(12) United States Patent  (10) Patent No.: US 8,309,739 B2
O'Sullivan et al.  (45) Date of Patent: Nov. 13, 2012

(54) CHEMICAL COMPOUNDS

(75) Inventors: Anthony Cornelius O'Sullivan, Basel (CH); Juergen Harry Schaetzer, Basel (CH); Christoph Luethy, Basel (CH); Allison Clare Elliott, Bracknell (GB); Christopher John Mathews, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 0 days.

(21) Appl. No.: 13/105,596

(22) Filed: May 11, 2011

(65) Prior Publication Data

US 2011/0218341 A1 Sep. 8, 2011

Related U.S. Application Data

(63) Continuation of application No. 12/063,869, filed as application No. PCT/GB2006/002886 on Aug. 2, 2006, now Pat. No. 7,960,310.

(30) Foreign Application Priority Data

Aug. 15, 2005 (GB) .................................. 0516706.9

(51) Int. Cl.
C07D 277/18 (2006.01)
(52) U.S. Cl. ...................................... 548/193; 548/190
(58) Field of Classification Search .................. 548/190, 548/193
See application file for complete search history.

(56) References Cited

U.S. PATENT DOCUMENTS 3,636,219 A 1/1972 Culik

FOREIGN PATENT DOCUMENTS

IN 179230 5/2008
WO 2005063724 7/2005

OTHER PUBLICATIONS

Shukla et al., Collection of Czechoslovak Chemical Communications (1992), vol. 57(2), p. 415-424.*
Collection of Czechoslovak Chemical Communications (1992); 57(2): 415-24.
Chapman, Arthur D., "Numbers of Living Species in Australia and the World," (2nd Ed.) Department of the Environment, Water, Heritage and the Arts, p. 1-84 (2009).
DE 2 658 138 A (Bayer AG) Jul. 6, 1978 (abstract) [online] Dialog IP, [retrieved on Jul. 14, 2010]. Retrieved from DialogSelect, Derwent Accession No. 1519289.

* cited by examiner

Primary Examiner — Yong Chu
(74) Attorney, Agent, or Firm — William A. Teoli, Jr.

(57) ABSTRACT

The use of a compound of formula I

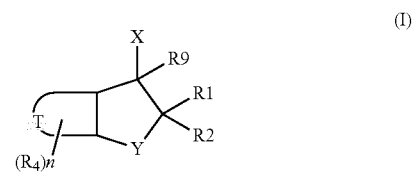

wherein
X is (i), (ii) or (iii)

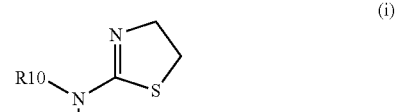

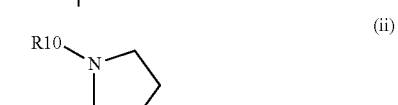

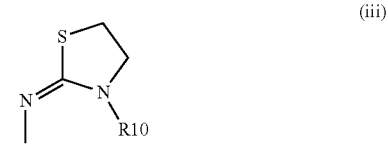

Y is O, $S(O)_m$, $NR^3$, $CR^5R^6$, $CR^5R^6$—$CR^7R^8$, O—$CR^7R^8$, $S(O)_m$—$CR^7R^8$, $NR^3$—$CR^7R^8$, $CR^5R^6$—O, $CR^5R^6$—$S(O)_m$, $CR^5R^6$—$NR^3$, $SO_2$—$NR^3$, $NR^3$—$SO_2$, $NR^3$—O or O—$NR^3$;
m is 0, 1, or 2;
the ring (T)

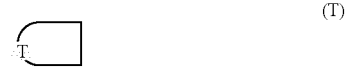

is a 5- or 6-membered aromatic or heteroaromatic ring; $R^1$ to $R^{10}$ are specified organic groups and n and is 0, 1, 2, 3 or 4; or salts or N-oxides thereof or compositions containing them in controlling insects, acarines, nematodes or molluscs. Novel compounds are also provided.

16 Claims, No Drawings

CHEMICAL COMPOUNDS

This application is a divisional application of U.S. Ser. No. 12/063,869, filed Jun. 16, 2008, which is a 371 of International Application No. PCT/GB2006/002886 filed Aug. 2, 2006, which claims priority to GB 0516706.9 filed Aug. 15, 2005, the contents of which are incorporated herein by reference.

The present invention relates to thiazoline derivatives, to processes for preparing them, to insecticidal, acaricidal, molluscicidal and nematicidal compositions comprising them and to methods of using them to combat and control insect, acarine, mollusc and nematode pests.

Thiazoline derivatives with pharmaceutical properties are disclosed in for example in U.S. Pat. No. 3,636,219, IN 179230 and Coll. Czech Chem. Comm, 1992, 57, 415.

It has now surprisingly been found that certain thiazolines have good insecticidal properties.

The present invention therefore provides a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I):

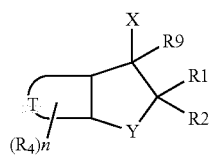

(I)

wherein
X is (i), (ii) or (iii)

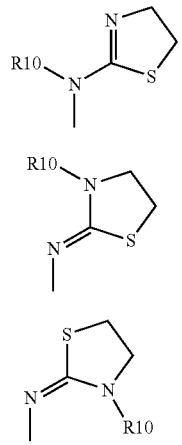

Y is O, $S(O)_m$, $NR^3$, $CR^5R^6$, $CR^5R^6$—$CR^7R^8$, O—$CR^7R^8$, $S(O)_m$—$CR^7R^8$, $NR^3$—$CR^7R^8$, $CR^5R^6$—O, $CR^5R^6$—$S(O)_m$, $CR^5R^6$—$NR^3$, $SO_2$—$NR^3$, $NR^3$—$SO_2$, $NR^3$—O or O—$NR^3$;
m is 0, 1, or 2;
the ring (T)

(T)

is a 5- or 6-membered aromatic or heteroaromatic ring;
$R^1$, $R^2$, $R^5$, $R^6$, $R^7$ and $R^8$ are each independently H, OH, halogen, nitro, cyano, rhodano, carboxy, formyl, formyloxy, G-, G-O—, G-S—, G-A-, $R^{21}R^{22}N$—, $R^{21}R^{22}N$-A-, G-O-A-, G-S-A-, G-A-O—, G-A-S—, G-A-$NR^{23}$—, $R^{21}R^{22}N$-A-O—, $R^{21}R^{22}N$-A-S—, $R^{21}R^{22}N$-A-$NR^{23}$—, G-O-A-O—, G-O-A-S—, G-O-A-$NR^{23}$—, G-S-A-O, G-S-A-$NR^{23}$—, or $R^{20}S(O)(=NR^{17})$—; or two of the groups $R^1$, $R^2$, $R^5$, $R^6$, $R^7$ and $R^8$ attached to the same carbon atom are =O, =S, =$NR^{11}$ or =$CR^{12}R^{13}$, or the groups $R^1$ and $R^2$, $R^5$ and $R^6$ or $R^7$ and $R^8$ together with the carbon atom to which they are attached form a three to six membered ring, containing at least 2 carbon atoms and optionally containing one or two sulfur and/or one or two non-adjacent oxygen atoms or a group $NR^{14}$, the ring being optionally substituted by $C_1$-$C_6$ alkyl; or two of the groups $R^1$, $R^2$, $R^5$, $R^6$, $R^7$ and $R^8$ attached to different atoms together with the atoms they are attached form a three to seven membered ring, that optionally contains one or two sulfur and/or one or two non-adjacent oxygen atoms or a group $NR^{14}$, the ring being optionally substituted by $C_1$-$C_6$ alkyl or two of the groups $R^1$, $R^2$, $R^5$, $R^6$, $R^7$ and $R^8$ attached to adjacent atoms combine to form a bond;
$R^{10}$ is H, OH, cyano, formyl, tri($C_1$-$C_6$ alkyl)silyl, G-, G-O—, G-S—, G-S—S—, G-A-, $R^{24}R^{25}N$—, $R^{24}R^{25}N$—S—, $R^{24}R^{25}N$-A-, $R^{18}N=C(R^{19})$—, G-A-$NR^{69}$—, $R^{70}R^{71}C=N$—, G-O-A- or G-S-A-,
$R^{11}$ is H, OH, nitro, cyano, formyl, formyloxy, G-, G-O—, G-A-, $R^{36}R^{37}N$—, G-C(O)—O—, G-C(O)—$NR^{26}$—, $R^{36}R^{37}N$—C(O)O—, G—OC(O)O—, G-OC(O)—$NR^{26}$—;
$R^{12}$ and $R^{13}$ are each independently H, halogen, nitro, cyano, formyl, formyloxy, G-, G-O—, G-S—, G-A-, $R^{40}R^{41}N$—, $R^{40}R^{41}N$-A-, G-O-A-, G-A-O—, $R^{40}R^{41}N$-A-O—, $R^{40}R^{41}N$-A-S—, G-O-A-O—, G-O-A-S—, G-O-A-$NR^{30}$—, or $R^{12}$ and $R^{13}$ together with the carbon atom to which they are attached form a 3 to 6 membered carbocyclic ring;
$R^3$, $R^{14}$, $R^{15}$ and $R^{16}$ are each independently H, OH, cyano, formyl, G-, G-O—, G-S—, G-A-, $R^{27}R^{28}N$—, $R^{27}R^{28}N$-A-, G-O-A-, G-S-A-, G-A-$NR^{29}$—, $R^{27}R^{28}NA$-$NR^{29}$—, G-O-A-$NR^{29}$— or G-S-A-$NR^{29}$—;
each $R^4$ is independently OH, halogen, nitro, cyano, azido, rhodano, isothiocyanato, carboxy, formyl, formyloxy, G-, G-O—, G-S—, G-A-, $R^{31}R^{32}N$—, $R^{31}R^{32}N$-A-, G-O-A-, G-S-A-, G-A-O—, G-A-S—, G-A-$NR^{33}$—, $R^{31}R^{32}N$-A-O—, $R^{31}R^{32}N$-A-S—, $R^{31}R^{32}N$-A-$NR^{33}$—, G-O-A-O—, G-O-A-S—, S—, G-O-A-$NR^{33}$—, G-S-A-O, G-S-A-$NR^{33}$—, $R^{20}S(O)(=NR^{17})$—, $R^{18}N=C(R^{19})$—, $R^{44}R^{45}P(O)$— or $R^{44}R^{45}P(S)$—, or 2 adjacent groups $R^4$ together with the carbon atoms to which they are attached form a 4, 5, 6, or 7 membered carbocyclic or heterocyclic ring which may be optionally substituted by halogen, or a group $R^4$ together with a group $R^3$, $R^5$ or $R^9$ and the atoms to which they are attached form a 5-7 membered ring optionally containing an $NR^{15}$ group or an S or O atom, the ring being optionally substituted by $C_1$-$C_6$ alkyl;
n is 0, 1, 2, 3 or 4;
$R^9$ is H, formyl, G, G-A-, $R^{34}R^{35}N$-A-, G-O-A- or G-S-A-, or $R^9$ together with a group $R^1$, $R^5$ or $R^7$ and the atoms to which they are attached may form a three to seven membered ring, that optionally may contain one or two sulfur and/or one or two non-adjacent oxygen atoms or a group $NR^{16}$;
$R^{17}$ is H, G-, G-C(O)—, or G-OC(O)—;
$R^{18}$ is H, OH, cyano, nitro, G-, G-O— or $R^{38}R^{39}N$—;
$R^{19}$ is H, cyano, G-, G-O—, G-S— or $R^{42}R^{43}N$—;
$R^{20}$ is $C_{1-6}$ alkyl, optionally substituted phenyl, optionally substituted benzyl;
each of the groups $R^{21}$ to $R^{43}$ inclusive are independently H or G-, or two $R^{21}$, $R^{22}$, $R^{27}$, $R^{28}$, $R^{31}$, $R^{32}$, $R^{34}$, $R^{35}$, $R^{36}$, $R^{37}$, $R^{38}$, $R^{39}$, $R^{42}$, $R^{43}$ groups, together with the N atom to which they are attached, form a group $N=CR^aR^b$ (where $R^a$ and $R^b$ are H, or $C_{1-6}$ alkyl) or two $R^{21}$, $R^{22}$, $R^{24}$, $R^{25}$, $R^{27}$, $R^{28}$, $R^{31}$, $R^{32}$, $R^{34}$, $R^{35}$, $R^{36}$, $R^{37}$, $R^{38}$, $R^{39}$, $R^{42}$, $R^{43}$ groups, together with the N atom to which they are attached, form a five, six or seven-membered heterocyclic ring which may contain one or two further heteroatoms selected from O, N or S and which may be optionally substituted by one to four $C_{1-6}$ alkyl groups;

$R^{44}$ and $R^{45}$ are independently $C_{1-6}$alkyl, $C_{1-6}$-alkoxy, phenyl, phenoxy;

G is optionally substituted $C_{1-12}$ alkyl, optionally substituted $C_{2-12}$ alkenyl, optionally substituted $C_{2-12}$ alkynyl, optionally substituted $C_{3-8}$ cycloalkyl, optionally substituted $C_{3-8}$ cycloalkenyl, optionally substituted aryl, optionally substituted heteroaryl or optionally substituted heterocyclyl;

$R^{69}$ is H, G-, G-C(O)—, or G-OC(O)—;

$R^{70}$ and $R^{71}$ are independently H, cyano, nitro, G-, G-O—, G-S—, or $R^{70}$ and $R^{71}$ together with the carbon atom to which they are attached form a five, six or seven-membered heterocyclic ring which may contain one or two further heteroatoms selected from O, N or S and which may be optionally substituted by one to four $C_{1-6}$ alkyl groups;

A is S(O), $SO_2$, C(O) or C(S);

or salts or N-oxides thereof.

The compounds of formula (I) may exist in different geometric or optical isomers or different tautomeric forms. One or more centres of chirality may be present, for example on the chiral carbon atoms $CR^1R^2$, $CR^5R^6$, $CR^7R^8$, $CR^9$, or a chiral carbon unit in the group G, or a chiral —S(O)— unit, in which case compounds of the formula (I) may be present as pure enantiomers, mixtures of enantiomers, pure diastereomers or mixtures of diastereomers. There may be double bonds present in the molecule, such as C=C or C=N bonds, in which case compounds of formula (I) may exist as single isomers of mixtures of isomers. Centres of tautomerisation may be present. This invention covers all such isomers and tautomers and mixtures thereof in all proportions as well as isotopic forms such as deuterated compounds.

The compounds of formula (I) contain an amidine moiety, which can exist in two tautomeric forms when $R^{10}$ is hydrogen. One of these forms contains an exocyclic C=N double bond, and one of them contains an endocyclic C=N double bond. When the C=N double bond is exocyclic this double bond can exist in two geometric forms E and Z as shown by formula (I') and (I''). Each form can be latentiated with a group $R^{10}$. This group $R^{10}$ is selected to allow its removal by one or a combination of biochemical, chemical or physical processes to afford compounds of formula I where $R^{10}$ is H before, during or following application to the treated area or plants. Examples of these processes include enzymatic cleavage, chemical hydrolysis and photolysis. Compounds bearing groups $R^{10}$ may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, increased movement in soils or reduced leaching in soils.

Suitable acid addition salts include those with an inorganic acid such as hydrochloric, hydrobromic, sulfuric, nitric and phosphoric acids, or an organic carboxylic acid such as oxalic, tartaric, lactic, butyric, toluic, hexanoic and phthalic acids, or sulphonic acids such as methane, benzene and toluene sulphonic acids. Other examples of organic carboxylic acids include haloacids such as trifluoroacetic acid.

N-oxides are oxidised forms of tertiary amines or oxidised forms of nitrogen containing heteroaromatic compounds. They are described in many books for example in "Heterocyclic N-oxides" by Angelo Albini and Silvio Pietra, CRC Press, Boca Raton, Fla., 1991.

Each alkyl moiety either alone or as part of a larger group (such as G, or alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are suitably $C_1$ to $C_{12}$ alkyl groups, but are preferably $C_1$-$C_{10}$, more preferably $C_1$-$C_8$, even more preferably $C_1$-$C_6$ and most preferably $C_1$-$C_4$ alkyl groups.

The ring or chain forming alkylene, alkenylene and alkinylene groups can optionally be further substituted by one or more halogen, $C_1$-$C_3$ alkyl, and/or $C_1$-$C_3$ alkoxy groups.

When present, the optional substituents on an alkyl moiety (alone or as part of a larger group such as alkoxy, alkoxycarbonyl, alkylcarbonyl, alkylaminocarbonyl, dialkylaminocarbonyl) include one or more of halogen, nitro, cyano, rhodano, isothiocyanato, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkylsilyl($C_{1-6}$) alkoxy, $C_{1-6}$ alkoxycarbonyl($C_{1-10}$)alkoxy, $C_{1-10}$ haloalkoxy, aryl($C_{1-4}$)-alkoxy (where the aryl group is optionally substituted), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl($C_{1-4}$)alkylthio (where the aryl group is optionally substituted), $C_{3-7}$ cycloalkylthio (where the cycloalkyl group is optionally substituted with $C_{1-6}$ alkyl or halogen), tri($C_{1-4}$)alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group may be optionally substituted), tri($C_{1-4}$)alkylsilyl, aryldi($C_{1-4}$)alkylsilyl, ($C_{1-4}$) alkyldiarylsilyl, triarylsilyl, formyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)aminocarbonyl, N—($C_{1-3}$ alkyl)-N—($C_{1-3}$ alkoxy)aminocarbonyl, $C_{1-6}$ alkylcarbonyloxy, arylcarbonyloxy (where the aryl group is optionally substituted), di($C_{1-6}$)alkylaminocarbonyloxy, oximes and oximethers such as =NOalkyl, =NOhaloalkyl and =NOaryl (itself optionally substituted), aryl (itself optionally substituted), heteroaryl (itself optionally substituted), heterocyclyl (itself optionally substituted with $C_{1-6}$ alkyl or halogen), aryloxy (where the aryl group is optionally substituted), heteroaryloxy, (where the heteroaryl group is optionally substituted), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, $C_{2-6}$ alkenylcarbonyl, $C_{2-6}$ alkynylcarbonyl, $C_{3-6}$ alkenyloxycarbonyl, $C_{3-6}$ alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. It is understood, that allenyl and alkylinylalkenyl are included in these terms.

When present, the optional substituents on alkenyl or alkynyl include those optional substituents given above for an alkyl moiety.

In the context of this specification acyl is optionally substituted $C_{1-6}$ alkylcarbonyl (for example acetyl), optionally substituted $C_{2-6}$ alkenylcarbonyl, optionally substituted $C_{3-6}$ cycloalkylcarbonyl (for example cyclopropylcarbonyl, optionally substituted $C_{2-6}$ alkynylcarbonyl, optionally substituted arylcarbonyl (for example benzoyl) or optionally substituted heteroarylcarbonyl.

Halogen is fluorine, chlorine, bromine or iodine.

Haloalkyl groups are alkyl groups which are substituted with one or more of the same or different halogen atoms and are, for example, $CF_3$, $CF_2Cl$, $CF_2H$, $CCl_2CH$, $FCH_2$, $ClCH_2$, $BrCH_2$, $CH_3CHF$, $CF_3CH_2$ or $CHF_2CH_2$.

In the context of the present specification the terms "aryl", "aromatic ring" and "aromatic ring system" refer to ring systems which may be mono-, bi- or tricyclic. Examples of such rings include phenyl, naphthalenyl, anthracenyl, indenyl or phenanthrenyl. A preferred aryl group is phenyl. In addition, the terms "heteroaryl", "heteroaromatic ring" or "heteroaromatic ring system" refer to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidyl, triazinyl, thienyl, furyl, oxazolyl, isoxazolyl, 2,1,3-benzoxadiazole and thiazolyl.

The terms heterocycle and heterocyclyl refer to a non-aromatic monocyclic or bicyclic ring system containing up to 10 atoms including one or more (preferably one or two) heteroatoms selected from O, S and N. Examples of such rings include 1,3-dioxolane, oxetane, tetrahydrofuran, morpholine, thiomorpholine and piperazine.

When present, the optional substituents on heterocyclyl include $C_{1-6}$ alkyl and $C_{1-6}$ haloalkyl as well as those optional substituents given above for an alkyl moiety.

Cycloalkyl includes cyclopropyl, cyclobutyl, cyclopentyl and cyclohexyl.

Cycloalkenyl includes cyclopentenyl and cyclohexenyl.

When present, the optional substituents on cycloalkyl or cycloalkenyl include $C_{1-3}$ alkyl as well as those optional substituents given above for an alkyl moiety.

Carbocyclic rings include aryl, cycloalkyl and cycloalkenyl groups.

When present, the optional substituents on aryl or heteroaryl are selected independently, from halogen, nitro, cyano, rhodano, isothiocyanato, $C_{1-6}$ alkyl, $C_{1-6}$ haloalkyl, $C_{1-6}$ alkoxy-$(C_{1-6})$alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy$(C_{1-10})$alkoxy, tri$(C_{1-4})$alkyl-silyl$(C_{1-6})$ alkoxy, $C_{1-6}$ alkoxycarbonyl$(C_{1-10})$alkoxy, $C_{1-10}$ haloalkoxy, aryl$(C_{1-4})$alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl$(C_{1-4})$alkylthio $C_{3-7}$ cycloalkylthio (where the cycloalkyl group is optionally substituted with $C_{1-6}$ alkyl or halogen), tri$(C_{1-4})$-alkylsilyl$(C_{1-6})$ alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, tri $(C_{1-4})$alkylsilyl, aryldi$(C_{1-4})$-alkylsilyl, $(C_{1-4})$alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di$(C_{1-6}$ alkyl)-aminocarbonyl, N—$(C_{1-3}$ alkyl)-N—$(C_{1-3}$ alkoxy) aminocarbonyl, $C_{1-6}$ alkylcarbonyloxy, arylcarbonyloxy, di$(C_{1-6})$alkylamino-carbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di$(C_{1-6})$alkylamino, $C_{1-6}$ alkylcarbonylamino, N—$(C_{1-6})$alkylcarbonyl-N—$(C_{1-6})$alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include aryl carbonyl amino (where the aryl group is substituted by $C_{1-6}$ alkyl or halogen), $(C_{1-6})$alkyloxycarbonylamino $(C_{1-6})$alkyloxycarbonyl-N—$(C_{1-6})$alkylamino, aryloxycarbonylamino (where the aryl group is substituted by $C_{1-6}$ alkyl or halogen), aryloxycarbonyl-N—$(C_{1-6})$alkylamino, (where the aryl group is substituted by $C_{1-6}$ alkyl or halogen), arylsulphonylamino (where the aryl group is substituted by $C_{1-6}$ alkyl or halogen), arylsulphonyl-N—$(C_{1-6})$alkylamino (where the aryl group is substituted by $C_{1-6}$ alkyl or halogen), aryl-N—$(C_{1-6})$alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$ alkylaminocarbonyl amino, di$(C_{1-6})$ alkylaminocarbonyl amino, arylaminocarbonyl amino where the aryl group is substituted by $C_{1-6}$ alkyl or halogen), aryl-N—$(C_{1-6})$alkylaminocarbonylamino where the aryl group is substituted by $C_{1-6}$ alkyl or halogen), $C_{1-6}$ alkylaminocarbonyl-N—$(C_{1-6})$alkyl amino, di$(C_{1-6})$alkylaminocarbonyl-N—$(C_{1-6})$alkyl amino, arylaminocarbonyl-N—$(C_{1-6})$alkyl amino where the aryl group is substituted by $C_{1-6}$ alkyl or halogen) and aryl-N—$(C_{1-6})$alkylaminocarbonyl-N—$(C_{1-6})$alkyl amino where the aryl group is substituted by $C_{1-6}$ alkyl or halogen).

For substituted phenyl moieties, heterocyclyl and heteroaryl groups it is preferred that one or more substituents are independently selected from halogen, $C_{1-6}$ alkyl, $C_{1-6}$ haloalkyl, $C_{1-6}$ alkoxy$(C_{1-6})$alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, $CO_2H$, $C_{1-6}$ alkylcarbonyl, $C_{1-6}$ alkoxycarbonyl, aryl, heteroaryl, $R^{50}R^{51}N$ or $R^{52}R^{53}NC(O)$; wherein $R^{50}$, $R^{51}$, $R^{52}$ and $R^{53}$ are, independently, hydrogen or $C_{1-6}$ alkyl.

Haloalkenyl groups are alkenyl groups which are substituted with one or more of the same or different halogen atoms.

It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_{1-6}$)alkyl groups. When heterocyclic rings are formed by joining two groups on an N atom, the resulting rings are suitably pyrrolidine, piperidine, thiomorpholine and morpholine each of which may be substituted by one or two independently selected ($C_{1-6}$) alkyl groups.

Preferably the optional substituents on an alkyl moiety include one or more of halogen, nitro, cyano, $HO_2C$, $C_{1-10}$ alkoxy (itself optionally substituted by $C_{1-10}$ alkoxy), aryl ($C_{1-4}$)alkoxy, $C_{1-10}$ alkylthio, $C_{1-10}$ alkylcarbonyl, $C_{3-5}$ cycloalkylcarbonyl, $C_{1-10}$ alkoxycarbonyl, $C_{1-6}$ alkylaminocarbonyl, di($C_{1-6}$ alkyl)aminocarbonyl, ($C_{1-6}$)alkylcarbonyloxy, optionally substituted phenyl, heteroaryl, aryloxy, arylcarbonyloxy, heteroaryloxy, heterocyclyl, heterocyclyloxy, $C_{3-7}$ cycloalkyl (itself optionally substituted with ($C_{1-6}$) alkyl or halogen), $C_{3-7}$ cycloalkyloxy, $C_{5-7}$ cycloalkenyl, $C_{1-6}$ alkylsulfonyl, $C_{1-6}$ alkylsulfinyl, tri($C_{1-4}$)alkylsilyl, tri($C_{1-4}$)alkylsilyl($C_{1-6}$)alkoxy, aryldi($C_{1-4}$)alkylsilyl, ($C_{1-4}$)alkyldiarylsilyl and triarylsilyl.

Preferably the optional substituents on alkenyl or alkynyl include one or more of halogen, aryl and $C_{3-7}$ cycloalkyl.

A preferred optional substituent for heterocyclyl is $C_{1-3}$ alkyl.

Preferably the optional substituents for cycloalkyl include halogen, cyano and $C_{1-6}$ alkyl.

The optional substituents for cycloalkenyl preferably include $C_{1-3}$ alkyl, halogen and cyano.

Preferred groups for T, Y, $R^1$, $R^2$, $R^4$, $R^9$, and $R^{10}$ in any combination thereof are set out below.

Y is preferably O, S, S(O), $SO_2$, $NR^3$ or $CR^5R^6$ where $R^3$, $R^5$ and $R^6$ are defined above. $R^3$ is especially hydrogen, formyl, $C_{1-6}$ alkylcarbonyl, cyclopropylcarbonyl, $C_{1-6}$ alkoxycarbonyl, $C_{1-6}$ alkylsulfonyl, $C_{1-6}$ alkyl, $C_{1-6}$ haloalkyl, $C_{3-4}$ alkenyl, $C_{3-4}$ haloalkenyl, $C_{3-4}$ alkynyl or benzyl, or phenyl (where the phenyl containing groups are optionally substituted by halogen, $C_{1-4}$ alkyl, $C_{1-4}$ alkoxy, $C_{1-4}$ haloalkyl, $C_{1-4}$ haloalkoxy, CN or $NO_2$). Especially $R^5$ and $R^6$ are independently hydrogen, hydroxy, halogen, cyano, $C_{1-6}$ alkyl, $C_{1-6}$ haloalkyl, $C_{1-6}$ alkoxy($C_{1-6}$)alkyl, phenyl ($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), $C_{3-5}$ cycloalkyl, 1,3-dioxolan-2-yl, phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), $C_{1-6}$ alkoxy, $C_{1-6}$ haloalkoxy, $C_{1-6}$ alkenyloxy, $C_{1-6}$ alkynyloxy, $C_{1-3}$ alkoxy($C_{1-3}$)alkoxy, benzyloxy (where phenyl is optionally substituted by halogen, $C_{1-4}$ alkyl, $C_{1-4}$ alkoxy, $C_{1-4}$ haloalkyl, $C_{1-4}$ haloalkoxy, CN, $NO_2$), $C_{1-6}$ alkylthio, $C_{1-6}$ haloalkylthio, $NR^{54}R^{55}$ (where $R^{54}$ and $R^{55}$ are independently hydrogen, $C_{1-6}$ alkyl or $C_{1-6}$ haloalkyl, $C_{1-4}$ alkoxy($C_{1-4}$alkyl, formyl, $C_{2-6}$ alkylcarbonyl, phenylcarbonyl (where the phenyl is optionally substituted by halogen, $C_{1-4}$ alkyl, $C_{1-4}$ alkoxy, $C_{1-4}$ haloalkyl, $C_{1-4}$ haloalkoxy, CN, $NO_2$)), or $R^5$ and $R^6$ together with the carbon atom to which they are attached form a three to six membered ring, that optionally may contain one or two sulfur or one or two not adjacent oxygen atoms or a group $NR^{56}$ (where $R^{56}$ is hydrogen, $C_{1-6}$ alkyl, $C_{1-6}$ haloalkyl, $C_{1-4}$ alkoxy($C_{1-4}$alkyl, formyl, $C_{2-6}$ alkylcarbonyl), or when $R^5$ together with $R^1$ forms a bond, or either $R^5$ or $R^6$ together with $R^1$ or $R^2$ and the carbon atom they are attached form a three to six membered ring, that optionally may contain one or two not adjacent oxygen atoms, or when $R^5$ and $R^6$ together form =O, =S, =$NR^{57}$ or =$CR^{58}R^{59}$, wherein $R^{57}$ is OH, optionally substituted $C_{1-6}$ alkoxy or $C_{1-4}$ alkylcarbonylamino, and $R^{58}$ and $R^{59}$ are independently H or $C_{1-6}$ alkyl.

More preferably Y is O or $CR^5R^6$ where $R^5$ and $R^6$ are hydrogen, hydroxy, fluoro, chloro, $C_{1-6}$ alkyl, $C_{1-6}$ haloalkyl, $C_{1-6}$ alkoxy, $C_{1-6}$ haloalkoxy, $C_{1-6}$ alkenyloxy, $C_{1-6}$ alkynyloxy, $C_{1-3}$ alkoxy($C_{1-3}$)alkoxy or benzyloxy, or $R^5$ and $R^6$ together with the carbon atom to which they are attached form a three to six membered carbocyclic ring, or $R^5$ and $R^1$ together form a bond, or $R^5$ together with $R^1$ and the carbon atoms to which they are attached form a three to six membered carbocyclic ring.

Most preferably Y is $CR^5R^6$ where $R^5$ and $R^6$ are independently hydrogen or methyl, especially hydrogen.

Preferably each $R^1$ and $R^2$ group is independently hydrogen, hydroxy, halogen, cyano, $C_{1-6}$ alkyl, $C_{1-6}$ haloalkyl, $C_{1-6}$ alkoxy($C_{1-6}$)alkyl, phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl), $C_{3-5}$ cycloalkyl, 1,3-dioxolan-2-yl, phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl), $C_{1-6}$ alkoxy, $C_{1-6}$ haloalkoxy, $C_{2-6}$ alkenyloxy, $C_{2-6}$ alkinyloxy, $C_{1-3}$ alkoxy($C_{1-3}$)alkoxy, benzyloxy (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$), $C_{1-6}$ alkylthio, $C_{1-6}$ haloalkylthio, formyl, $C_{2-6}$ alkylcarbonyl, phenylcarbonyl (where the phenyl is optionally substituted by halogen, $C_{1-4}$ alkyl, $C_{1-4}$ alkoxy, $C_{1-4}$ haloalkyl, $C_{1-4}$ haloalkoxy, CN, $NO_2$), or $R^1$ and $R^2$ together are =O, =S, =$NR^{60}$ or =$CR^{61}R^{62}$, wherein $R^{60}$ is OH, $C_1$-$C_6$-alkoxy or $C_1$-$C_6$-alkylcarbonylamino, and $R^{61}$ and $R^{62}$ are independently H, $C_1$-$C_6$-alkyl, or $C_1$-$C_6$-haloalkyl; or $R^1$ and $R^9$ together with the carbon atom they are attached form a three to six membered ring, that optionally may contain one or two not adjacent oxygen atoms; or $R^1$ and $R^2$ together form a three to six membered ring, that optionally may contain one or two non-adjacent oxygen atoms.

More preferably each $R^1$ and $R^2$ group is independently hydrogen, hydroxy, halogen, $C_{1-6}$ alkyl, $C_{1-6}$ haloalkyl, $C_{1-6}$ alkoxy, $C_{1-6}$ haloalkoxy, $C_{1-6}$ alkenyloxy, $C_{1-6}$ alkynyloxy, $C_{1-3}$ alkoxy($C_{1-3}$)alkoxy or benzyloxy.

Most preferably each $R^1$ and $R^2$ group is independently hydrogen or methyl.

$R^9$ is preferably hydrogen, $C_{1-6}$ alkyl, $C_{1-6}$ cyanoalkyl, $C_{1-6}$ haloalkyl, $C_{3-7}$ cycloalkyl($C_{1-4}$alkyl, $C_{1-6}$ alkoxy($C_{1-6}$)alkyl, aryl($C_{1-6}$)alkyl (wherein the aryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl), $C_{2-6}$ alkylcarbonyl, phenylcarbonyl (where the phenyl is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{1-6}$ alkoxycarbonyl, C(O)$NR^{63}R^{64}$ (where $R^{63}$ and $R^{64}$ are independently hydrogen, $C_{1-6}$ alkyl or $C_{1-6}$ haloalkyl or $C_{1-6}$ alkoxy($C_{1-6}$) alkyl or $R^{63}$ and $R^{64}$ together with the N atom to which they are attached form a five, six or seven-membered ring containing an O or S atom), or $R^9$ and $R^1$ together with the carbon atoms to which they are attached form a three to six membered ring.

More preferably $R^9$ is independently hydrogen, $C_{1-6}$ alkyl, $C_{1-6}$ haloalkyl, $C_{3-7}$ cycloalkyl($C_{1-4}$)alkyl, $C_{1-6}$ alkoxy($C_{1-6}$) alkyl, aryl($C_{1-6}$)alkyl (wherein the aryl group may be optionally substituted by halo, nitro, cyano, $C_{1-6}$ alkyl, $C_{1-6}$ haloalkyl, $C_{1-6}$ alkoxy), $C_{2-6}$ alkylcarbonyl, phenylcarbonyl (where the phenyl is optionally substituted by halogen, $C_{1-4}$ alkyl, $C_{1-4}$ alkoxy, $C_{1-4}$ haloalkyl), $C_{1-6}$ alkoxycarbonyl, or $R^9$ and $R^1$ together with the carbon atoms to which they are attached form a three to six membered ring.

Most preferably $R_9$ is independently hydrogen or methyl.

Preferably each $R^4$ is independently halogen, cyano, $C_{1-8}$ alkyl, $C_{1-8}$ haloalkyl, cyano($C_{1-6}$)alkyl, $C_{1-3}$ alkoxy($C_{1-3}$) alkyl, $C_{2-6}$ alkynyl, $C_{3-6}$ cycloalkyl, $C_{1-3}$ alkyl ($C_{3-6}$) cycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), formyl, $C_{1-6}$ alkylcarbonyl, $C_{1-6}$ alkoxycarbonyl, $C_{1-6}$ alkylthiocarbonyl, $C_{1-6}$ alkoxythiocarbonyl, carbamoyl, $C_{1-6}$ alkylaminocarbonyl, di-$C_{1-6}$ alkylaminocarbonyl, thiocarbamoyl, $C_{1-6}$ alkylaminothiocarbonyl, di-$C_{1-6}$ alkylaminothiocarbonyl, $C_{1-8}$ alkoxy, $C_{1-6}$ haloalkoxy, phenoxy (optionally substituted by halogen, $C_{1-4}$ alkyl, $C_{1-4}$ alkoxy, $C_{1-4}$ haloalkyl, $C_{1-4}$ haloalkoxy, CN, $NO_2$, phenyl), heteroaryloxy (optionally substituted by halo, nitro, cyano, $C_{1-3}$ alkyl, $C_{1-3}$ haloalkyl, $C_{1-3}$ alkoxy or $C_{1-3}$ haloalkoxy), $C_{1-6}$ alkylcarbonyloxy, $C_{1-6}$ alkoxycarbonyloxy, $C_{1-6}$ alkylaminocarbonyloxy, di-$C_{1-6}$ alkylaminocarbonyloxy, $C_{1-6}$ alkylaminothiocarbonyloxy, di-$C_{1-6}$ alkylaminothiocarbonyloxy, $C_{1-8}$ alkylthio, $C_{1-6}$ haloalkylthio, arylthio or heteroarylthio (where the aryl is optionally substituted by halogen, $C_{1-4}$ alkyl, $C_{1-4}$ alkoxy, $C_{1-4}$ haloalkyl, $C_{1-4}$ haloalkoxy, CN, $NO_2$ or phenyl), $C_{1-6}$ alkylcarbonylthio, $C_{1-6}$ alkylaminocarbonylthio, di-$C_{1-6}$ alkylaminocarbonylthio, di($C_{1-8}$)alkylamino, $C_{1-6}$ alkylcarbonylamino, $C_{1-6}$ alkoxycarbonylamino, $C_{1-6}$ alkylaminocarbonylamino, di-$C_{1-6}$ alkylaminocarbonylamino, aminothiocarbonylamino, $C_{1-6}$ alkylaminothiocarbonylamino, di-$C_{1-6}$ alkylaminothiocarbonylamino, or 2 adjacent groups $R^4$ together with the carbon atoms to which they are attached form a 4, 5, 6 or 7 membered carbocyclic or heterocyclic ring which may be optionally substituted by halogen; n is 0, 1, 2 or 3.

More preferably each $R^4$ is independently halogen, cyano, $C_{1-8}$ alkyl, $C_{1-8}$ haloalkyl, cyano($C_{1-6}$)alkyl, $C_{1-6}$ alkoxy ($C_{1-6}$)alkyl, $C_{2-6}$ alkynyl, heterocyclyl (optionally substituted by $C_{1-6}$ alkyl), $C_{1-8}$ alkoxy, $C_{1-6}$ haloalkoxy, phenoxy (optionally substituted by halo, cyano, $C_{1-3}$ alkyl or $C_{1-3}$ haloalkyl), heteroaryloxy (optionally substituted by halo, cyano, $C_{1-3}$ alkyl or $C_{1-3}$ haloalkyl), $C_{1-3}$ alkoxy, $C_{1-3}$ haloalkoxy, $C_{1-3}$ alkylthio, $C_{1-3}$ haloalkylthio, $C_{1-3}$ alksulfonyl, di($C_{1-8}$)alkylamino, or 2 adjacent groups $R^4$ together with the carbon atoms to which they are attached form a 4, 5, 6 or 7 membered carbocyclic or heterocyclic ring which may be optionally substituted by halogen; n is 0, 1, 2 or 3.

Most preferably each $R^4$ is independently fluoro, chloro, bromo, $C_{1-4}$ alkyl or $C_{1-4}$ haloalkyl; n is 1, 2 or 3, preferably 1 or 2.

Preferably at least one group $R^4$ is positioned adjacent to the group Y.

$R^{10}$ is preferably hydrogen, hydroxy, cyano, $C_{1-6}$ alkyl, $C_{1-6}$ haloalkyl, $C_{1-6}$ alkoxy($C_{1-6}$)alkyl, phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl), $C_{1-6}$ alkoxy, $C_{1-6}$ haloalkoxy, $C_{2-6}$ alkenyloxy, $C_{2-6}$ alkinyloxy, $C_{1-3}$ alkoxy ($C_{1-3}$)alkoxy, benzyloxy (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$), $C_{1-6}$ alkylthio, $C_{1-6}$ haloalkylthio, phenylthio (where the phenyl is optionally substituted by halogen, $C_{1-4}$ alkyl, $C_{1-4}$ alkoxy, $C_{1-4}$ haloalkyl, $C_{1-4}$ haloalkoxy, CN, $NO_2$), $C_{1-6}$ alkyldithio, $C_{1-6}$ haloalkyldithio, formyl, $C_{2-6}$ alkylcarbonyl, $C_{2-6}$ haloalkylcarbonyl, $C_{1-6}$ alkoxycarbonyl, arylcarbonyl (where the aryl is optionally substituted by halogen, $C_{1-4}$ alkyl, $C_{1-4}$ alkoxy, $C_{1-4}$ haloalkyl, $C_{1-4}$ haloalkoxy, CN, $NO_2$), $NR^{65}R^{66}$ (where $R^{65}$ and $R^{66}$ are independently hydrogen, $C_{1-6}$ alkyl or $C_{1-6}$ haloalkyl, $C_{1-6}$ alkoxy($C_{1-6}$)alkyl, $C_{1-6}$ alkylcarbonyl or $R^{65}$ and $R^{66}$ together with the N atom to which they are attached form a five, six or seven-membered ring containing an O or S atom), $R^{65}R^{66}NS$, $R^{65}R^{66}NC(O)$, $R^{65}R^{66}NC(S)$, $R^{67}N=C(R^{68})$—, where $R^{67}$ is $C_{1-6}$ alkyl or phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$), and $R^{68}$ is H, $C_{1-6}$ alkyl or $C_{1-6}$ alkylthio.

More preferably $R^{10}$ is hydrogen, hydroxy, cyano, $C_{1-6}$ alkyl, $C_{1-6}$ alkoxy($C_{1-6}$)alkyl, $C_{1-6}$ alkoxy, $C_{1-6}$ alkylthio, $C_{1-6}$ haloalkylthio, formyl, $C_{2-6}$ alkylcarbonyl, $C_{1-6}$ alkoxycarbonyl, $NR^{65}R^{66}$ (where $R^{65}$ and $R^{66}$ are independently hydrogen, $C_{1-6}$ alkyl or $C_{1-6}$ haloalkyl, $C_{1-6}$ alkoxy($C_{1-6}$)alkyl, $C_{1-6}$ alkylcarbonyl or $R^{65}$ and $R^{66}$ together with the N atom to which they are attached form a five, six or seven-membered ring containing an O or S atom).

Most preferably $R^{10}$ is hydrogen, cyano, or formyl, especially hydrogen.

It is preferred that the ring

is a 6-membered aromatic ring or is 5 or 6 membered heteroaromatic ring wherein the ring members are each independently CH, S, N, $NR^4$, O, or $CR^4$ provided that there are no more than one O or S atoms present in the ring.

More preferably the ring

is a benzene, thiophene, furan, pyridine, pyrimidine, pyrazine, pyridazine, triazine, pyrrole, imidazole, pyrazole, oxazole, thiazole, isoxazole, isothiazole, [1,2,3]triazole, [1,2,3]oxadiazole or [1,2,3]thiadiazole Most preferably the ring

is a benzene, pyridine or thiophene ring, especially a benzene ring.

Another especially preferred group of compounds are those compounds of formula (IB)

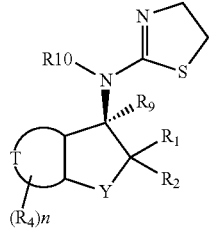
(IB)

where the chirality on the $R^9$ bearing carbon atom is that shown in the above structure and $R^1$, $R^2$, $R^4$, $R^9$, $R^{10}$, Y and n are as defined above in relation to formula (I).

Certain compounds of formula (I) are novel and as such form a further aspect of the invention. One group of novel compounds are compounds of formula IC

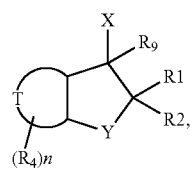
(IC)

wherein $R^1$, $R^2$, $R^4$, $R^9$, T, X, Y and n are as defined in in claim 1 or salts or N-oxides thereof, with the proviso that the following compounds (IC1) to (IC3) are excluded:

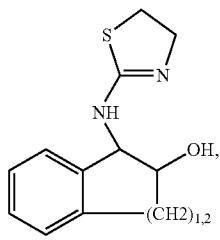
(IC1)

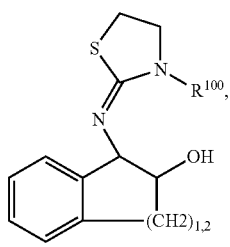
(IC2)

wherein $R^{100}$ is hydrogen or acetyl, and

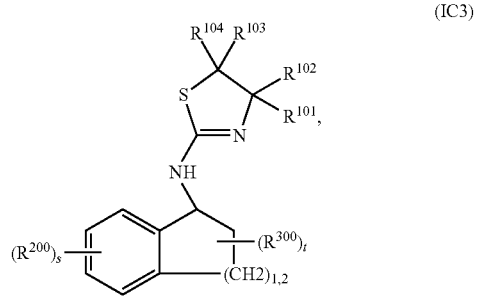
(IC3)

wherein $R^{101}$, $R^{102}$, $R^{103}$ and $R^{104}$ are hydrogen, $R^{200}$ and $R^{300}$ are independently of each other halogen, $C_{1-4}$ alkyl, $C_{1-4}$ alkoxy, $C_{1-4}$ alkylthio, trifluoromethyl or trifluoromethoxy, where s and t are independently of each other 0, 1, 2 or 3, and the total of s+t is not greater than 3.

A preferred group of new compounds of the formula IC are those of the formula ID

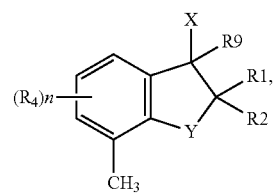
(ID)

or salts or N-oxides thereof, wherein Y is $CR^5R^6$ or $CR^5R^6CR^7R^8$, and $R^1$, $R^2$, $R^4$, $R^9$, X and n are as defined above, where at least one of $R^1$, $R^2$, $R^4$, $R^5$, $R^6$, $R^7$, $R^8$ or $R^9$ is fluorine, and those of formula IE (IE)

or salts or N-oxides thereof, wherein Y is $CR^5R^6$, and $R^1$, $R^2$, $R^4$, $R^9$, X are as defined above and n is 0, 1, 2 or 3.

The compounds in Tables I to LXIII below illustrate the compounds of the invention.

Table I provides 612 compounds of formula Ia

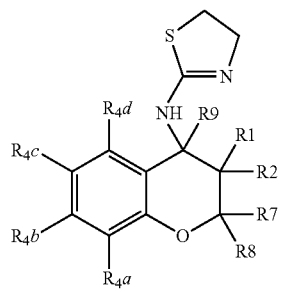
(Ia)

wherein the values of $R^1$, $R^2$, $R^{4a}$, $R^{4b}$, $R^{4c}$, $R^{4d}$, $R^7$, $R^8$ and $R^9$ are given in Table 1.

TABLE 1

| Compound No | R9 | R1 | R2 | R7 | R8 | R4a | R4b | R4c | R4d |
|---|---|---|---|---|---|---|---|---|---|
| I-1 | Me | H | H | H | H | H | H | H | H |
| I-2 | Et | H | H | H | H | H | H | H | H |
| I-3 | Vinyl | H | H | H | H | H | H | H | H |
| I-4 | Allyl | H | H | H | H | H | H | H | H |
| I-5 | cyclopropyl | H | H | H | H | H | H | H | H |
| I-6 | CN | H | H | H | H | H | H | H | H |
| I-7 | $CONH_2$ | H | H | H | H | H | H | H | H |
| I-8 | CONHMe | H | H | H | H | H | H | H | H |
| I-9 | $CONMe_2$ | H | H | H | H | H | H | H | H |
| I-10 | COMe | H | H | H | H | H | H | H | H |
| I-11 | COOH | H | H | H | H | H | H | H | H |
| I-12 | COOMe | H | H | H | H | H | H | H | H |
| I-13 | CSNHMe | H | H | H | H | H | H | H | H |
| I-14 | H | Me | H | H | H | H | H | H | H |
| I-15 | H | Et | H | H | H | H | H | H | H |
| I-16 | H | vinyl | H | H | H | H | H | H | H |
| I-17 | H | allyl | H | H | H | H | H | H | H |
| I-18 | H | cyclopropyl | H | H | H | H | H | H | H |
| I-19 | H | F | H | H | H | H | H | H | H |
| I-20 | H | Cl | H | H | H | H | H | H | H |
| I-21 | H | $NO_2$ | H | H | H | H | H | H | H |
| I-22 | H | CN | H | H | H | H | H | H | H |
| I-23 | H | $CONH_2$ | H | H | H | H | H | H | H |
| I-24 | H | CONHMe | H | H | H | H | H | H | H |
| I-25 | H | $CONMe_2$ | H | H | H | H | H | H | H |
| I-26 | H | COMe | H | H | H | H | H | H | H |
| I-27 | H | COOH | H | H | H | H | H | H | H |
| I-28 | H | COOMe | H | H | H | H | H | H | H |
| I-29 | H | CSOMe | H | H | H | H | H | H | H |
| I-30 | H | $CSNH_2$ | H | H | H | H | H | H | H |
| I-31 | H | $CSNMe_2$ | H | H | H | H | H | H | H |
| I-32 | H | CSNHMe | H | H | H | H | H | H | H |
| I-33 | H | OMe | H | H | H | H | H | H | H |
| I-34 | H | OEt | H | H | H | H | H | H | H |
| I-35 | H | OCOMe | H | H | H | H | H | H | H |
| I-36 | H | OCOOMe | H | H | H | H | H | H | H |
| I-37 | H | OCONHMe | H | H | H | H | H | H | H |
| I-38 | H | $OCONMe_2$ | H | H | H | H | H | H | H |
| I-39 | H | OCSMe | H | H | H | H | H | H | H |
| I-40 | H | $OCSNMe_2$ | H | H | H | H | H | H | H |
| I-41 | H | SMe | H | H | H | H | H | H | H |
| I-42 | H | SEt | H | H | H | H | H | H | H |
| I-43 | H | SCOMe | H | H | H | H | H | H | H |
| I-44 | H | $SCSNMe_2$ | H | H | H | H | H | H | H |
| I-45 | H | SCSNHMe | H | H | H | H | H | H | H |
| I-46 | H | NHMe | H | H | H | H | H | H | H |
| I-47 | H | $NH_2$ | H | H | H | H | H | H | H |
| I-48 | H | $NMe_2$ | H | H | H | H | H | H | H |
| I-49 | H | NHCOMe | H | H | H | H | H | H | H |
| I-50 | H | $NHCONH_2$ | H | H | H | H | H | H | H |
| I-51 | H | NHCONHMe | H | H | H | H | H | H | H |
| I-52 | H | $NHCONMe_2$ | H | H | H | H | H | H | H |
| I-53 | H | phenyl | H | H | H | H | H | H | H |
| I-54 | H | 2-chloro-phenyl | H | H | H | H | H | H | H |
| I-55 | H | 4-nitrophenyl | H | H | H | H | H | H | H |
| I-56 | H | 2-pyridyl | H | H | H | H | H | H | H |
| I-57 | H | 3-pyridyl | H | H | H | H | H | H | H |
| I-58 | H | 4-pyridyl | H | H | H | H | H | H | H |
| I-59 | H | 2-furyl | H | H | H | H | H | H | H |
| I-60 | H | PhO | H | H | H | H | H | H | H |
| I-61 | H | $CH_2$ | | H | H | H | H | H | H |
| I-62 | H | | =O | H | H | H | H | H | H |
| I-63 | H | | =NOH | H | H | H | H | H | H |
| I-64 | H | | =NOMe | H | H | H | H | H | H |
| I-65 | H | | $=CH_2$ | H | H | H | H | H | H |
| I-66 | H | | =CHMe | H | H | H | H | H | H |
| I-67 | H | H | H | H | H | H | H | H | H |
| I-68 | H | H | H | H | Me | H | H | H | H |
| I-69 | H | H | H | H | Et | H | H | H | H |
| I-70 | H | H | H | H | Vinyl | H | H | H | H |
| I-71 | H | H | H | H | Allyl | H | H | H | H |
| I-72 | H | H | H | H | cyclopropyl | H | H | H | H |
| I-73 | H | H | H | H | F | H | H | H | H |
| I-74 | H | H | H | H | Cl | H | H | H | H |
| I-75 | H | H | H | H | $NO_2$ | H | H | H | H |
| I-76 | H | H | H | H | CN | H | H | H | H |

TABLE 1-continued

| Compound No | R9 | R1 | R2 | R7 | R8 | R4a | R4b | R4c | R4d |
|---|---|---|---|---|---|---|---|---|---|
| I-77 | H | H | H | CONH$_2$ | H | H | H | H | H |
| I-78 | H | H | H | CONHMe | H | H | H | H | H |
| I-79 | H | H | H | CONMe$_2$ | H | H | H | H | H |
| I-80 | H | H | H | COMe | H | H | H | H | H |
| I-81 | H | H | H | COOH | H | H | H | H | H |
| I-82 | H | H | H | COOMe | H | H | H | H | H |
| I-83 | H | H | H | CSOMe | H | H | H | H | H |
| I-84 | H | H | H | CSNH$_2$ | H | H | H | H | H |
| I-85 | H | H | H | CSNMe$_2$ | H | H | H | H | H |
| I-86 | H | H | H | CSNHMe | H | H | H | H | H |
| I-87 | H | H | H | OMe | H | H | H | H | H |
| I-88 | H | H | H | OEt | H | H | H | H | H |
| I-89 | H | H | H | OCOMe | H | H | H | H | H |
| I-90 | H | H | H | OCOOMe | H | H | H | H | H |
| I-91 | H | H | H | OCONHMe | H | H | H | H | H |
| I-92 | H | H | H | OCONMe$_2$ | H | H | H | H | H |
| I-93 | H | H | H | OCSMe | H | H | H | H | H |
| I-94 | H | H | H | OCSNMe$_2$ | H | H | H | H | H |
| I-95 | H | H | H | SMe | H | H | H | H | H |
| I-96 | H | H | H | SEt | H | H | H | H | H |
| I-97 | H | H | H | SCOMe | H | H | H | H | H |
| I-98 | H | H | H | SCSNMe$_2$ | H | H | H | H | H |
| I-99 | H | H | H | SCSNHMe | H | H | H | H | H |
| I-100 | H | H | H | NHMe | H | H | H | H | H |
| I-101 | H | H | H | NH$_2$ | H | H | H | H | H |
| I-102 | H | H | H | NMe$_2$ | H | H | H | H | H |
| I-103 | H | H | H | NHCOMe | H | H | H | H | H |
| I-104 | H | H | H | NHCONH$_2$ | H | H | H | H | H |
| I-105 | H | H | H | NHCONHMe | H | H | H | H | H |
| I-106 | H | H | H | NHCONMe$_2$ | H | H | H | H | H |
| I-107 | H | H | H | Phenyl | H | H | H | H | H |
| I-108 | H | H | H | 2-chloro-phenyl | H | H | H | H | H |
| I-109 | H | H | H | 4-nitrophenyl | H | H | H | H | H |
| I-110 | H | H | H | 2-pyridyl | H | H | H | H | H |
| I-111 | H | H | H | 3-pyridyl | H | H | H | H | H |
| I-112 | H | H | H | 4-pyridyl | H | H | H | H | H |
| I-113 | H | H | H | 2-furyl | H | H | H | H | H |
| I-114 | H | H | H | PhO | H | H | H | H | H |
| I-115 | H | H | H | =O | H | H | H | H | H |
| I-116 | H | H | H | =NOH | H | H | H | H | H |
| I-117 | H | H | H | =NOMe | H | H | H | H | H |
| I-118 | H | H | H | =CH$_2$ | H | H | H | H | H |
| I-119 | H | H | H | =CHMe | H | H | H | H | H |
| I-120 | H | Me | H | Me | H | H | H | H | H |
| I-121 | H | Me | F | Me | H | H | H | H | H |
| I-122 | H | Me | Me | F | H | H | H | H | H |
| I-123 | H | Me | F | H | H | H | H | H | H |
| I-124 | H | Me | Me | H | H | H | H | H | H |
| I-125 | H | F | H | Me | H | H | H | H | H |
| I-126 | H | F | H | F | H | H | H | H | H |
| I-127 | Me | H | H | H | H | F | H | H | H |
| I-128 | Et | H | H | H | H | F | H | H | H |
| I-129 | vinyl | H | H | H | H | F | H | H | H |
| I-130 | allyl | H | H | H | H | F | H | H | H |
| I-131 | cyclopropyl | H | H | H | H | F | H | H | H |
| I-132 | CN | H | H | H | H | F | H | H | H |
| I-133 | CONH$_2$ | H | H | H | H | F | H | H | H |
| I-134 | CONHMe | H | H | H | H | F | H | H | H |
| I-135 | CONMe$_2$ | H | H | H | H | F | H | H | H |
| I-136 | COMe | H | H | H | H | F | H | H | H |
| I-137 | COOH | H | H | H | H | F | H | H | H |
| I-138 | COOMe | H | H | H | H | F | H | H | H |
| I-139 | CSNHMe | H | H | H | H | F | H | H | H |
| I-140 | H | Me | H | H | H | F | H | H | H |
| I-141 | H | Et | H | H | H | F | H | H | H |
| I-142 | H | vinyl | H | H | H | F | H | H | H |
| I-143 | H | allyl | H | H | H | F | H | H | H |
| I-144 | H | cyclopropyl | H | H | H | F | H | H | H |
| I-145 | H | F | H | H | H | F | H | H | H |
| I-146 | H | Cl | H | H | H | F | H | H | H |
| I-147 | H | NO$_2$ | H | H | H | F | H | H | H |
| I-148 | H | CN | H | H | H | F | H | H | H |
| I-149 | H | CONH$_2$ | H | H | H | F | H | H | H |
| I-150 | H | CONHMe | H | H | H | F | H | H | H |
| I-151 | H | CONMe$_2$ | H | H | H | F | H | H | H |

TABLE 1-continued

| Compound No | R9 | R1 | R2 | R7 | R8 | R4a | R4b | R4c | R4d |
|---|---|---|---|---|---|---|---|---|---|
| I-152 | H | COMe | H | H | H | F | H | H | H |
| I-153 | H | COOH | H | H | H | F | H | H | H |
| I-154 | H | COOMe | H | H | H | F | H | H | H |
| I-155 | H | CSOMe | H | H | H | F | H | H | H |
| I-156 | H | $CSNH_2$ | H | H | H | F | H | H | H |
| I-157 | H | $CSNMe_2$ | H | H | H | F | H | H | H |
| I-158 | H | CSNHMe | H | H | H | F | H | H | H |
| I-159 | H | OMe | H | H | H | F | H | H | H |
| I-160 | H | OEt | H | H | H | F | H | H | H |
| I-161 | H | OCOMe | H | H | H | F | H | H | H |
| I-162 | H | OCOOMe | H | H | H | F | H | H | H |
| I-163 | H | OCONHMe | H | H | H | F | H | H | H |
| I-164 | H | $OCONMe_2$ | H | H | H | F | H | H | H |
| I-165 | H | OCSMe | H | H | H | F | H | H | H |
| I-166 | H | $OCSNMe_2$ | H | H | H | F | H | H | H |
| I-167 | H | SMe | H | H | H | F | H | H | H |
| I-168 | H | SEt | H | H | H | F | H | H | H |
| I-169 | H | SCOMe | H | H | H | F | H | H | H |
| I-170 | H | $SCSNMe_2$ | H | H | H | F | H | H | H |
| I-171 | H | SCSNHMe | H | H | H | F | H | H | H |
| I-172 | H | NHMe | H | H | H | F | H | H | H |
| I-173 | H | $NH_2$ | H | H | H | F | H | H | H |
| I-174 | H | $NMe_2$ | H | H | H | F | H | H | H |
| I-175 | H | NHCOMe | H | H | H | F | H | H | H |
| I-176 | H | $NHCONH_2$ | H | H | H | F | H | H | H |
| I-177 | H | NHCONHMe | H | H | H | F | H | H | H |
| I-178 | H | $NHCONMe_2$ | H | H | H | F | H | H | H |
| I-179 | H | phenyl | H | H | H | F | H | H | H |
| I-180 | H | 2-chloro-phenyl | H | H | H | F | H | H | H |
| I-181 | H | 4-nitrophenyl | H | H | H | F | H | H | H |
| I-182 | H | 2-pyridyl | H | H | H | F | H | H | H |
| I-183 | H | 3-pyridyl | H | H | H | F | H | H | H |
| I-184 | H | 4-pyridyl | H | H | H | F | H | H | H |
| I-185 | H | 2-furyl | H | H | H | F | H | H | H |
| I-186 | H | PhO | H | H | H | F | H | H | H |
| I-187 |  | $CH_2$ | H | H | H | F | H | H | H |
| I-188 | H | H | H | Me | H | F | H | H | H |
| I-190 | H | H | H | Vinyl | H | F | H | H | H |
| I-191 | H | H | H | Allyl | H | F | H | H | H |
| I-192 | H | H | H | Cyclopropyl | H | F | H | H | H |
| I-193 | H | H | H | F | H | F | H | H | H |
| I-194 | H | H | H | Cl | H | F | H | H | H |
| I-195 | H | H | H | $NO_2$ | H | F | H | H | H |
| I-196 | H | H | H | CN | H | F | H | H | H |
| I-197 | H | H | H | $CONH_2$ | H | F | H | H | H |
| I-198 | H | H | H | CONHMe | H | F | H | H | H |
| I-199 | H | H | H | $CONMe_2$ | H | F | H | H | H |
| I-200 | H | H | H | COMe | H | F | H | H | H |
| I-201 | H | H | H | COOH | H | F | H | H | H |
| I-202 | H | H | H | COOMe | H | F | H | H | H |
| I-203 | H | H | H | CSOMe | H | F | H | H | H |
| I-204 | H | H | H | $CSNH_2$ | H | F | H | H | H |
| I-205 | H | H | H | $CSNMe_2$ | H | F | H | H | H |
| I-206 | H | H | H | CSNHMe | H | F | H | H | H |
| I-207 | H | H | H | OMe | H | F | H | H | H |
| I-208 | H | H | H | OEt | H | F | H | H | H |
| I-209 | H | H | H | OCOMe | H | F | H | H | H |
| I-210 | H | H | H | OCOOMe | H | F | H | H | H |
| I-211 | H | H | H | OCONHMe | H | F | H | H | H |
| I-212 | H | H | H | $OCONMe_2$ | H | F | H | H | H |
| I-213 | H | H | H | OCSMe | H | F | H | H | H |
| I-214 | H | H | H | OCSNMe2 | H | F | H | H | H |
| I-215 | H | H | H | SMe | H | F | H | H | H |
| I-216 | H | H | H | SEt | H | F | H | H | H |
| I-217 | H | H | H | SCOMe | H | F | H | H | H |
| I-218 | H | H | H | $SCSNMe_2$ | H | F | H | H | H |
| I-219 | H | H | H | SCSNHMe | H | F | H | H | H |
| I-220 | H | H | H | NHMe | H | F | H | H | H |
| I-221 | H | H | H | $NH_2$ | H | F | H | H | H |
| I-222 | H | H | H | $NMe_2$ | H | F | H | H | H |
| I-223 | H | H | H | NHCOMe | H | F | H | H | H |
| I-224 | H | H | H | $NHCONH_2$ | H | F | H | H | H |
| I-225 | H | H | H | NHCONHMe | H | F | H | H | H |
| I-226 | H | H | H | $NHCONMe_2$ | H | F | H | H | H |
| I-227 | H | H | H | Phenyl | H | F | H | H | H |

TABLE 1-continued

| Compound No | R9 | R1 | R2 | R7 | R8 | R4a | R4b | R4c | R4d |
|---|---|---|---|---|---|---|---|---|---|
| I-228 | H | H | H | 2-chloro-phenyl | H | F | H | H | H |
| I-229 | H | H | H | 4-nitrophenyl | H | F | H | H | H |
| I-230 | H | H | H | 2-pyridyl | H | F | H | H | H |
| I-231 | H | H | H | 3-pyridyl | H | F | H | H | H |
| I-232 | H | H | H | 4-pyridyl | H | F | H | H | H |
| I-233 | H | H | H | 2-furyl | H | F | H | H | H |
| I-234 | H | H | H | PhO | H | F | H | H | H |
| I-235 | H | Me | H | Me | H | F | H | H | H |
| I-236 | H | Me | F | Me | H | F | H | H | H |
| I-237 | H | Me | H | F | H | F | H | H | H |
| I-238 | H | Me | F | H | H | F | H | H | H |
| I-239 | H | Me | Me | H | H | F | H | H | H |
| I-240 | H | F | H | Me | H | F | H | H | H |
| I-241 | H | F | H | F | H | F | H | H | H |
| I-242 | Me | H | H | H | H | Me | H | H | H |
| I-243 | Et | H | H | H | H | Me | H | H | H |
| I-244 | vinyl | H | H | H | H | Me | H | H | H |
| I-245 | allyl | H | H | H | H | Me | H | H | H |
| I-246 | cyclopropyl | H | H | H | H | Me | H | H | H |
| I-247 | CN | H | H | H | H | Me | H | H | H |
| I-248 | $CONH_2$ | H | H | H | H | Me | H | H | H |
| I-249 | CONHMe | H | H | H | H | Me | H | H | H |
| I-250 | $CONMe_2$ | H | H | H | H | Me | H | H | H |
| I-251 | COMe | H | H | H | H | Me | H | H | H |
| I-252 | COOH | H | H | H | H | Me | H | H | H |
| I-253 | COOMe | H | H | H | H | Me | H | H | H |
| I-254 | CSNHMe | H | H | H | H | Me | H | H | H |
| I-255 | H | Me | H | H | H | Me | H | H | H |
| I-256 | H | Et | H | H | H | Me | H | H | H |
| I-257 | H | vinyl | H | H | H | Me | H | H | H |
| I-258 | H | allyl | H | H | H | Me | H | H | H |
| I-259 | H | cyclopropyl | H | H | H | Me | H | H | H |
| I-260 | H | F | H | H | H | Me | H | H | H |
| I-261 | H | Cl | H | H | H | Me | H | H | H |
| I-262 | H | $NO_2$ | H | H | H | Me | H | H | H |
| I-263 | H | CN | H | H | H | Me | H | H | H |
| I-264 | H | $CONH_2$ | H | H | H | Me | H | H | H |
| I-265 | H | CONHMe | H | H | H | Me | H | H | H |
| I-266 | H | $CONMe_2$ | H | H | H | Me | H | H | H |
| I-267 | H | COMe | H | H | H | Me | H | H | H |
| I-268 | H | COOH | H | H | H | Me | H | H | H |
| I-269 | H | COOMe | H | H | H | Me | H | H | H |
| I-270 | H | CSOMe | H | H | H | Me | H | H | H |
| I-271 | H | $CSNH_2$ | H | H | H | Me | H | H | H |
| I-272 | H | $CSNMe_2$ | H | H | H | Me | H | H | H |
| I-273 | H | CSNHMe | H | H | H | Me | H | H | H |
| I-274 | H | OMe | H | H | H | Me | H | H | H |
| I-275 | H | OEt | H | H | H | Me | H | H | H |
| I-276 | H | OCOMe | H | H | H | Me | H | H | H |
| I-277 | H | OCOOMe | H | H | H | Me | H | H | H |
| I-278 | H | OCONHMe | H | H | H | Me | H | H | H |
| I-279 | H | $OCONMe_2$ | H | H | H | Me | H | H | H |
| I-280 | H | OCSMe | H | H | H | Me | H | H | H |
| I-281 | H | $OCSNMe_2$ | H | H | H | Me | H | H | H |
| I-282 | H | SMe | H | H | H | Me | H | H | H |
| I-283 | H | SEt | H | H | H | Me | H | H | H |
| I-284 | H | SCOMe | H | H | H | Me | H | H | H |
| I-285 | H | $SCSNMe_2$ | H | H | H | Me | H | H | H |
| I-286 | H | SCSNHMe | H | H | H | Me | H | H | H |
| I-287 | H | NHMe | H | H | H | Me | H | H | H |
| I-288 | H | $NH_2$ | H | H | H | Me | H | H | H |
| I-289 | H | $NMe_2$ | H | H | H | Me | H | H | H |
| I-290 | H | NHCOMe | H | H | H | Me | H | H | H |
| I-291 | H | $NHCONH_2$ | H | H | H | Me | H | H | H |
| I-292 | H | NHCONHMe | H | H | H | Me | H | H | H |
| I-293 | H | $NHCONMe_2$ | H | H | H | Me | H | H | H |
| I-294 | H | phenyl | H | H | H | Me | H | H | H |
| I-295 | H | 2-chloro-phenyl | H | H | H | Me | H | H | H |
| I-296 | H | 4-nitrophenyl | H | H | H | Me | H | H | H |
| I-297 | H | 2-pyridyl | H | H | H | Me | H | H | H |
| I-298 | H | 3-pyridyl | H | H | H | Me | H | H | H |
| I-299 | H | 4-pyridyl | H | H | H | Me | H | H | H |
| I-300 | H | 2-furyl | H | H | H | Me | H | H | H |
| I-301 | H | PhO | H | H | H | Me | H | H | H |
| I-302 | | $CH_2$ | H | H | H | Me | H | H | H |

TABLE 1-continued

| Compound No | R9 | R1 | R2 | R7 | R8 | R4a | R4b | R4c | R4d |
|---|---|---|---|---|---|---|---|---|---|
| I-303 | H | H | H | Me | H | Me | H | H | H |
| I-304 | H | H | H | Et | H | Me | H | H | H |
| I-305 | H | H | H | Vinyl | H | Me | H | H | H |
| I-306 | H | H | H | Allyl | H | Me | H | H | H |
| I-307 | H | H | H | Cyclopropyl | H | Me | H | H | H |
| I-308 | H | H | H | F | H | Me | H | H | H |
| I-309 | H | H | H | Cl | H | Me | H | H | H |
| I-310 | H | H | H | $NO_2$ | H | Me | H | H | H |
| I-311 | H | H | H | CN | H | Me | H | H | H |
| I-312 | H | H | H | $CONH_2$ | H | Me | H | H | H |
| I-313 | H | H | H | CONHMe | H | Me | H | H | H |
| I-314 | H | H | H | $CONMe_2$ | H | Me | H | H | H |
| I-315 | H | H | H | COMe | H | Me | H | H | H |
| I-316 | H | H | H | COOH | H | Me | H | H | H |
| I-317 | H | H | H | COOMe | H | Me | H | H | H |
| I-318 | H | H | H | CSOMe | H | Me | H | H | H |
| I-319 | H | H | H | $CSNH_2$ | H | Me | H | H | H |
| I-320 | H | H | H | $CSNMe_2$ | H | Me | H | H | H |
| I-321 | H | H | H | CSNHMe | H | Me | H | H | H |
| I-322 | H | H | H | OMe | H | Me | H | H | H |
| I-323 | H | H | H | OEt | H | Me | H | H | H |
| I-324 | H | H | H | OCOMe | H | Me | H | H | H |
| I-325 | H | H | H | OCOOMe | H | Me | H | H | H |
| I-326 | H | H | H | OCONHMe | H | Me | H | H | H |
| I-327 | H | H | H | $OCONMe_2$ | H | Me | H | H | H |
| I-328 | H | H | H | OCSMe | H | Me | H | H | H |
| I-329 | H | H | H | OCSNMe2 | H | Me | H | H | H |
| I-330 | H | H | H | SMe | H | Me | H | H | H |
| I-331 | H | H | H | SEt | H | Me | H | H | H |
| I-332 | H | H | H | SCOMe | H | Me | H | H | H |
| I-333 | H | H | H | $SCSNMe_2$ | H | Me | H | H | H |
| I-334 | H | H | H | SCSNHMe | H | Me | H | H | H |
| I-335 | H | H | H | NHMe | H | Me | H | H | H |
| I-336 | H | H | H | $NH_2$ | H | Me | H | H | H |
| I-337 | H | H | H | $NMe_2$ | H | Me | H | H | H |
| I-338 | H | H | H | NHCOMe | H | Me | H | H | H |
| I-339 | H | H | H | $NHCONH_2$ | H | Me | H | H | H |
| I-340 | H | H | H | NHCONHMe | H | Me | H | H | H |
| I-341 | H | H | H | $NHCONMe_2$ | H | Me | H | H | H |
| I-342 | H | H | H | Phenyl | H | Me | H | H | H |
| I-343 | H | H | H | 2-chloro-phenyl | H | Me | H | H | H |
| I-344 | H | H | H | 4-nitrophenyl | H | Me | H | H | H |
| I-345 | H | H | H | 2-pyridyl | H | Me | H | H | H |
| I-346 | H | H | H | 3-pyridyl | H | Me | H | H | H |
| I-347 | H | H | H | 4-pyridyl | H | Me | H | H | H |
| I-348 | H | H | H | 2-furyl | H | Me | H | H | H |
| I-349 | H | H | H | PhO | H | Me | H | H | H |
| I-350 | H | Me | H | Me | H | Me | H | H | H |
| I-351 | H | Me | F | Me | H | Me | H | H | H |
| I-352 | H | Me | H | F | H | Me | H | H | H |
| I-353 | H | Me | F | H | H | Me | H | H | H |
| I-354 | H | Me | Me | H | H | Me | H | H | H |
| I-355 | H | F | H | Me | H | Me | H | H | H |
| I-356 | H | F | H | F | H | Me | H | H | H |
| I-357 | Me | H | H | H | H | F | H | F | H |
| I-358 | Et | H | H | H | H | F | H | F | H |
| I-359 | vinyl | H | H | H | H | F | H | F | H |
| I-360 | allyl | H | H | H | H | F | H | F | H |
| I-361 | cyclopropyl | H | H | H | H | F | H | F | H |
| I-362 | CN | H | H | H | H | F | H | F | H |
| I-363 | $CONH_2$ | H | H | H | H | F | H | F | H |
| I-364 | CONHMe | H | H | H | H | F | H | F | H |
| I-365 | $CONMe_2$ | H | H | H | H | F | H | F | H |
| I-366 | COMe | H | H | H | H | F | H | F | H |
| I-367 | COOH | H | H | H | H | F | H | F | H |
| I-368 | COOMe | H | H | H | H | F | H | F | H |
| I-369 | CSNHMe | H | H | H | H | F | H | F | H |
| I-370 | H | Me | H | H | H | F | H | F | H |
| I-371 | H | Et | H | H | H | F | H | F | H |
| I-372 | H | vinyl | H | H | H | F | H | F | H |
| I-373 | H | allyl | H | H | H | F | H | F | H |
| I-374 | H | cyclopropyl | H | H | H | F | H | F | H |
| I-375 | H | F | H | H | H | F | H | F | H |
| I-376 | H | Cl | H | H | H | F | H | F | H |
| I-377 | H | $NO_2$ | H | H | H | F | H | F | H |
| I-378 | H | CN | H | H | H | F | H | F | H |

TABLE 1-continued

| Compound No | R9 | R1 | R2 | R7 | R8 | R4a | R4b | R4c | R4d |
|---|---|---|---|---|---|---|---|---|---|
| I-379 | H | CONH$_2$ | H | H | H | F | H | F | H |
| I-380 | H | CONHMe | H | H | H | F | H | F | H |
| I-381 | H | CONMe$_2$ | H | H | H | F | H | F | H |
| I-382 | H | COMe | H | H | H | F | H | F | H |
| I-383 | H | COOH | H | H | H | F | H | F | H |
| I-384 | H | COOMe | H | H | H | F | H | F | H |
| I-385 | H | CSOMe | H | H | H | F | H | F | H |
| I-386 | H | CSNH$_2$ | H | H | H | F | H | F | H |
| I-387 | H | CSNMe$_2$ | H | H | H | F | H | F | H |
| I-388 | H | CSNHMe | H | H | H | F | H | F | H |
| I-389 | H | OMe | H | H | H | F | H | F | H |
| I-390 | H | OEt | H | H | H | F | H | F | H |
| I-391 | H | OCOMe | H | H | H | F | H | F | H |
| I-392 | H | OCOOMe | H | H | H | F | H | F | H |
| I-393 | H | OCONHMe | H | H | H | F | H | F | H |
| I-394 | H | OCONMe$_2$ | H | H | H | F | H | F | H |
| I-395 | H | OCSMe | H | H | H | F | H | F | H |
| I-396 | H | OCSNMe$_2$ | H | H | H | F | H | F | H |
| I-397 | H | SMe | H | H | H | F | H | F | H |
| I-398 | H | SEt | H | H | H | F | H | F | H |
| I-399 | H | SCOMe | H | H | H | F | H | F | H |
| I-400 | H | SCSNMe$_2$ | H | H | H | F | H | F | H |
| I-401 | H | SCSNHMe | H | H | H | F | H | F | H |
| I-402 | H | NHMe | H | H | H | F | H | F | H |
| I-403 | H | NH$_2$ | H | H | H | F | H | F | H |
| I-404 | H | NMe$_2$ | H | H | H | F | H | F | H |
| I-405 | H | NHCOMe | H | H | H | F | H | F | H |
| I-406 | H | NHCONH$_2$ | H | H | H | F | H | F | H |
| I-407 | H | NHCONHMe | H | H | H | F | H | F | H |
| I-408 | H | NHCONMe$_2$ | H | H | H | F | H | F | H |
| I-409 | H | phenyl | H | H | H | F | H | F | H |
| I-410 | H | 2-chloro-phenyl | H | H | H | F | H | F | H |
| I-411 | H | 4-nitrophenyl | H | H | H | F | H | F | H |
| I-412 | H | 2-pyridyl | H | H | H | F | H | F | H |
| I-413 | H | 3-pyridyl | H | H | H | F | H | F | H |
| I-414 | H | 4-pyridyl | H | H | H | F | H | F | H |
| I-415 | H | 2-furyl | H | H | H | F | H | F | H |
| I-416 | H | PhO | H | H | H | F | H | F | H |
| I-417 |  | CH$_2$ | H | H | H | F | H | F | H |
| I-418 | H | H | H | Me | H | F | H | F | H |
| I-419 | H | H | H | Et | H | F | H | F | H |
| I-420 | H | H | H | Vinyl | H | F | H | F | H |
| I-421 | H | H | H | Allyl | H | F | H | F | H |
| I-422 | H | H | H | Cyclopropyl | H | F | H | F | H |
| I-423 | H | H | H | F | H | F | H | F | H |
| I-424 | H | H | H | Cl | H | F | H | F | H |
| I-425 | H | H | H | NO$_2$ | H | F | H | F | H |
| I-426 | H | H | H | CN | H | F | H | F | H |
| I-427 | H | H | H | CONH$_2$ | H | F | H | F | H |
| I-428 | H | H | H | CONHMe | H | F | H | F | H |
| I-429 | H | H | H | CONMe$_2$ | H | F | H | F | H |
| I-430 | H | H | H | COMe | H | F | H | F | H |
| I-431 | H | H | H | COOH | H | F | H | F | H |
| I-432 | H | H | H | COOMe | H | F | H | F | H |
| I-433 | H | H | H | CSOMe | H | F | H | F | H |
| I-434 | H | H | H | CSNH$_2$ | H | F | H | F | H |
| I-435 | H | H | H | CSNMe$_2$ | H | F | H | F | H |
| I-436 | H | H | H | CSNHMe | H | F | H | F | H |
| I-437 | H | H | H | OMe | H | F | H | F | H |
| I-438 | H | H | H | OEt | H | F | H | F | H |
| I-439 | H | H | H | OCOMe | H | F | H | F | H |
| I-440 | H | H | H | OCOOMe | H | F | H | F | H |
| I-441 | H | H | H | OCONHMe | H | F | H | F | H |
| I-442 | H | H | H | OCONMe$_2$ | H | F | H | F | H |
| I-443 | H | H | H | OCSMe | H | F | H | F | H |
| I-444 | H | H | H | OCSNMe$_2$ | H | F | H | F | H |
| I-445 | H | H | H | SMe | H | F | H | F | H |
| I-446 | H | H | H | SEt | H | F | H | F | H |
| I-447 | H | H | H | SCOMe | H | F | H | F | H |
| I-448 | H | H | H | SCSNMe$_2$ | H | F | H | F | H |
| I-449 | H | H | H | SCSNHMe | H | F | H | F | H |
| I-450 | H | H | H | NHMe | H | F | H | F | H |
| I-451 | H | H | H | NH$_2$ | H | F | H | F | H |
| I-452 | H | H | H | NMe$_2$ | H | F | H | F | H |
| I-453 | H | H | H | NHCOMe | H | F | H | F | H |

TABLE 1-continued

| Compound No | R9 | R1 | R2 | R7 | R8 | R4a | R4b | R4c | R4d |
|---|---|---|---|---|---|---|---|---|---|
| I-454 | H | H | H | NHCONH₂ | H | F | H | F | H |
| I-455 | H | H | H | NHCONHMe | H | F | H | F | H |
| I-456 | H | H | H | NHCONMe₂ | H | F | H | F | H |
| I-457 | H | H | H | Phenyl | H | F | H | F | H |
| I-458 | H | H | H | 2-chlorophenyl | H | F | H | F | H |
| I-459 | H | H | H | 4-nitrophenyl | H | F | H | F | H |
| I-460 | H | H | H | 2-pyridyl | H | F | H | F | H |
| I-461 | H | H | H | 3-pyridyl | H | F | H | F | H |
| I-462 | H | H | H | 4-pyridyl | H | F | H | F | H |
| I-463 | H | H | H | 2-furyl | H | F | H | F | H |
| I-464 | H | H | H | PhO | H | F | H | F | H |
| I-465 | H | Me | H | Me | H | F | H | F | H |
| I-466 | H | Me | F | Me | H | F | H | F | H |
| I-467 | H | Me | Me | F | H | F | H | F | H |
| I-468 | H | Me | F | H | H | F | H | F | H |
| I-469 | H | Me | Me | H | H | F | H | F | H |
| I-470 | H | F | H | Me | H | F | H | F | H |
| I-471 | H | F | F | F | H | F | H | F | H |
| I-472 | H | H | H | H | H | Me | H | H | H |
| I-473 | H | H | H | H | H | Et | H | H | H |
| I-474 | H | H | H | H | H | vinyl | H | H | H |
| I-475 | H | H | H | H | H | allyl | H | H | H |
| I-476 | H | H | H | H | H | cyclopropyl | H | H | H |
| I-477 | H | H | H | H | H | F | H | H | H |
| I-478 | H | H | H | H | H | Cl | H | H | H |
| I-479 | H | H | H | H | H | NO₂ | H | H | H |
| I-480 | H | H | H | H | H | CN | H | H | H |
| I-481 | H | H | H | H | H | CONH₂ | H | H | H |
| I-482 | H | H | H | H | H | CONHMe | H | H | H |
| I-483 | H | H | H | H | H | CONMe₂ | H | H | H |
| I-484 | H | H | H | H | H | COMe | H | H | H |
| I-485 | H | H | H | H | H | COOH | H | H | H |
| I-486 | H | H | H | H | H | COOMe | H | H | H |
| I-487 | H | H | H | H | H | CSOMe | H | H | H |
| I-488 | H | H | H | H | H | CSNH₂ | H | H | H |
| I-489 | H | H | H | H | H | CSNMe₂ | H | H | H |
| I-490 | H | H | H | H | H | CSNHMe | H | H | H |
| I-491 | H | H | H | H | H | OMe | H | H | H |
| I-492 | H | H | H | H | H | OEt | H | H | H |
| I-493 | H | H | H | H | H | OCOMe | H | H | H |
| I-494 | H | H | H | H | H | OCOOMe | H | H | H |
| I-495 | H | H | H | H | H | OCONHMe | H | H | H |
| I-496 | H | H | H | H | H | OCONMe₂ | H | H | H |
| I-497 | H | H | H | H | H | OCSMe | H | H | H |
| I-498 | H | H | H | H | H | OCSNMe₂ | H | H | H |
| I-499 | H | H | H | H | H | SMe | H | H | H |
| I-500 | H | H | H | H | H | SEt | H | H | H |
| I-501 | H | H | H | H | H | SCOMe | H | H | H |
| I-502 | H | H | H | H | H | SCSNMe₂ | H | H | H |
| I-503 | H | H | H | H | H | SCSNHMe | H | H | H |
| I-504 | H | H | H | H | H | NHMe | H | H | H |
| I-505 | H | H | H | H | H | NH₂ | H | H | H |
| I-506 | H | H | H | H | H | NMe₂ | H | H | H |
| I-507 | H | H | H | H | H | NHCOMe | H | H | H |
| I-508 | H | H | H | H | H | NHCONH₂ | H | H | H |
| I-509 | H | H | H | H | H | NHCONHMe | H | H | H |
| I-510 | H | H | H | H | H | NHCONMe₂ | H | H | H |
| I-511 | H | H | H | H | H | phenyl | H | H | H |
| I-512 | H | H | H | H | H | 2-chlorophenyl | H | H | H |
| I-513 | H | H | H | H | H | 4-nitrophenyl | H | H | H |
| I-514 | H | H | H | H | H | 2-pyridyl | H | H | H |
| I-515 | H | H | H | H | H | 3-pyridyl | H | H | H |
| I-516 | H | H | H | H | H | 4-pyridyl | H | H | H |
| I-517 | H | H | H | H | H | 2-furyl | H | H | H |
| I-518 | H | H | H | H | H | PhO | H | H | H |
| I-519 | H | H | H | H | H | H | H | Me | H |
| I-520 | H | H | H | H | H | H | H | Et | H |
| I-521 | H | H | H | H | H | H | H | vinyl | H |
| I-522 | H | H | H | H | H | H | H | allyl | H |
| I-523 | H | H | H | H | H | H | H | cyclopropyl | H |
| I-524 | H | H | H | H | H | H | H | F | H |
| I-525 | H | H | H | H | H | H | H | Cl | H |
| I-526 | H | H | H | H | H | H | H | NO₂ | H |
| I-527 | H | H | H | H | H | H | H | CN | H |

TABLE 1-continued

| Compound No | R9 | R1 | R2 | R7 | R8 | R4a | R4b | R4c | R4d |
|---|---|---|---|---|---|---|---|---|---|
| I-528 | H | H | H | H | H | H | H | CONH$_2$ | H |
| I-529 | H | H | H | H | H | H | H | CONHMe | H |
| I-530 | H | H | H | H | H | H | H | CONMe$_2$ | H |
| I-531 | H | H | H | H | H | H | H | COMe | H |
| I-532 | H | H | H | H | H | H | H | COOH | H |
| I-533 | H | H | H | H | H | H | H | COOMe | H |
| I-534 | H | H | H | H | H | H | H | CSOMe | H |
| I-535 | H | H | H | H | H | H | H | CSNH$_2$ | H |
| I-536 | H | H | H | H | H | H | H | CSNMe$_2$ | H |
| I-537 | H | H | H | H | H | H | H | CSNHMe | H |
| I-538 | H | H | H | H | H | H | H | OMe | H |
| I-539 | H | H | H | H | H | H | H | OEt | H |
| I-540 | H | H | H | H | H | H | H | OCOMe | H |
| I-541 | H | H | H | H | H | H | H | OCOOMe | H |
| I-542 | H | H | H | H | H | H | H | OCONHMe | H |
| I-543 | H | H | H | H | H | H | H | OCONMe$_2$ | H |
| I-544 | H | H | H | H | H | H | H | OCSMe | H |
| I-545 | H | H | H | H | H | H | H | OCSNMe$_2$ | H |
| I-546 | H | H | H | H | H | H | H | SMe | H |
| I-547 | H | H | H | H | H | H | H | SEt | H |
| I-548 | H | H | H | H | H | H | H | SCOMe | H |
| I-549 | H | H | H | H | H | H | H | SCSNMe$_2$ | H |
| I-550 | H | H | H | H | H | H | H | SCSNHMe | H |
| I-551 | H | H | H | H | H | H | H | NHMe | H |
| I-552 | H | H | H | H | H | H | H | NH$_2$ | H |
| I-553 | H | H | H | H | H | H | H | NMe$_2$ | H |
| I-554 | H | H | H | H | H | H | H | NHCOMe | H |
| I-555 | H | H | H | H | H | H | H | NHCONH$_2$ | H |
| I-556 | H | H | H | H | H | H | H | NHCONHMe | H |
| I-557 | H | H | H | H | H | H | H | NHCONMe$_2$ | H |
| I-558 | H | H | H | H | H | H | H | phenyl | H |
| I-559 | H | H | H | H | H | H | H | 2-chlorophenyl | H |
| I-560 | H | H | H | H | H | H | H | 4-nitrophenyl | H |
| I-561 | H | H | H | H | H | H | H | 2-pyridyl | H |
| I-562 | H | H | H | H | H | H | H | 3-pyridyl | H |
| I-563 | H | H | H | H | H | H | H | 4-pyridyl | H |
| I-564 | H | H | H | H | H | H | H | 2-furyl | H |
| I-565 | H | H | H | H | H | H | H | PhO | H |
| I-566 | H | H | H | H | H | H | H | H | Me |
| I-567 | H | H | H | H | H | H | H | H | Et |
| I-568 | H | H | H | H | H | H | H | H | vinyl |
| I-569 | H | H | H | H | H | H | H | H | allyl |
| I-570 | H | H | H | H | H | H | H | H | cyclopropyl |
| I-571 | H | H | H | H | H | H | H | H | F |
| I-572 | H | H | H | H | H | H | H | H | Cl |
| I-573 | H | H | H | H | H | H | H | H | NO$_2$ |
| I-574 | H | H | H | H | H | H | H | H | CN |
| I-575 | H | H | H | H | H | H | H | H | CONH$_2$ |
| I-576 | H | H | H | H | H | H | H | H | CONHMe |
| I-577 | H | H | H | H | H | H | H | H | CONMe$_2$ |
| I-578 | H | H | H | H | H | H | H | H | COMe |
| I-579 | H | H | H | H | H | H | H | H | COOH |
| I-580 | H | H | H | H | H | H | H | H | COOMe |
| I-581 | H | H | H | H | H | H | H | H | CSOMe |
| I-582 | H | H | H | H | H | H | H | H | CSNH$_2$ |
| I-583 | H | H | H | H | H | H | H | H | CSNMe$_2$ |
| I-584 | H | H | H | H | H | H | H | H | CSNHMe |
| I-585 | H | H | H | H | H | H | H | H | OMe |
| I-586 | H | H | H | H | H | H | H | H | OEt |
| I-587 | H | H | H | H | H | H | H | H | OCOMe |
| I-588 | H | H | H | H | H | H | H | H | OCOOMe |
| I-589 | H | H | H | H | H | H | H | H | OCONHMe |
| I-590 | H | H | H | H | H | H | H | H | OCONMe$_2$ |
| I-591 | H | H | H | H | H | H | H | H | OCSMe |
| I-592 | H | H | H | H | H | H | H | H | OCSNMe$_2$ |
| I-593 | H | H | H | H | H | H | H | H | SMe |
| I-594 | H | H | H | H | H | H | H | H | SEt |
| I-595 | H | H | H | H | H | H | H | H | SCOMe |
| I-596 | H | H | H | H | H | H | H | H | SCSNMe$_2$ |
| I-597 | H | H | H | H | H | H | H | H | SCSNHMe |
| I-598 | H | H | H | H | H | H | H | H | NHMe |

TABLE 1-continued

| Compound No | R9 | R1 | R2 | R7 | R8 | R4a | R4b | R4c | R4d |
|---|---|---|---|---|---|---|---|---|---|
| I-599 | H | H | H | H | H | H | H | H | NH$_2$ |
| I-600 | H | H | H | H | H | H | H | H | NMe$_2$ |
| I-601 | H | H | H | H | H | H | H | H | NHCOMe |
| I-602 | H | H | H | H | H | H | H | H | NHCONH$_2$ |
| I-603 | H | H | H | H | H | H | H | H | NHCONHMe |
| I-604 | H | H | H | H | H | H | H | H | NHCONMe$_2$ |
| I-605 | H | H | H | H | H | H | H | H | phenyl |
| I-606 | H | H | H | H | H | H | H | H | 2-chlorophenyl |
| I-607 | H | H | H | H | H | H | H | H | 4-nitrophenyl |
| I-608 | H | H | H | H | H | H | H | H | 2-pyridyl |
| I-609 | H | H | H | H | H | H | H | H | 3-pyridyl |
| I-610 | H | H | H | H | H | H | H | H | 4-pyridyl |
| I-611 | H | H | H | H | H | H | H | H | 2-furyl |
| I-612 | H | H | H | H | H | H | H | H | PhO |

Table II provides 612 compounds of formula Ib

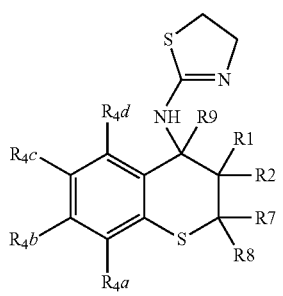

(Ib)

wherein the values of $R^1$, $R^2$, $R^{4a}$, $R^{4b}$, $R^{4c}$, $R^{4d}$, $R^7$, $R^8$ and $R^9$ are given in Table 1.

Table III provides 612 compounds of formula Ic

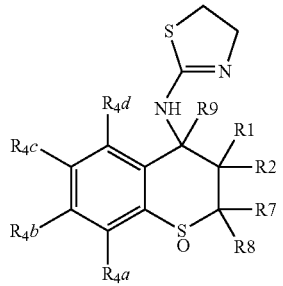

(Ic)

wherein the values of $R^1$, $R^2$, $R^{4a}$, $R^{4b}$, $R^{4c}$, $R^{4d}$, $R^7$, $R^8$ and $R^9$ are given in Table 1.

Table IV provides 612 compounds of formula Id

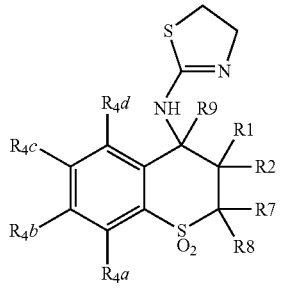

(Id)

wherein the values of $R^1$, $R^2$, $R^{4a}$, $R^{4b}$, $R^{4c}$, $R^{4d}$, $R^7$, $R^8$ and $R^9$ are given in Table 1.

Table V provides 612 compounds of formula Ie

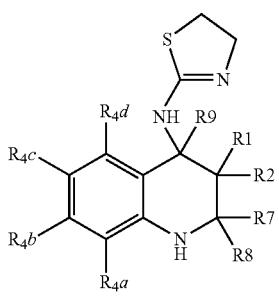

(Ie)

wherein the values of $R^1$, $R^2$, $R^{4a}$, $R^{4b}$, $R^{4c}$, $R^{4d}$, $R^7$, $R^8$ and $R^9$ are given in Table 1.

Table VI provides 612 compounds of formula If

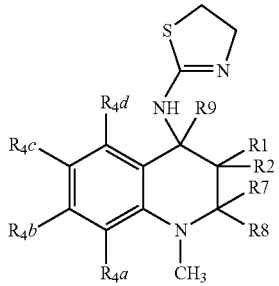

(If)

wherein the values of $R^1$, $R^2$, $R^{4a}$, $R^{4b}$, $R^{4c}$, $R^{4d}$, $R^7$, $R^8$ and $R^9$ are given in Table 1.

Table VII provides 612 compounds of formula Ig

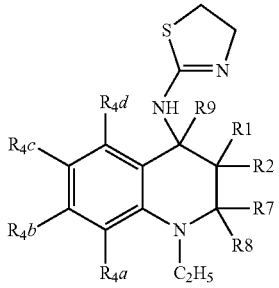

(Ig)

wherein the values of $R^1$, $R^2$, $R^{4a}$, $R^{4b}$, $R^{4c}$, $R^{4d}$, $R^7$, $R^8$ and $R^9$ are given in Table 1.

Table VIII provides 612 compounds of formula Ih

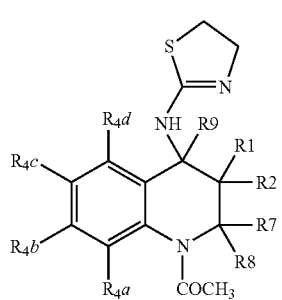
(Ih)

wherein the values of $R^1$, $R^2$, $R^{4a}$, $R^{4b}$, $R^{4c}$, $R^{4d}$, $R^7$, $R^8$ and $R^9$ are given in Table 1.

Table IX provides 612 compounds of formula Ii

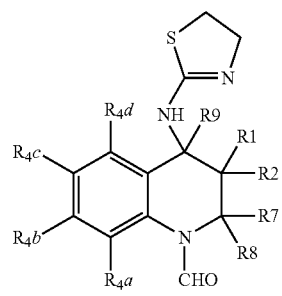
(Ii)

wherein the values of $R^1$, $R^2$, $R^{4a}$, $R^{4b}$, $R^{4c}$, $R^{4d}$, $R^7$, $R^8$ and $R^9$ are given in Table 1.

Table X provides 612 compounds of formula Ij

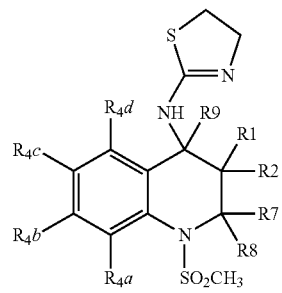
(Ij)

wherein the values of $R^1$, $R^2$, $R^{4a}$, $R^{4b}$, $R^{4c}$, $R^{4d}$, $R^7$, $R^8$ and $R^9$ are given in Table 1.

Table XI provides 612 compounds of formula Ik

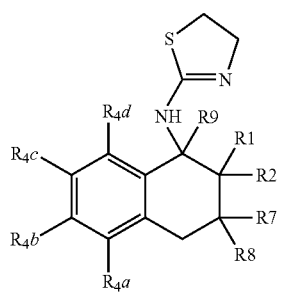
(Ik)

wherein the values of $R^1$, $R^2$, $R^{4a}$, $R^{4b}$, $R^{4c}$, $R^{4d}$, $R^7$, $R^8$ and $R^9$ are given in Table 1.

Table XII provides 612 compounds of formula Il

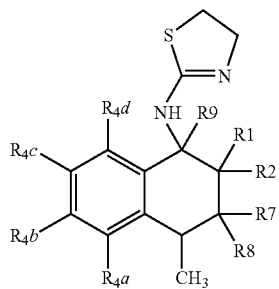
(Il)

wherein the values of $R^1$, $R^2$, $R^{4a}$, $R^{4b}$, $R^{4c}$, $R^{4d}$, $R^7$, $R^8$ and $R^9$ are given in Table 1.

Table XIII provides 612 compounds of formula Im

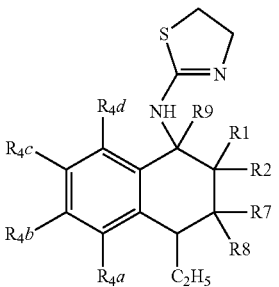
(Im)

wherein the values of $R^1$, $R^2$, $R^{4a}$, $R^{4b}$, $R^{4c}$, $R^{4d}$, $R^7$, $R^8$ and $R^9$ are given in Table 1.

Table XIV provides 612 compounds of formula In

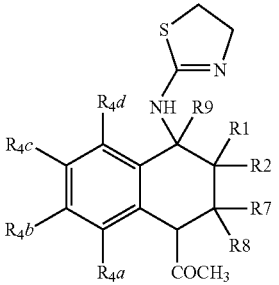
(Im)

wherein the values of $R^1$, $R^2$, $R^{4a}$, $R^{4b}$, $R^{4c}$, $R^{4d}$, $R^7$, $R^8$ and $R^9$ are given in Table 1.

Table XV provides 612 compounds of formula Io

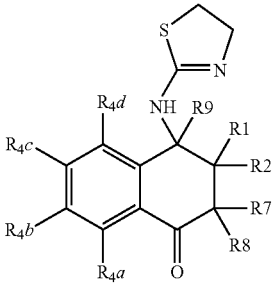
(Im)

wherein the values of $R^1$, $R^2$, $R^{4a}$, $R^{4b}$, $R^{4c}$, $R^{4d}$, $R^7$, $R^8$ and $R^9$ are given in Table 1.

Table XVI provides 612 compounds of formula Ip

Table XVII provides 612 compounds of formula Iq wherein the values of $R^1$, $R^2$, $R^{4a}$, $R^{4b}$, $R^{4c}$, $R^{4d}$, $R^7$, $R^8$ and $R^9$ are given in Table 1.

wherein the values of $R^1$, $R^2$, $R^{4a}$, $R^{4b}$, $R^{4c}$, $R^{4d}$, $R^5$, $R^6$ and $R^9$ are given in Table 2.

TABLE 2

| Compound No | R9 | R1 | R2 | R5 | R6 | R4a | R4b | R4c | R4d |
|---|---|---|---|---|---|---|---|---|---|
| XVII-1 | Me | H | H | H | H | H | H | H | H |
| XVII-2 | Et | H | H | H | H | H | H | H | H |
| XVII-3 | vinyl | H | H | H | H | H | H | H | H |
| XVII-4 | allyl | H | H | H | H | H | H | H | H |
| XVII-5 | cyclopropyl | H | H | H | H | H | H | H | H |
| XVII-6 | CN | H | H | H | H | H | H | H | H |
| XVII-7 | CONH$_2$ | H | H | H | H | H | H | H | H |
| XVII-8 | CONHMe | H | H | H | H | H | H | H | H |
| XVII-9 | CONMe$_2$ | H | H | H | H | H | H | H | H |
| XVII-10 | COMe | H | H | H | H | H | H | H | H |
| XVII-11 | COOH | H | H | H | H | H | H | H | H |
| XVII-12 | COOMe | H | H | H | H | H | H | H | H |
| XVII-13 | CSNHMe | H | H | H | H | H | H | H | H |
| XVII-14 | H | Me | H | H | H | H | H | H | H |
| XVII-15 | H | Et | H | H | H | H | H | H | H |
| XVII-16 | H | vinyl | H | H | H | H | H | H | H |
| XVII-17 | H | allyl | H | H | H | H | H | H | H |
| XVII-18 | H | cyclopropyl | H | H | H | H | H | H | H |
| XVII-19 | H | F | H | H | H | H | H | H | H |
| XVII-20 | H | Cl | H | H | H | H | H | H | H |
| XVII-21 | H | NO$_2$ | H | H | H | H | H | H | H |
| XVII-22 | H | CN | H | H | H | H | H | H | H |
| XVII-23 | H | CONH$_2$ | H | H | H | H | H | H | H |
| XVII-24 | H | CONHMe | H | H | H | H | H | H | H |
| XVII-25 | H | CONMe$_2$ | H | H | H | H | H | H | H |
| XVII-26 | H | COMe | H | H | H | H | H | H | H |
| XVII-27 | H | COOH | H | H | H | H | H | H | H |
| XVII-28 | H | COOMe | H | H | H | H | H | H | H |
| XVII-29 | H | CSOMe | H | H | H | H | H | H | H |
| XVII-30 | H | CSNH$_2$ | H | H | H | H | H | H | H |
| XVII-31 | H | CSNMe$_2$ | H | H | H | H | H | H | H |
| XVII-32 | H | CSNHMe | H | H | H | H | H | H | H |
| XVII-33 | H | OMe | H | H | H | H | H | H | H |
| XVII-34 | H | OEt | H | H | H | H | H | H | H |
| XVII-35 | H | OCOMe | H | H | H | H | H | H | H |
| XVII-36 | H | OCOOMe | H | H | H | H | H | H | H |
| XVII-37 | H | OCONHMe | H | H | H | H | H | H | H |
| XVII-38 | H | OCONMe$_2$ | H | H | H | H | H | H | H |
| XVII-39 | H | OCSMe | H | H | H | H | H | H | H |
| XVII-40 | H | OCSNMe$_2$ | H | H | H | H | H | H | H |
| XVII-41 | H | SMe | H | H | H | H | H | H | H |
| XVII-42 | H | SEt | H | H | H | H | H | H | H |
| XVII-43 | H | SCOMe | H | H | H | H | H | H | H |
| XVII-44 | H | SCSNMe$_2$ | H | H | H | H | H | H | H |
| XVII-45 | H | SCSNHMe | H | H | H | H | H | H | H |
| XVII-46 | H | NHMe | H | H | H | H | H | H | H |
| XVII-47 | H | NH$_2$ | H | H | H | H | H | H | H |
| XVII-48 | H | NMe$_2$ | H | H | H | H | H | H | H |
| XVII-49 | H | NHCOMe | H | H | H | H | H | H | H |
| XVII-50 | H | NHCONH$_2$ | H | H | H | H | H | H | H |
| XVII-51 | H | NHCONHMe | H | H | H | H | H | H | H |
| XVII-52 | H | NHCONMe$_2$ | H | H | H | H | H | H | H |
| XVII-53 | H | phenyl | H | H | H | H | H | H | H |

TABLE 2-continued

| Compound No | R9 | R1 | R2 | R5 | R6 | R4a | R4b | R4c | R4d |
|---|---|---|---|---|---|---|---|---|---|
| XVII-54 | H | 2-chloro-phenyl | H | H | H | H | H | H | H |
| XVII-55 | H | 4-nitrophenyl | H | H | H | H | H | H | H |
| XVII-56 | H | 2-pyridyl | H | H | H | H | H | H | H |
| XVII-57 | H | 3-pyridyl | H | H | H | H | H | H | H |
| XVII-58 | H | 4-pyridyl | H | H | H | H | H | H | H |
| XVII-59 | H | 2-furyl | H | H | H | H | H | H | H |
| XVII-60 | H | PhO | H | H | H | H | H | H | H |
| XVII-61 | | CH$_2$ | H | H | H | H | H | H | H |
| XVII-62 | H | =O | | H | H | H | H | H | H |
| XVII-63 | H | =NOH | | H | H | H | H | H | H |
| XVII-64 | H | =NOMe | | H | H | H | H | H | H |
| XVII-65 | H | =CH$_2$ | | H | H | H | H | H | H |
| XVII-66 | H | =CHMe | | H | H | H | H | H | H |
| XVII-67 | H | H | H | H | H | H | H | H | H |
| XVII-68 | H | H | H | Me | H | H | H | H | H |
| XVII-69 | H | H | H | Et | H | H | H | H | H |
| XVII-70 | H | H | H | vinyl | H | H | H | H | H |
| XVII-71 | H | H | H | allyl | H | H | H | H | H |
| XVII-72 | H | H | H | cyclopropyl | H | H | H | H | H |
| XVII-73 | H | H | H | F | H | H | H | H | H |
| XVII-74 | H | H | H | Cl | H | H | H | H | H |
| XVII-75 | H | H | H | NO$_2$ | H | H | H | H | H |
| XVII-76 | H | H | H | CN | H | H | H | H | H |
| XVII-77 | H | H | H | CONH$_2$ | H | H | H | H | H |
| XVII-78 | H | H | H | CONHMe | H | H | H | H | H |
| XVII-79 | H | H | H | CONMe$_2$ | H | H | H | H | H |
| XVII-80 | H | H | H | COMe | H | H | H | H | H |
| XVII-81 | H | H | H | COOH | H | H | H | H | H |
| XVII-82 | H | H | H | COOMe | H | H | H | H | H |
| XVII-83 | H | H | H | CSOMe | H | H | H | H | H |
| XVII-84 | H | H | H | CSNH$_2$ | H | H | H | H | H |
| XVII-85 | H | H | H | CSNMe$_2$ | H | H | H | H | H |
| XVII-86 | H | H | H | CSNHMe | H | H | H | H | H |
| XVII-87 | H | H | H | OMe | H | H | H | H | H |
| XVII-88 | H | H | H | OEt | H | H | H | H | H |
| XVII-89 | H | H | H | OCOMe | H | H | H | H | H |
| XVII-90 | H | H | H | OCOOMe | H | H | H | H | H |
| XVII-91 | H | H | H | OCONHMe | H | H | H | H | H |
| XVII-92 | H | H | H | OCONMe$_2$ | H | H | H | H | H |
| XVII-93 | H | H | H | OCSMe | H | H | H | H | H |
| XVII-94 | H | H | H | OCSNMe$_2$ | H | H | H | H | H |
| XVII-95 | H | H | H | SMe | H | H | H | H | H |
| XVII-96 | H | H | H | SEt | H | H | H | H | H |
| XVII-97 | H | H | H | SCOMe | H | H | H | H | H |
| XVII-98 | H | H | H | SCSNMe$_2$ | H | H | H | H | H |
| XVII-99 | H | H | H | SCSNHMe | H | H | H | H | H |
| XVII-100 | H | H | H | NHMe | H | H | H | H | H |
| XVII-101 | H | H | H | NH$_2$ | H | H | H | H | H |
| XVII-102 | H | H | H | NMe$_2$ | H | H | H | H | H |
| XVII-103 | H | H | H | NHCOMe | H | H | H | H | H |
| XVII-104 | H | H | H | NHCONH$_2$ | H | H | H | H | H |
| XVII-105 | H | H | H | NHCONHMe | H | H | H | H | H |
| XVII-106 | H | H | H | NHCONMe$_2$ | H | H | H | H | H |
| XVII-107 | H | H | H | phenyl | H | H | H | H | H |
| XVII-108 | H | H | H | 2-chloro-phenyl | H | H | H | H | H |
| XVII-109 | H | H | H | 4-nitrophenyl | H | H | H | H | H |
| XVII-110 | H | H | H | 2-pyridyl | H | H | H | H | H |
| XVII-111 | H | H | H | 3-pyridyl | H | H | H | H | H |
| XVII-112 | H | H | H | 4-pyridyl | H | H | H | H | H |
| XVII-113 | H | H | H | 2-furyl | H | H | H | H | H |
| XVII-114 | H | H | H | PhO | H | H | H | H | H |
| XVII-115 | H | H | H | =O | | H | H | H | H |
| XVII-116 | H | H | H | =NOH | | H | H | H | H |
| XVII-117 | H | H | H | =NOMe | | H | H | H | H |
| XVII-118 | H | H | H | =CH$_2$ | | H | H | H | H |
| XVII-119 | H | H | H | =CHMe | | H | H | H | H |
| XVII-120 | H | Me | H | Me | H | H | H | H | H |
| XVII-121 | H | Me | F | Me | H | H | H | H | H |
| XVII-122 | H | Me | H | F | H | H | H | H | H |
| XVII-123 | H | Me | F | H | H | H | H | H | H |
| XVII-124 | H | Me | Me | H | H | H | H | H | H |
| XVII-125 | H | F | H | Me | H | H | H | H | H |
| XVII-126 | H | F | H | F | H | H | H | H | H |
| XVII-127 | Me | H | H | H | H | F | H | H | H |

TABLE 2-continued

| Compound No | R9 | R1 | R2 | R5 | R6 | R4a | R4b | R4c | R4d |
|---|---|---|---|---|---|---|---|---|---|
| XVII-128 | Et | H | H | H | H | F | H | H | H |
| XVII-129 | vinyl | H | H | H | H | F | H | H | H |
| XVII-130 | allyl | H | H | H | H | F | H | H | H |
| XVII-131 | cyclopropyl | H | H | H | H | F | H | H | H |
| XVII-132 | CN | H | H | H | H | F | H | H | H |
| XVII-133 | CONH$_2$ | H | H | H | H | F | H | H | H |
| XVII-134 | CONHMe | H | H | H | H | F | H | H | H |
| XVII-135 | CONMe$_2$ | H | H | H | H | F | H | H | H |
| XVII-136 | COMe | H | H | H | H | F | H | H | H |
| XVII-137 | COOH | H | H | H | H | F | H | H | H |
| XVII-138 | COOMe | H | H | H | H | F | H | H | H |
| XVII-139 | CSNHMe | H | H | H | H | F | H | H | H |
| XVII-140 | H | Me | H | H | H | F | H | H | H |
| XVII-141 | H | Et | H | H | H | F | H | H | H |
| XVII-142 | H | vinyl | H | H | H | F | H | H | H |
| XVII-143 | H | allyl | H | H | H | F | H | H | H |
| XVII-144 | H | cyclopropyl | H | H | H | F | H | H | H |
| XVII-145 | H | F | H | H | H | F | H | H | H |
| XVII-146 | H | Cl | H | H | H | F | H | H | H |
| XVII-147 | H | NO$_2$ | H | H | H | F | H | H | H |
| XVII-148 | H | CN | H | H | H | F | H | H | H |
| XVII-149 | H | CONH$_2$ | H | H | H | F | H | H | H |
| XVII-150 | H | CONHMe | H | H | H | F | H | H | H |
| XVII-151 | H | CONMe$_2$ | H | H | H | F | H | H | H |
| XVII-152 | H | COMe | H | H | H | F | H | H | H |
| XVII-153 | H | COOH | H | H | H | F | H | H | H |
| XVII-154 | H | COOMe | H | H | H | F | H | H | H |
| XVII-155 | H | CSOMe | H | H | H | F | H | H | H |
| XVII-156 | H | CSNH$_2$ | H | H | H | F | H | H | H |
| XVII-157 | H | CSNMe$_2$ | H | H | H | F | H | H | H |
| XVII-158 | H | CSNHMe | H | H | H | F | H | H | H |
| XVII-159 | H | OMe | H | H | H | F | H | H | H |
| XVII-160 | H | OEt | H | H | H | F | H | H | H |
| XVII-161 | H | OCOMe | H | H | H | F | H | H | H |
| XVII-162 | H | OCOOMe | H | H | H | F | H | H | H |
| XVII-163 | H | OCONHMe | H | H | H | F | H | H | H |
| XVII-164 | H | OCONMe$_2$ | H | H | H | F | H | H | H |
| XVII-165 | H | OCSMe | H | H | H | F | H | H | H |
| XVII-166 | H | OCSNMe$_2$ | H | H | H | F | H | H | H |
| XVII-167 | H | SMe | H | H | H | F | H | H | H |
| XVII-168 | H | SEt | H | H | H | F | H | H | H |
| XVII-169 | H | SCOMe | H | H | H | F | H | H | H |
| XVII-170 | H | SCSNMe$_2$ | H | H | H | F | H | H | H |
| XVII-171 | H | SCSNHMe | H | H | H | F | H | H | H |
| XVII-172 | H | NHMe | H | H | H | F | H | H | H |
| XVII-173 | H | NH$_2$ | H | H | H | F | H | H | H |
| XVII-174 | H | NMe$_2$ | H | H | H | F | H | H | H |
| XVII-175 | H | NHCOMe | H | H | H | F | H | H | H |
| XVII-176 | H | NHCONH$_2$ | H | H | H | F | H | H | H |
| XVII-177 | H | NHCONHMe | H | H | H | F | H | H | H |
| XVII-178 | H | NHCONMe$_2$ | H | H | H | F | H | H | H |
| XVII-179 | H | phenyl | H | H | H | F | H | H | H |
| XVII-180 | H | 2-chloro-phenyl | H | H | H | F | H | H | H |
| XVII-181 | H | 4-nitrophenyl | H | H | H | F | H | H | H |
| XVII-182 | H | 2-pyridyl | H | H | H | F | H | H | H |
| XVII-183 | H | 3-pyridyl | H | H | H | F | H | H | H |
| XVII-184 | H | 4-pyridyl | H | H | H | F | H | H | H |
| XVII-185 | H | 2-furyl | H | H | H | F | H | H | H |
| XVII-186 | H | PhO | H | H | H | F | H | H | H |
| XVII-187 | | CH$_2$ | H | H | H | F | H | H | H |
| XVII-188 | H | H | H | Me | H | F | H | H | H |
| XVII-189 | H | H | H | Et | H | F | H | H | H |
| XVII-190 | H | H | H | vinyl | H | F | H | H | H |
| XVII-191 | H | H | H | allyl | H | F | H | H | H |
| XVII-192 | H | H | H | cyclopropyl | H | F | H | H | H |
| XVII-193 | H | H | H | F | H | F | H | H | H |
| XVII-194 | H | H | H | Cl | H | F | H | H | H |
| XVII-195 | H | H | H | NO$_2$ | H | F | H | H | H |
| XVII-196 | H | H | H | CN | H | F | H | H | H |
| XVII-197 | H | H | H | CONH$_2$ | H | F | H | H | H |
| XVII-198 | H | H | H | CONHMe | H | F | H | H | H |
| XVII-199 | H | H | H | CONMe$_2$ | H | F | H | H | H |
| XVII-200 | H | H | H | COMe | H | F | H | H | H |
| XVII-201 | H | H | H | COOH | H | F | H | H | H |
| XVII-202 | H | H | H | COOMe | H | F | H | H | H |
| XVII-203 | H | H | H | CSOMe | H | F | H | H | H |

TABLE 2-continued

| Compound No | R9 | R1 | R2 | R5 | R6 | R4a | R4b | R4c | R4d |
|---|---|---|---|---|---|---|---|---|---|
| XVII-204 | H | H | H | CSNH$_2$ | H | F | H | H | H |
| XVII-205 | H | H | H | CSNMe$_2$ | H | F | H | H | H |
| XVII-206 | H | H | H | CSNHMe | H | F | H | H | H |
| XVII-207 | H | H | H | OMe | H | F | H | H | H |
| XVII-208 | H | H | H | OEt | H | F | H | H | H |
| XVII-209 | H | H | H | OCOMe | H | F | H | H | H |
| XVII-210 | H | H | H | OCOOMe | H | F | H | H | H |
| XVII-211 | H | H | H | OCONHMe | H | F | H | H | H |
| XVII-212 | H | H | H | OCONMe$_2$ | H | F | H | H | H |
| XVII-213 | H | H | H | OCSMe | H | F | H | H | H |
| XVII-214 | H | H | H | OCSNMe$_2$ | H | F | H | H | H |
| XVII-215 | H | H | H | SMe | H | F | H | H | H |
| XVII-216 | H | H | H | SEt | H | F | H | H | H |
| XVII-217 | H | H | H | SCOMe | H | F | H | H | H |
| XVII-218 | H | H | H | SCSNMe$_2$ | H | F | H | H | H |
| XVII-219 | H | H | H | SCSNHMe | H | F | H | H | H |
| XVII-220 | H | H | H | NHMe | H | F | H | H | H |
| XVII-221 | H | H | H | NH$_2$ | H | F | H | H | H |
| XVII-222 | H | H | H | NMe$_2$ | H | F | H | H | H |
| XVII-223 | H | H | H | NHCOMe | H | F | H | H | H |
| XVII-224 | H | H | H | NHCONH$_2$ | H | F | H | H | H |
| XVII-225 | H | H | H | NHCONHMe | H | F | H | H | H |
| XVII-226 | H | H | H | NHCONMe$_2$ | H | F | H | H | H |
| XVII-227 | H | H | H | phenyl | H | F | H | H | H |
| XVII-228 | H | H | H | 2-chloro-phenyl | H | F | H | H | H |
| XVII-229 | H | H | H | 4-nitrophenyl | H | F | H | H | H |
| XVII-230 | H | H | H | 2-pyridyl | H | F | H | H | H |
| XVII-231 | H | H | H | 3-pyridyl | H | F | H | H | H |
| XVII-232 | H | H | H | 4-pyridyl | H | F | H | H | H |
| XVII-233 | H | H | H | 2-furyl | H | F | H | H | H |
| XVII-234 | H | H | H | PhO | H | F | H | H | H |
| XVII-235 | H | Me | H | Me | H | F | H | H | H |
| XVII-236 | H | Me | F | Me | H | F | H | H | H |
| XVII-237 | H | Me | H | F | H | F | H | H | H |
| XVII-238 | H | Me | F | H | H | F | H | H | H |
| XVII-239 | H | Me | Me | H | H | F | H | H | H |
| XVII-240 | H | F | H | Me | H | F | H | H | H |
| XVII-241 | H | F | H | F | H | F | H | H | H |
| XVII-242 | Me | H | H | H | H | Me | H | H | H |
| XVII-243 | Et | H | H | H | H | Me | H | H | H |
| XVII-244 | vinyl | H | H | H | H | Me | H | H | H |
| XVII-245 | allyl | H | H | H | H | Me | H | H | H |
| XVII-246 | cyclopropyl | H | H | H | H | Me | H | H | H |
| XVII-247 | CN | H | H | H | H | Me | H | H | H |
| XVII-248 | CONH$_2$ | H | H | H | H | Me | H | H | H |
| XVII-249 | CONHMe | H | H | H | H | Me | H | H | H |
| XVII-250 | CONMe$_2$ | H | H | H | H | Me | H | H | H |
| XVII-251 | COMe | H | H | H | H | Me | H | H | H |
| XVII-252 | COOH | H | H | H | H | Me | H | H | H |
| XVII-253 | COOMe | H | H | H | H | Me | H | H | H |
| XVII-254 | CSNHMe | H | H | H | H | Me | H | H | H |
| XVII-255 | H | Me | H | H | H | Me | H | H | H |
| XVII-256 | H | Et | H | H | H | Me | H | H | H |
| XVII-257 | H | vinyl | H | H | H | Me | H | H | H |
| XVII-258 | H | allyl | H | H | H | Me | H | H | H |
| XVII-259 | H | cyclopropyl | H | H | H | Me | H | H | H |
| XVII-260 | H | F | H | H | H | Me | H | H | H |
| XVII-261 | H | Cl | H | H | H | Me | H | H | H |
| XVII-262 | H | NO$_2$ | H | H | H | Me | H | H | H |
| XVII-263 | H | CN | H | H | H | Me | H | H | H |
| XVII-264 | H | CONH$_2$ | H | H | H | Me | H | H | H |
| XVII-265 | H | CONHMe | H | H | H | Me | H | H | H |
| XVII-266 | H | CONMe$_2$ | H | H | H | Me | H | H | H |
| XVII-267 | H | COMe | H | H | H | Me | H | H | H |
| XVII-268 | H | COOH | H | H | H | Me | H | H | H |
| XVII-269 | H | COOMe | H | H | H | Me | H | H | H |
| XVII-270 | H | CSOMe | H | H | H | Me | H | H | H |
| XVII-271 | H | CSNH$_2$ | H | H | H | Me | H | H | H |
| XVII-272 | H | CSNMe$_2$ | H | H | H | Me | H | H | H |
| XVII-273 | H | CSNHMe | H | H | H | Me | H | H | H |
| XVII-274 | H | OMe | H | H | H | Me | H | H | H |
| XVII-275 | H | OEt | H | H | H | Me | H | H | H |
| XVII-276 | H | OCOMe | H | H | H | Me | H | H | H |
| XVII-277 | H | OCOOMe | H | H | H | Me | H | H | H |
| XVII-278 | H | OCONHMe | H | H | H | Me | H | H | H |

TABLE 2-continued

| Compound No | R9 | R1 | R2 | R5 | R6 | R4a | R4b | R4c | R4d |
|---|---|---|---|---|---|---|---|---|---|
| XVII-279 | H | OCONMe$_2$ | H | H | H | Me | H | H | H |
| XVII-280 | H | OCSMe | H | H | H | Me | H | H | H |
| XVII-281 | H | OCSNMe2 | H | H | H | Me | H | H | H |
| XVII-282 | H | SMe | H | H | H | Me | H | H | H |
| XVII-283 | H | SEt | H | H | H | Me | H | H | H |
| XVII-284 | H | SCOMe | H | H | H | Me | H | H | H |
| XVII-285 | H | SCSNMe$_2$ | H | H | H | Me | H | H | H |
| XVII-286 | H | SCSNHMe | H | H | H | Me | H | H | H |
| XVII-287 | H | NHMe | H | H | H | Me | H | H | H |
| XVII-288 | H | NH$_2$ | H | H | H | Me | H | H | H |
| XVII-289 | H | NMe$_2$ | H | H | H | Me | H | H | H |
| XVII-290 | H | NHCOMe | H | H | H | Me | H | H | H |
| XVII-291 | H | NHCONH$_2$ | H | H | H | Me | H | H | H |
| XVII-292 | H | NHCONHMe | H | H | H | Me | H | H | H |
| XVII-293 | H | NHCONMe$_2$ | H | H | H | Me | H | H | H |
| XVII-294 | H | phenyl | H | H | H | Me | H | H | H |
| XVII-295 | H | 2-chloro-phenyl | H | H | H | Me | H | H | H |
| XVII-296 | H | 4-nitrophenyl | H | H | H | Me | H | H | H |
| XVII-297 | H | 2-pyridyl | H | H | H | Me | H | H | H |
| XVII-298 | H | 3-pyridyl | H | H | H | Me | H | H | H |
| XVII-299 | H | 4-pyridyl | H | H | H | Me | H | H | H |
| XVII-300 | H | 2-furyl | H | H | H | Me | H | H | H |
| XVII-301 | H | PhO | H | H | H | Me | H | H | H |
| XVII-302 |  | CH$_2$ | H | H | H | Me | H | H | H |
| XVII-303 | H | H | H | Me | H | Me | H | H | H |
| XVII-304 | H | H | H | Et | H | Me | H | H | H |
| XVII-305 | H | H | H | vinyl | H | Me | H | H | H |
| XVII-306 | H | H | H | allyl | H | Me | H | H | H |
| XVII-307 | H | H | H | cyclopropyl | H | Me | H | H | H |
| XVII-308 | H | H | H | F | H | Me | H | H | H |
| XVII-309 | H | H | H | Cl | H | Me | H | H | H |
| XVII-310 | H | H | H | NO$_2$ | H | Me | H | H | H |
| XVII-311 | H | H | H | CN | H | Me | H | H | H |
| XVII-312 | H | H | H | CONH$_2$ | H | Me | H | H | H |
| XVII-313 | H | H | H | CONHMe | H | Me | H | H | H |
| XVII-314 | H | H | H | CONMe$_2$ | H | Me | H | H | H |
| XVII-315 | H | H | H | COMe | H | Me | H | H | H |
| XVII-316 | H | H | H | COOH | H | Me | H | H | H |
| XVII-317 | H | H | H | COOMe | H | Me | H | H | H |
| XVII-318 | H | H | H | CSOMe | H | Me | H | H | H |
| XVII-319 | H | H | H | CSNH$_2$ | H | Me | H | H | H |
| XVII-320 | H | H | H | CSNMe$_2$ | H | Me | H | H | H |
| XVII-321 | H | H | H | CSNHMe | H | Me | H | H | H |
| XVII-322 | H | H | H | OMe | H | Me | H | H | H |
| XVII-323 | H | H | H | OEt | H | Me | H | H | H |
| XVII-324 | H | H | H | OCOMe | H | Me | H | H | H |
| XVII-325 | H | H | H | OCOOMe | H | Me | H | H | H |
| XVII-326 | H | H | H | OCONHMe | H | Me | H | H | H |
| XVII-327 | H | H | H | OCONMe$_2$ | H | Me | H | H | H |
| XVII-328 | H | H | H | OCSMe | H | Me | H | H | H |
| XVII-329 | H | H | H | OCSNMe2 | H | Me | H | H | H |
| XVII-330 | H | H | H | SMe | H | Me | H | H | H |
| XVII-331 | H | H | H | SEt | H | Me | H | H | H |
| XVII-332 | H | H | H | SCOMe | H | Me | H | H | H |
| XVII-333 | H | H | H | SCSNMe$_2$ | H | Me | H | H | H |
| XVII-334 | H | H | H | SCSNHMe | H | Me | H | H | H |
| XVII-335 | H | H | H | NHMe | H | Me | H | H | H |
| XVII-336 | H | H | H | NH$_2$ | H | Me | H | H | H |
| XVII-337 | H | H | H | NMe$_2$ | H | Me | H | H | H |
| XVII-338 | H | H | H | NHCOMe | H | Me | H | H | H |
| XVII-339 | H | H | H | NHCONH$_2$ | H | Me | H | H | H |
| XVII-340 | H | H | H | NHCONHMe | H | Me | H | H | H |
| XVII-341 | H | H | H | NHCONMe$_2$ | H | Me | H | H | H |
| XVII-342 | H | H | H | phenyl | H | Me | H | H | H |
| XVII-343 | H | H | H | 2-chloro-phenyl | H | Me | H | H | H |
| XVII-344 | H | H | H | 4-nitrophenyl | H | Me | H | H | H |
| XVII-345 | H | H | H | 2-pyridyl | H | Me | H | H | H |
| XVII-346 | H | H | H | 3-pyridyl | H | Me | H | H | H |
| XVII-347 | H | H | H | 4-pyridyl | H | Me | H | H | H |
| XVII-348 | H | H | H | 2-furyl | H | Me | H | H | H |
| XVII-349 | H | H | H | PhO | H | Me | H | H | H |
| XVII-350 | H | Me | H | Me | H | Me | H | H | H |
| XVII-351 | H | Me | F | Me | H | Me | H | H | H |
| XVII-352 | H | Me | H | F | H | Me | H | H | H |

TABLE 2-continued

| Compound No | R9 | R1 | R2 | R5 | R6 | R4a | R4b | R4c | R4d |
|---|---|---|---|---|---|---|---|---|---|
| XVII-353 | H | Me | F | H | H | Me | H | H | H |
| XVII-354 | H | Me | Me | H | H | Me | H | H | H |
| XVII-355 | H | F | H | Me | H | Me | H | H | H |
| XVII-356 | H | F | H | F | H | Me | H | H | H |
| XVII-357 | Me | H | H | H | H | F | H | F | H |
| XVII-358 | Et | H | H | H | H | F | H | F | H |
| XVII-359 | vinyl | H | H | H | H | F | H | F | H |
| XVII-360 | allyl | H | H | H | H | F | H | F | H |
| XVII-361 | cyclopropyl | H | H | H | H | F | H | F | H |
| XVII-362 | CN | H | H | H | H | F | H | F | H |
| XVII-363 | CONH$_2$ | H | H | H | H | F | H | F | H |
| XVII-364 | CONHMe | H | H | H | H | F | H | F | H |
| XVII-365 | CONMe$_2$ | H | H | H | H | F | H | F | H |
| XVII-366 | COMe | H | H | H | H | F | H | F | H |
| XVII-367 | COOH | H | H | H | H | F | H | F | H |
| XVII-368 | COOMe | H | H | H | H | F | H | F | H |
| XVII-369 | CSNHMe | H | H | H | H | F | H | F | H |
| XVII-370 | H | Me | H | H | H | F | H | F | H |
| XVII-371 | H | Et | H | H | H | F | H | F | H |
| XVII-372 | H | vinyl | H | H | H | F | H | F | H |
| XVII-373 | H | allyl | H | H | H | F | H | F | H |
| XVII-374 | H | cyclopropyl | H | H | H | F | H | F | H |
| XVII-375 | H | F | H | H | H | F | H | F | H |
| XVII-376 | H | Cl | H | H | H | F | H | F | H |
| XVII-377 | H | NO$_2$ | H | H | H | F | H | F | H |
| XVII-378 | H | CN | H | H | H | F | H | F | H |
| XVII-379 | H | CONH$_2$ | H | H | H | F | H | F | H |
| XVII-380 | H | CONHMe | H | H | H | F | H | F | H |
| XVII-381 | H | CONMe$_2$ | H | H | H | F | H | F | H |
| XVII-382 | H | COMe | H | H | H | F | H | F | H |
| XVII-383 | H | COOH | H | H | H | F | H | F | H |
| XVII-384 | H | COOMe | H | H | H | F | H | F | H |
| XVII-385 | H | CSOMe | H | H | H | F | H | F | H |
| XVII-386 | H | CSNH$_2$ | H | H | H | F | H | F | H |
| XVII-387 | H | CSNMe$_2$ | H | H | H | F | H | F | H |
| XVII-388 | H | CSNHMe | H | H | H | F | H | F | H |
| XVII-389 | H | OMe | H | H | H | F | H | F | H |
| XVII-390 | H | OEt | H | H | H | F | H | F | H |
| XVII-391 | H | OCOMe | H | H | H | F | H | F | H |
| XVII-392 | H | OCOOMe | H | H | H | F | H | F | H |
| XVII-393 | H | OCONHMe | H | H | H | F | H | F | H |
| XVII-394 | H | OCONMe$_2$ | H | H | H | F | H | F | H |
| XVII-395 | H | OCSMe | H | H | H | F | H | F | H |
| XVII-396 | H | OCSNMe2 | H | H | H | F | H | F | H |
| XVII-397 | H | SMe | H | H | H | F | H | F | H |
| XVII-398 | H | SEt | H | H | H | F | H | F | H |
| XVII-399 | H | SCOMe | H | H | H | F | H | F | H |
| XVII-400 | H | SCSNMe$_2$ | H | H | H | F | H | F | H |
| XVII-401 | H | SCSNHMe | H | H | H | F | H | F | H |
| XVII-402 | H | NHMe | H | H | H | F | H | F | H |
| XVII-403 | H | NH$_2$ | H | H | H | F | H | F | H |
| XVII-404 | H | NMe$_2$ | H | H | H | F | H | F | H |
| XVII-405 | H | NHCOMe | H | H | H | F | H | F | H |
| XVII-406 | H | NHCONH$_2$ | H | H | H | F | H | F | H |
| XVII-407 | H | NHCONHMe | H | H | H | F | H | F | H |
| XVII-408 | H | NHCONMe$_2$ | H | H | H | F | H | F | H |
| XVII-409 | H | phenyl | H | H | H | F | H | F | H |
| XVII-410 | H | 2-chloro-phenyl | H | H | H | F | H | F | H |
| XVII-411 | H | 4-nitrophenyl | H | H | H | F | H | F | H |
| XVII-412 | H | 2-pyridyl | H | H | H | F | H | F | H |
| XVII-413 | H | 3-pyridyl | H | H | H | F | H | F | H |
| XVII-414 | H | 4-pyridyl | H | H | H | F | H | F | H |
| XVII-415 | H | 2-furyl | H | H | H | F | H | F | H |
| XVII-416 | H | PhO | H | H | H | F | H | F | H |
| XVII-417 |  | CH$_2$ | H | H | H | F | H | F | H |
| XVII-418 | H | H | H | Me | H | F | H | F | H |
| XVII-419 | H | H | H | Et | H | F | H | F | H |
| XVII-420 | H | H | H | vinyl | H | F | H | F | H |
| XVII-421 | H | H | H | allyl | H | F | H | F | H |
| XVII-422 | H | H | H | cyclopropyl | H | F | H | F | H |
| XVII-423 | H | H | H | F | H | F | H | F | H |
| XVII-424 | H | H | H | Cl | H | F | H | F | H |
| XVII-425 | H | H | H | NO$_2$ | H | F | H | F | H |
| XVII-426 | H | H | H | CN | H | F | H | F | H |
| XVII-427 | H | H | H | CONH$_2$ | H | F | H | F | H |
| XVII-428 | H | H | H | CONHMe | H | F | H | F | H |

TABLE 2-continued

| Compound No | R9 | R1 | R2 | R5 | R6 | R4a | R4b | R4c | R4d |
|---|---|---|---|---|---|---|---|---|---|
| XVII-429 | H | H | H | CONMe₂ | H | F | H | F | H |
| XVII-430 | H | H | H | COMe | H | F | H | F | H |
| XVII-431 | H | H | H | COOH | H | F | H | F | H |
| XVII-432 | H | H | H | COOMe | H | F | H | F | H |
| XVII-433 | H | H | H | CSOMe | H | F | H | F | H |
| XVII-434 | H | H | H | CSNH₂ | H | F | H | F | H |
| XVII-435 | H | H | H | CSNMe₂ | H | F | H | F | H |
| XVII-436 | H | H | H | CSNHMe | H | F | H | F | H |
| XVII-437 | H | H | H | OMe | H | F | H | F | H |
| XVII-438 | H | H | H | OEt | H | F | H | F | H |
| XVII-439 | H | H | H | OCOMe | H | F | H | F | H |
| XVII-440 | H | H | H | OCOOMe | H | F | H | F | H |
| XVII-441 | H | H | H | OCONHMe | H | F | H | F | H |
| XVII-442 | H | H | H | OCONMe₂ | H | F | H | F | H |
| XVII-443 | H | H | H | OCSMe | H | F | H | F | H |
| XVII-444 | H | H | H | OCSNMe₂ | H | F | H | F | H |
| XVII-445 | H | H | H | SMe | H | F | H | F | H |
| XVII-446 | H | H | H | SEt | H | F | H | F | H |
| XVII-447 | H | H | H | SCOMe | H | F | H | F | H |
| XVII-448 | H | H | H | SCSNMe₂ | H | F | H | F | H |
| XVII-449 | H | H | H | SCSNHMe | H | F | H | F | H |
| XVII-450 | H | H | H | NHMe | H | F | H | F | H |
| XVII-451 | H | H | H | NH₂ | H | F | H | F | H |
| XVII-452 | H | H | H | NMe₂ | H | F | H | F | H |
| XVII-453 | H | H | H | NHCOMe | H | F | H | F | H |
| XVII-454 | H | H | H | NHCONH₂ | H | F | H | F | H |
| XVII-455 | H | H | H | NHCONHMe | H | F | H | F | H |
| XVII-456 | H | H | H | NHCONMe₂ | H | F | H | F | H |
| XVII-457 | H | H | H | phenyl | H | F | H | F | H |
| XVII-458 | H | H | H | 2-chloro-phenyl | H | F | H | F | H |
| XVII-459 | H | H | H | 4-nitrophenyl | H | F | H | F | H |
| XVII-460 | H | H | H | 2-pyridyl | H | F | H | F | H |
| XVII-461 | H | H | H | 3-pyridyl | H | F | H | F | H |
| XVII-462 | H | H | H | 4-pyridyl | H | F | H | F | H |
| XVII-463 | H | H | H | 2-furyl | H | F | H | F | H |
| XVII-464 | H | H | H | PhO | H | F | H | F | H |
| XVII-465 | H | Me | H | Me | H | F | H | F | H |
| XVII-466 | H | Me | F | Me | H | F | H | F | H |
| XVII-467 | H | Me | H | F | H | F | H | F | H |
| XVII-468 | H | Me | F | H | H | F | H | F | H |
| XVII-469 | H | Me | Me | H | H | F | H | F | H |
| XVII-470 | H | F | H | Me | H | F | H | F | H |
| XVII-471 | H | F | H | F | H | F | H | F | H |
| XVII-472 | H | H | H | H | H | Me | H | H | H |
| XVII-473 | H | H | H | H | H | Et | H | H | H |
| XVII-474 | H | H | H | H | H | vinyl | H | H | H |
| XVII-475 | H | H | H | H | H | allyl | H | H | H |
| XVII-476 | H | H | H | H | H | cyclopropyl | H | H | H |
| XVII-477 | H | H | H | H | H | F | H | H | H |
| XVII-478 | H | H | H | H | H | Cl | H | H | H |
| XVII-479 | H | H | H | H | H | NO₂ | H | H | H |
| XVII-480 | H | H | H | H | H | CN | H | H | H |
| XVII-481 | H | H | H | H | H | CONH₂ | H | H | H |
| XVII-482 | H | H | H | H | H | CONHMe | H | H | H |
| XVII-483 | H | H | H | H | H | CONMe₂ | H | H | H |
| XVII-484 | H | H | H | H | H | COMe | H | H | H |
| XVII-485 | H | H | H | H | H | COOH | H | H | H |
| XVII-486 | H | H | H | H | H | COOMe | H | H | H |
| XVII-487 | H | H | H | H | H | CSOMe | H | H | H |
| XVII-488 | H | H | H | H | H | CSNH₂ | H | H | H |
| XVII-489 | H | H | H | H | H | CSNMe₂ | H | H | H |
| XVII-490 | H | H | H | H | H | CSNHMe | H | H | H |
| XVII-491 | H | H | H | H | H | OMe | H | H | H |
| XVII-492 | H | H | H | H | H | OEt | H | H | H |
| XVII-493 | H | H | H | H | H | OCOMe | H | H | H |
| XVII-494 | H | H | H | H | H | OCOOMe | H | H | H |
| XVII-495 | H | H | H | H | H | OCONHMe | H | H | H |
| XVII-496 | H | H | H | H | H | OCONMe₂ | H | H | H |
| XVII-497 | H | H | H | H | H | OCSMe | H | H | H |
| XVII-498 | H | H | H | H | H | OCSNMe₂ | H | H | H |
| XVII-499 | H | H | H | H | H | SMe | H | H | H |
| XVII-500 | H | H | H | H | H | SEt | H | H | H |
| XVII-501 | H | H | H | H | H | SCOMe | H | H | H |
| XVII-502 | H | H | H | H | H | SCSNMe₂ | H | H | H |
| XVII-503 | H | H | H | H | H | SCSNHMe | H | H | H |

TABLE 2-continued

| Compound No | R9 | R1 | R2 | R5 | R6 | R4a | R4b | R4c | R4d |
|---|---|---|---|---|---|---|---|---|---|
| XVII-504 | H | H | H | H | H | NHMe | H | H | H |
| XVII-505 | H | H | H | H | H | NH$_2$ | H | H | H |
| XVII-506 | H | H | H | H | H | NMe$_2$ | H | H | H |
| XVII-507 | H | H | H | H | H | NHCOMe | H | H | H |
| XVII-508 | H | H | H | H | H | NHCONH$_2$ | H | H | H |
| XVII-509 | H | H | H | H | H | NHCONHMe | H | H | H |
| XVII-510 | H | H | H | H | H | NHCONMe$_2$ | H | H | H |
| XVII-511 | H | H | H | H | H | phenyl | H | H | H |
| XVII-512 | H | H | H | H | H | 2-chloro-phenyl | H | H | H |
| XVII-513 | H | H | H | H | H | 4-nitrophenyl | H | H | H |
| XVII-514 | H | H | H | H | H | 2-pyridyl | H | H | H |
| XVII-515 | H | H | H | H | H | 3-pyridyl | H | H | H |
| XVII-516 | H | H | H | H | H | 4-pyridyl | H | H | H |
| XVII-517 | H | H | H | H | H | 2-furyl | H | H | H |
| XVII-518 | H | H | H | H | H | PhO | H | H | H |
| XVII-519 | H | H | H | H | H | H | H | Me | H |
| XVII-520 | H | H | H | H | H | H | H | Et | H |
| XVII-521 | H | H | H | H | H | H | H | vinyl | H |
| XVII-522 | H | H | H | H | H | H | H | allyl | H |
| XVII-523 | H | H | H | H | H | H | H | cyclopropyl | H |
| XVII-524 | H | H | H | H | H | H | H | F | H |
| XVII-525 | H | H | H | H | H | H | H | Cl | H |
| XVII-526 | H | H | H | H | H | H | H | NO$_2$ | H |
| XVII-527 | H | H | H | H | H | H | H | CN | H |
| XVII-528 | H | H | H | H | H | H | H | CONH$_2$ | H |
| XVII-529 | H | H | H | H | H | H | H | CONHMe | H |
| XVII-530 | H | H | H | H | H | H | H | CONMe$_2$ | H |
| XVII-531 | H | H | H | H | H | H | H | COMe | H |
| XVII-532 | H | H | H | H | H | H | H | COOH | H |
| XVII-533 | H | H | H | H | H | H | H | COOMe | H |
| XVII-534 | H | H | H | H | H | H | H | CSOMe | H |
| XVII-535 | H | H | H | H | H | H | H | CSNH$_2$ | H |
| XVII-536 | H | H | H | H | H | H | H | CSNMe$_2$ | H |
| XVII-537 | H | H | H | H | H | H | H | CSNHMe | H |
| XVII-538 | H | H | H | H | H | H | H | OMe | H |
| XVII-539 | H | H | H | H | H | H | H | OEt | H |
| XVII-540 | H | H | H | H | H | H | H | OCOMe | H |
| XVII-541 | H | H | H | H | H | H | H | OCOOMe | H |
| XVII-542 | H | H | H | H | H | H | H | OCONHMe | H |
| XVII-543 | H | H | H | H | H | H | H | OCONMe$_2$ | H |
| XVII-544 | H | H | H | H | H | H | H | OCSMe | H |
| XVII-545 | H | H | H | H | H | H | H | OCSNMe2 | H |
| XVII-546 | H | H | H | H | H | H | H | SMe | H |
| XVII-547 | H | H | H | H | H | H | H | SEt | H |
| XVII-548 | H | H | H | H | H | H | H | SCOMe | H |
| XVII-549 | H | H | H | H | H | H | H | SCSNMe$_2$ | H |
| XVII-550 | H | H | H | H | H | H | H | SCSNHMe | H |
| XVII-551 | H | H | H | H | H | H | H | NHMe | H |
| XVII-552 | H | H | H | H | H | H | H | NH$_2$ | H |
| XVII-553 | H | H | H | H | H | H | H | NMe$_2$ | H |
| XVII-554 | H | H | H | H | H | H | H | NHCOMe | H |
| XVII-555 | H | H | H | H | H | H | H | NHCONH$_2$ | H |
| XVII-556 | H | H | H | H | H | H | H | NHCONHMe | H |
| XVII-557 | H | H | H | H | H | H | H | NHCONMe$_2$ | H |
| XVII-558 | H | H | H | H | H | H | H | phenyl | H |
| XVII-559 | H | H | H | H | H | H | H | 2-chloro-phenyl | H |
| XVII-560 | H | H | H | H | H | H | H | 4-nitrophenyl | H |
| XVII-561 | H | H | H | H | H | H | H | 2-pyridyl | H |
| XVII-562 | H | H | H | H | H | H | H | 3-pyridyl | H |
| XVII-563 | H | H | H | H | H | H | H | 4-pyridyl | H |
| XVII-564 | H | H | H | H | H | H | H | 2-furyl | H |
| XVII-565 | H | H | H | H | H | H | H | PhO | H |
| XVII-566 | H | H | H | H | H | H | H | H | Me |
| XVII-567 | H | H | H | H | H | H | H | H | Et |
| XVII-568 | H | H | H | H | H | H | H | H | vinyl |

TABLE 2-continued

| Compound No | R9 | R1 | R2 | R5 | R6 | R4a | R4b | R4c | R4d |
|---|---|---|---|---|---|---|---|---|---|
| XVII-569 | H | H | H | H | H | H | H | H | allyl |
| XVII-570 | H | H | H | H | H | H | H | H | cyclopropyl |
| XVII-571 | H | H | H | H | H | H | H | H | F |
| XVII-572 | H | H | H | H | H | H | H | H | Cl |
| XVII-573 | H | H | H | H | H | H | H | H | $NO_2$ |
| XVII-574 | H | H | H | H | H | H | H | H | CN |
| XVII-575 | H | H | H | H | H | H | H | H | $CONH_2$ |
| XVII-576 | H | H | H | H | H | H | H | H | CONHMe |
| XVII-577 | H | H | H | H | H | H | H | H | $CONMe_2$ |
| XVII-578 | H | H | H | H | H | H | H | H | COMe |
| XVII-579 | H | H | H | H | H | H | H | H | COOH |
| XVII-580 | H | H | H | H | H | H | H | H | COOMe |
| XVII-581 | H | H | H | H | H | H | H | H | CSOMe |
| XVII-582 | H | H | H | H | H | H | H | H | $CSNH_2$ |
| XVII-583 | H | H | H | H | H | H | H | H | $CSNMe_2$ |
| XVII-584 | H | H | H | H | H | H | H | H | CSNHMe |
| XVII-585 | H | H | H | H | H | H | H | H | OMe |
| XVII-586 | H | H | H | H | H | H | H | H | OEt |
| XVII-587 | H | H | H | H | H | H | H | H | OCOMe |
| XVII-588 | H | H | H | H | H | H | H | H | OCOOMe |
| XVII-589 | H | H | H | H | H | H | H | H | OCONHMe |
| XVII-590 | H | H | H | H | H | H | H | H | $OCONMe_2$ |
| XVII-591 | H | H | H | H | H | H | H | H | OCSMe |
| XVII-592 | H | H | H | H | H | H | H | H | OCSNMe2 |
| XVII-593 | H | H | H | H | H | H | H | H | SMe |
| XVII-594 | H | H | H | H | H | H | H | H | SEt |
| XVII-595 | H | H | H | H | H | H | H | H | SCOMe |
| XVII-596 | H | H | H | H | H | H | H | H | $SCSNMe_2$ |
| XVII-597 | H | H | H | H | H | H | H | H | SCSNHMe |
| XVII-598 | H | H | H | H | H | H | H | H | NHMe |
| XVII-599 | H | H | H | H | H | H | H | H | $NH_2$ |
| XVII-600 | H | H | H | H | H | H | H | H | $NMe_2$ |
| XVII-601 | H | H | H | H | H | H | H | H | NHCOMe |
| XVII-602 | H | H | H | H | H | H | H | H | $NHCONH_2$ |
| XVII-603 | H | H | H | H | H | H | H | H | NHCONHMe |
| XVII-604 | H | H | H | H | H | H | H | H | $NHCONMe_2$ |
| XVII-605 | H | H | H | H | H | H | H | H | phenyl |
| XVII-606 | H | H | H | H | H | H | H | H | 2-chlorophenyl |
| XVII-607 | H | H | H | H | H | H | H | H | 4-nitrophenyl |
| XVII-608 | H | H | H | H | H | H | H | H | 2-pyridyl |
| XVII-609 | H | H | H | H | H | H | H | H | 3-pyridyl |
| XVII-610 | H | H | H | H | H | H | H | H | 4-pyridyl |
| XVII-611 | H | H | H | H | H | H | H | H | 2-furyl |
| XVII-612 | H | H | H | H | H | H | H | H | PhO |

Table XVIII provides 612 compounds of formula Ir

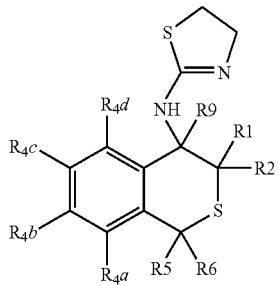

(Ir)

wherein the values of $R^1$, $R^2$, $R^{4a}$, $R^{4b}$, $R^{4c}$, $R^{4a}$, $R^5$, $R^6$ and $R^9$ are given in Table 2.

Table XIX provides 612 compounds of formula Is

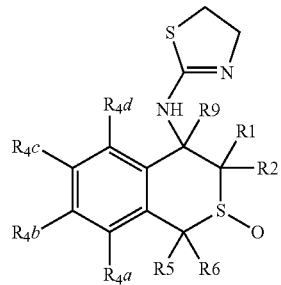

(Is)

wherein the values of $R^1$, $R^2$, $R^{4a}$, $R^{4b}$, $R^{4c}$, $R^{4d}$, $R^5$, $R^6$ and $R^9$ are given in Table 2.

Table XX provides 612 compounds of formula It

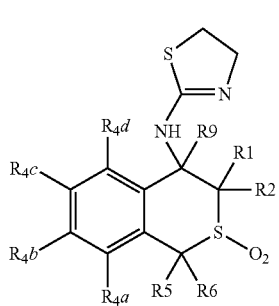
(It)

wherein the values of $R^1, R^2, R^{4a}, R^{4b}, R^{4c}, R^{4d}, R^5, R^6$ and $R^9$ are given in Table 2.

Table XXI provides 612 compounds of formula Iu

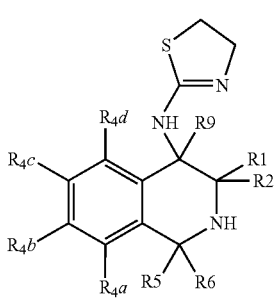
(Iu)

wherein the values of $R^1, R^2, R^{4a}, R^{4b}, R^{4c}, R^{4d}, R^5, R^6$ and $R^9$ are given in Table 2.

Table XXII provides 612 compounds of formula Iv

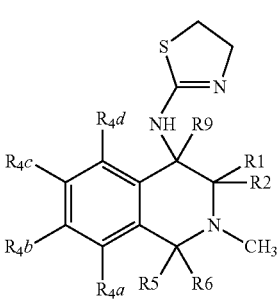
(Iv)

wherein the values of $R^1, R^2, R^{4a}, R^{4b}, R^{4c}, R^{4d}, R^5, R^6$ and $R^9$ are given in Table 2.

Table XXIII provides 612 compounds of formula Iw

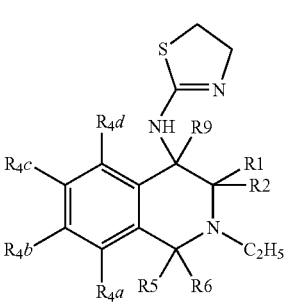
(Iw)

wherein the values of $R^1, R^2, R^{4a}, R^{4b}, R^{4c}, R^{4d}, R^5, R^6$ and $R^9$ are given in Table 2.

Table XXIV provides 612 compounds of formula Ix

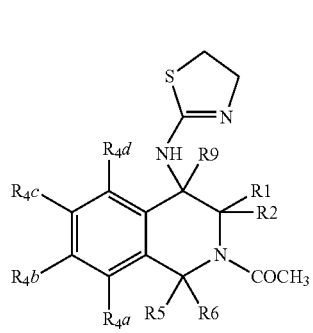
(Ix)

wherein the values of $R^1, R^2, R^{4a}, R^{4b}, R^{4c}, R^{4d}, R^5, R^6$ and $R^9$ are given in Table 2.

Table XXV provides 612 compounds of formula Iy

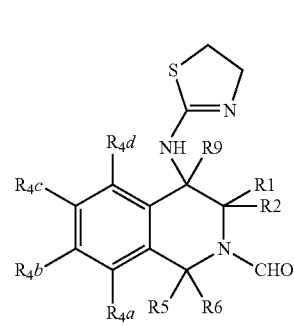
(Iy)

wherein the values of $R^1, R^2, R^{4a}, R^{4b}, R^{4c}, R^{4d}, R^5, R^6$ and $R^9$ are given in Table 2.

Table XXVI provides 612 compounds of formula Iz

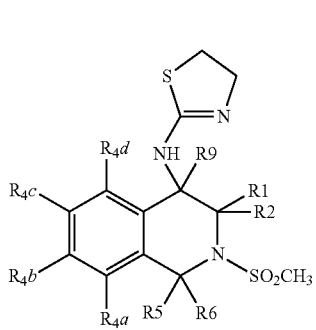
(Iz)

wherein the values of $R^1, R^2, R^{4a}, R^{4b}, R^{4c}, R^{4d}, R^5, R^6$ and $R^9$ are given in Table 2.

Table XXVII provides 612 compounds of formula Iaa

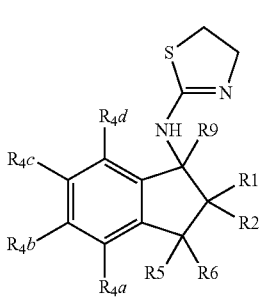
(Iaa)

wherein the values of $R^1, R^2, R^{4a}, R^{4b}, R^{4c}, R^{4d}, R^5, R^6$ and $R^9$ are given in Table 3.

TABLE 3

| Compound No | R9 | R1 | R2 | R5 | R6 | R4a | R4b | R4c | R4d |
|---|---|---|---|---|---|---|---|---|---|
| XXVII-1 | Me | H | H | H | H | H | H | H | H |
| XXVII-2 | Et | H | H | H | H | H | H | H | H |
| XXVII-3 | vinyl | H | H | H | H | H | H | H | H |
| XXVII-4 | allyl | H | H | H | H | H | H | H | H |
| XXVII-5 | cyclopropyl | H | H | H | H | H | H | H | H |
| XXVII-6 | CN | H | H | H | H | H | H | H | H |
| XXVII-7 | $CONH_2$ | H | H | H | H | H | H | H | H |
| XXVII-8 | CONHMe | H | H | H | H | H | H | H | H |
| XXVII-9 | $CONMe_2$ | H | H | H | H | H | H | H | H |
| XXVII-10 | COMe | H | H | H | H | H | H | H | H |
| XXVII-11 | COOH | H | H | H | H | H | H | H | H |
| XXVII-12 | COOMe | H | H | H | H | H | H | H | H |
| XXVII-13 | CSNHMe | H | H | H | H | H | H | H | H |
| XXVII-14 | H | Me | H | H | H | H | H | H | H |
| XXVII-15 | H | Et | H | H | H | H | H | H | H |
| XXVII-16 | H | vinyl | H | H | H | H | H | H | H |
| XXVII-17 | H | allyl | H | H | H | H | H | H | H |
| XXVII-18 | H | cyclopropyl | H | H | H | H | H | H | H |
| XXVII-19 | H | F | H | H | H | H | H | H | H |
| XXVII-20 | H | Cl | H | H | H | H | H | H | H |
| XXVII-21 | H | $NO_2$ | H | H | H | H | H | H | H |
| XXVII-22 | H | CN | H | H | H | H | H | H | H |
| XXVII-23 | H | $CONH_2$ | H | H | H | H | H | H | H |
| XXVII-24 | H | CONHMe | H | H | H | H | H | H | H |
| XXVII-25 | H | $CONMe_2$ | H | H | H | H | H | H | H |
| XXVII-26 | H | COMe | H | H | H | H | H | H | H |
| XXVII-27 | H | COOH | H | H | H | H | H | H | H |
| XXVII-28 | H | COOMe | H | H | H | H | H | H | H |
| XXVII-29 | H | CSOMe | H | H | H | H | H | H | H |
| XXVII-30 | H | $CSNH_2$ | H | H | H | H | H | H | H |
| XXVII-31 | H | $CSNMe_2$ | H | H | H | H | H | H | H |
| XXVII-32 | H | CSNHMe | H | H | H | H | H | H | H |
| XXVII-33 | H | OMe | H | H | H | H | H | H | H |
| XXVII-34 | H | OEt | H | H | H | H | H | H | H |
| XXVII-35 | H | OCOMe | H | H | H | H | H | H | H |
| XXVII-36 | H | OCOOMe | H | H | H | H | H | H | H |
| XXVII-37 | H | OCONHMe | H | H | H | H | H | H | H |
| XXVII-38 | H | $OCONMe_2$ | H | H | H | H | H | H | H |
| XXVII-39 | H | OCSMe | H | H | H | H | H | H | H |
| XXVII-40 | H | OCSNMe2 | H | H | H | H | H | H | H |
| XXVII-41 | H | SMe | H | H | H | H | H | H | H |
| XXVII-42 | H | SEt | H | H | H | H | H | H | H |
| XXVII-43 | H | SCOMe | H | H | H | H | H | H | H |
| XXVII-44 | H | $SCSNMe_2$ | H | H | H | H | H | H | H |
| XXVII-45 | H | SCSNHMe | H | H | H | H | H | H | H |
| XXVII-46 | H | NHMe | H | H | H | H | H | H | H |
| XXVII-47 | H | $NH_2$ | H | H | H | H | H | H | H |
| XXVII-48 | H | $NMe_2$ | H | H | H | H | H | H | H |
| XXVII-49 | H | NHCOMe | H | H | H | H | H | H | H |
| XXVII-50 | H | $NHCONH_2$ | H | H | H | H | H | H | H |
| XXVII-51 | H | NHCONHMe | H | H | H | H | H | H | H |
| XXVII-52 | H | $NHCONMe_2$ | H | H | H | H | H | H | H |
| XXVII-53 | H | phenyl | H | H | H | H | H | H | H |
| XXVII-54 | H | 2-chloro-phenyl | H | H | H | H | H | H | H |
| XXVII-55 | H | 4-nitrophenyl | H | H | H | H | H | H | H |
| XXVII-56 | H | 2-pyridyl | H | H | H | H | H | H | H |
| XXVII-57 | H | 3-pyridyl | H | H | H | H | H | H | H |
| XXVII-58 | H | 4-pyridyl | H | H | H | H | H | H | H |
| XXVII-59 | H | 2-furyl | H | H | H | H | H | H | H |
| XXVII-60 | H | PhO | H | H | H | H | H | H | H |
| XXVII-61 | H | $CH_2$ | H | H | H | H | H | H | H |
| XXVII-62 | H | | =O | H | H | H | H | H | H |
| XXVII-63 | H | | =NOH | H | H | H | H | H | H |
| XXVII-64 | H | | =NOMe | H | H | H | H | H | H |
| XXVII-65 | H | | $=CH_2$ | H | H | H | H | H | H |
| XXVII-66 | H | | =CHMe | H | H | H | H | H | H |
| XXVII-67 | H | H | H | H | H | H | H | H | H |
| XXVII-68 | H | H | H | Me | H | H | H | H | H |
| XXVII-69 | H | H | H | Et | H | H | H | H | H |
| XXVII-70 | H | H | H | vinyl | H | H | H | H | H |
| XXVII-71 | H | H | H | allyl | H | H | H | H | H |

TABLE 3-continued

| Compound No | R9 | R1 | R2 | R5 | R6 | R4a | R4b | R4c | R4d |
|---|---|---|---|---|---|---|---|---|---|
| XXVII-72 | H | H | H | cyclopropyl | H | H | H | H | H |
| XXVII-73 | H | H | H | F | H | H | H | H | H |
| XXVII-74 | H | H | H | Cl | H | H | H | H | H |
| XXVII-75 | H | H | H | NO$_2$ | H | H | H | H | H |
| XXVII-76 | H | H | H | CN | H | H | H | H | H |
| XXVII-77 | H | H | H | CONH$_2$ | H | H | H | H | H |
| XXVII-78 | H | H | H | CONHMe | H | H | H | H | H |
| XXVII-79 | H | H | H | CONMe$_2$ | H | H | H | H | H |
| XXVII-80 | H | H | H | COMe | H | H | H | H | H |
| XXVII-81 | H | H | H | COOH | H | H | H | H | H |
| XXVII-82 | H | H | H | COOMe | H | H | H | H | H |
| XXVII-83 | H | H | H | CSOMe | H | H | H | H | H |
| XXVII-84 | H | H | H | CSNH$_2$ | H | H | H | H | H |
| XXVII-85 | H | H | H | CSNMe$_2$ | H | H | H | H | H |
| XXVII-86 | H | H | H | CSNHMe | H | H | H | H | H |
| XXVII-87 | H | H | H | OMe | H | H | H | H | H |
| XXVII-88 | H | H | H | OEt | H | H | H | H | H |
| XXVII-89 | H | H | H | OCOMe | H | H | H | H | H |
| XXVII-90 | H | H | H | OCOOMe | H | H | H | H | H |
| XXVII-91 | H | H | H | OCONHMe | H | H | H | H | H |
| XXVII-92 | H | H | H | OCONMe$_2$ | H | H | H | H | H |
| XXVII-93 | H | H | H | OCSMe | H | H | H | H | H |
| XXVII-94 | H | H | H | OCSNMe2 | H | H | H | H | H |
| XXVII-95 | H | H | H | SMe | H | H | H | H | H |
| XXVII-96 | H | H | H | SEt | H | H | H | H | H |
| XXVII-97 | H | H | H | SCOMe | H | H | H | H | H |
| XXVII-98 | H | H | H | SCSNMe$_2$ | H | H | H | H | H |
| XXVII-99 | H | H | H | SCSNHMe | H | H | H | H | H |
| XXVII-100 | H | H | H | NHMe | H | H | H | H | H |
| XXVII-101 | H | H | H | NH$_2$ | H | H | H | H | H |
| XXVII-102 | H | H | H | NMe$_2$ | H | H | H | H | H |
| XXVII-103 | H | H | H | NHCOMe | H | H | H | H | H |
| XXVII-104 | H | H | H | NHCONH$_2$ | H | H | H | H | H |
| XXVII-105 | H | H | H | NHCONHMe | H | H | H | H | H |
| XXVII-106 | H | H | H | NHCONMe$_2$ | H | H | H | H | H |
| XXVII-107 | H | H | H | phenyl | H | H | H | H | H |
| XXVII-108 | H | H | H | 2-chloro-phenyl | H | H | H | H | H |
| XXVII-109 | H | H | H | 4-nitrophenyl | H | H | H | H | H |
| XXVII-110 | H | H | H | 2-pyridyl | H | H | H | H | H |
| XXVII-111 | H | H | H | 3-pyridyl | H | H | H | H | H |
| XXVII-112 | H | H | H | 4-pyridyl | H | H | H | H | H |
| XXVII-113 | H | H | H | 2-furyl | H | H | H | H | H |
| XXVII-114 | H | H | H | PhO | H | H | H | H | H |
| XXVII-115 | H | H | H | =O | H | H | H | H | H |
| XXVII-116 | H | H | H | =NOH | H | H | H | H | H |
| XXVII-117 | H | H | H | =NOMe | H | H | H | H | H |
| XXVII-118 | H | H | H | =CH$_2$ | H | H | H | H | H |
| XXVII-119 | H | H | H | =CHMe | H | H | H | H | H |
| XXVII-120 | H | Me | H | Me | H | H | H | H | H |
| XXVII-121 | H | Me | F | Me | H | H | H | H | H |
| XXVII-122 | H | Me | F | H | H | H | H | H | H |
| XXVII-123 | H | Me | F | H | H | H | H | H | H |
| XXVII-124 | H | Me | Me | H | H | H | H | H | H |
| XXVII-125 | H | F | H | Me | H | H | H | H | H |
| XXVII-126 | H | F | H | F | H | H | H | H | H |
| XXVII-127 | Me | H | H | H | H | F | H | H | H |
| XXVII-128 | Et | H | H | H | H | F | H | H | H |
| XXVII-129 | vinyl | H | H | H | H | F | H | H | H |
| XXVII-130 | allyl | H | H | H | H | F | H | H | H |
| XXVII-131 | cyclopropyl | H | H | H | H | F | H | H | H |
| XXVII-132 | CN | H | H | H | H | F | H | H | H |
| XXVII-133 | CONH$_2$ | H | H | H | H | F | H | H | H |
| XXVII-134 | CONHMe | H | H | H | H | F | H | H | H |
| XXVII-135 | CONMe$_2$ | H | H | H | H | F | H | H | H |
| XXVII-136 | COMe | H | H | H | H | F | H | H | H |
| XXVII-137 | COOH | H | H | H | H | F | H | H | H |
| XXVII-138 | COOMe | H | H | H | H | F | H | H | H |
| XXVII-139 | CSNHMe | H | H | H | H | F | H | H | H |
| XXVII-140 | H | Me | H | H | H | F | H | H | H |
| XXVII-141 | H | Et | H | H | H | F | H | H | H |
| XXVII-142 | H | vinyl | H | H | H | F | H | H | H |

TABLE 3-continued

| Compound No | R9 | R1 | R2 | R5 | R6 | R4a | R4b | R4c | R4d |
|---|---|---|---|---|---|---|---|---|---|
| XXVII-143 | H | allyl | H | H | H | F | H | H | H |
| XXVII-144 | H | cyclopropyl | H | H | H | F | H | H | H |
| XXVII-145 | H | F | H | H | H | F | H | H | H |
| XXVII-146 | H | Cl | H | H | H | F | H | H | H |
| XXVII-147 | H | NO$_2$ | H | H | H | F | H | H | H |
| XXVII-148 | H | CN | H | H | H | F | H | H | H |
| XXVII-149 | H | CONH$_2$ | H | H | H | F | H | H | H |
| XXVII-150 | H | CONHMe | H | H | H | F | H | H | H |
| XXVII-151 | H | CONMe$_2$ | H | H | H | F | H | H | H |
| XXVII-152 | H | COMe | H | H | H | F | H | H | H |
| XXVII-153 | H | COOH | H | H | H | F | H | H | H |
| XXVII-154 | H | COOMe | H | H | H | F | H | H | H |
| XXVII-155 | H | CSOMe | H | H | H | F | H | H | H |
| XXVII-156 | H | CSNH$_2$ | H | H | H | F | H | H | H |
| XXVII-157 | H | CSNMe$_2$ | H | H | H | F | H | H | H |
| XXVII-158 | H | CSNHMe | H | H | H | F | H | H | H |
| XXVII-159 | H | OMe | H | H | H | F | H | H | H |
| XXVII-160 | H | OEt | H | H | H | F | H | H | H |
| XXVII-161 | H | OCOMe | H | H | H | F | H | H | H |
| XXVII-162 | H | OCOOMe | H | H | H | F | H | H | H |
| XXVII-163 | H | OCONHMe | H | H | H | F | H | H | H |
| XXVII-164 | H | OCONMe$_2$ | H | H | H | F | H | H | H |
| XXVII-165 | H | OCSMe | H | H | H | F | H | H | H |
| XXVII-166 | H | OCSNMe2 | H | H | H | F | H | H | H |
| XXVII-167 | H | SMe | H | H | H | F | H | H | H |
| XXVII-168 | H | SEt | H | H | H | F | H | H | H |
| XXVII-169 | H | SCOMe | H | H | H | F | H | H | H |
| XXVII-170 | H | SCSNMe$_2$ | H | H | H | F | H | H | H |
| XXVII-171 | H | SCSNHMe | H | H | H | F | H | H | H |
| XXVII-172 | H | NHMe | H | H | H | F | H | H | H |
| XXVII-173 | H | NH$_2$ | H | H | H | F | H | H | H |
| XXVII-174 | H | NMe$_2$ | H | H | H | F | H | H | H |
| XXVII-175 | H | NHCOMe | H | H | H | F | H | H | H |
| XXVII-176 | H | NHCONH$_2$ | H | H | H | F | H | H | H |
| XXVII-177 | H | NHCONHMe | H | H | H | F | H | H | H |
| XXVII-178 | H | NHCONMe$_2$ | H | H | H | F | H | H | H |
| XXVII-179 | H | phenyl | H | H | H | F | H | H | H |
| XXVII-180 | H | 2-chloro-phenyl | H | H | H | F | H | H | H |
| XXVII-181 | H | 4-nitrophenyl | H | H | H | F | H | H | H |
| XXVII-182 | H | 2-pyridyl | H | H | H | F | H | H | H |
| XXVII-183 | H | 3-pyridyl | H | H | H | F | H | H | H |
| XXVII-184 | H | 4-pyridyl | H | H | H | F | H | H | H |
| XXVII-185 | H | 2-furyl | H | H | H | F | H | H | H |
| XXVII-186 | H | PhO | H | H | H | F | H | H | H |
| XXVII-187 |  | CH$_2$ | H | H | H | F | H | H | H |
| XXVII-188 | H | H | H | Me | H | F | H | H | H |
| XXVII-189 | H | H | H | Et | H | F | H | H | H |
| XXVII-190 | H | H | H | vinyl | H | F | H | H | H |
| XXVII-191 | H | H | H | allyl | H | F | H | H | H |
| XXVII-192 | H | H | H | cyclopropyl | H | F | H | H | H |
| XXVII-193 | H | H | H | F | H | F | H | H | H |
| XXVII-194 | H | H | H | Cl | H | F | H | H | H |
| XXVII-195 | H | H | H | NO$_2$ | H | F | H | H | H |
| XXVII-196 | H | H | H | CN | H | F | H | H | H |
| XXVII-197 | H | H | H | CONH$_2$ | H | F | H | H | H |
| XXVII-198 | H | H | H | CONHMe | H | F | H | H | H |
| XXVII-199 | H | H | H | CONMe$_2$ | H | F | H | H | H |
| XXVII-200 | H | H | H | COMe | H | F | H | H | H |
| XXVII-201 | H | H | H | COOH | H | F | H | H | H |
| XXVII-202 | H | H | H | COOMe | H | F | H | H | H |
| XXVII-203 | H | H | H | CSOMe | H | F | H | H | H |
| XXVII-204 | H | H | H | CSNH$_2$ | H | F | H | H | H |
| XXVII-205 | H | H | H | CSNMe$_2$ | H | F | H | H | H |
| XXVII-206 | H | H | H | CSNHMe | H | F | H | H | H |
| XXVII-207 | H | H | H | OMe | H | F | H | H | H |
| XXVII-208 | H | H | H | OEt | H | F | H | H | H |
| XXVII-209 | H | H | H | OCOMe | H | F | H | H | H |
| XXVII-210 | H | H | H | OCOOMe | H | F | H | H | H |
| XXVII-211 | H | H | H | OCONHMe | H | F | H | H | H |
| XXVII-212 | H | H | H | OCONMe$_2$ | H | F | H | H | H |
| XXVII-213 | H | H | H | OCSMe | H | F | H | H | H |

TABLE 3-continued

| Compound No | R9 | R1 | R2 | R5 | R6 | R4a | R4b | R4c | R4d |
|---|---|---|---|---|---|---|---|---|---|
| XXVII-214 | H | H | H | OCSNMe2 | H | F | H | H | H |
| XXVII-215 | H | H | H | SMe | H | F | H | H | H |
| XXVII-216 | H | H | H | SEt | H | F | H | H | H |
| XXVII-217 | H | H | H | SCOMe | H | F | H | H | H |
| XXVII-218 | H | H | H | SCSNMe$_2$ | H | F | H | H | H |
| XXVII-219 | H | H | H | SCSNHMe | H | F | H | H | H |
| XXVII-220 | H | H | H | NHMe | H | F | H | H | H |
| XXVII-221 | H | H | H | NH$_2$ | H | F | H | H | H |
| XXVII-222 | H | H | H | NMe$_2$ | H | F | H | H | H |
| XXVII-223 | H | H | H | NHCOMe | H | F | H | H | H |
| XXVII-224 | H | H | H | NHCONH$_2$ | H | F | H | H | H |
| XXVII-225 | H | H | H | NHCONHMe | H | F | H | H | H |
| XXVII-226 | H | H | H | NHCONMe$_2$ | H | F | H | H | H |
| XXVII-227 | H | H | H | phenyl | H | F | H | H | H |
| XXVII-228 | H | H | H | 2-chloro-phenyl | H | F | H | H | H |
| XXVII-229 | H | H | H | 4-nitrophenyl | H | F | H | H | H |
| XXVII-230 | H | H | H | 2-pyridyl | H | F | H | H | H |
| XXVII-231 | H | H | H | 3-pyridyl | H | F | H | H | H |
| XXVII-232 | H | H | H | 4-pyridyl | H | F | H | H | H |
| XXVII-233 | H | H | H | 2-furyl | H | F | H | H | H |
| XXVII-234 | H | H | H | PhO | H | F | H | H | H |
| XXVII-235 | H | Me | H | Me | H | F | H | H | H |
| XXVII-236 | H | Me | F | Me | H | F | H | H | H |
| XXVII-237 | H | Me | H | F | H | F | H | H | H |
| XXVII-238 | H | Me | F | H | H | F | H | H | H |
| XXVII-239 | H | Me | Me | H | H | F | H | H | H |
| XXVII-240 | H | F | H | Me | H | F | H | H | H |
| XXVII-241 | H | F | H | F | H | F | H | H | H |
| XXVII-242 | Me | H | H | H | H | Me | H | H | H |
| XXVII-243 | Et | H | H | H | H | Me | H | H | H |
| XXVII-244 | vinyl | H | H | H | H | Me | H | H | H |
| XXVII-245 | allyl | H | H | H | H | Me | H | H | H |
| XXVII-246 | cyclopropyl | H | H | H | H | Me | H | H | H |
| XXVII-247 | CN | H | H | H | H | Me | H | H | H |
| XXVII-248 | CONH$_2$ | H | H | H | H | Me | H | H | H |
| XXVII-249 | CONHMe | H | H | H | H | Me | H | H | H |
| XXVII-250 | CONMe$_2$ | H | H | H | H | Me | H | H | H |
| XXVII-251 | COMe | H | H | H | H | Me | H | H | H |
| XXVII-252 | COOH | H | H | H | H | Me | H | H | H |
| XXVII-253 | COOMe | H | H | H | H | Me | H | H | H |
| XXVII-254 | CSNHMe | H | H | H | H | Me | H | H | H |
| XXVII-255 | H | Me | H | H | H | Me | H | H | H |
| XXVII-256 | H | Et | H | H | H | Me | H | H | H |
| XXVII-257 | H | vinyl | H | H | H | Me | H | H | H |
| XXVII-258 | H | allyl | H | H | H | Me | H | H | H |
| XXVII-259 | H | cyclopropyl | H | H | H | Me | H | H | H |
| XXVII-260 | H | F | H | H | H | Me | H | H | H |
| XXVII-261 | H | Cl | H | H | H | Me | H | H | H |
| XXVII-262 | H | NO$_2$ | H | H | H | Me | H | H | H |
| XXVII-263 | H | CN | H | H | H | Me | H | H | H |
| XXVII-264 | H | CONH$_2$ | H | H | H | Me | H | H | H |
| XXVII-265 | H | CONHMe | H | H | H | Me | H | H | H |
| XXVII-266 | H | CONMe$_2$ | H | H | H | Me | H | H | H |
| XXVII-267 | H | COMe | H | H | H | Me | H | H | H |
| XXVII-268 | H | COOH | H | H | H | Me | H | H | H |
| XXVII-269 | H | COOMe | H | H | H | Me | H | H | H |
| XXVII-270 | H | CSOMe | H | H | H | Me | H | H | H |
| XXVII-271 | H | CSNH$_2$ | H | H | H | Me | H | H | H |
| XXVII-272 | H | CSNMe$_2$ | H | H | H | Me | H | H | H |
| XXVII-273 | H | CSNHMe | H | H | H | Me | H | H | H |
| XXVII-274 | H | OMe | H | H | H | Me | H | H | H |
| XXVII-275 | H | OEt | H | H | H | Me | H | H | H |
| XXVII-276 | H | OCOMe | H | H | H | Me | H | H | H |
| XXVII-277 | H | OCOOMe | H | H | H | Me | H | H | H |
| XXVII-278 | H | OCONHMe | H | H | H | Me | H | H | H |
| XXVII-279 | H | OCONMe$_2$ | H | H | H | Me | H | H | H |
| XXVII-280 | H | OCSMe | H | H | H | Me | H | H | H |
| XXVII-281 | H | OCSNMe$_2$ | H | H | H | Me | H | H | H |
| XXVII-282 | H | SMe | H | H | H | Me | H | H | H |
| XXVII-283 | H | SEt | H | H | H | Me | H | H | H |
| XXVII-284 | H | SCOMe | H | H | H | Me | H | H | H |

TABLE 3-continued

| Compound No | R9 | R1 | R2 | R5 | R6 | R4a | R4b | R4c | R4d |
|---|---|---|---|---|---|---|---|---|---|
| XXVII-285 | H | SCSNMe$_2$ | H | H | H | Me | H | H | H |
| XXVII-286 | H | SCSNHMe | H | H | H | Me | H | H | H |
| XXVII-287 | H | NHMe | H | H | H | Me | H | H | H |
| XXVII-288 | H | NH$_2$ | H | H | H | Me | H | H | H |
| XXVII-289 | H | NMe$_2$ | H | H | H | Me | H | H | H |
| XXVII-290 | H | NHCOMe | H | H | H | Me | H | H | H |
| XXVII-291 | H | NHCONH$_2$ | H | H | H | Me | H | H | H |
| XXVII-292 | H | NHCONHMe | H | H | H | Me | H | H | H |
| XXVII-293 | H | NHCONMe$_2$ | H | H | H | Me | H | H | H |
| XXVII-294 | H | phenyl | H | H | H | Me | H | H | H |
| XXVII-295 | H | 2-chlorophenyl | H | H | H | Me | H | H | H |
| XXVII-296 | H | 4-nitrophenyl | H | H | H | Me | H | H | H |
| XXVII-297 | H | 2-pyridyl | H | H | H | Me | H | H | H |
| XXVII-298 | H | 3-pyridyl | H | H | H | Me | H | H | H |
| XXVII-299 | H | 4-pyridyl | H | H | H | Me | H | H | H |
| XXVII-300 | H | 2-furyl | H | H | H | Me | H | H | H |
| XXVII-301 | H | PhO | H | H | H | Me | H | H | H |
| XXVII-302 | | CH$_2$ | H | H | H | Me | H | H | H |
| XXVII-303 | H | H | H | Me | H | Me | H | H | H |
| XXVII-304 | H | H | H | Et | H | Me | H | H | H |
| XXVII-305 | H | H | H | vinyl | H | Me | H | H | H |
| XXVII-306 | H | H | H | allyl | H | Me | H | H | H |
| XXVII-307 | H | H | H | cyclopropyl | H | Me | H | H | H |
| XXVII-308 | H | H | H | F | H | Me | H | H | H |
| XXVII-309 | H | H | H | Cl | H | Me | H | H | H |
| XXVII-310 | H | H | H | NO$_2$ | H | Me | H | H | H |
| XXVII-311 | H | H | H | CN | H | Me | H | H | H |
| XXVII-312 | H | H | H | CONH$_2$ | H | Me | H | H | H |
| XXVII-313 | H | H | H | CONHMe | H | Me | H | H | H |
| XXVII-314 | H | H | H | CONMe$_2$ | H | Me | H | H | H |
| XXVII-315 | H | H | H | COMe | H | Me | H | H | H |
| XXVII-316 | H | H | H | COOH | H | Me | H | H | H |
| XXVII-317 | H | H | H | COOMe | H | Me | H | H | H |
| XXVII-318 | H | H | H | CSOMe | H | Me | H | H | H |
| XXVII-319 | H | H | H | CSNH$_2$ | H | Me | H | H | H |
| XXVII-320 | H | H | H | CSNMe$_2$ | H | Me | H | H | H |
| XXVII-321 | H | H | H | CSNHMe | H | Me | H | H | H |
| XXVII-322 | H | H | H | OMe | H | Me | H | H | H |
| XXVII-323 | H | H | H | OEt | H | Me | H | H | H |
| XXVII-324 | H | H | H | OCOMe | H | Me | H | H | H |
| XXVII-325 | H | H | H | OCOOMe | H | Me | H | H | H |
| XXVII-326 | H | H | H | OCONHMe | H | Me | H | H | H |
| XXVII-327 | H | H | H | OCONMe$_2$ | H | Me | H | H | H |
| XXVII-328 | H | H | H | OCSMe | H | Me | H | H | H |
| XXVII-329 | H | H | H | OCSNMe$_2$ | H | Me | H | H | H |
| XXVII-330 | H | H | H | SMe | H | Me | H | H | H |
| XXVII-331 | H | H | H | SEt | H | Me | H | H | H |
| XXVII-332 | H | H | H | SCOMe | H | Me | H | H | H |
| XXVII-333 | H | H | H | SCSNMe$_2$ | H | Me | H | H | H |
| XXVII-334 | H | H | H | SCSNHMe | H | Me | H | H | H |
| XXVII-335 | H | H | H | NHMe | H | Me | H | H | H |
| XXVII-336 | H | H | H | NH$_2$ | H | Me | H | H | H |
| XXVII-337 | H | H | H | NMe$_2$ | H | Me | H | H | H |
| XXVII-338 | H | H | H | NHCOMe | H | Me | H | H | H |
| XXVII-339 | H | H | H | NHCONH$_2$ | H | Me | H | H | H |
| XXVII-340 | H | H | H | NHCONHMe | H | Me | H | H | H |
| XXVII-341 | H | H | H | NHCONMe$_2$ | H | Me | H | H | H |
| XXVII-342 | H | H | H | phenyl | H | Me | H | H | H |
| XXVII-343 | H | H | H | 2-chlorophenyl | H | Me | H | H | H |
| XXVII-344 | H | H | H | 4-nitrophenyl | H | Me | H | H | H |
| XXVII-345 | H | H | H | 2-pyridyl | H | Me | H | H | H |
| XXVII-346 | H | H | H | 3-pyridyl | H | Me | H | H | H |
| XXVII-347 | H | H | H | 4-pyridyl | H | Me | H | H | H |
| XXVII-348 | H | H | H | 2-furyl | H | Me | H | H | H |
| XXVII-349 | H | H | H | PhO | H | Me | H | H | H |

TABLE 3-continued

| Compound No | R9 | R1 | R2 | R5 | R6 | R4a | R4b | R4c | R4d |
|---|---|---|---|---|---|---|---|---|---|
| XXVII-350 | H | Me | H | Me | H | Me | H | H | H |
| XXVII-351 | H | Me | F | Me | H | Me | H | H | H |
| XXVII-352 | H | Me | H | F | H | Me | H | H | H |
| XXVII-353 | H | Me | F | H | H | Me | H | H | H |
| XXVII-354 | H | Me | Me | H | H | Me | H | H | H |
| XXVII-355 | H | F | H | Me | H | Me | H | H | H |
| XXVII-356 | H | F | H | F | H | Me | H | H | H |
| XXVII-357 | Me | H | H | H | H | F | H | F | H |
| XXVII-358 | Et | H | H | H | H | F | H | F | H |
| XXVII-359 | vinyl | H | H | H | H | F | H | F | H |
| XXVII-360 | allyl | H | H | H | H | F | H | F | H |
| XXVII-361 | cyclopropyl | H | H | H | H | F | H | F | H |
| XXVII-362 | CN | H | H | H | H | F | H | F | H |
| XXVII-363 | CONH$_2$ | H | H | H | H | F | H | F | H |
| XXVII-364 | CONHMe | H | H | H | H | F | H | F | H |
| XXVII-365 | CONMe$_2$ | H | H | H | H | F | H | F | H |
| XXVII-366 | COMe | H | H | H | H | F | H | F | H |
| XXVII-367 | COOH | H | H | H | H | F | H | F | H |
| XXVII-368 | COOMe | H | H | H | H | F | H | F | H |
| XXVII-369 | CSNHMe | H | H | H | H | F | H | F | H |
| XXVII-370 | H | Me | H | H | H | F | H | F | H |
| XXVII-371 | H | Et | H | H | H | F | H | F | H |
| XXVII-372 | H | vinyl | H | H | H | F | H | F | H |
| XXVII-373 | H | allyl | H | H | H | F | H | F | H |
| XXVII-374 | H | cyclopropyl | H | H | H | F | H | F | H |
| XXVII-375 | H | F | H | H | H | F | H | F | H |
| XXVII-376 | H | Cl | H | H | H | F | H | F | H |
| XXVII-377 | H | NO$_2$ | H | H | H | F | H | F | H |
| XXVII-378 | H | CN | H | H | H | F | H | F | H |
| XXVII-379 | H | CONH$_2$ | H | H | H | F | H | F | H |
| XXVII-380 | H | CONHMe | H | H | H | F | H | F | H |
| XXVII-381 | H | CONMe$_2$ | H | H | H | F | H | F | H |
| XXVII-382 | H | COMe | H | H | H | F | H | F | H |
| XXVII-383 | H | COOH | H | H | H | F | H | F | H |
| XXVII-384 | H | COOMe | H | H | H | F | H | F | H |
| XXVII-385 | H | CSOMe | H | H | H | F | H | F | H |
| XXVII-386 | H | CSNH$_2$ | H | H | H | F | H | F | H |
| XXVII-387 | H | CSNMe$_2$ | H | H | H | F | H | F | H |
| XXVII-388 | H | CSNHMe | H | H | H | F | H | F | H |
| XXVII-389 | H | OMe | H | H | H | F | H | F | H |
| XXVII-390 | H | OEt | H | H | H | F | H | F | H |
| XXVII-391 | H | OCOMe | H | H | H | F | H | F | H |
| XXVII-392 | H | OCOOMe | H | H | H | F | H | F | H |
| XXVII-393 | H | OCONHMe | H | H | H | F | H | F | H |
| XXVII-394 | H | OCONMe$_2$ | H | H | H | F | H | F | H |
| XXVII-395 | H | OCSMe | H | H | H | F | H | F | H |
| XXVII-396 | H | OCSNMe$_2$ | H | H | H | F | H | F | H |
| XXVII-397 | H | SMe | H | H | H | F | H | F | H |
| XXVII-398 | H | SEt | H | H | H | F | H | F | H |
| XXVII-399 | H | SCOMe | H | H | H | F | H | F | H |
| XXVII-400 | H | SCSNMe$_2$ | H | H | H | F | H | F | H |
| XXVII-401 | H | SCSNHMe | H | H | H | F | H | F | H |
| XXVII-402 | H | NHMe | H | H | H | F | H | F | H |
| XXVII-403 | H | NH$_2$ | H | H | H | F | H | F | H |
| XXVII-404 | H | NMe$_2$ | H | H | H | F | H | F | H |
| XXVII-405 | H | NHCOMe | H | H | H | F | H | F | H |
| XXVII-406 | H | NHCONH$_2$ | H | H | H | F | H | F | H |
| XXVII-407 | H | NHCONHMe | H | H | H | F | H | F | H |
| XXVII-408 | H | NHCONMe$_2$ | H | H | H | F | H | F | H |
| XXVII-409 | H | phenyl | H | H | H | F | H | F | H |
| XXVII-410 | H | 2-chloro-phenyl | H | H | H | F | H | F | H |
| XXVII-411 | H | 4-nitrophenyl | H | H | H | F | H | F | H |
| XXVII-412 | H | 2-pyridyl | H | H | H | F | H | F | H |
| XXVII-413 | H | 3-pyridyl | H | H | H | F | H | F | H |
| XXVII-414 | H | 4-pyridyl | H | H | H | F | H | F | H |
| XXVII-415 | H | 2-furyl | H | H | H | F | H | F | H |
| XXVII-416 | H | PhO | H | H | H | F | H | F | H |
| XXVII-417 | | CH$_2$ | H | H | H | F | H | F | H |
| XXVII-418 | H | H | H | Me | H | F | H | F | H |
| XXVII-419 | H | H | H | Et | H | F | H | F | H |
| XXVII-420 | H | H | H | vinyl | H | F | H | F | H |

TABLE 3-continued

| Compound No | R9 | R1 | R2 | R5 | R6 | R4a | R4b | R4c | R4d |
|---|---|---|---|---|---|---|---|---|---|
| XXVII-421 | H | H | H | allyl | H | F | H | F | H |
| XXVII-422 | H | H | H | cyclopropyl | H | F | H | F | H |
| XXVII-423 | H | H | H | F | H | F | H | F | H |
| XXVII-424 | H | H | H | Cl | H | F | H | F | H |
| XXVII-425 | H | H | H | NO$_2$ | H | F | H | F | H |
| XXVII-426 | H | H | H | CN | H | F | H | F | H |
| XXVII-427 | H | H | H | CONH$_2$ | H | F | H | F | H |
| XXVII-428 | H | H | H | CONHMe | H | F | H | F | H |
| XXVII-429 | H | H | H | CONMe$_2$ | H | F | H | F | H |
| XXVII-430 | H | H | H | COMe | H | F | H | F | H |
| XXVII-431 | H | H | H | COOH | H | F | H | F | H |
| XXVII-432 | H | H | H | COOMe | H | F | H | F | H |
| XXVII-433 | H | H | H | CSOMe | H | F | H | F | H |
| XXVII-434 | H | H | H | CSNH$_2$ | H | F | H | F | H |
| XXVII-435 | H | H | H | CSNMe$_2$ | H | F | H | F | H |
| XXVII-436 | H | H | H | CSNHMe | H | F | H | F | H |
| XXVII-437 | H | H | H | OMe | H | F | H | F | H |
| XXVII-438 | H | H | H | OEt | H | F | H | F | H |
| XXVII-439 | H | H | H | OCOMe | H | F | H | F | H |
| XXVII-440 | H | H | H | OCOOMe | H | F | H | F | H |
| XXVII-441 | H | H | H | OCONHMe | H | F | H | F | H |
| XXVII-442 | H | H | H | OCONMe$_2$ | H | F | H | F | H |
| XXVII-443 | H | H | H | OCSMe | H | F | H | F | H |
| XXVII-444 | H | H | H | OCSNMe2 | H | F | H | F | H |
| XXVII-445 | H | H | H | SMe | H | F | H | F | H |
| XXVII-446 | H | H | H | SEt | H | F | H | F | H |
| XXVII-447 | H | H | H | SCOMe | H | F | H | F | H |
| XXVII-448 | H | H | H | SCSNMe$_2$ | H | F | H | F | H |
| XXVII-449 | H | H | H | SCSNHMe | H | F | H | F | H |
| XXVII-450 | H | H | H | NHMe | H | F | H | F | H |
| XXVII-451 | H | H | H | NH$_2$ | H | F | H | F | H |
| XXVII-452 | H | H | H | NMe$_2$ | H | F | H | F | H |
| XXVII-453 | H | H | H | NHCOMe | H | F | H | F | H |
| XXVII-454 | H | H | H | NHCONH$_2$ | H | F | H | F | H |
| XXVII-455 | H | H | H | NHCONHMe | H | F | H | F | H |
| XXVII-456 | H | H | H | NHCONMe$_2$ | H | F | H | F | H |
| XXVII-457 | H | H | H | phenyl | H | F | H | F | H |
| XXVII-458 | H | H | H | 2-chloro-phenyl | H | F | H | F | H |
| XXVII-459 | H | H | H | 4-nitrophenyl | H | F | H | F | H |
| XXVII-460 | H | H | H | 2-pyridyl | H | F | H | F | H |
| XXVII-461 | H | H | H | 3-pyridyl | H | F | H | F | H |
| XXVII-462 | H | H | H | 4-pyridyl | H | F | H | F | H |
| XXVII-463 | H | H | H | 2-furyl | H | F | H | F | H |
| XXVII-464 | H | H | H | PhO | H | F | H | F | H |
| XXVII-465 | H | Me | H | Me | H | F | H | F | H |
| XXVII-466 | H | Me | F | Me | H | F | H | F | H |
| XXVII-467 | H | Me | F | F | H | F | H | F | H |
| XXVII-468 | H | Me | F | H | H | F | H | F | H |
| XXVII-469 | H | Me | Me | H | H | F | H | F | H |
| XXVII-470 | H | F | H | Me | H | F | H | F | H |
| XXVII-471 | H | F | H | F | H | F | H | F | H |
| XXVII-472 | H | H | H | H | H | Me | H | H | H |
| XXVII-473 | H | H | H | H | H | Et | H | H | H |
| XXVII-474 | H | H | H | H | H | vinyl | H | H | H |
| XXVII-475 | H | H | H | H | H | allyl | H | H | H |
| XXVII-476 | H | H | H | H | H | cyclopropyl | H | H | H |
| XXVII-477 | H | H | H | H | H | F | H | H | H |
| XXVII-478 | H | H | H | H | H | Cl | H | H | H |
| XXVII-479 | H | H | H | H | H | NO$_2$ | H | H | H |
| XXVII-480 | H | H | H | H | H | CN | H | H | H |
| XXVII-481 | H | H | H | H | H | CONH$_2$ | H | H | H |
| XXVII-482 | H | H | H | H | H | CONHMe | H | H | H |
| XXVII-483 | H | H | H | H | H | CONMe$_2$ | H | H | H |
| XXVII-484 | H | H | H | H | H | COMe | H | H | H |
| XXVII-485 | H | H | H | H | H | COOH | H | H | H |
| XXVII-486 | H | H | H | H | H | COOMe | H | H | H |
| XXVII-487 | H | H | H | H | H | CSOMe | H | H | H |
| XXVII-488 | H | H | H | H | H | CSNH$_2$ | H | H | H |
| XXVII-489 | H | H | H | H | H | CSNMe$_2$ | H | H | H |
| XXVII-490 | H | H | H | H | H | CSNHMe | H | H | H |
| XXVII-491 | H | H | H | H | H | OMe | H | H | H |

TABLE 3-continued

| Compound No | R9 | R1 | R2 | R5 | R6 | R4a | R4b | R4c | R4d |
|---|---|---|---|---|---|---|---|---|---|
| XXVII-492 | H | H | H | H | H | OEt | H | H | H |
| XXVII-493 | H | H | H | H | H | OCOMe | H | H | H |
| XXVII-494 | H | H | H | H | H | OCOOMe | H | H | H |
| XXVII-495 | H | H | H | H | H | OCONHMe | H | H | H |
| XXVII-496 | H | H | H | H | H | OCONMe$_2$ | H | H | H |
| XXVII-497 | H | H | H | H | H | OCSMe | H | H | H |
| XXVII-498 | H | H | H | H | H | OCSNMe2 | H | H | H |
| XXVII-499 | H | H | H | H | H | SMe | H | H | H |
| XXVII-500 | H | H | H | H | H | SEt | H | H | H |
| XXVII-501 | H | H | H | H | H | SCOMe | H | H | H |
| XXVII-502 | H | H | H | H | H | SCSNMe$_2$ | H | H | H |
| XXVII-503 | H | H | H | H | H | SCSNHMe | H | H | H |
| XXVII-504 | H | H | H | H | H | NHMe | H | H | H |
| XXVII-505 | H | H | H | H | H | NH$_2$ | H | H | H |
| XXVII-506 | H | H | H | H | H | NMe$_2$ | H | H | H |
| XXVII-507 | H | H | H | H | H | NHCOMe | H | H | H |
| XXVII-508 | H | H | H | H | H | NHCONH$_2$ | H | H | H |
| XXVII-509 | H | H | H | H | H | NHCONHMe | H | H | H |
| XXVII-510 | H | H | H | H | H | NHCONMe$_2$ | H | H | H |
| XXVII-511 | H | H | H | H | H | phenyl | H | H | H |
| XXVII-512 | H | H | H | H | H | 2-chloro-phenyl | H | H | H |
| XXVII-513 | H | H | H | H | H | 4-nitrophenyl | H | H | H |
| XXVII-514 | H | H | H | H | H | 2-pyridyl | H | H | H |
| XXVII-515 | H | H | H | H | H | 3-pyridyl | H | H | H |
| XXVII-516 | H | H | H | H | H | 4-pyridyl | H | H | H |
| XXVII-517 | H | H | H | H | H | 2-furyl | H | H | H |
| XXVII-518 | H | H | H | H | H | PhO | H | H | H |
| XXVII-519 | H | H | H | H | H | H | H | Me | H |
| XXVII-520 | H | H | H | H | H | H | H | Et | H |
| XXVII-521 | H | H | H | H | H | H | H | vinyl | H |
| XXVII-522 | H | H | H | H | H | H | H | allyl | H |
| XXVII-523 | H | H | H | H | H | H | H | cyclopropyl | H |
| XXVII-524 | H | H | H | H | H | H | H | F | H |
| XXVII-525 | H | H | H | H | H | H | H | Cl | H |
| XXVII-526 | H | H | H | H | H | H | H | NO$_2$ | H |
| XXVII-527 | H | H | H | H | H | H | H | CN | H |
| XXVII-528 | H | H | H | H | H | H | H | CONH$_2$ | H |
| XXVII-529 | H | H | H | H | H | H | H | CONHMe | H |
| XXVII-530 | H | H | H | H | H | H | H | CONMe$_2$ | H |
| XXVII-531 | H | H | H | H | H | H | H | COMe | H |
| XXVII-532 | H | H | H | H | H | H | H | COOH | H |
| XXVII-533 | H | H | H | H | H | H | H | COOMe | H |
| XXVII-534 | H | H | H | H | H | H | H | CSOMe | H |
| XXVII-535 | H | H | H | H | H | H | H | CSNH$_2$ | H |
| XXVII-536 | H | H | H | H | H | H | H | CSNMe$_2$ | H |
| XXVII-537 | H | H | H | H | H | H | H | CSNHMe | H |
| XXVII-538 | H | H | H | H | H | H | H | OMe | H |
| XXVII-539 | H | H | H | H | H | H | H | OEt | H |
| XXVII-540 | H | H | H | H | H | H | H | OCOMe | H |
| XXVII-541 | H | H | H | H | H | H | H | OCOOMe | H |
| XXVII-542 | H | H | H | H | H | H | H | OCONHMe | H |
| XXVII-543 | H | H | H | H | H | H | H | OCONMe$_2$ | H |
| XXVII-544 | H | H | H | H | H | H | H | OCSMe | H |
| XXVII-545 | H | H | H | H | H | H | H | OCSNMe2 | H |
| XXVII-546 | H | H | H | H | H | H | H | SMe | H |
| XXVII-547 | H | H | H | H | H | H | H | SEt | H |
| XXVII-548 | H | H | H | H | H | H | H | SCOMe | H |
| XXVII-549 | H | H | H | H | H | H | H | SCSNMe$_2$ | H |
| XXVII-550 | H | H | H | H | H | H | H | SCSNHMe | H |
| XXVII-551 | H | H | H | H | H | H | H | NHMe | H |
| XXVII-552 | H | H | H | H | H | H | H | NH$_2$ | H |
| XXVII-553 | H | H | H | H | H | H | H | NMe$_2$ | H |
| XXVII-554 | H | H | H | H | H | H | H | NHCOMe | H |
| XXVII-555 | H | H | H | H | H | H | H | NHCONH$_2$ | H |
| XXVII-556 | H | H | H | H | H | H | H | NHCONHMe | H |
| XXVII-557 | H | H | H | H | H | H | H | NHCONMe$_2$ | H |
| XXVII-558 | H | H | H | H | H | H | H | phenyl | H |
| XXVII-559 | H | H | H | H | H | H | H | 2-chloro-phenyl | H |
| XXVII-560 | H | H | H | H | H | H | H | 4-nitrophenyl | H |
| XXVII-561 | H | H | H | H | H | H | H | 2-pyridyl | H |
| XXVII-562 | H | H | H | H | H | H | H | 3-pyridyl | H |

TABLE 3-continued

| Compound No | R9 | R1 | R2 | R5 | R6 | R4a | R4b | R4c | R4d |
|---|---|---|---|---|---|---|---|---|---|
| XXVII-563 | H | H | H | H | H | H | H | 4-pyridyl | H |
| XXVII-564 | H | H | H | H | H | H | H | 2-furyl | H |
| XXVII-565 | H | H | H | H | H | H | H | PhO | H |
| XXVII-566 | H | H | H | H | H | H | H | H | Me |
| XXVII-567 | H | H | H | H | H | H | H | H | Et |
| XXVII-568 | H | H | H | H | H | H | H | H | vinyl |
| XXVII-569 | H | H | H | H | H | H | H | H | allyl |
| XXVII-570 | H | H | H | H | H | H | H | H | cyclopropyl |
| XXVII-571 | H | H | H | H | H | H | H | H | F |
| XXVII-572 | H | H | H | H | H | H | H | H | Cl |
| XXVII-573 | H | H | H | H | H | H | H | H | $NO_2$ |
| XXVII-574 | H | H | H | H | H | H | H | H | CN |
| XXVII-575 | H | H | H | H | H | H | H | H | $CONH_2$ |
| XXVII-576 | H | H | H | H | H | H | H | H | CONHMe |
| XXVII-577 | H | H | H | H | H | H | H | H | $CONMe_2$ |
| XXVII-578 | H | H | H | H | H | H | H | H | COMe |
| XXVII-579 | H | H | H | H | H | H | H | H | COOH |
| XXVII-580 | H | H | H | H | H | H | H | H | COOMe |
| XXVII-581 | H | H | H | H | H | H | H | H | CSOMe |
| XXVII-582 | H | H | H | H | H | H | H | H | $CSNH_2$ |
| XXVII-583 | H | H | H | H | H | H | H | H | $CSNMe_2$ |
| XXVII-584 | H | H | H | H | H | H | H | H | CSNHMe |
| XXVII-585 | H | H | H | H | H | H | H | H | OMe |
| XXVII-586 | H | H | H | H | H | H | H | H | OEt |
| XXVII-587 | H | H | H | H | H | H | H | H | OCOMe |
| XXVII-588 | H | H | H | H | H | H | H | H | OCOOMe |
| XXVII-589 | H | H | H | H | H | H | H | H | OCONHMe |
| XXVII-590 | H | H | H | H | H | H | H | H | $OCONMe_2$ |
| XXVII-591 | H | H | H | H | H | H | H | H | OCSMe |
| XXVII-592 | H | H | H | H | H | H | H | H | $OCSNMe_2$ |
| XXVII-593 | H | H | H | H | H | H | H | H | SMe |
| XXVII-594 | H | H | H | H | H | H | H | H | SEt |
| XXVII-595 | H | H | H | H | H | H | H | H | SCOMe |
| XXVII-596 | H | H | H | H | H | H | H | H | $SCSNMe_2$ |
| XXVII-597 | H | H | H | H | H | H | H | H | SCSNHMe |
| XXVII-598 | H | H | H | H | H | H | H | H | NHMe |
| XXVII-599 | H | H | H | H | H | H | H | H | $NH_2$ |
| XXVII-600 | H | H | H | H | H | H | H | H | $NMe_2$ |
| XXVII-601 | H | H | H | H | H | H | H | H | NHCOMe |
| XXVII-602 | H | H | H | H | H | H | H | H | $NHCONH_2$ |
| XXVII-603 | H | H | H | H | H | H | H | H | NHCONHMe |
| XXVII-604 | H | H | H | H | H | H | H | H | $NHCONMe_2$ |
| XXVII-605 | H | H | H | H | H | H | H | H | phenyl |
| XXVII-606 | H | H | H | H | H | H | H | H | 2-chloro-phenyl |
| XXVII-607 | H | H | H | H | H | H | H | H | 4-nitrophenyl |
| XXVII-608 | H | H | H | H | H | H | H | H | 2-pyridyl |
| XXVII-609 | H | H | H | H | H | H | H | H | 3-pyridyl |
| XXVII-610 | H | H | H | H | H | H | H | H | 4-pyridyl |
| XXVII-611 | H | H | H | H | H | H | H | H | 2-furyl |
| XXVII-612 | H | H | H | H | H | H | H | H | PhO |

Table XXVIII provides 422 compounds of formula Iab

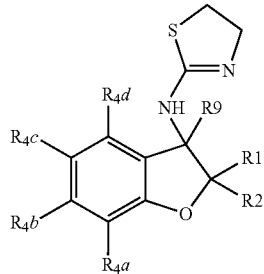

(Iab)

wherein the values of $R^1$, $R^2$, $R^{4a}$, $R^{4b}$, $R^{4c}$, $R^{4d}$ and $R^9$ are given in Table 4

TABLE 4

| Compound No | R9 | R1 | R2 | R4a | R4b | R4c | R4d |
|---|---|---|---|---|---|---|---|
| XXVIII-1 | Me | H | H | H | H | H | H |
| XXVIII-2 | Et | H | H | H | H | H | H |
| XXVIII-3 | vinyl | H | H | H | H | H | H |
| XXVIII-4 | allyl | H | H | H | H | H | H |
| XXVIII-5 | cyclopropyl | H | H | H | H | H | H |
| XXVIII-6 | CN | H | H | H | H | H | H |
| XXVIII-7 | CONH$_2$ | H | H | H | H | H | H |
| XXVIII-8 | CONHMe | H | H | H | H | H | H |
| XXVIII-9 | CONMe$_2$ | H | H | H | H | H | H |
| XXVIII-10 | COMe | H | H | H | H | H | H |
| XXVIII-11 | COOH | H | H | H | H | H | H |
| XXVIII-12 | COOMe | H | H | H | H | H | H |
| XXVIII-13 | CSNHMe | H | H | H | H | H | H |
| XXVIII-14 | H | Me | H | H | H | H | H |
| XXVIII-15 | H | Et | H | H | H | H | H |
| XXVIII-16 | H | Vinyl | H | H | H | H | H |
| XXVIII-17 | H | Allyl | H | H | H | H | H |
| XXVIII-18 | H | Cyclopropyl | H | H | H | H | H |
| XXVIII-19 | H | F | H | H | H | H | H |
| XXVIII-20 | H | Cl | H | H | H | H | H |
| XXVIII-21 | H | NO$_2$ | H | H | H | H | H |
| XXVIII-22 | H | CN | H | H | H | H | H |
| XXVIII-23 | H | CONH$_2$ | H | H | H | H | H |
| XXVIII-24 | H | CONHMe | H | H | H | H | H |
| XXVIII-25 | H | CONMe$_2$ | H | H | H | H | H |
| XXVIII-26 | H | COMe | H | H | H | H | H |
| XXVIII-27 | H | COOH | H | H | H | H | H |
| XXVIII-28 | H | COOMe | H | H | H | H | H |
| XXVIII-29 | H | CSOMe | H | H | H | H | H |
| XXVIII-30 | H | CSNH$_2$ | H | H | H | H | H |
| XXVIII-31 | H | CSNMe$_2$ | H | H | H | H | H |
| XXVIII-32 | H | CSNHMe | H | H | H | H | H |
| XXVIII-33 | H | OMe | H | H | H | H | H |
| XXVIII-34 | H | OEt | H | H | H | H | H |
| XXVIII-35 | H | OCOMe | H | H | H | H | H |
| XXVIII-36 | H | OCOOMe | H | H | H | H | H |
| XXVIII-37 | H | OCONHMe | H | H | H | H | H |
| XXVIII-38 | H | OCONMe$_2$ | H | H | H | H | H |
| XXVIII-39 | H | OCSMe | H | H | H | H | H |
| XXVIII-40 | H | OCSNMe$_2$ | H | H | H | H | H |
| XXVIII-41 | H | SMe | H | H | H | H | H |
| XXVIII-42 | H | SEt | H | H | H | H | H |
| XXVIII-43 | H | SCOMe | H | H | H | H | H |
| XXVIII-44 | H | SCSNMe$_2$ | H | H | H | H | H |
| XXVIII-45 | H | SCSNHMe | H | H | H | H | H |
| XXVIII-46 | H | NHMe | H | H | H | H | H |
| XXVIII-47 | H | NH$_2$ | H | H | H | H | H |
| XXVIII-48 | H | NMe$_2$ | H | H | H | H | H |
| XXVIII-49 | H | NHCOMe | H | H | H | H | H |
| XXVIII-50 | H | NHCONH$_2$ | H | H | H | H | H |
| XXVIII-51 | H | NHCONHMe | H | H | H | H | H |
| XXVIII-52 | H | NHCONMe$_2$ | H | H | H | H | H |
| XXVIII-53 | H | Phenyl | H | H | H | H | H |
| XXVIII-54 | H | 2-chloro-phenyl | H | H | H | H | H |
| XXVIII-55 | H | 4-nitrophenyl | H | H | H | H | H |
| XXVIII-56 | H | 2-pyridyl | H | H | H | H | H |
| XXVIII-57 | H | 3-pyridyl | H | H | H | H | H |
| XXVIII-58 | H | 4-pyridyl | H | H | H | H | H |
| XXVIII-59 | H | 2-furyl | H | H | H | H | H |
| XXVIII-60 | H | PhO | H | H | H | H | H |
| XXVIII-61 | | CH$_2$ | H | H | H | H | H |
| XXVIII-62 | H | =O | | H | H | H | H |
| XXVIII-63 | H | =NOH | | H | H | H | H |
| XXVIII-64 | H | =NOMe | | H | H | H | H |
| XXVIII-65 | H | =CH$_2$ | | H | H | H | H |
| XXVIII-66 | H | =CHMe | | H | H | H | H |
| XXVIII-67 | H | H | H | H | H | H | H |
| XXVIII-68 | H | Me | H | H | H | H | H |
| XXVIII-69 | H | Me | F | H | H | H | H |
| XXVIII-70 | H | Et | H | H | H | H | H |
| XXVIII-71 | H | Me | Me | H | H | H | H |
| XXVIII-72 | Me | H | Me | H | H | H | H |
| XXVIII-73 | H | F | H | H | H | H | H |
| XXVIII-74 | Me | F | H | H | H | H | H |
| XXVIII-75 | Me | H | H | F | H | H | H |
| XXVIII-76 | Et | H | H | F | H | H | H |

TABLE 4-continued

| Compound No | R9 | R1 | R2 | R4a | R4b | R4c | R4d |
|---|---|---|---|---|---|---|---|
| XXVIII-77 | vinyl | H | H | F | H | H | H |
| XXVIII-78 | allyl | H | H | F | H | H | H |
| XXVIII-79 | cyclopropyl | H | H | F | H | H | H |
| XXVIII-80 | CN | H | H | F | H | H | H |
| XXVIII-81 | $CONH_2$ | H | H | F | H | H | H |
| XXVIII-82 | CONHMe | H | H | F | H | H | H |
| XXVIII-83 | $CONMe_2$ | H | H | F | H | H | H |
| XXVIII-84 | COMe | H | H | F | H | H | H |
| XXVIII-85 | COOH | H | H | F | H | H | H |
| XXVIII-86 | COOMe | H | H | F | H | H | H |
| XXVIII-87 | CSNHMe | H | H | F | H | H | H |
| XXVIII-88 | H | Me | H | F | H | H | H |
| XXVIII-89 | H | Et | H | F | H | H | H |
| XXVIII-90 | H | vinyl | H | F | H | H | H |
| XXVIII-91 | H | allyl | H | F | H | H | H |
| XXVIII-92 | H | cyclopropyl | H | F | H | H | H |
| XXVIII-93 | H | F | H | F | H | H | H |
| XXVIII-94 | H | Cl | H | F | H | H | H |
| XXVIII-95 | H | $NO_2$ | H | F | H | H | H |
| XXVIII-96 | H | CN | H | F | H | H | H |
| XXVIII-97 | H | $CONH_2$ | H | F | H | H | H |
| XXVIII-98 | H | CONHMe | H | F | H | H | H |
| XXVIII-99 | H | $CONMe_2$ | H | F | H | H | H |
| XXVIII-100 | H | COMe | H | F | H | H | H |
| XXVIII-101 | H | COOH | H | F | H | H | H |
| XXVIII-102 | H | COOMe | H | F | H | H | H |
| XXVIII-103 | H | CSOMe | H | F | H | H | H |
| XXVIII-104 | H | $CSNH_2$ | H | F | H | H | H |
| XXVIII-105 | H | $CSNMe_2$ | H | F | H | H | H |
| XXVIII-106 | H | CSNHMe | H | F | H | H | H |
| XXVIII-107 | H | OMe | H | F | H | H | H |
| XXVIII-108 | H | OEt | H | F | H | H | H |
| XXVIII-109 | H | OCOMe | H | F | H | H | H |
| XXVIII-110 | H | OCOOMe | H | F | H | H | H |
| XXVIII-111 | H | OCONHMe | H | F | H | H | H |
| XXVIII-112 | H | $OCONMe_2$ | H | F | H | H | H |
| XXVIII-113 | H | OCSMe | H | F | H | H | H |
| XXVIII-114 | H | $OCSNMe_2$ | H | F | H | H | H |
| XXVIII-115 | H | SMe | H | F | H | H | H |
| XXVIII-116 | H | SEt | H | F | H | H | H |
| XXVIII-117 | H | SCOMe | H | F | H | H | H |
| XXVIII-118 | H | $SCSNMe_2$ | H | F | H | H | H |
| XXVIII-119 | H | SCSNHMe | H | F | H | H | H |
| XXVIII-120 | H | NHMe | H | F | H | H | H |
| XXVIII-121 | H | $NH_2$ | H | F | H | H | H |
| XXVIII-122 | H | $NMe_2$ | H | F | H | H | H |
| XXVIII-123 | H | NHCOMe | H | F | H | H | H |
| XXVIII-124 | H | $NHCONH_2$ | H | F | H | H | H |
| XXVIII-125 | H | NHCONHMe | H | F | H | H | H |
| XXVIII-126 | H | $NHCONMe_2$ | H | F | H | H | H |
| XXVIII-127 | H | phenyl | H | F | H | H | H |
| XXVIII-128 | H | 2-chloro-phenyl | H | F | H | H | H |
| XXVIII-129 | H | 4-nitrophenyl | H | F | H | H | H |
| XXVIII-130 | H | 2-pyridyl | H | F | H | H | H |
| XXVIII-131 | H | 3-pyridyl | H | F | H | H | H |
| XXVIII-132 | H | 4-pyridyl | H | F | H | H | H |
| XXVIII-133 | H | 2-furyl | H | F | H | H | H |
| XXVIII-134 | H | PhO | H | F | H | H | H |
| XXVIII-135 | | $CH_2$ | H | F | H | H | H |
| XXVIII-136 | H | H | H | F | H | H | H |
| XXVIII-137 | H | Me | H | F | H | H | H |
| XXVIII-138 | H | Me | F | F | H | H | H |
| XXVIII-139 | H | Et | H | F | H | H | H |
| XXVIII-140 | H | Me | Me | F | H | H | H |
| XXVIII-141 | Me | H | Me | F | H | H | H |
| XXVIII-142 | H | F | H | F | H | H | H |
| XXVIII-143 | Me | F | H | F | H | H | H |
| XXVIII-144 | Me | H | H | Me | H | H | H |
| XXVIII-145 | Et | H | H | Me | H | H | H |
| XXVIII-146 | vinyl | H | H | Me | H | H | H |
| XXVIII-147 | allyl | H | H | Me | H | H | H |
| XXVIII-148 | cyclopropyl | H | H | Me | H | H | H |
| XXVIII-149 | CN | H | H | Me | H | H | H |
| XXVIII-150 | $CONH_2$ | H | H | Me | H | H | H |
| XXVIII-151 | CONHMe | H | H | Me | H | H | H |
| XXVIII-152 | $CONMe_2$ | H | H | Me | H | H | H |

TABLE 4-continued

| Compound No | R9 | R1 | R2 | R4a | R4b | R4c | R4d |
|---|---|---|---|---|---|---|---|
| XXVIII-153 | COMe | H | H | Me | H | H | H |
| XXVIII-154 | COOH | H | H | Me | H | H | H |
| XXVIII-155 | COOMe | H | H | Me | H | H | H |
| XXVIII-156 | CSNHMe | H | H | Me | H | H | H |
| XXVIII-157 | H | Me | H | Me | H | H | H |
| XXVIII-158 | H | Et | H | Me | H | H | H |
| XXVIII-159 | H | vinyl | H | Me | H | H | H |
| XXVIII-160 | H | allyl | H | Me | H | H | H |
| XXVIII-161 | H | cyclopropyl | H | Me | H | H | H |
| XXVIII-162 | H | F | H | Me | H | H | H |
| XXVIII-163 | H | Cl | H | Me | H | H | H |
| XXVIII-164 | H | $NO_2$ | H | Me | H | H | H |
| XXVIII-165 | H | CN | H | Me | H | H | H |
| XXVIII-166 | H | $CONH_2$ | H | Me | H | H | H |
| XXVIII-167 | H | CONHMe | H | Me | H | H | H |
| XXVIII-168 | H | $CONMe_2$ | H | Me | H | H | H |
| XXVIII-169 | H | COMe | H | Me | H | H | H |
| XXVIII-170 | H | COOH | H | Me | H | H | H |
| XXVIII-171 | H | COOMe | H | Me | H | H | H |
| XXVIII-172 | H | CSOMe | H | Me | H | H | H |
| XXVIII-173 | H | $CSNH_2$ | H | Me | H | H | H |
| XXVIII-174 | H | $CSNMe_2$ | H | Me | H | H | H |
| XXVIII-175 | H | CSNHMe | H | Me | H | H | H |
| XXVIII-176 | H | OMe | H | Me | H | H | H |
| XXVIII-177 | H | OEt | H | Me | H | H | H |
| XXVIII-178 | H | OCOMe | H | Me | H | H | H |
| XXVIII-179 | H | OCOOMe | H | Me | H | H | H |
| XXVIII-180 | H | OCONHMe | H | Me | H | H | H |
| XXVIII-181 | H | $OCONMe_2$ | H | Me | H | H | H |
| XXVIII-182 | H | OCSMe | H | Me | H | H | H |
| XXVIII-183 | H | $OCSNMe_2$ | H | Me | H | H | H |
| XXVIII-184 | H | SMe | H | Me | H | H | H |
| XXVIII-185 | H | SEt | H | Me | H | H | H |
| XXVIII-186 | H | SCOMe | H | Me | H | H | H |
| XXVIII-187 | H | $SCSNMe_2$ | H | Me | H | H | H |
| XXVIII-188 | H | SCSNHMe | H | Me | H | H | H |
| XXVIII-189 | H | NHMe | H | Me | H | H | H |
| XXVIII-190 | H | $NH_2$ | H | Me | H | H | H |
| XXVIII-191 | H | $NMe_2$ | H | Me | H | H | H |
| XXVIII-192 | H | NHCOMe | H | Me | H | H | H |
| XXVIII-193 | H | $NHCONH_2$ | H | Me | H | H | H |
| XXVIII-194 | H | NHCONHMe | H | Me | H | H | H |
| XXVIII-195 | H | $NHCONMe_2$ | H | Me | H | H | H |
| XXVIII-196 | H | phenyl | H | Me | H | H | H |
| XXVIII-197 | H | 2-chloro-phenyl | H | Me | H | H | H |
| XXVIII-198 | H | 4-nitrophenyl | H | Me | H | H | H |
| XXVIII-199 | H | 2-pyridyl | H | Me | H | H | H |
| XXVIII-200 | H | 3-pyridyl | H | Me | H | H | H |
| XXVIII-201 | H | 4-pyridyl | H | Me | H | H | H |
| XXVIII-202 | H | 2-furyl | H | Me | H | H | H |
| XXVIII-203 | H | PhO | H | Me | H | H | H |
| XXVIII-204 | | $CH_2$ | H | Me | H | H | H |
| XXVIII-205 | H | H | H | Me | H | H | H |
| XXVIII-206 | H | Me | H | Me | H | H | H |
| XXVIII-207 | H | Me | F | Me | H | H | H |
| XXVIII-208 | H | Et | H | Me | H | H | H |
| XXVIII-209 | H | Me | Me | Me | H | H | H |
| XXVIII-210 | Me | H | Me | Me | H | H | H |
| XXVIII-211 | H | F | H | Me | H | H | H |
| XXVIII-212 | Me | F | H | Me | H | H | H |
| XXVIII-213 | Me | H | H | F | H | F | H |
| XXVIII-214 | Et | H | H | F | H | F | H |
| XXVIII-215 | vinyl | H | H | F | H | F | H |
| XXVIII-216 | allyl | H | H | F | H | F | H |
| XXVIII-217 | cyclopropyl | H | H | F | H | F | H |
| XXVIII-218 | CN | H | H | F | H | F | H |
| XXVIII-219 | $CONH_2$ | H | H | F | H | F | H |
| XXVIII-220 | CONHMe | H | H | F | H | F | H |
| XXVIII-221 | $CONMe_2$ | H | H | F | H | F | H |
| XXVIII-222 | COMe | H | H | F | H | F | H |
| XXVIII-223 | COOH | H | H | F | H | F | H |
| XXVIII-224 | COOMe | H | H | F | H | F | H |
| XXVIII-225 | CSNHMe | H | H | F | H | F | H |
| XXVIII-226 | H | Me | H | F | H | F | H |
| XXVIII-227 | H | Et | H | F | H | F | H |
| XXVIII-228 | H | vinyl | H | F | H | F | H |

TABLE 4-continued

| Compound No | R9 | R1 | R2 | R4a | R4b | R4c | R4d |
|---|---|---|---|---|---|---|---|
| XXVIII-229 | H | allyl | H | F | H | F | H |
| XXVIII-230 | H | cyclopropyl | H | F | H | F | H |
| XXVIII-231 | H | F | H | F | H | F | H |
| XXVIII-232 | H | Cl | H | F | H | F | H |
| XXVIII-233 | H | NO$_2$ | H | F | H | F | H |
| XXVIII-234 | H | CN | H | F | H | F | H |
| XXVIII-235 | H | CONH$_2$ | H | F | H | F | H |
| XXVIII-236 | H | CONHMe | H | F | H | F | H |
| XXVIII-237 | H | CONMe$_2$ | H | F | H | F | H |
| XXVIII-238 | H | COMe | H | F | H | F | H |
| XXVIII-239 | H | COOH | H | F | H | F | H |
| XXVIII-240 | H | COOMe | H | F | H | F | H |
| XXVIII-241 | H | CSOMe | H | F | H | F | H |
| XXVIII-242 | H | CSNH$_2$ | H | F | H | F | H |
| XXVIII-243 | H | CSNMe$_2$ | H | F | H | F | H |
| XXVIII-244 | H | CSNHMe | H | F | H | F | H |
| XXVIII-245 | H | OMe | H | F | H | F | H |
| XXVIII-246 | H | OEt | H | F | H | F | H |
| XXVIII-247 | H | OCOMe | H | F | H | F | H |
| XXVIII-248 | H | OCOOMe | H | F | H | F | H |
| XXVIII-249 | H | OCONHMe | H | F | H | F | H |
| XXVIII-250 | H | OCONMe$_2$ | H | F | H | F | H |
| XXVIII-251 | H | OCSMe | H | F | H | F | H |
| XXVIII-252 | H | OCSNMe$_2$ | H | F | H | F | H |
| XXVIII-253 | H | SMe | H | F | H | F | H |
| XXVIII-254 | H | SEt | H | F | H | F | H |
| XXVIII-255 | H | SCOMe | H | F | H | F | H |
| XXVIII-256 | H | SCSNMe$_2$ | H | F | H | F | H |
| XXVIII-257 | H | SCSNHMe | H | F | H | F | H |
| XXVIII-258 | H | NHMe | H | F | H | F | H |
| XXVIII-259 | H | NH$_2$ | H | F | H | F | H |
| XXVIII-260 | H | NMe$_2$ | H | F | H | F | H |
| XXVIII-261 | H | NHCOMe | H | F | H | F | H |
| XXVIII-262 | H | NHCONH$_2$ | H | F | H | F | H |
| XXVIII-263 | H | NHCONHMe | H | F | H | F | H |
| XXVIII-264 | H | NHCONMe$_2$ | H | F | H | F | H |
| XXVIII-265 | H | phenyl | H | F | H | F | H |
| XXVIII-266 | H | 2-chloro-phenyl | H | F | H | F | H |
| XXVIII-267 | H | 4-nitrophenyl | H | F | H | F | H |
| XXVIII-268 | H | 2-pyridyl | H | F | H | F | H |
| XXVIII-269 | H | 3-pyridyl | H | F | H | F | H |
| XXVIII-270 | H | 4-pyridyl | H | F | H | F | H |
| XXVIII-271 | H | 2-furyl | H | F | H | F | H |
| XXVIII-272 | H | PhO | H | F | H | F | H |
| XXVIII-273 | | CH$_2$ | H | F | H | F | H |
| XXVIII-274 | H | H | H | F | H | F | H |
| XXVIII-275 | H | Me | H | F | H | F | H |
| XXVIII-276 | H | Me | F | F | H | F | H |
| XXVIII-277 | H | Et | H | F | H | F | H |
| XXVIII-278 | H | Me | Me | F | H | F | H |
| XXVIII-279 | Me | H | Me | F | H | F | H |
| XXVIII-280 | H | F | H | F | H | F | H |
| XXVIII-281 | Me | F | H | F | H | F | H |
| XXVIII-282 | H | H | H | Me | H | H | H |
| XXVIII-283 | H | H | H | Et | H | H | H |
| XXVIII-284 | H | H | H | vinyl | H | H | H |
| XXVIII-285 | H | H | H | allyl | H | H | H |
| XXVIII-286 | H | H | H | cyclopropyl | H | H | H |
| XXVIII-287 | H | H | H | F | H | H | H |
| XXVIII-288 | H | H | H | Cl | H | H | H |
| XXVIII-289 | H | H | H | NO$_2$ | H | H | H |
| XXVIII-290 | H | H | H | CN | H | H | H |
| XXVIII-291 | H | H | H | CONH$_2$ | H | H | H |
| XXVIII-292 | H | H | H | CONHMe | H | H | H |
| XXVIII-293 | H | H | H | CONMe$_2$ | H | H | H |
| XXVIII-294 | H | H | H | COMe | H | H | H |
| XXVIII-295 | H | H | H | COOH | H | H | H |
| XXVIII-296 | H | H | H | COOMe | H | H | H |
| XXVIII-297 | H | H | H | CSOMe | H | H | H |
| XXVIII-298 | H | H | H | CSNH$_2$ | H | H | H |
| XXVIII-299 | H | H | H | CSNMe$_2$ | H | H | H |
| XXVIII-300 | H | H | H | CSNHMe | H | H | H |
| XXVIII-301 | H | H | H | OMe | H | H | H |
| XXVIII-302 | H | H | H | OEt | H | H | H |
| XXVIII-303 | H | H | H | OCOMe | H | H | H |
| XXVIII-304 | H | H | H | OCOOMe | H | H | H |

TABLE 4-continued

| Compound No | R9 | R1 | R2 | R4a | R4b | R4c | R4d |
|---|---|---|---|---|---|---|---|
| XXVIII-305 | H | H | H | OCONHMe | H | H | H |
| XXVIII-306 | H | H | H | OCONMe$_2$ | H | H | H |
| XXVIII-307 | H | H | H | OCSMe | H | H | H |
| XXVIII-308 | H | H | H | OCSNMe$_2$ | H | H | H |
| XXVIII-309 | H | H | H | SMe | H | H | H |
| XXVIII-310 | H | H | H | SEt | H | H | H |
| XXVIII-311 | H | H | H | SCOMe | H | H | H |
| XXVIII-312 | H | H | H | SCSNMe$_2$ | H | H | H |
| XXVIII-313 | H | H | H | SCSNHMe | H | H | H |
| XXVIII-314 | H | H | H | NHMe | H | H | H |
| XXVIII-315 | H | H | H | NH$_2$ | H | H | H |
| XXVIII-316 | H | H | H | NMe$_2$ | H | H | H |
| XXVIII-317 | H | H | H | NHCOMe | H | H | H |
| XXVIII-318 | H | H | H | NHCONH$_2$ | H | H | H |
| XXVIII-319 | H | H | H | NHCONHMe | H | H | H |
| XXVIII-320 | H | H | H | NHCONMe$_2$ | H | H | H |
| XXVIII-321 | H | H | H | phenyl | H | H | H |
| XXVIII-322 | H | H | H | 2-chloro-phenyl | H | H | H |
| XXVIII-323 | H | H | H | 4-nitrophenyl | H | H | H |
| XXVIII-324 | H | H | H | 2-pyridyl | H | H | H |
| XXVIII-325 | H | H | H | 3-pyridyl | H | H | H |
| XXVIII-326 | H | H | H | 4-pyridyl | H | H | H |
| XXVIII-327 | H | H | H | 2-furyl | H | H | H |
| XXVIII-328 | H | H | H | PhO | H | H | H |
| XXVIII-329 | H | H | H | H | H | Me | H |
| XXVIII-330 | H | H | H | H | H | Et | H |
| XXVIII-331 | H | H | H | H | H | vinyl | H |
| XXVIII-332 | H | H | H | H | H | allyl | H |
| XXVIII-333 | H | H | H | H | H | cyclopropyl | H |
| XXVIII-334 | H | H | H | H | H | F | H |
| XXVIII-335 | H | H | H | H | H | Cl | H |
| XXVIII-336 | H | H | H | H | H | NO$_2$ | H |
| XXVIII-337 | H | H | H | H | H | CN | H |
| XXVIII-338 | H | H | H | H | H | CONH$_2$ | H |
| XXVIII-339 | H | H | H | H | H | CONHMe | H |
| XXVIII-340 | H | H | H | H | H | CONMe$_2$ | H |
| XXVIII-341 | H | H | H | H | H | COMe | H |
| XXVIII-342 | H | H | H | H | H | COOH | H |
| XXVIII-343 | H | H | H | H | H | COOMe | H |
| XXVIII-344 | H | H | H | H | H | CSOMe | H |
| XXVIII-345 | H | H | H | H | H | CSNH$_2$ | H |
| XXVIII-346 | H | H | H | H | H | CSNMe$_2$ | H |
| XXVIII-347 | H | H | H | H | H | CSNHMe | H |
| XXVIII-348 | H | H | H | H | H | OMe | H |
| XXVIII-349 | H | H | H | H | H | OEt | H |
| XXVIII-350 | H | H | H | H | H | OCOMe | H |
| XXVIII-351 | H | H | H | H | H | OCOOMe | H |
| XXVIII-352 | H | H | H | H | H | OCONHMe | H |
| XXVIII-353 | H | H | H | H | H | OCONMe$_2$ | H |
| XXVIII-354 | H | H | H | H | H | OCSMe | H |
| XXVIII-355 | H | H | H | H | H | OCSNMe$_2$ | H |
| XXVIII-356 | H | H | H | H | H | SMe | H |
| XXVIII-357 | H | H | H | H | H | SEt | H |
| XXVIII-358 | H | H | H | H | H | SCOMe | H |
| XXVIII-359 | H | H | H | H | H | SCSNMe$_2$ | H |
| XXVIII-360 | H | H | H | H | H | SCSNHMe | H |
| XXVIII-361 | H | H | H | H | H | NHMe | H |
| XXVIII-362 | H | H | H | H | H | NH$_2$ | H |
| XXVIII-363 | H | H | H | H | H | NMe$_2$ | H |
| XXVIII-364 | H | H | H | H | H | NHCOMe | H |
| XXVIII-365 | H | H | H | H | H | NHCONH$_2$ | H |
| XXVIII-366 | H | H | H | H | H | NHCONHMe | H |
| XXVIII-367 | H | H | H | H | H | NHCONMe$_2$ | H |
| XXVIII-368 | H | H | H | H | H | phenyl | H |
| XXVIII-369 | H | H | H | H | H | 2-chloro-phenyl | H |
| XXVIII-370 | H | H | H | H | H | 4-nitrophenyl | H |
| XXVIII-371 | H | H | H | H | H | 2-pyridyl | H |
| XXVIII-372 | H | H | H | H | H | 3-pyridyl | H |
| XXVIII-373 | H | H | H | H | H | 4-pyridyl | H |
| XXVIII-374 | H | H | H | H | H | 2-furyl | H |
| XXVIII-375 | H | H | H | H | H | PhO | H |
| XXVIII-376 | H | H | H | H | H | H | Me |
| XXVIII-377 | H | H | H | H | H | H | Et |
| XXVIII-378 | H | H | H | H | H | H | Vinyl |
| XXVIII-379 | H | H | H | H | H | H | Allyl |

TABLE 4-continued

| Compound No | R9 | R1 | R2 | R4a | R4b | R4c | R4d |
|---|---|---|---|---|---|---|---|
| XXVIII-380 | H | H | H | H | H | H | Cyclopropyl |
| XXVIII-381 | H | H | H | H | H | H | F |
| XXVIII-382 | H | H | H | H | H | H | Cl |
| XXVIII-383 | H | H | H | H | H | H | $NO_2$ |
| XXVIII-384 | H | H | H | H | H | H | CN |
| XXVIII-385 | H | H | H | H | H | H | $CONH_2$ |
| XXVIII-386 | H | H | H | H | H | H | CONHMe |
| XXVIII-387 | H | H | H | H | H | H | $CONMe_2$ |
| XXVIII-388 | H | H | H | H | H | H | COMe |
| XXVIII-389 | H | H | H | H | H | H | COOH |
| XXVIII-390 | H | H | H | H | H | H | COOMe |
| XXVIII-391 | H | H | H | H | H | H | CSOMe |
| XXVIII-392 | H | H | H | H | H | H | $CSNH_2$ |
| XXVIII-393 | H | H | H | H | H | H | $CSNMe_2$ |
| XXVIII-394 | H | H | H | H | H | H | CSNHMe |
| XXVIII-395 | H | H | H | H | H | H | OMe |
| XXVIII-396 | H | H | H | H | H | H | OEt |
| XXVIII-397 | H | H | H | H | H | H | OCOMe |
| XXVIII-398 | H | H | H | H | H | H | OCOOMe |
| XXVIII-399 | H | H | H | H | H | H | OCONHMe |
| XXVIII-400 | H | H | H | H | H | H | $OCONMe_2$ |
| XXVIII-401 | H | H | H | H | H | H | OCSMe |
| XXVIII-402 | H | H | H | H | H | H | $OCSNMe_2$ |
| XXVIII-403 | H | H | H | H | H | H | SMe |
| XXVIII-404 | H | H | H | H | H | H | SEt |
| XXVIII-405 | H | H | H | H | H | H | SCOMe |
| XXVIII-406 | H | H | H | H | H | H | $SCSNMe_2$ |
| XXVIII-407 | H | H | H | H | H | H | SCSNHMe |
| XXVIII-408 | H | H | H | H | H | H | NHMe |
| XXVIII-409 | H | H | H | H | H | H | $NH_2$ |
| XXVIII-410 | H | H | H | H | H | H | $NMe_2$ |
| XXVIII-411 | H | H | H | H | H | H | NHCOMe |
| XXVIII-412 | H | H | H | H | H | H | $NHCONH_2$ |
| XXVIII-413 | H | H | H | H | H | H | NHCONHMe |
| XXVIII-414 | H | H | H | H | H | H | $NHCONMe_2$ |
| XXVIII-415 | H | H | H | H | H | H | phenyl |
| XXVIII-416 | H | H | H | H | H | H | 2-chloro-phenyl |
| XXVIII-417 | H | H | H | H | H | H | 4-nitrophenyl |
| XXVIII-418 | H | H | H | H | H | H | 2-pyridyl |
| XXVIII-419 | H | H | H | H | H | H | 3-pyridyl |
| XXVIII-420 | H | H | H | H | H | H | 4-pyridyl |
| XXVIII-421 | H | H | H | H | H | H | 2-furyl |
| XXVIII-422 | H | H | H | H | H | H | PhO |

Table XXIX provides 422 compounds of formula Iac

Table XXX provides 422 compounds of formula Iad

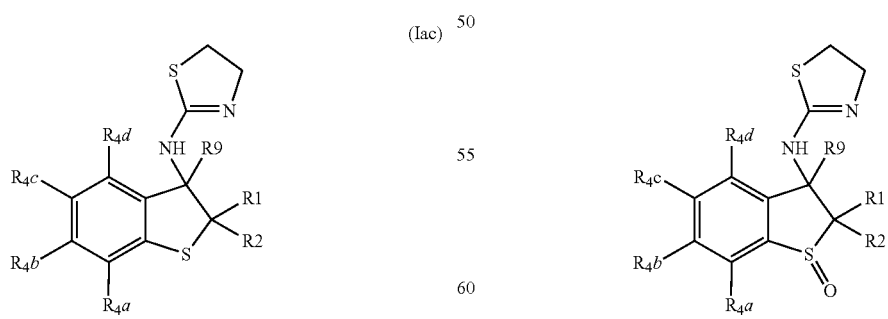

wherein the values of $R^1$, $R^2$, $R^{4a}$, $R^{4b}$, $R^{4c}$, $R^{4d}$ and $R^9$ are given in Table 4.

wherein the values of $R^1$, $R^2$, $R^{4a}$, $R^{4b}$, $R^{4c}$, $R^{4d}$ and $R^9$ are given in Table 4.

Table XXXI provides 422 compounds of formula Iae

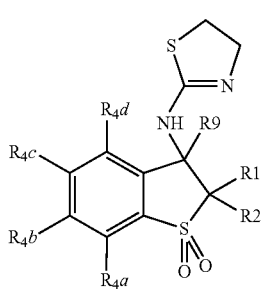
(Iae)

wherein the values of $R^1$, $R^2$, $R^{4a}$, $R^{4b}$, $R^{4c}$, $R^{4d}$ and $R^9$ are given in Table 4.

Table XXXII provides 422 compounds of formula Iaf

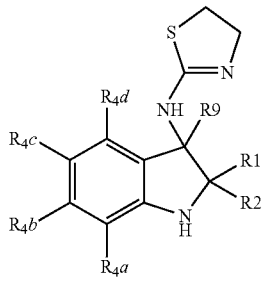
(Iaf)

wherein the values of $R^1$, $R^2$, $R^{4a}$, $R^{4b}$, $R^{4c}$, $R^{4d}$ and $R^9$ are given in Table 4.

Table XXXIII provides 422 compounds of formula Iag

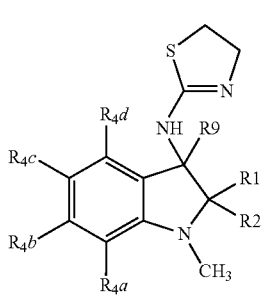
(Iag)

wherein the values of $R^1$, $R^2$, $R^{4a}$, $R^{4b}$, $R^{4c}$, $R^{4d}$ and $R^9$ are given in Table 4.

Table XXXIV provides 422 compounds of formula Iah

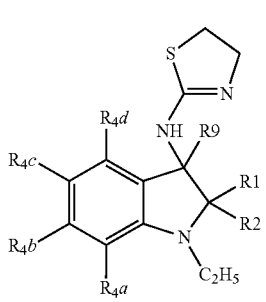
(Iah)

wherein the values of $R^1$, $R^2$, $R^{4a}$, $R^{4b}$, $R^{4c}$, $R^{4d}$ and $R^9$ are given in Table 4.

Table XXXV provides 422 compounds of formula Iai

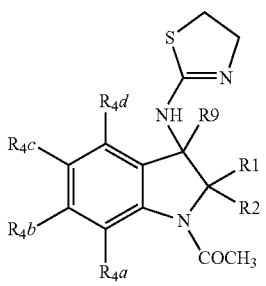
(Iai)

wherein the values of $R^1$, $R^2$, $R^{4a}$, $R^{4b}$, $R^{4c}$, $R^{4d}$ and $R^9$ are given in Table 4.

Table XXXVI provides 4222 compounds of formula Iaj

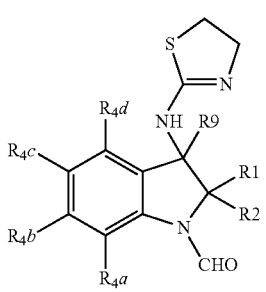
(Iaj)

wherein the values of $R^1$, $R^2$, $R^{4a}$, $R^{4b}$, $R^{4c}$, $R^{4d}$ and $R^9$ are given in Table 4.

Table XXXVII provides 422 compounds of formula Iak

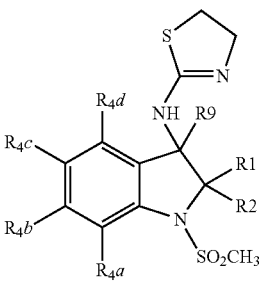
(Iak)

wherein the values of $R^1$, $R^2$, $R^{4a}$, $R^{4b}$, $R^{4c}$, $R^{4d}$ and $R^9$ are given in Table 4.

Table XXXVIII provides 391 compounds of formula Ial

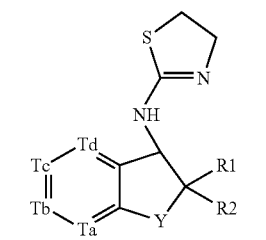
(Ial)

wherein the values of Y, $R^1$, $R^2$, $T^a$, $T^b$, $T^c$ and $T^d$ are given in Table 5.

TABLE 5

| Compound No | Y | R1 | R2 | Ta | Tb | Tc | Td |
|---|---|---|---|---|---|---|---|
| XXXVIII-1 | CH$_2$ | H | H | N | CH | CH | CH |
| XXXVIII-2 | CHMe | H | H | N | CH | CH | CH |
| XXXVIII-3 | CHEt | H | H | N | CH | CH | CH |
| XXXVIII-4 | CHF | H | H | N | CH | CH | CH |
| XXXVIII-5 | C=CH$_2$ | H | H | N | CH | CH | CH |
| XXXVIII-6 | O | H | H | N | CH | CH | CH |
| XXXVIII-7 | S | H | H | N | CH | CH | CH |
| XXXVIII-8 | NH | H | H | N | CH | CH | CH |
| XXXVIII-9 | NMe | H | H | N | CH | CH | CH |
| XXXVIII-10 | NCHO | H | H | N | CH | CH | CH |
| XXXVIII-11 | NCOMe | H | H | N | CH | CH | CH |
| XXXVIII-12 | CH$_2$ | Me | H | N | CH | CH | CH |
| XXXVIII-13 | O | Me | H | N | CH | CH | CH |
| XXXVIII-14 | CHMe | Me | H | N | CH | CH | CH |
| XXXVIII-15 | CH$_2$ | =O | | N | CH | CH | CH |
| XXXVIII-16 | CH$_2$ | =CH$_2$ | | N | CH | CH | CH |
| XXXVIII-17 | CH$_2$ | =CHMe | | N | CH | CH | CH |
| XXXVIII-18 | CH$_2$ | H | H | N | CH | CF | CH |
| XXXVIII-19 | CHMe | H | H | N | CH | CF | CH |
| XXXVIII-20 | CHEt | H | H | N | CH | CF | CH |
| XXXVIII-21 | CHF | H | H | N | CH | CF | CH |
| XXXVIII-22 | C=CH$_2$ | H | H | N | CH | CF | CH |
| XXXVIII-23 | O | H | H | N | CH | CF | CH |
| XXXVIII-24 | S | H | H | N | CH | CF | CH |
| XXXVIII-25 | NH | H | H | N | CH | CF | CH |
| XXXVIII-26 | NMe | H | H | N | CH | CF | CH |
| XXXVIII-27 | NCHO | H | H | N | CH | CF | CH |
| XXXVIII-28 | NCOMe | H | H | N | CH | CF | CH |
| XXXVIII-29 | CH$_2$ | Me | H | N | CH | CF | CH |
| XXXVIII-30 | O | Me | H | N | CH | CF | CH |
| XXXVIII-31 | CHMe | Me | H | N | CH | CF | CH |
| XXXVIII-32 | CH$_2$ | =O | | N | CH | CF | CH |
| XXXVIII-33 | CH$_2$ | =CH$_2$ | | N | CH | CF | CH |
| XXXVIII-34 | CH$_2$ | =CHMe | | N | CH | CF | CH |
| XXXVIII-35 | CH$_2$ | H | H | N | CH | CH | CF |
| XXXVIII-36 | CHMe | H | H | N | CH | CH | CF |
| XXXVIII-37 | CHEt | H | H | N | CH | CH | CF |
| XXXVIII-38 | CHF | H | H | N | CH | CH | CF |
| XXXVIII-39 | C=CH$_2$ | H | H | N | CH | CH | CF |
| XXXVIII-40 | O | H | H | N | CH | CH | CF |
| XXXVIII-41 | S | H | H | N | CH | CH | CF |
| XXXVIII-42 | NH | H | H | N | CH | CH | CF |
| XXXVIII-43 | NMe | H | H | N | CH | CH | CF |
| XXXVIII-44 | NCHO | H | H | N | CH | CH | CF |
| XXXVIII-45 | NCOMe | H | H | N | CH | CH | CF |
| XXXVIII-46 | CH$_2$ | Me | H | N | CH | CH | CF |
| XXXVIII-47 | O | Me | H | N | CH | CH | CF |
| XXXVIII-48 | CHMe | Me | H | N | CH | CH | CF |
| XXXVIII-49 | CH$_2$ | =O | | N | CH | CH | CF |
| XXXVIII-50 | CH$_2$ | =CH$_2$ | | N | CH | CH | CF |
| XXXVIII-51 | CH$_2$ | =CHMe | | N | CH | CH | CF |
| XXXVIII-52 | CH$_2$ | H | H | CH | N | CH | CH |
| XXXVIII-53 | CHMe | H | H | CH | N | CH | CH |
| XXXVIII-54 | CHEt | H | H | CH | N | CH | CH |
| XXXVIII-55 | CHF | H | H | CH | N | CH | CH |
| XXXVIII-56 | C=CH$_2$ | H | H | CH | N | CH | CH |
| XXXVIII-57 | O | H | H | CH | N | CH | CH |
| XXXVIII-58 | S | H | H | CH | N | CH | CH |
| XXXVIII-59 | NH | H | H | CH | N | CH | CH |
| XXXVIII-60 | NMe | H | H | CH | N | CH | CH |
| XXXVIII-61 | NCHO | H | H | CH | N | CH | CH |
| XXXVIII-62 | NCOMe | H | H | CH | N | CH | CH |
| XXXVIII-63 | CH$_2$ | Me | H | CH | N | CH | CH |
| XXXVIII-64 | O | Me | H | CH | N | CH | CH |
| XXXVIII-65 | CHMe | Me | H | CH | N | CH | CH |
| XXXVIII-66 | CH$_2$ | =O | | CH | N | CH | CH |
| XXXVIII-67 | CH$_2$ | =CH$_2$ | | CH | N | CH | CH |
| XXXVIII-68 | CH$_2$ | =CHMe | | CH | N | CH | CH |
| XXXVIII-69 | CH$_2$ | H | H | CF | N | CH | CH |
| XXXVIII-70 | CHMe | H | H | CF | N | CH | CH |
| XXXVIII-71 | CHEt | H | H | CF | N | CH | CH |
| XXXVIII-72 | CHF | H | H | CF | N | CH | CH |
| XXXVIII-73 | C=CH$_2$ | H | H | CF | N | CH | CH |
| XXXVIII-74 | O | H | H | CF | N | CH | CH |
| XXXVIII-75 | S | H | H | CF | N | CH | CH |
| XXXVIII-76 | NH | H | H | CF | N | CH | CH |
| XXXVIII-77 | NMe | H | H | CF | N | CH | CH |
| XXXVIII-78 | NCHO | H | H | CF | N | CH | CH |
| XXXVIII-79 | NCOMe | H | H | CF | N | CH | CH |
| XXXVIII-80 | CH$_2$ | Me | H | CF | N | CH | CH |
| XXXVIII-81 | O | Me | H | CF | N | CH | CH |
| XXXVIII-82 | CHMe | Me | H | CF | N | CH | CH |
| XXXVIII-83 | CH$_2$ | =O | | CF | N | CH | CH |
| XXXVIII-84 | CH$_2$ | =CH$_2$ | | CF | N | CH | CH |
| XXXVIII-85 | CH$_2$ | =CHMe | | CF | N | CH | CH |
| XXXVIII-86 | CH$_2$ | H | H | CMe | N | CH | CH |
| XXXVIII-87 | CHMe | H | H | CMe | N | CH | CH |
| XXXVIII-88 | CHEt | H | H | CMe | N | CH | CH |
| XXXVIII-89 | CHF | H | H | CMe | N | CH | CH |
| XXXVIII-90 | C=CH$_2$ | H | H | CMe | N | CH | CH |
| XXXVIII-91 | O | H | H | CMe | N | CH | CH |
| XXXVIII-92 | S | H | H | CMe | N | CH | CH |
| XXXVIII-93 | NH | H | H | CMe | N | CH | CH |
| XXXVIII-94 | NMe | H | H | CMe | N | CH | CH |
| XXXVIII-95 | NCHO | H | H | CMe | N | CH | CH |
| XXXVIII-96 | NCOMe | H | H | CMe | N | CH | CH |
| XXXVIII-97 | CH$_2$ | Me | H | CMe | N | CH | CH |
| XXXVIII-98 | O | Me | H | CMe | N | CH | CH |
| XXXVIII-99 | CHMe | Me | H | CMe | N | CH | CH |
| XXXVIII-100 | CH$_2$ | =O | | CMe | N | CH | CH |
| XXXVIII-101 | CH$_2$ | =CH$_2$ | | CMe | N | CH | CH |
| XXXVIII-102 | CH$_2$ | =CHMe | | CMe | N | CH | CH |
| XXXVIII-103 | CH$_2$ | H | H | CH | N | CF | CH |
| XXXVIII-104 | CHMe | H | H | CH | N | CF | CH |
| XXXVIII-105 | CHEt | H | H | CH | N | CF | CH |
| XXXVIII-106 | CHF | H | H | CH | N | CF | CH |
| XXXVIII-107 | C=CH$_2$ | H | H | CH | N | CF | CH |
| XXXVIII-108 | O | H | H | CH | N | CF | CH |
| XXXVIII-109 | S | H | H | CH | N | CF | CH |
| XXXVIII-110 | NH | H | H | CH | N | CF | CH |
| XXXVIII-111 | NMe | H | H | CH | N | CF | CH |
| XXXVIII-112 | NCHO | H | H | CH | N | CF | CH |
| XXXVIII-113 | NCOMe | H | H | CH | N | CF | CH |
| XXXVIII-114 | CH$_2$ | Me | H | CH | N | CF | CH |
| XXXVIII-115 | O | Me | H | CH | N | CF | CH |
| XXXVIII-116 | CHMe | Me | H | CH | N | CF | CH |
| XXXVIII-117 | CH$_2$ | =O | | CH | N | CF | CH |
| XXXVIII-118 | CH$_2$ | =CH$_2$ | | CH | N | CF | CH |
| XXXVIII-119 | CH$_2$ | =CHMe | | CH | N | CF | CH |
| XXXVIII-120 | CH$_2$ | H | H | CH | N | CH | CF |
| XXXVIII-121 | CHMe | H | H | CH | N | CH | CF |
| XXXVIII-122 | CHEt | H | H | CH | N | CH | CF |
| XXXVIII-123 | CHF | H | H | CH | N | CH | CF |
| XXXVIII-124 | C=CH$_2$ | H | H | CH | N | CH | CF |
| XXXVIII-125 | O | H | H | CH | N | CH | CF |
| XXXVIII-126 | S | H | H | CH | N | CH | CF |
| XXXVIII-127 | NH | H | H | CH | N | CH | CF |
| XXXVIII-128 | NMe | H | H | CH | N | CH | CF |
| XXXVIII-129 | NCHO | H | H | CH | N | CH | CF |
| XXXVIII-130 | NCOMe | H | H | CH | N | CH | CF |
| XXXVIII-131 | CH$_2$ | Me | H | CH | N | CH | CF |
| XXXVIII-132 | O | Me | H | CH | N | CH | CF |
| XXXVIII-133 | CHMe | Me | H | CH | N | CH | CF |
| XXXVIII-134 | CH$_2$ | =O | | CH | N | CH | CF |
| XXXVIII-135 | CH$_2$ | =CH$_2$ | | CH | N | CH | CF |
| XXXVIII-136 | CH$_2$ | =CHMe | | CH | N | CH | CF |
| XXXVIII-137 | CH$_2$ | H | H | CH | CH | N | CH |
| XXXVIII-138 | CHMe | H | H | CH | CH | N | CH |
| XXXVIII-139 | CHEt | H | H | CH | CH | N | CH |
| XXXVIII-140 | CHF | H | H | CH | CH | N | CH |
| XXXVIII-141 | C=CH$_2$ | H | H | CH | CH | N | CH |
| XXXVIII-142 | O | H | H | CH | CH | N | CH |
| XXXVIII-143 | S | H | H | CH | CH | N | CH |
| XXXVIII-144 | NH | H | H | CH | CH | N | CH |
| XXXVIII-145 | NMe | H | H | CH | CH | N | CH |
| XXXVIII-146 | NCHO | H | H | CH | CH | N | CH |
| XXXVIII-147 | NCOMe | H | H | CH | CH | N | CH |
| XXXVIII-148 | CH$_2$ | Me | H | CH | CH | N | CH |
| XXXVIII-149 | O | Me | H | CH | CH | N | CH |
| XXXVIII-150 | CHMe | Me | H | CH | CH | N | CH |
| XXXVIII-151 | CH$_2$ | =O | | CH | CH | N | CH |
| XXXVIII-152 | CH$_2$ | =CH$_2$ | | CH | CH | N | CH |
| XXXVIII-153 | CH$_2$ | =CHMe | | CH | CH | N | CH |
| XXXVIII-154 | CH$_2$ | H | H | CF | CH | N | CH |
| XXXVIII-155 | CHMe | H | H | CF | CH | N | CH |
| XXXVIII-156 | CHEt | H | H | CF | CH | N | CH |

TABLE 5-continued

| Compound No | Y | R1 | R2 | Ta | Tb | Tc | Td |
|---|---|---|---|---|---|---|---|
| XXXVIII-157 | CHF | H | H | CF | CH | N | CH |
| XXXVIII-158 | C=CH$_2$ | H | H | CF | CH | N | CH |
| XXXVIII-159 | O | H | H | CF | CH | N | CH |
| XXXVIII-160 | S | H | H | CF | CH | N | CH |
| XXXVIII-161 | NH | H | H | CF | CH | N | CH |
| XXXVIII-162 | NMe | H | H | CF | CH | N | CH |
| XXXVIII-163 | NCHO | H | H | CF | CH | N | CH |
| XXXVIII-164 | NCOMe | H | H | CF | CH | N | CH |
| XXXVIII-165 | CH$_2$ | Me | H | CF | CH | N | CH |
| XXXVIII-166 | O | Me | H | CF | CH | N | CH |
| XXXVIII-167 | CHMe | Me | H | CF | CH | N | CH |
| XXXVIII-168 | CH$_2$ | =O | | CF | CH | N | CH |
| XXXVIII-169 | CH$_2$ | =CH$_2$ | | CF | CH | N | CH |
| XXXVIII-170 | CH$_2$ | =CHMe | | CF | CH | N | CH |
| XXXVIII-171 | CH$_2$ | H | H | CMe | CH | N | CH |
| XXXVIII-172 | CHMe | H | H | CMe | CH | N | CH |
| XXXVIII-173 | CHEt | H | H | CMe | CH | N | CH |
| XXXVIII-174 | CHF | H | H | CMe | CH | N | CH |
| XXXVIII-175 | C=CH$_2$ | H | H | CMe | CH | N | CH |
| XXXVIII-176 | O | H | H | CMe | CH | N | CH |
| XXXVIII-177 | S | H | H | CMe | CH | N | CH |
| XXXVIII-178 | NH | H | H | CMe | CH | N | CH |
| XXXVIII-179 | NMe | H | H | CMe | CH | N | CH |
| XXXVIII-180 | NCHO | H | H | CMe | CH | N | CH |
| XXXVIII-181 | NCOMe | H | H | CMe | CH | N | CH |
| XXXVIII-182 | CH$_2$ | Me | H | CMe | CH | N | CH |
| XXXVIII-183 | O | Me | H | CMe | CH | N | CH |
| XXXVIII-184 | CHMe | Me | H | CMe | CH | N | CH |
| XXXVIII-185 | CH$_2$ | =O | | CMe | CH | N | CH |
| XXXVIII-186 | CH$_2$ | =CH$_2$ | | CMe | CH | N | CH |
| XXXVIII-187 | CH$_2$ | =CHMe | | CMe | CH | N | CH |
| XXXVIII-188 | CH$_2$ | H | H | CH | CH | N | CF |
| XXXVIII-189 | CHMe | H | H | CH | CH | N | CF |
| XXXVIII-190 | CHEt | H | H | CH | CH | N | CF |
| XXXVIII-191 | CHF | H | H | CH | CH | N | CF |
| XXXVIII-192 | C=CH$_2$ | H | H | CH | CH | N | CF |
| XXXVIII-193 | O | H | H | CH | CH | N | CF |
| XXXVIII-194 | S | H | H | CH | CH | N | CF |
| XXXVIII-195 | NH | H | H | CH | CH | N | CF |
| XXXVIII-196 | NMe | H | H | CH | CH | N | CF |
| XXXVIII-197 | NCHO | H | H | CH | CH | N | CF |
| XXXVIII-198 | NCOMe | H | H | CH | CH | N | CF |
| XXXVIII-199 | CH$_2$ | Me | H | CH | CH | N | CF |
| XXXVIII-200 | O | Me | H | CH | CH | N | CF |
| XXXVIII-201 | CHMe | Me | H | CH | CH | N | CF |
| XXXVIII-202 | CH$_2$ | =O | | CH | CH | N | CF |
| XXXVIII-203 | CH$_2$ | =CH$_2$ | | CH | CH | N | CF |
| XXXVIII-204 | CH$_2$ | =CHMe | | CH | CH | N | CF |
| XXXVIII-205 | CH$_2$ | H | H | CH | CH | CH | N |
| XXXVIII-206 | CHMe | H | H | CH | CH | CH | N |
| XXXVIII-207 | CHEt | H | H | CH | CH | CH | N |
| XXXVIII-208 | CHF | H | H | CH | CH | CH | N |
| XXXVIII-209 | C=CH$_2$ | H | H | CH | CH | CH | N |
| XXXVIII-210 | O | H | H | CH | CH | CH | N |
| XXXVIII-211 | S | H | H | CH | CH | CH | N |
| XXXVIII-212 | NH | H | H | CH | CH | CH | N |
| XXXVIII-213 | NMe | H | H | CH | CH | CH | N |
| XXXVIII-214 | NCHO | H | H | CH | CH | CH | N |
| XXXVIII-215 | NCOMe | H | H | CH | CH | CH | N |
| XXXVIII-216 | CH$_2$ | Me | H | CH | CH | CH | N |
| XXXVIII-217 | O | Me | H | CH | CH | CH | N |
| XXXVIII-218 | CHMe | Me | H | CH | CH | CH | N |
| XXXVIII-219 | CH$_2$ | =O | | CH | CH | CH | N |
| XXXVIII-220 | CH$_2$ | =CH$_2$ | | CH | CH | CH | N |
| XXXVIII-221 | CH$_2$ | =CHMe | | CH | CH | CH | N |
| XXXVIII-222 | CH$_2$ | H | H | CF | CH | CH | N |
| XXXVIII-223 | CHMe | H | H | CF | CH | CH | N |
| XXXVIII-224 | CHEt | H | H | CF | CH | CH | N |
| XXXVIII-225 | CHF | H | H | CF | CH | CH | N |
| XXXVIII-226 | C=CH$_2$ | H | H | CF | CH | CH | N |
| XXXVIII-227 | O | H | H | CF | CH | CH | N |
| XXXVIII-228 | S | H | H | CF | CH | CH | N |
| XXXVIII-229 | NH | H | H | CF | CH | CH | N |
| XXXVIII-230 | NMe | H | H | CF | CH | CH | N |
| XXXVIII-231 | NCHO | H | H | CF | CH | CH | N |
| XXXVIII-232 | NCOMe | H | H | CF | CH | CH | N |
| XXXVIII-233 | CH$_2$ | Me | H | CF | CH | CH | N |
| XXXVIII-234 | O | Me | H | CF | CH | CH | N |
| XXXVIII-235 | CHMe | Me | H | CF | CH | CH | N |
| XXXVIII-236 | CH$_2$ | =O | | CF | CH | CH | N |
| XXXVIII-237 | CH$_2$ | =CH$_2$ | | CF | CH | CH | N |
| XXXVIII-238 | CH$_2$ | =CHMe | | CF | CH | CH | N |
| XXXVIII-239 | CH$_2$ | H | H | CMe | CH | CH | N |
| XXXVIII-240 | CHMe | H | H | CMe | CH | CH | N |
| XXXVIII-241 | CHEt | H | H | CMe | CH | CH | N |
| XXXVIII-242 | CHF | H | H | CMe | CH | CH | N |
| XXXVIII-243 | C=CH$_2$ | H | H | CMe | CH | CH | N |
| XXXVIII-244 | O | H | H | CMe | CH | CH | N |
| XXXVIII-245 | S | H | H | CMe | CH | CH | N |
| XXXVIII-246 | NH | H | H | CMe | CH | CH | N |
| XXXVIII-247 | NMe | H | H | CMe | CH | CH | N |
| XXXVIII-248 | NCHO | H | H | CMe | CH | CH | N |
| XXXVIII-249 | NCOMe | H | H | CMe | CH | CH | N |
| XXXVIII-250 | CH$_2$ | Me | H | CMe | CH | CH | N |
| XXXVIII-251 | O | Me | H | CMe | CH | CH | N |
| XXXVIII-252 | CHMe | Me | H | CMe | CH | CH | N |
| XXXVIII-253 | CH$_2$ | =O | | CMe | CH | CH | N |
| XXXVIII-254 | CH$_2$ | =CH$_2$ | | CMe | CH | CH | N |
| XXXVIII-255 | CH$_2$ | =CHMe | | CMe | CH | CH | N |
| XXXVIII-256 | CH$_2$ | H | H | CH | CH | CF | N |
| XXXVIII-257 | CHMe | H | H | CH | CH | CF | N |
| XXXVIII-258 | CHEt | H | H | CH | CH | CF | N |
| XXXVIII-259 | CHF | H | H | CH | CH | CF | N |
| XXXVIII-260 | C=CH$_2$ | H | H | CH | CH | CF | N |
| XXXVIII-261 | O | H | H | CH | CH | CF | N |
| XXXVIII-262 | S | H | H | CH | CH | CF | N |
| XXXVIII-263 | NH | H | H | CH | CH | CF | N |
| XXXVIII-264 | NMe | H | H | CH | CH | CF | N |
| XXXVIII-265 | NCHO | H | H | CH | CH | CF | N |
| XXXVIII-266 | NCOMe | H | H | CH | CH | CF | N |
| XXXVIII-267 | CH$_2$ | Me | H | CH | CH | CF | N |
| XXXVIII-268 | O | Me | H | CH | CH | CF | N |
| XXXVIII-269 | CHMe | Me | H | CH | CH | CF | N |
| XXXVIII-270 | CH$_2$ | =O | | CH | CH | CF | N |
| XXXVIII-271 | CH$_2$ | =CH$_2$ | | CH | CH | CF | N |
| XXXVIII-272 | CH$_2$ | =CHMe | | CH | CH | CF | N |
| XXXVIII-273 | CH$_2$ | H | H | N | CH | N | CH |
| XXXVIII-274 | CHMe | H | H | N | CH | N | CH |
| XXXVIII-275 | CHEt | H | H | N | CH | N | CH |
| XXXVIII-276 | CHF | H | H | N | CH | N | CH |
| XXXVIII-277 | C=CH$_2$ | H | H | N | CH | N | CH |
| XXXVIII-278 | O | H | H | N | CH | N | CH |
| XXXVIII-279 | S | H | H | N | CH | N | CH |
| XXXVIII-280 | NH | H | H | N | CH | N | CH |
| XXXVIII-281 | NMe | H | H | N | CH | N | CH |
| XXXVIII-282 | NCHO | H | H | N | CH | N | CH |
| XXXVIII-283 | NCOMe | H | H | N | CH | N | CH |
| XXXVIII-284 | CH$_2$ | Me | H | N | CH | N | CH |
| XXXVIII-285 | O | Me | H | N | CH | N | CH |
| XXXVIII-286 | CHMe | Me | H | N | CH | N | CH |
| XXXVIII-287 | CH$_2$ | =O | | N | CH | N | CH |
| XXXVIII-288 | CH$_2$ | =CH$_2$ | | N | CH | N | CH |
| XXXVIII-289 | CH$_2$ | =CHMe | | N | CH | N | CH |
| XXXVIII-290 | CH$_2$ | H | H | N | CH | N | CF |
| XXXVIII-291 | CHMe | H | H | N | CH | N | CF |
| XXXVIII-292 | CHEt | H | H | N | CH | N | CF |
| XXXVIII-293 | CHF | H | H | N | CH | N | CF |
| XXXVIII-294 | C=CH$_2$ | H | H | N | CH | N | CF |
| XXXVIII-295 | O | H | H | N | CH | N | CF |
| XXXVIII-296 | S | H | H | N | CH | N | CF |
| XXXVIII-297 | NH | H | H | N | CH | N | CF |
| XXXVIII-298 | NMe | H | H | N | CH | N | CF |
| XXXVIII-299 | NCHO | H | H | N | CH | N | CF |
| XXXVIII-300 | NCOMe | H | H | N | CH | N | CF |
| XXXVIII-301 | CH$_2$ | Me | H | N | CH | N | CF |
| XXXVIII-302 | O | Me | H | N | CH | N | CF |
| XXXVIII-303 | CHMe | Me | H | N | CH | N | CF |
| XXXVIII-304 | CH$_2$ | =O | | N | CH | N | CF |
| XXXVIII-305 | CH$_2$ | =CH$_2$ | | N | CH | N | CF |
| XXXVIII-306 | CH$_2$ | =CHMe | | N | CH | N | CF |
| XXXVIII-307 | CH$_2$ | H | H | N | N | CH | CH |
| XXXVIII-308 | CHMe | H | H | N | N | CH | CH |
| XXXVIII-309 | CHEt | H | H | N | N | CH | CH |
| XXXVIII-310 | CHF | H | H | N | N | CH | CH |
| XXXVIII-311 | C=CH$_2$ | H | H | N | N | CH | CH |
| XXXVIII-312 | O | H | H | N | N | CH | CH |

TABLE 5-continued

| Compound No | Y | R1 | R2 | Ta | Tb | Tc | Td |
|---|---|---|---|---|---|---|---|
| XXXVIII-313 | S | H | H | N | N | CH | CH |
| XXXVIII-314 | NH | H | H | N | N | CH | CH |
| XXXVIII-315 | NMe | H | H | N | N | CH | CH |
| XXXVIII-316 | NCHO | H | H | N | N | CH | CH |
| XXXVIII-317 | NCOMe | H | H | N | N | CH | CH |
| XXXVIII-318 | CH$_2$ | Me | H | N | N | CH | CH |
| XXXVIII-319 | O | Me | H | N | N | CH | CH |
| XXXVIII-320 | CHMe | Me | H | N | N | CH | CH |
| XXXVIII-321 | CH$_2$ | =O | | N | N | CH | CH |
| XXXVIII-322 | CH$_2$ | =CH$_2$ | | N | N | CH | CH |
| XXXVIII-323 | CH$_2$ | =CHMe | | N | N | CH | CH |
| XXXVIII-324 | CH$_2$ | H | H | N | N | CF | CH |
| XXXVIII-325 | CHMe | H | H | N | N | CF | CH |
| XXXVIII-326 | CHEt | H | H | N | N | CF | CH |
| XXXVIII-327 | CHF | H | H | N | N | CF | CH |
| XXXVIII-328 | C=CH$_2$ | H | H | N | N | CF | CH |
| XXXVIII-329 | O | H | H | N | N | CF | CH |
| XXXVIII-330 | S | H | H | N | N | CF | CH |
| XXXVIII-331 | NH | H | H | N | N | CF | CH |
| XXXVIII-332 | NMe | H | H | N | N | CF | CH |
| XXXVIII-333 | NCHO | H | H | N | N | CF | CH |
| XXXVIII-334 | NCOMe | H | H | N | N | CF | CH |
| XXXVIII-335 | CH$_2$ | Me | H | N | N | CF | CH |
| XXXVIII-336 | O | Me | H | N | N | CF | CH |
| XXXVIII-337 | CHMe | Me | H | N | N | CF | CH |
| XXXVIII-338 | CH$_2$ | =O | | N | N | CF | CH |
| XXXVIII-339 | CH$_2$ | =CH$_2$ | | N | N | CF | CH |
| XXXVIII-340 | CH$_2$ | =CHMe | | N | N | CF | CH |
| XXXVIII-341 | CH$_2$ | H | H | N | N | CH | CF |
| XXXVIII-342 | CHMe | H | H | N | N | CH | CF |
| XXXVIII-343 | CHEt | H | H | N | N | CH | CF |
| XXXVIII-344 | CHF | H | H | N | N | CH | CF |
| XXXVIII-345 | C=CH$_2$ | H | H | N | N | CH | CF |
| XXXVIII-346 | O | H | H | N | N | CH | CF |
| XXXVIII-347 | S | H | H | N | N | CH | CF |
| XXXVIII-348 | NH | H | H | N | N | CH | CF |
| XXXVIII-349 | NMe | H | H | N | N | CH | CF |
| XXXVIII-350 | NCHO | H | H | N | N | CH | CF |
| XXXVIII-351 | NCOMe | H | H | N | N | CH | CF |
| XXXVIII-352 | CH$_2$ | Me | H | N | N | CH | CF |
| XXXVIII-353 | O | Me | H | N | N | CH | CF |
| XXXVIII-354 | CHMe | Me | H | N | N | CH | CF |
| XXXVIII-355 | CH$_2$ | =O | | N | N | CH | CF |
| XXXVIII-356 | CH$_2$ | =CH$_2$ | | N | N | CH | CF |
| XXXVIII-357 | CH$_2$ | =CHMe | | N | N | CH | CF |
| XXXVIII-358 | CH$_2$ | H | H | N | CH | CH | N |
| XXXVIII-359 | CHMe | H | H | N | CH | CH | N |
| XXXVIII-360 | CHEt | H | H | N | CH | CH | N |
| XXXVIII-361 | CHF | H | H | N | CH | CH | N |
| XXXVIII-362 | C=CH$_2$ | H | H | N | CH | CH | N |
| XXXVIII-363 | O | H | H | N | CH | CH | N |
| XXXVIII-364 | S | H | H | N | CH | CH | N |
| XXXVIII-365 | NH | H | H | N | CH | CH | N |
| XXXVIII-366 | NMe | H | H | N | CH | CH | N |
| XXXVIII-367 | NCHO | H | H | N | CH | CH | N |
| XXXVIII-368 | NCOMe | H | H | N | CH | CH | N |
| XXXVIII-369 | CH$_2$ | Me | H | N | CH | CH | N |
| XXXVIII-370 | O | Me | H | N | CH | CH | N |
| XXXVIII-371 | CHMe | Me | H | N | CH | CH | N |
| XXXVIII-372 | CH$_2$ | =O | | N | CH | CH | N |
| XXXVIII-373 | CH$_2$ | =CH$_2$ | | N | CH | CH | N |
| XXXVIII-374 | CH$_2$ | =CHMe | | N | CH | CH | N |
| XXXVIII-375 | CH$_2$ | H | H | CH | N | CH | N |
| XXXVIII-376 | CHMe | H | H | CH | N | CH | N |
| XXXVIII-377 | CHEt | H | H | CH | N | CH | N |
| XXXVIII-378 | CHF | H | H | CH | N | CH | N |
| XXXVIII-379 | C=CH$_2$ | H | H | CH | N | CH | N |
| XXXVIII-380 | O | H | H | CH | N | CH | N |
| XXXVIII-381 | S | H | H | CH | N | CH | N |
| XXXVIII-382 | NH | H | H | CH | N | CH | N |
| XXXVIII-383 | NMe | H | H | CH | N | CH | N |
| XXXVIII-384 | NCHO | H | H | CH | N | CH | N |
| XXXVIII-385 | NCOMe | H | H | CH | N | CH | N |
| XXXVIII-386 | CH$_2$ | Me | H | CH | N | CH | N |
| XXXVIII-387 | O | Me | H | CH | N | CH | N |
| XXXVIII-388 | CHMe | Me | H | CH | N | CH | N |
| XXXVIII-389 | CH$_2$ | =O | | CH | N | CH | N |
| XXXVIII-390 | CH$_2$ | =CH$_2$ | | CH | N | CH | N |
| XXXVIII-391 | CH$_2$ | =CHMe | | CH | N | CH | N |

Table XXXIX provides 578 compounds of formula Iam

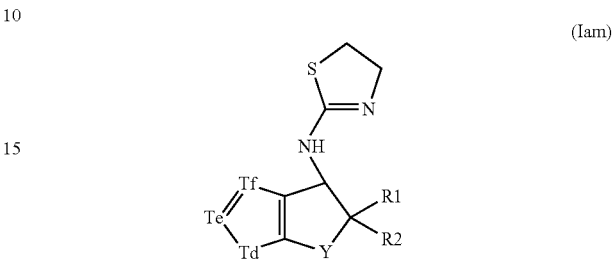

(Iam)

wherein the values of Y, $R^1$, $R^2$, $T^d$, $T^e$ and $T^f$ are given in Table 6.

TABLE 6

| Compound No | Y | R1 | R2 | Td | Te | Tf |
|---|---|---|---|---|---|---|
| XXXIX-1 | CH$_2$ | H | H | NH | CH | CH |
| XXXIX-2 | CHMe | H | H | NH | CH | CH |
| XXXIX-3 | CHEt | H | H | NH | CH | CH |
| XXXIX-4 | CHF | H | H | NH | CH | CH |
| XXXIX-5 | C=CH$_2$ | H | H | NH | CH | CH |
| XXXIX-6 | O | H | H | NH | CH | CH |
| XXXIX-7 | S | H | H | NH | CH | CH |
| XXXIX-8 | NH | H | H | NH | CH | CH |
| XXXIX-9 | NMe | H | H | NH | CH | CH |
| XXXIX-10 | NCHO | H | H | NH | CH | CH |
| XXXIX-11 | NCOMe | H | H | NH | CH | CH |
| XXXIX-12 | CH$_2$ | Me | H | NH | CH | CH |
| XXXIX-13 | O | Me | H | NH | CH | CH |
| XXXIX-14 | CHMe | Me | H | NH | CH | CH |
| XXXIX-15 | CH$_2$ | =O | | NH | CH | CH |
| XXXIX-16 | CH$_2$ | =CH$_2$ | | NH | CH | CH |
| XXXIX-17 | CH$_2$ | =CHMe | | NH | CH | CH |
| XXXIX-18 | CH$_2$ | H | H | NH | CF | CH |
| XXXIX-19 | CHMe | H | H | NH | CF | CH |
| XXXIX-20 | CHEt | H | H | NH | CF | CH |
| XXXIX-21 | CHF | H | H | NH | CF | CH |
| XXXIX-22 | C=CH$_2$ | H | H | NH | CF | CH |
| XXXIX-23 | O | H | H | NH | CF | CH |
| XXXIX-24 | S | H | H | NH | CF | CH |
| XXXIX-25 | NH | H | H | NH | CF | CH |
| XXXIX-26 | NMe | H | H | NH | CF | CH |
| XXXIX-27 | NCHO | H | H | NH | CF | CH |
| XXXIX-28 | NCOMe | H | H | NH | CF | CH |
| XXXIX-29 | CH$_2$ | Me | H | NH | CF | CH |
| XXXIX-30 | O | Me | H | NH | CF | CH |
| XXXIX-31 | CHMe | Me | H | NH | CF | CH |
| XXXIX-32 | CH$_2$ | =O | | NH | CF | CH |
| XXXIX-33 | CH$_2$ | =CH$_2$ | | NH | CF | CH |
| XXXIX-34 | CH$_2$ | =CHMe | | NH | CF | CH |
| XXXIX-35 | CH$_2$ | H | H | NH | CMe | CH |
| XXXIX-36 | CHMe | H | H | NH | CMe | CH |
| XXXIX-37 | CHEt | H | H | NH | CMe | CH |
| XXXIX-38 | CHF | H | H | NH | CMe | CH |
| XXXIX-39 | C=CH$_2$ | H | H | NH | CMe | CH |
| XXXIX-40 | O | H | H | NH | CMe | CH |
| XXXIX-41 | S | H | H | NH | CMe | CH |
| XXXIX-42 | NH | H | H | NH | CMe | CH |
| XXXIX-43 | NMe | H | H | NH | CMe | CH |
| XXXIX-44 | NCHO | H | H | NH | CMe | CH |
| XXXIX-45 | NCOMe | H | H | NH | CMe | CH |
| XXXIX-46 | CH$_2$ | Me | H | NH | CMe | CH |
| XXXIX-47 | O | Me | H | NH | CMe | CH |
| XXXIX-48 | CHMe | Me | H | NH | CMe | CH |
| XXXIX-49 | CH$_2$ | =O | | NH | CMe | CH |

TABLE 6-continued

| Compound No | Y | R1 | R2 | Td | Te | Tf |
|---|---|---|---|---|---|---|
| XXXIX-50 | CH$_2$ | | =CH$_2$ | NH | CMe | CH |
| XXXIX-51 | CH$_2$ | | =CHMe | NH | CMe | CH |
| XXXIX-52 | CH$_2$ | H | H | NH | CH | CMe |
| XXXIX-53 | CHMe | H | H | NH | CH | CMe |
| XXXIX-54 | CHEt | H | H | NH | CH | CMe |
| XXXIX-55 | CHF | H | H | NH | CH | CMe |
| XXXIX-56 | C=CH$_2$ | H | H | NH | CH | CMe |
| XXXIX-57 | O | H | H | NH | CH | CMe |
| XXXIX-58 | S | H | H | NH | CH | CMe |
| XXXIX-59 | NH | H | H | NH | CH | CMe |
| XXXIX-60 | NMe | H | H | NH | CH | CMe |
| XXXIX-61 | NCHO | H | H | NH | CH | CMe |
| XXXIX-62 | NCOMe | H | H | NH | CH | CMe |
| XXXIX-63 | CH$_2$ | Me | H | NH | CH | CMe |
| XXXIX-64 | O | Me | H | NH | CH | CMe |
| XXXIX-65 | CHMe | Me | H | NH | CH | CMe |
| XXXIX-66 | CH$_2$ | | =O | NH | CH | CMe |
| XXXIX-67 | CH$_2$ | | =CH$_2$ | NH | CH | CMe |
| XXXIX-68 | CH$_2$ | | =CHMe | NH | CH | CMe |
| XXXIX-69 | CH$_2$ | H | H | NMe | CH | CH |
| XXXIX-70 | CHMe | H | H | NMe | CH | CH |
| XXXIX-71 | CHEt | H | H | NMe | CH | CH |
| XXXIX-72 | CHF | H | H | NMe | CH | CH |
| XXXIX-73 | C=CH$_2$ | H | H | NMe | CH | CH |
| XXXIX-74 | O | H | H | NMe | CH | CH |
| XXXIX-75 | S | H | H | NMe | CH | CH |
| XXXIX-76 | NH | H | H | NMe | CH | CH |
| XXXIX-77 | NMe | H | H | NMe | CH | CH |
| XXXIX-78 | NCHO | H | H | NMe | CH | CH |
| XXXIX-79 | NCOMe | H | H | NMe | CH | CH |
| XXXIX-80 | CH$_2$ | Me | H | NMe | CH | CH |
| XXXIX-81 | O | Me | H | NMe | CH | CH |
| XXXIX-82 | CHMe | Me | H | NMe | CH | CH |
| XXXIX-83 | CH$_2$ | | =O | NMe | CH | CH |
| XXXIX-84 | CH$_2$ | | =CH$_2$ | NMe | CH | CH |
| XXXIX-85 | CH$_2$ | | =CHMe | NMe | CH | CH |
| XXXIX-86 | CH$_2$ | H | H | NMe | CF | CH |
| XXXIX-87 | CHMe | H | H | NMe | CF | CH |
| XXXIX-88 | CHEt | H | H | NMe | CF | CH |
| XXXIX-89 | CHF | H | H | NMe | CF | CH |
| XXXIX-90 | C=CH$_2$ | H | H | NMe | CF | CH |
| XXXIX-91 | O | H | H | NMe | CF | CH |
| XXXIX-92 | S | H | H | NMe | CF | CH |
| XXXIX-93 | NH | H | H | NMe | CF | CH |
| XXXIX-94 | NMe | H | H | NMe | CF | CH |
| XXXIX-95 | NCHO | H | H | NMe | CF | CH |
| XXXIX-96 | NCOMe | H | H | NMe | CF | CH |
| XXXIX-97 | CH$_2$ | Me | H | NMe | CF | CH |
| XXXIX-98 | O | Me | H | NMe | CF | CH |
| XXXIX-99 | CHMe | Me | H | NMe | CF | CH |
| XXXIX-100 | CH$_2$ | | =O | NMe | CF | CH |
| XXXIX-101 | CH$_2$ | | =CH$_2$ | NMe | CF | CH |
| XXXIX-102 | CH$_2$ | | =CHMe | NMe | CF | CH |
| XXXIX-103 | CH$_2$ | H | H | NMe | CMe | CH |
| XXXIX-104 | CHMe | H | H | NMe | CMe | CH |
| XXXIX-105 | CHEt | H | H | NMe | CMe | CH |
| XXXIX-106 | CHF | H | H | NMe | CMe | CH |
| XXXIX-107 | C=CH$_2$ | H | H | NMe | CMe | CH |
| XXXIX-108 | O | H | H | NMe | CMe | CH |
| XXXIX-109 | S | H | H | NMe | CMe | CH |
| XXXIX-110 | NH | H | H | NMe | CMe | CH |
| XXXIX-111 | NMe | H | H | NMe | CMe | CH |
| XXXIX-112 | NCHO | H | H | NMe | CMe | CH |
| XXXIX-113 | NCOMe | H | H | NMe | CMe | CH |
| XXXIX-114 | CH$_2$ | Me | H | NMe | CMe | CH |
| XXXIX-115 | O | Me | H | NMe | CMe | CH |
| XXXIX-116 | CHMe | Me | H | NMe | CMe | CH |
| XXXIX-117 | CH$_2$ | | =O | NMe | CMe | CH |
| XXXIX-118 | CH$_2$ | | =CH$_2$ | NMe | CMe | CH |
| XXXIX-119 | CH$_2$ | | =CHMe | NMe | CMe | CH |
| XXXIX-120 | CH$_2$ | H | H | NMe | CH | CMe |
| XXXIX-121 | CHMe | H | H | NMe | CH | CMe |
| XXXIX-122 | CHEt | H | H | NMe | CH | CMe |
| XXXIX-123 | CHF | H | H | NMe | CH | CMe |
| XXXIX-124 | C=CH$_2$ | H | H | NMe | CH | CMe |
| XXXIX-125 | O | H | H | NMe | CH | CMe |
| XXXIX-126 | S | H | H | NMe | CH | CMe |
| XXXIX-127 | NH | H | H | NMe | CH | CMe |
| XXXIX-128 | NMe | H | H | NMe | CH | CMe |
| XXXIX-129 | NCHO | H | H | NMe | CH | CMe |
| XXXIX-130 | NCOMe | H | H | NMe | CH | CMe |
| XXXIX-131 | CH$_2$ | Me | H | NMe | CH | CMe |
| XXXIX-132 | O | Me | H | NMe | CH | CMe |
| XXXIX-133 | CHMe | Me | H | NMe | CH | CMe |
| XXXIX-134 | CH$_2$ | | =O | NMe | CH | CMe |
| XXXIX-135 | CH$_2$ | | =CH$_2$ | NMe | CH | CMe |
| XXXIX-136 | CH$_2$ | | =CHMe | NMe | CH | CMe |
| XXXIX-137 | CH$_2$ | H | H | O | CH | CH |
| XXXIX-138 | CHMe | H | H | O | CH | CH |
| XXXIX-139 | CHEt | H | H | O | CH | CH |
| XXXIX-140 | CHF | H | H | O | CH | CH |
| XXXIX-141 | C=CH$_2$ | H | H | O | CH | CH |
| XXXIX-142 | O | H | H | O | CH | CH |
| XXXIX-143 | S | H | H | O | CH | CH |
| XXXIX-144 | NH | H | H | O | CH | CH |
| XXXIX-145 | NMe | H | H | O | CH | CH |
| XXXIX-146 | NCHO | H | H | O | CH | CH |
| XXXIX-147 | NCOMe | H | H | O | CH | CH |
| XXXIX-148 | CH$_2$ | Me | H | O | CH | CH |
| XXXIX-149 | O | Me | H | O | CH | CH |
| XXXIX-150 | CHMe | Me | H | O | CH | CH |
| XXXIX-151 | CH$_2$ | | =O | O | CH | CH |
| XXXIX-152 | CH$_2$ | | =CH$_2$ | O | CH | CH |
| XXXIX-153 | CH$_2$ | | =CHMe | O | CH | CH |
| XXXIX-154 | CH$_2$ | H | H | O | CF | CH |
| XXXIX-155 | CHMe | H | H | O | CF | CH |
| XXXIX-156 | CHEt | H | H | O | CF | CH |
| XXXIX-157 | CHF | H | H | O | CF | CH |
| XXXIX-158 | C=CH$_2$ | H | H | O | CF | CH |
| XXXIX-159 | O | H | H | O | CF | CH |
| XXXIX-160 | S | H | H | O | CF | CH |
| XXXIX-161 | NH | H | H | O | CF | CH |
| XXXIX-162 | NMe | H | H | O | CF | CH |
| XXXIX-163 | NCHO | H | H | O | CF | CH |
| XXXIX-164 | NCOMe | H | H | O | CF | CH |
| XXXIX-165 | CH$_2$ | Me | H | O | CF | CH |
| XXXIX-166 | O | Me | H | O | CF | CH |
| XXXIX-167 | CHMe | Me | H | O | CF | CH |
| XXXIX-168 | CH$_2$ | | =O | O | CF | CH |
| XXXIX-169 | CH$_2$ | | =CH$_2$ | O | CF | CH |
| XXXIX-170 | CH$_2$ | | =CHMe | O | CF | CH |
| XXXIX-171 | CH$_2$ | H | H | O | CMe | CH |
| XXXIX-172 | CHMe | H | H | O | CMe | CH |
| XXXIX-173 | CHEt | H | H | O | CMe | CH |
| XXXIX-174 | CHF | H | H | O | CMe | CH |
| XXXIX-175 | C=CH$_2$ | H | H | O | CMe | CH |
| XXXIX-176 | O | H | H | O | CMe | CH |
| XXXIX-177 | S | H | H | O | CMe | CH |
| XXXIX-178 | NH | H | H | O | CMe | CH |
| XXXIX-179 | NMe | H | H | O | CMe | CH |
| XXXIX-180 | NCHO | H | H | O | CMe | CH |
| XXXIX-181 | NCOMe | H | H | O | CMe | CH |
| XXXIX-182 | CH$_2$ | Me | H | O | CMe | CH |
| XXXIX-183 | O | Me | H | O | CMe | CH |
| XXXIX-184 | CHMe | Me | H | O | CMe | CH |
| XXXIX-185 | CH$_2$ | | =O | O | CMe | CH |
| XXXIX-186 | CH$_2$ | | =CH$_2$ | O | CMe | CH |
| XXXIX-187 | CH$_2$ | | =CHMe | O | CMe | CH |
| XXXIX-188 | CH$_2$ | H | H | O | CH | CMe |
| XXXIX-189 | CHMe | H | H | O | CH | CMe |
| XXXIX-190 | CHEt | H | H | O | CH | CMe |
| XXXIX-191 | CHF | H | H | O | CH | CMe |
| XXXIX-192 | C=CH$_2$ | H | H | O | CH | CMe |
| XXXIX-193 | O | H | H | O | CH | CMe |
| XXXIX-194 | S | H | H | O | CH | CMe |
| XXXIX-195 | NH | H | H | O | CH | CMe |
| XXXIX-196 | NMe | H | H | O | CH | CMe |
| XXXIX-197 | NCHO | H | H | O | CH | CMe |
| XXXIX-198 | NCOMe | H | H | O | CH | CMe |
| XXXIX-199 | CH$_2$ | Me | H | O | CH | CMe |
| XXXIX-200 | O | Me | H | O | CH | CMe |
| XXXIX-201 | CHMe | Me | H | O | CH | CMe |
| XXXIX-202 | CH$_2$ | | =O | O | CH | CMe |
| XXXIX-203 | CH$_2$ | | =CH$_2$ | O | CH | CMe |
| XXXIX-204 | CH$_2$ | | =CHMe | O | CH | CMe |
| XXXIX-205 | CH$_2$ | H | H | S | CH | CH |

TABLE 6-continued

| Compound No | Y | R1 | R2 | Td | Te | Tf |
|---|---|---|---|---|---|---|
| XXXIX-206 | CHMe | H | H | S | CH | CH |
| XXXIX-207 | CHEt | H | H | S | CH | CH |
| XXXIX-208 | CHF | H | H | S | CH | CH |
| XXXIX-209 | C=CH$_2$ | H | H | S | CH | CH |
| XXXIX-210 | O | H | H | S | CH | CH |
| XXXIX-211 | S | H | H | S | CH | CH |
| XXXIX-212 | NH | H | H | S | CH | CH |
| XXXIX-213 | NMe | H | H | S | CH | CH |
| XXXIX-214 | NCHO | H | H | S | CH | CH |
| XXXIX-215 | NCOMe | H | H | S | CH | CH |
| XXXIX-216 | CH$_2$ | Me | H | S | CH | CH |
| XXXIX-217 | O | Me | H | S | CH | CH |
| XXXIX-218 | CHMe | Me | H | S | CH | CH |
| XXXIX-219 | CH$_2$ | =O | | S | CH | CH |
| XXXIX-220 | CH$_2$ | =CH$_2$ | | S | CH | CH |
| XXXIX-221 | CH$_2$ | =CHMe | | S | CH | CH |
| XXXIX-222 | CH$_2$ | H | H | S | CF | CH |
| XXXIX-223 | CHMe | H | H | S | CF | CH |
| XXXIX-224 | CHEt | H | H | S | CF | CH |
| XXXIX-225 | CHF | H | H | S | CF | CH |
| XXXIX-226 | C=CH$_2$ | H | H | S | CF | CH |
| XXXIX-227 | O | H | H | S | CF | CH |
| XXXIX-228 | S | H | H | S | CF | CH |
| XXXIX-229 | NH | H | H | S | CF | CH |
| XXXIX-230 | NMe | H | H | S | CF | CH |
| XXXIX-231 | NCHO | H | H | S | CF | CH |
| XXXIX-232 | NCOMe | H | H | S | CF | CH |
| XXXIX-233 | CH$_2$ | Me | H | S | CF | CH |
| XXXIX-234 | O | Me | H | S | CF | CH |
| XXXIX-235 | CHMe | Me | H | S | CF | CH |
| XXXIX-236 | CH$_2$ | =O | | S | CF | CH |
| XXXIX-237 | CH$_2$ | =CH$_2$ | | S | CF | CH |
| XXXIX-238 | CH$_2$ | =CHMe | | S | CF | CH |
| XXXIX-239 | CH$_2$ | H | H | S | CMe | CH |
| XXXIX-240 | CHMe | H | H | S | CMe | CH |
| XXXIX-241 | CHEt | H | H | S | CMe | CH |
| XXXIX-242 | CHF | H | H | S | CMe | CH |
| XXXIX-243 | C=CH$_2$ | H | H | S | CMe | CH |
| XXXIX-244 | O | H | H | S | CMe | CH |
| XXXIX-245 | S | H | H | S | CMe | CH |
| XXXIX-246 | NH | H | H | S | CMe | CH |
| XXXIX-247 | NMe | H | H | S | CMe | CH |
| XXXIX-248 | NCHO | H | H | S | CMe | CH |
| XXXIX-249 | NCOMe | H | H | S | CMe | CH |
| XXXIX-250 | CH$_2$ | Me | H | S | CMe | CH |
| XXXIX-251 | O | Me | H | S | CMe | CH |
| XXXIX-252 | CHMe | Me | H | S | CMe | CH |
| XXXIX-253 | CH$_2$ | =O | | S | CMe | CH |
| XXXIX-254 | CH$_2$ | =CH$_2$ | | S | CMe | CH |
| XXXIX-255 | CH$_2$ | =CHMe | | S | CMe | CH |
| XXXIX-256 | CH$_2$ | H | H | S | CH | CMe |
| XXXIX-257 | CHMe | H | H | S | CH | CMe |
| XXXIX-258 | CHEt | H | H | S | CH | CMe |
| XXXIX-259 | CHF | H | H | S | CH | CMe |
| XXXIX-260 | C=CH$_2$ | H | H | S | CH | CMe |
| XXXIX-261 | O | H | H | S | CH | CMe |
| XXXIX-262 | S | H | H | S | CH | CMe |
| XXXIX-263 | NH | H | H | S | CH | CMe |
| XXXIX-264 | NMe | H | H | S | CH | CMe |
| XXXIX-265 | NCHO | H | H | S | CH | CMe |
| XXXIX-266 | NCOMe | H | H | S | CH | CMe |
| XXXIX-267 | CH$_2$ | Me | H | S | CH | CMe |
| XXXIX-268 | O | Me | H | S | CH | CMe |
| XXXIX-269 | CHMe | Me | H | S | CH | CMe |
| XXXIX-270 | CH$_2$ | =O | | S | CH | CMe |
| XXXIX-271 | CH$_2$ | =CH$_2$ | | S | CH | CMe |
| XXXIX-272 | CH$_2$ | =CHMe | | S | CH | CMe |
| XXXIX-273 | CH$_2$ | H | H | NH | N | CH |
| XXXIX-274 | CHMe | H | H | NH | N | CH |
| XXXIX-275 | CHEt | H | H | NH | N | CH |
| XXXIX-276 | CHF | H | H | NH | N | CH |
| XXXIX-277 | C=CH$_2$ | H | H | NH | N | CH |
| XXXIX-278 | O | H | H | NH | N | CH |
| XXXIX-279 | S | H | H | NH | N | CH |
| XXXIX-280 | NH | H | H | NH | N | CH |
| XXXIX-281 | NMe | H | H | NH | N | CH |
| XXXIX-282 | NCHO | H | H | NH | N | CH |
| XXXIX-283 | NCOMe | H | H | NH | N | CH |
| XXXIX-284 | CH$_2$ | Me | H | NH | N | CH |
| XXXIX-285 | O | Me | H | NH | N | CH |
| XXXIX-286 | CHMe | Me | H | NH | N | CH |
| XXXIX-287 | CH$_2$ | =O | | NH | N | CH |
| XXXIX-288 | CH$_2$ | =CH$_2$ | | NH | N | CH |
| XXXIX-289 | CH$_2$ | =CHMe | | NH | N | CH |
| XXXIX-290 | CH$_2$ | H | H | NH | N | CMe |
| XXXIX-291 | CHMe | H | H | NH | N | CMe |
| XXXIX-292 | CHEt | H | H | NH | N | CMe |
| XXXIX-293 | CHF | H | H | NH | N | CMe |
| XXXIX-294 | C=CH$_2$ | H | H | NH | N | CMe |
| XXXIX-295 | O | H | H | NH | N | CMe |
| XXXIX-296 | S | H | H | NH | N | CMe |
| XXXIX-297 | NH | H | H | NH | N | CMe |
| XXXIX-298 | NMe | H | H | NH | N | CMe |
| XXXIX-299 | NCHO | H | H | NH | N | CMe |
| XXXIX-300 | NCOMe | H | H | NH | N | CMe |
| XXXIX-301 | CH$_2$ | Me | H | NH | N | CMe |
| XXXIX-302 | O | Me | H | NH | N | CMe |
| XXXIX-303 | CHMe | Me | H | NH | N | CMe |
| XXXIX-304 | CH$_2$ | =O | | NH | N | CMe |
| XXXIX-305 | CH$_2$ | =CH$_2$ | | NH | N | CMe |
| XXXIX-306 | CH$_2$ | =CHMe | | NH | N | CMe |
| XXXIX-307 | CH$_2$ | H | H | NMe | N | CH |
| XXXIX-308 | CHMe | H | H | NMe | N | CH |
| XXXIX-309 | CHEt | H | H | NMe | N | CH |
| XXXIX-310 | CHF | H | H | NMe | N | CH |
| XXXIX-311 | C=CH$_2$ | H | H | NMe | N | CH |
| XXXIX-312 | O | H | H | NMe | N | CH |
| XXXIX-313 | S | H | H | NMe | N | CH |
| XXXIX-314 | NH | H | H | NMe | N | CH |
| XXXIX-315 | NMe | H | H | NMe | N | CH |
| XXXIX-316 | NCHO | H | H | NMe | N | CH |
| XXXIX-317 | NCOMe | H | H | NMe | N | CH |
| XXXIX-318 | CH$_2$ | Me | H | NMe | N | CH |
| XXXIX-319 | O | Me | H | NMe | N | CH |
| XXXIX-320 | CHMe | Me | H | NMe | N | CH |
| XXXIX-321 | CH$_2$ | =O | | NMe | N | CH |
| XXXIX-322 | CH$_2$ | =CH$_2$ | | NMe | N | CH |
| XXXIX-323 | CH$_2$ | =CHMe | | NMe | N | CH |
| XXXIX-324 | CH$_2$ | H | H | NMe | N | CMe |
| XXXIX-325 | CHMe | H | H | NMe | N | CMe |
| XXXIX-326 | CHEt | H | H | NMe | N | CMe |
| XXXIX-327 | CHF | H | H | NMe | N | CMe |
| XXXIX-328 | C=CH$_2$ | H | H | NMe | N | CMe |
| XXXIX-329 | O | H | H | NMe | N | CMe |
| XXXIX-330 | S | H | H | NMe | N | CMe |
| XXXIX-331 | NH | H | H | NMe | N | CMe |
| XXXIX-332 | NMe | H | H | NMe | N | CMe |
| XXXIX-333 | NCHO | H | H | NMe | N | CMe |
| XXXIX-334 | NCOMe | H | H | NMe | N | CMe |
| XXXIX-335 | CH$_2$ | Me | H | NMe | N | CMe |
| XXXIX-336 | O | Me | H | NMe | N | CMe |
| XXXIX-337 | CHMe | Me | H | NMe | N | CMe |
| XXXIX-338 | CH$_2$ | =O | | NMe | N | CMe |
| XXXIX-339 | CH$_2$ | =CH$_2$ | | NMe | N | CMe |
| XXXIX-340 | CH$_2$ | =CHMe | | NMe | N | CMe |
| XXXIX-341 | CH$_2$ | H | H | O | N | CH |
| XXXIX-342 | CHMe | H | H | O | N | CH |
| XXXIX-343 | CHEt | H | H | O | N | CH |
| XXXIX-344 | CHF | H | H | O | N | CH |
| XXXIX-345 | C=CH$_2$ | H | H | O | N | CH |
| XXXIX-346 | O | H | H | O | N | CH |
| XXXIX-347 | S | H | H | O | N | CH |
| XXXIX-348 | NH | H | H | O | N | CH |
| XXXIX-349 | NMe | H | H | O | N | CH |
| XXXIX-350 | NCHO | H | H | O | N | CH |
| XXXIX-351 | NCOMe | H | H | O | N | CH |
| XXXIX-352 | CH$_2$ | Me | H | O | N | CH |
| XXXIX-353 | O | Me | H | O | N | CH |
| XXXIX-354 | CHMe | Me | H | O | N | CH |
| XXXIX-355 | CH$_2$ | =O | | O | N | CH |
| XXXIX-356 | CH$_2$ | =CH$_2$ | | O | N | CH |
| XXXIX-357 | CH$_2$ | =CHMe | | O | N | CH |
| XXXIX-358 | CH$_2$ | H | H | O | N | CMe |
| XXXIX-359 | CHMe | H | H | O | N | CMe |
| XXXIX-360 | CHEt | H | H | O | N | CMe |
| XXXIX-361 | CHF | H | H | O | N | CMe |

TABLE 6-continued

| Compound No | Y | R1 | R2 | Td | Te | Tf |
|---|---|---|---|---|---|---|
| XXXIX-362 | C=CH$_2$ | H | H | O | N | CMe |
| XXXIX-363 | O | H | H | O | N | CMe |
| XXXIX-364 | S | H | H | O | N | CMe |
| XXXIX-365 | NH | H | H | O | N | CMe |
| XXXIX-366 | NMe | H | H | O | N | CMe |
| XXXIX-367 | NCHO | H | H | O | N | CMe |
| XXXIX-368 | NCOMe | H | H | O | N | CMe |
| XXXIX-369 | CH$_2$ | Me | H | O | N | CMe |
| XXXIX-370 | O | Me | H | O | N | CMe |
| XXXIX-371 | CHMe | Me | H | O | N | CMe |
| XXXIX-372 | CH$_2$ | =O | | O | N | CMe |
| XXXIX-373 | CH$_2$ | =CH$_2$ | | O | N | CMe |
| XXXIX-374 | CH$_2$ | =CHMe | | O | N | CMe |
| XXXIX-375 | CH$_2$ | H | H | S | N | CH |
| XXXIX-376 | CHMe | H | H | S | N | CH |
| XXXIX-377 | CHEt | H | H | S | N | CH |
| XXXIX-378 | CHF | H | H | S | N | CH |
| XXXIX-379 | C=CH$_2$ | H | H | S | N | CH |
| XXXIX-380 | O | H | H | S | N | CH |
| XXXIX-381 | S | H | H | S | N | CH |
| XXXIX-382 | NH | H | H | S | N | CH |
| XXXIX-383 | NMe | H | H | S | N | CH |
| XXXIX-384 | NCHO | H | H | S | N | CH |
| XXXIX-385 | NCOMe | H | H | S | N | CH |
| XXXIX-386 | CH$_2$ | Me | H | S | N | CH |
| XXXIX-387 | O | Me | H | S | N | CH |
| XXXIX-388 | CHMe | Me | H | S | N | CH |
| XXXIX-389 | CH$_2$ | =O | | S | N | CH |
| XXXIX-390 | CH$_2$ | =CH$_2$ | | S | N | CH |
| XXXIX-391 | CH$_2$ | =CHMe | | S | N | CH |
| XXXIX-392 | CH$_2$ | H | H | S | N | CMe |
| XXXIX-393 | CHMe | H | H | S | N | CMe |
| XXXIX-394 | CHEt | H | H | S | N | CMe |
| XXXIX-395 | CHF | H | H | S | N | CMe |
| XXXIX-396 | C=CH$_2$ | H | H | S | N | CMe |
| XXXIX-397 | O | H | H | S | N | CMe |
| XXXIX-398 | S | H | H | S | N | CMe |
| XXXIX-399 | NH | H | H | S | N | CMe |
| XXXIX-400 | NMe | H | H | S | N | CMe |
| XXXIX-401 | NCHO | H | H | S | N | CMe |
| XXXIX-402 | NCOMe | H | H | S | N | CMe |
| XXXIX-403 | CH$_2$ | Me | H | S | N | CMe |
| XXXIX-404 | O | Me | H | S | N | CMe |
| XXXIX-405 | CHMe | Me | H | S | N | CMe |
| XXXIX-406 | CH$_2$ | =O | | S | N | CMe |
| XXXIX-407 | CH$_2$ | =CH$_2$ | | S | N | CMe |
| XXXIX-408 | CH$_2$ | =CHMe | | S | N | CMe |
| XXXIX-409 | CH$_2$ | H | H | NH | CH | N |
| XXXIX-410 | CHMe | H | H | NH | CH | N |
| XXXIX-411 | CHEt | H | H | NH | CH | N |
| XXXIX-412 | CHF | H | H | NH | CH | N |
| XXXIX-413 | C=CH$_2$ | H | H | NH | CH | N |
| XXXIX-414 | O | H | H | NH | CH | N |
| XXXIX-415 | S | H | H | NH | CH | N |
| XXXIX-416 | NH | H | H | NH | CH | N |
| XXXIX-417 | NMe | H | H | NH | CH | N |
| XXXIX-418 | NCHO | H | H | NH | CH | N |
| XXXIX-419 | NCOMe | H | H | NH | CH | N |
| XXXIX-420 | CH$_2$ | Me | H | NH | CH | N |
| XXXIX-421 | O | Me | H | NH | CH | N |
| XXXIX-422 | CHMe | Me | H | NH | CH | N |
| XXXIX-423 | CH$_2$ | =O | | NH | CH | N |
| XXXIX-424 | CH$_2$ | =CH$_2$ | | NH | CH | N |
| XXXIX-425 | CH$_2$ | =CHMe | | NH | CH | N |
| XXXIX-426 | CH$_2$ | H | H | NH | CMe | N |
| XXXIX-427 | CHMe | H | H | NH | CMe | N |
| XXXIX-428 | CHEt | H | H | NH | CMe | N |
| XXXIX-429 | CHF | H | H | NH | CMe | N |
| XXXIX-430 | C=CH$_2$ | H | H | NH | CMe | N |
| XXXIX-431 | O | H | H | NH | CMe | N |
| XXXIX-432 | S | H | H | NH | CMe | N |
| XXXIX-433 | NH | H | H | NH | CMe | N |
| XXXIX-434 | NMe | H | H | NH | CMe | N |
| XXXIX-435 | NCHO | H | H | NH | CMe | N |
| XXXIX-436 | NCOMe | H | H | NH | CMe | N |
| XXXIX-437 | CH$_2$ | Me | H | NH | CMe | N |
| XXXIX-438 | O | Me | H | NH | CMe | N |
| XXXIX-439 | CHMe | Me | H | NH | CMe | N |
| XXXIX-440 | CH$_2$ | =O | | NH | CMe | N |
| XXXIX-441 | CH$_2$ | =CH$_2$ | | NH | CMe | N |
| XXXIX-442 | CH$_2$ | =CHMe | | NH | CMe | N |
| XXXIX-443 | CH$_2$ | H | H | O | CH | N |
| XXXIX-444 | CHMe | H | H | O | CH | N |
| XXXIX-445 | CHEt | H | H | O | CH | N |
| XXXIX-446 | CHF | H | H | O | CH | N |
| XXXIX-447 | C=CH$_2$ | H | H | O | CH | N |
| XXXIX-448 | O | H | H | O | CH | N |
| XXXIX-449 | S | H | H | O | CH | N |
| XXXIX-450 | NH | H | H | O | CH | N |
| XXXIX-451 | NMe | H | H | O | CH | N |
| XXXIX-452 | NCHO | H | H | O | CH | N |
| XXXIX-453 | NCOMe | H | H | O | CH | N |
| XXXIX-454 | CH$_2$ | Me | H | O | CH | N |
| XXXIX-455 | O | Me | H | O | CH | N |
| XXXIX-456 | CHMe | Me | H | O | CH | N |
| XXXIX-457 | CH$_2$ | =O | | O | CH | N |
| XXXIX-458 | CH$_2$ | =CH$_2$ | | O | CH | N |
| XXXIX-459 | CH$_2$ | =CHMe | | O | CH | N |
| XXXIX-460 | CH$_2$ | H | H | O | CMe | N |
| XXXIX-461 | CHMe | H | H | O | CMe | N |
| XXXIX-462 | CHEt | H | H | O | CMe | N |
| XXXIX-463 | CHF | H | H | O | CMe | N |
| XXXIX-464 | C=CH$_2$ | H | H | O | CMe | N |
| XXXIX-465 | O | H | H | O | CMe | N |
| XXXIX-466 | S | H | H | O | CMe | N |
| XXXIX-467 | NH | H | H | O | CMe | N |
| XXXIX-468 | NMe | H | H | O | CMe | N |
| XXXIX-469 | NCHO | H | H | O | CMe | N |
| XXXIX-470 | NCOMe | H | H | O | CMe | N |
| XXXIX-471 | CH$_2$ | Me | H | O | CMe | N |
| XXXIX-472 | O | Me | H | O | CMe | N |
| XXXIX-473 | CHMe | Me | H | O | CMe | N |
| XXXIX-474 | CH$_2$ | =O | | O | CMe | N |
| XXXIX-475 | CH$_2$ | =CH$_2$ | | O | CMe | N |
| XXXIX-476 | CH$_2$ | =CHMe | | O | CMe | N |
| XXXIX-477 | CH$_2$ | H | H | S | CH | N |
| XXXIX-478 | CHMe | H | H | S | CH | N |
| XXXIX-479 | CHEt | H | H | S | CH | N |
| XXXIX-480 | CHF | H | H | S | CH | N |
| XXXIX-481 | C=CH$_2$ | H | H | S | CH | N |
| XXXIX-482 | O | H | H | S | CH | N |
| XXXIX-483 | S | H | H | S | CH | N |
| XXXIX-484 | NH | H | H | S | CH | N |
| XXXIX-485 | NMe | H | H | S | CH | N |
| XXXIX-486 | NCHO | H | H | S | CH | N |
| XXXIX-487 | NCOMe | H | H | S | CH | N |
| XXXIX-488 | CH$_2$ | Me | H | S | CH | N |
| XXXIX-489 | O | Me | H | S | CH | N |
| XXXIX-490 | CHMe | Me | H | S | CH | N |
| XXXIX-491 | CH$_2$ | =O | | S | CH | N |
| XXXIX-492 | CH$_2$ | =CH$_2$ | | S | CH | N |
| XXXIX-493 | CH$_2$ | =CHMe | | S | CH | N |
| XXXIX-494 | CH$_2$ | H | H | S | CMe | N |
| XXXIX-495 | CHMe | H | H | S | CMe | N |
| XXXIX-496 | CHEt | H | H | S | CMe | N |
| XXXIX-497 | CHF | H | H | S | CMe | N |
| XXXIX-498 | C=CH$_2$ | H | H | S | CMe | N |
| XXXIX-499 | O | H | H | S | CMe | N |
| XXXIX-500 | S | H | H | S | CMe | N |
| XXXIX-501 | NH | H | H | S | CMe | N |
| XXXIX-502 | NMe | H | H | S | CMe | N |
| XXXIX-503 | NCHO | H | H | S | CMe | N |
| XXXIX-504 | NCOMe | H | H | S | CMe | N |
| XXXIX-505 | CH$_2$ | Me | H | S | CMe | N |
| XXXIX-506 | O | Me | H | S | CMe | N |
| XXXIX-507 | CHMe | Me | H | S | CMe | N |
| XXXIX-508 | CH$_2$ | =O | | S | CMe | N |
| XXXIX-509 | CH$_2$ | =CH$_2$ | | S | CMe | N |
| XXXIX-510 | CH$_2$ | =CHMe | | S | CMe | N |
| XXXIX-511 | CH$_2$ | H | H | NH | N | N |
| XXXIX-512 | CHMe | H | H | NH | N | N |
| XXXIX-513 | CHEt | H | H | NH | N | N |
| XXXIX-514 | CHF | H | H | NH | N | N |
| XXXIX-515 | C=CH$_2$ | H | H | NH | N | N |
| XXXIX-516 | O | H | H | NH | N | N |
| XXXIX-517 | S | H | H | NH | N | N |

TABLE 6-continued

| Compound No | Y | R1 | R2 | Td | Te | Tf |
|---|---|---|---|---|---|---|
| XXXIX-518 | NH | H | H | NH | N | N |
| XXXIX-519 | NMe | H | H | NH | N | N |
| XXXIX-520 | NCHO | H | H | NH | N | N |
| XXXIX-521 | NCOMe | H | H | NH | N | N |
| XXXIX-522 | $CH_2$ | Me | H | NH | N | N |
| XXXIX-523 | O | Me | H | NH | N | N |
| XXXIX-524 | CHMe | Me | H | NH | N | N |
| XXXIX-525 | $CH_2$ | =O | | NH | N | N |
| XXXIX-526 | $CH_2$ | =$CH_2$ | | NH | N | N |
| XXXIX-527 | $CH_2$ | =CHMe | | NH | N | N |
| XXXIX-528 | $CH_2$ | H | H | NMe | N | N |
| XXXIX-529 | CHMe | H | H | NMe | N | N |
| XXXIX-530 | CHEt | H | H | NMe | N | N |
| XXXIX-531 | CHF | H | H | NMe | N | N |
| XXXIX-532 | C=$CH_2$ | H | H | NMe | N | N |
| XXXIX-533 | O | H | H | NMe | N | N |
| XXXIX-534 | S | H | H | NMe | N | N |
| XXXIX-535 | NH | H | H | NMe | N | N |
| XXXIX-536 | NMe | H | H | NMe | N | N |
| XXXIX-537 | NCHO | H | H | NMe | N | N |
| XXXIX-538 | NCOMe | H | H | NMe | N | N |
| XXXIX-539 | $CH_2$ | Me | H | NMe | N | N |
| XXXIX-540 | O | Me | H | NMe | N | N |
| XXXIX-541 | CHMe | Me | H | NMe | N | N |
| XXXIX-542 | $CH_2$ | =O | | NMe | N | N |
| XXXIX-543 | $CH_2$ | =$CH_2$ | | NMe | N | N |
| XXXIX-544 | $CH_2$ | =CHMe | | NMe | N | N |
| XXXIX-545 | $CH_2$ | H | H | O | N | N |
| XXXIX-546 | CHMe | H | H | O | N | N |
| XXXIX-547 | CHEt | H | H | O | N | N |
| XXXIX-548 | CHF | H | H | O | N | N |
| XXXIX-549 | C=$CH_2$ | H | H | O | N | N |
| XXXIX-550 | O | H | H | O | N | N |
| XXXIX-551 | S | H | H | O | N | N |
| XXXIX-552 | NH | H | H | O | N | N |
| XXXIX-553 | NMe | H | H | O | N | N |
| XXXIX-554 | NCHO | H | H | O | N | N |
| XXXIX-555 | NCOMe | H | H | O | N | N |
| XXXIX-556 | $CH_2$ | Me | H | O | N | N |
| XXXIX-557 | O | Me | H | O | N | N |
| XXXIX-558 | CHMe | Me | H | O | N | N |
| XXXIX-559 | $CH_2$ | =O | | O | N | N |
| XXXIX-560 | $CH_2$ | =$CH_2$ | | O | N | N |
| XXXIX-561 | $CH_2$ | =CHMe | | O | N | N |
| XXXIX-562 | $CH_2$ | H | H | S | N | N |
| XXXIX-563 | CHMe | H | H | S | N | N |
| XXXIX-564 | CHEt | H | H | S | N | N |
| XXXIX-565 | CHF | H | H | S | N | N |
| XXXIX-566 | C=$CH_2$ | H | H | S | N | N |
| XXXIX-567 | O | H | H | S | N | N |
| XXXIX-568 | S | H | H | S | N | N |
| XXXIX-569 | NH | H | H | S | N | N |
| XXXIX-570 | NMe | H | H | S | N | N |
| XXXIX-571 | NCHO | H | H | S | N | N |
| XXXIX-572 | NCOMe | H | H | S | N | N |
| XXXIX-573 | $CH_2$ | Me | H | S | N | N |
| XXXIX-574 | O | Me | H | S | N | N |
| XXXIX-575 | CHMe | Me | H | S | N | N |
| XXXIX-576 | $CH_2$ | =O | | S | N | N |
| XXXIX-577 | $CH_2$ | =$CH_2$ | | S | N | N |
| XXXIX-578 | $CH_2$ | =CHMe | | S | N | N |

Table XL provides 392 compounds of formula Ian

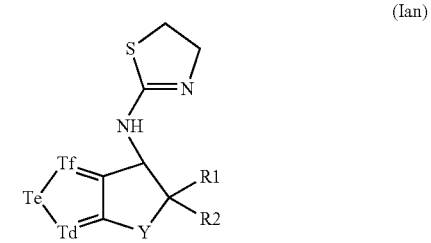

(Ian)

wherein the values of Y, $R^1$, $R_2$, $T^d$, $T^e$ and $T^f$ are given in Table 7.

TABLE 7

| Compound No | Y | R1 | R2 | Td | Te | Tf |
|---|---|---|---|---|---|---|
| XL-1 | $CH_2$ | H | H | CH | NH | CH |
| XL-2 | CHMe | H | H | CH | NH | CH |
| XL-3 | CHEt | H | H | CH | NH | CH |
| XL-4 | CHF | H | H | CH | NH | CH |
| XL-5 | C=$CH_2$ | H | H | CH | NH | CH |
| XL-6 | O | H | H | CH | NH | CH |
| XL-7 | S | H | H | CH | NH | CH |
| XL-8 | NH | H | H | CH | NH | CH |
| XL-9 | NMe | H | H | CH | NH | CH |
| XL-10 | NCHO | H | H | CH | NH | CH |
| XL-11 | NCOMe | H | H | CH | NH | CH |
| XL-12 | $CH_2$ | Me | H | CH | NH | CH |
| XL-13 | O | Me | H | CH | NH | CH |
| XL-14 | CHMe | Me | H | CH | NH | CH |
| XL-15 | $CH_2$ | H | H | CMe | NH | CH |
| XL-16 | CHMe | H | H | CMe | NH | CH |
| XL-17 | CHEt | H | H | CMe | NH | CH |
| XL-18 | CHF | H | H | CMe | NH | CH |
| XL-19 | C=$CH_2$ | H | H | CMe | NH | CH |
| XL-20 | O | H | H | CMe | NH | CH |
| XL-21 | S | H | H | CMe | NH | CH |
| XL-22 | NH | H | H | CMe | NH | CH |
| XL-23 | NMe | H | H | CMe | NH | CH |
| XL-24 | NCHO | H | H | CMe | NH | CH |
| XL-25 | NCOMe | H | H | CMe | NH | CH |
| XL-26 | $CH_2$ | Me | H | CMe | NH | CH |
| XL-27 | O | Me | H | CMe | NH | CH |
| XL-28 | CHMe | Me | H | CMe | NH | CH |
| XL-29 | $CH_2$ | H | H | CH | NH | CMe |
| XL-30 | CHMe | H | H | CH | NH | CMe |
| XL-31 | CHEt | H | H | CH | NH | CMe |
| XL-32 | CHF | H | H | CH | NH | CMe |
| XL-33 | C=$CH_2$ | H | H | CH | NH | CMe |
| XL-34 | O | H | H | CH | NH | CMe |
| XL-35 | S | H | H | CH | NH | CMe |
| XL-36 | NH | H | H | CH | NH | CMe |
| XL-37 | NMe | H | H | CH | NH | CMe |
| XL-38 | NCHO | H | H | CH | NH | CMe |
| XL-39 | NCOMe | H | H | CH | NH | CMe |
| XL-40 | $CH_2$ | Me | H | CH | NH | CMe |
| XL-41 | O | Me | H | CH | NH | CMe |
| XL-42 | CHMe | Me | H | CH | NH | CMe |
| XL-43 | $CH_2$ | H | H | CMe | NH | CMe |
| XL-44 | CHMe | H | H | CMe | NH | CMe |
| XL-45 | CHEt | H | H | CMe | NH | CMe |
| XL-46 | CHF | H | H | CMe | NH | CMe |
| XL-47 | C=$CH_2$ | H | H | CMe | NH | CMe |
| XL-48 | O | H | H | CMe | NH | CMe |
| XL-49 | S | H | H | CMe | NH | CMe |
| XL-50 | NH | H | H | CMe | NH | CMe |
| XL-51 | NMe | H | H | CMe | NH | CMe |
| XL-52 | NCHO | H | H | CMe | NH | CMe |
| XL-53 | NCOMe | H | H | CMe | NH | CMe |
| XL-54 | $CH_2$ | Me | H | CMe | NH | CMe |
| XL-55 | O | Me | H | CMe | NH | CMe |
| XL-56 | CHMe | Me | H | CMe | NH | CMe |
| XL-57 | $CH_2$ | H | H | CH | NMe | CH |

TABLE 7-continued

| Compound No | Y | R1 | R2 | Td | Te | Tf |
|---|---|---|---|---|---|---|
| XL-58 | CHMe | H | H | CH | NMe | CH |
| XL-59 | CHEt | H | H | CH | NMe | CH |
| XL-60 | CHF | H | H | CH | NMe | CH |
| XL-61 | C=CH$_2$ | H | H | CH | NMe | CH |
| XL-62 | O | H | H | CH | NMe | CH |
| XL-63 | S | H | H | CH | NMe | CH |
| XL-64 | NH | H | H | CH | NMe | CH |
| XL-65 | NMe | H | H | CH | NMe | CH |
| XL-66 | NCHO | H | H | CH | NMe | CH |
| XL-67 | NCOMe | H | H | CH | NMe | CH |
| XL-68 | CH$_2$ | Me | H | CH | NMe | CH |
| XL-69 | O | Me | H | CH | NMe | CH |
| XL-70 | CHMe | Me | H | CH | NMe | CH |
| XL-71 | CH$_2$ | H | H | CMe | NMe | CH |
| XL-72 | CHMe | H | H | CMe | NMe | CH |
| XL-73 | CHEt | H | H | CMe | NMe | CH |
| XL-74 | CHF | H | H | CMe | NMe | CH |
| XL-75 | C=CH$_2$ | H | H | CMe | NMe | CH |
| XL-76 | O | H | H | CMe | NMe | CH |
| XL-77 | S | H | H | CMe | NMe | CH |
| XL-78 | NH | H | H | CMe | NMe | CH |
| XL-79 | NMe | H | H | CMe | NMe | CH |
| XL-80 | NCHO | H | H | CMe | NMe | CH |
| XL-81 | NCOMe | H | H | CMe | NMe | CH |
| XL-82 | CH$_2$ | Me | H | CMe | NMe | CH |
| XL-83 | O | Me | H | CMe | NMe | CH |
| XL-84 | CHMe | Me | H | CMe | NMe | CH |
| XL-85 | CH$_2$ | H | H | CH | NMe | CMe |
| XL-86 | CHMe | H | H | CH | NMe | CMe |
| XL-87 | CHEt | H | H | CH | NMe | CMe |
| XL-88 | CHF | H | H | CH | NMe | CMe |
| XL-89 | C=CH$_2$ | H | H | CH | NMe | CMe |
| XL-90 | O | H | H | CH | NMe | CMe |
| XL-91 | S | H | H | CH | NMe | CMe |
| XL-92 | NH | H | H | CH | NMe | CMe |
| XL-93 | NMe | H | H | CH | NMe | CMe |
| XL-94 | NCHO | H | H | CH | NMe | CMe |
| XL-95 | NCOMe | H | H | CH | NMe | CMe |
| XL-96 | CH$_2$ | Me | H | CH | NMe | CMe |
| XL-97 | O | Me | H | CH | NMe | CMe |
| XL-98 | CHMe | Me | H | CH | NMe | CMe |
| XL-99 | CH$_2$ | H | H | CMe | NMe | CMe |
| XL-100 | CHMe | H | H | CMe | NMe | CMe |
| XL-101 | CHEt | H | H | CMe | NMe | CMe |
| XL-102 | CHF | H | H | CMe | NMe | CMe |
| XL-103 | C=CH$_2$ | H | H | CMe | NMe | CMe |
| XL-104 | O | H | H | CMe | NMe | CMe |
| XL-105 | S | H | H | CMe | NMe | CMe |
| XL-106 | NH | H | H | CMe | NMe | CMe |
| XL-107 | NMe | H | H | CMe | NMe | CMe |
| XL-108 | NCHO | H | H | CMe | NMe | CMe |
| XL-109 | NCOMe | H | H | CMe | NMe | CMe |
| XL-110 | CH$_2$ | Me | H | CMe | NMe | CMe |
| XL-111 | O | Me | H | CMe | NMe | CMe |
| XL-112 | CHMe | Me | H | CMe | NMe | CMe |
| XL-113 | CH$_2$ | H | H | CH | O | CH |
| XL-114 | CHMe | H | H | CH | O | CH |
| XL-115 | CHEt | H | H | CH | O | CH |
| XL-116 | CHF | H | H | CH | O | CH |
| XL-117 | C=CH$_2$ | H | H | CH | O | CH |
| XL-118 | O | H | H | CH | O | CH |
| XL-119 | S | H | H | CH | O | CH |
| XL-120 | NH | H | H | CH | O | CH |
| XL-121 | NMe | H | H | CH | O | CH |
| XL-122 | NCHO | H | H | CH | O | CH |
| XL-123 | NCOMe | H | H | CH | O | CH |
| XL-124 | CH$_2$ | Me | H | CH | O | CH |
| XL-125 | O | Me | H | CH | O | CH |
| XL-126 | CHMe | Me | H | CH | O | CH |
| XL-127 | CH$_2$ | H | H | CMe | O | CH |
| XL-128 | CHMe | H | H | CMe | O | CH |
| XL-129 | CHEt | H | H | CMe | O | CH |
| XL-130 | CHF | H | H | CMe | O | CH |
| XL-131 | C=CH$_2$ | H | H | CMe | O | CH |
| XL-132 | O | H | H | CMe | O | CH |
| XL-133 | S | H | H | CMe | O | CH |
| XL-134 | NH | H | H | CMe | O | CH |
| XL-135 | NMe | H | H | CMe | O | CH |
| XL-136 | NCHO | H | H | CMe | O | CH |
| XL-137 | NCOMe | H | H | CMe | O | CH |
| XL-138 | CH$_2$ | Me | H | CMe | O | CH |
| XL-139 | O | Me | H | CMe | O | CH |
| XL-140 | CHMe | Me | H | CMe | O | CH |
| XL-141 | CH$_2$ | H | H | CH | O | CMe |
| XL-142 | CHMe | H | H | CH | O | CMe |
| XL-143 | CHEt | H | H | CH | O | CMe |
| XL-144 | CHF | H | H | CH | O | CMe |
| XL-145 | C=CH$_2$ | H | H | CH | O | CMe |
| XL-146 | O | H | H | CH | O | CMe |
| XL-147 | S | H | H | CH | O | CMe |
| XL-148 | NH | H | H | CH | O | CMe |
| XL-149 | NMe | H | H | CH | O | CMe |
| XL-150 | NCHO | H | H | CH | O | CMe |
| XL-151 | NCOMe | H | H | CH | O | CMe |
| XL-152 | CH$_2$ | Me | H | CH | O | CMe |
| XL-153 | O | Me | H | CH | O | CMe |
| XL-154 | CHMe | Me | H | CH | O | CMe |
| XL-155 | CH$_2$ | H | H | CMe | O | CMe |
| XL-156 | CHMe | H | H | CMe | O | CMe |
| XL-157 | CHEt | H | H | CMe | O | CMe |
| XL-158 | CHF | H | H | CMe | O | CMe |
| XL-159 | C=CH$_2$ | H | H | CMe | O | CMe |
| XL-160 | O | H | H | CMe | O | CMe |
| XL-161 | S | H | H | CMe | O | CMe |
| XL-162 | NH | H | H | CMe | O | CMe |
| XL-163 | NMe | H | H | CMe | O | CMe |
| XL-164 | NCHO | H | H | CMe | O | CMe |
| XL-165 | NCOMe | H | H | CMe | O | CMe |
| XL-166 | CH$_2$ | Me | H | CMe | O | CMe |
| XL-167 | O | Me | H | CMe | O | CMe |
| XL-168 | CHMe | Me | H | CMe | O | CMe |
| XL-169 | CH$_2$ | H | H | CH | S | CH |
| XL-170 | CHMe | H | H | CH | S | CH |
| XL-171 | CHEt | H | H | CH | S | CH |
| XL-172 | CHF | H | H | CH | S | CH |
| XL-173 | C=CH$_2$ | H | H | CH | S | CH |
| XL-174 | O | H | H | CH | S | CH |
| XL-175 | S | H | H | CH | S | CH |
| XL-176 | NH | H | H | CH | S | CH |
| XL-177 | NMe | H | H | CH | S | CH |
| XL-178 | NCHO | H | H | CH | S | CH |
| XL-179 | NCOMe | H | H | CH | S | CH |
| XL-180 | CH$_2$ | Me | H | CH | S | CH |
| XL-181 | O | Me | H | CH | S | CH |
| XL-182 | CHMe | Me | H | CH | S | CH |
| XL-183 | CH$_2$ | H | H | CMe | S | CH |
| XL-184 | CHMe | H | H | CMe | S | CH |
| XL-185 | CHEt | H | H | CMe | S | CH |
| XL-186 | CHF | H | H | CMe | S | CH |
| XL-187 | C=CH$_2$ | H | H | CMe | S | CH |
| XL-188 | O | H | H | CMe | S | CH |
| XL-189 | S | H | H | CMe | S | CH |
| XL-190 | NH | H | H | CMe | S | CH |
| XL-191 | NMe | H | H | CMe | S | CH |
| XL-192 | NCHO | H | H | CMe | S | CH |
| XL-193 | NCOMe | H | H | CMe | S | CH |
| XL-194 | CH$_2$ | Me | H | CMe | S | CH |
| XL-195 | O | Me | H | CMe | S | CH |
| XL-196 | CHMe | Me | H | CMe | S | CH |
| XL-197 | CH$_2$ | H | H | CH | S | CMe |
| XL-198 | CHMe | H | H | CH | S | CMe |
| XL-199 | CHEt | H | H | CH | S | CMe |
| XL-200 | CHF | H | H | CH | S | CMe |
| XL-201 | C=CH$_2$ | H | H | CH | S | CMe |
| XL-202 | O | H | H | CH | S | CMe |
| XL-203 | S | H | H | CH | S | CMe |
| XL-204 | NH | H | H | CH | S | CMe |
| XL-205 | NMe | H | H | CH | S | CMe |
| XL-206 | NCHO | H | H | CH | S | CMe |
| XL-207 | NCOMe | H | H | CH | S | CMe |
| XL-208 | CH$_2$ | Me | H | CH | S | CMe |
| XL-209 | O | Me | H | CH | S | CMe |
| XL-210 | CHMe | Me | H | CH | S | CMe |
| XL-211 | CH$_2$ | H | H | CMe | S | CMe |
| XL-212 | CHMe | H | H | CMe | S | CMe |
| XL-213 | CHEt | H | H | CMe | S | CMe |

TABLE 7-continued

| Compound No | Y | R1 | R2 | Td | Te | Tf |
|---|---|---|---|---|---|---|
| XL-214 | CHF | H | H | CMe | S | CMe |
| XL-215 | C=CH$_2$ | H | H | CMe | S | CMe |
| XL-216 | O | H | H | CMe | S | CMe |
| XL-217 | S | H | H | CMe | S | CMe |
| XL-218 | NH | H | H | CMe | S | CMe |
| XL-219 | NMe | H | H | CMe | S | CMe |
| XL-220 | NCHO | H | H | CMe | S | CMe |
| XL-221 | NCOMe | H | H | CMe | S | CMe |
| XL-222 | CH$_2$ | Me | H | CMe | S | CMe |
| XL-223 | O | Me | H | CMe | S | CMe |
| XL-224 | CHMe | Me | H | CMe | S | CMe |
| XL-225 | CH$_2$ | H | H | N | NMe | CH |
| XL-226 | CHMe | H | H | N | NMe | CH |
| XL-227 | CHEt | H | H | N | NMe | CH |
| XL-228 | CHF | H | H | N | NMe | CH |
| XL-229 | C=CH$_2$ | H | H | N | NMe | CH |
| XL-230 | O | H | H | N | NMe | CH |
| XL-231 | S | H | H | N | NMe | CH |
| XL-232 | NH | H | H | N | NMe | CH |
| XL-233 | NMe | H | H | N | NMe | CH |
| XL-234 | NCHO | H | H | N | NMe | CH |
| XL-235 | NCOMe | H | H | N | NMe | CH |
| XL-236 | CH$_2$ | Me | H | N | NMe | CH |
| XL-237 | O | Me | H | N | NMe | CH |
| XL-238 | CHMe | Me | H | N | NMe | CH |
| XL-239 | CH$_2$ | H | H | N | NMe | CMe |
| XL-240 | CHMe | H | H | N | NMe | CMe |
| XL-241 | CHEt | H | H | N | NMe | CMe |
| XL-242 | CHF | H | H | N | NMe | CMe |
| XL-243 | C=CH$_2$ | H | H | N | NMe | CMe |
| XL-244 | O | H | H | N | NMe | CMe |
| XL-245 | S | H | H | N | NMe | CMe |
| XL-246 | NH | H | H | N | NMe | CMe |
| XL-247 | NMe | H | H | N | NMe | CMe |
| XL-248 | NCHO | H | H | N | NMe | CMe |
| XL-249 | NCOMe | H | H | N | NMe | CMe |
| XL-250 | CH$_2$ | Me | H | N | NMe | CMe |
| XL-251 | O | Me | H | N | NMe | CMe |
| XL-252 | CHMe | Me | H | N | NMe | CMe |
| XL-253 | CH$_2$ | H | H | N | O | CH |
| XL-254 | CHMe | H | H | N | O | CH |
| XL-255 | CHEt | H | H | N | O | CH |
| XL-256 | CHF | H | H | N | O | CH |
| XL-257 | C=CH$_2$ | H | H | N | O | CH |
| XL-258 | O | H | H | N | O | CH |
| XL-259 | S | H | H | N | O | CH |
| XL-260 | NH | H | H | N | O | CH |
| XL-261 | NMe | H | H | N | O | CH |
| XL-262 | NCHO | H | H | N | O | CH |
| XL-263 | NCOMe | H | H | N | O | CH |
| XL-264 | CH$_2$ | Me | H | N | O | CH |
| XL-265 | O | Me | H | N | O | CH |
| XL-266 | CHMe | Me | H | N | O | CH |
| XL-267 | CH$_2$ | H | H | N | O | CMe |
| XL-268 | CHMe | H | H | N | O | CMe |
| XL-269 | CHEt | H | H | N | O | CMe |
| XL-270 | CHF | H | H | N | O | CMe |
| XL-271 | C=CH$_2$ | H | H | N | O | CMe |
| XL-272 | O | H | H | N | O | CMe |
| XL-273 | S | H | H | N | O | CMe |
| XL-274 | NH | H | H | N | O | CMe |
| XL-275 | NMe | H | H | N | O | CMe |
| XL-276 | NCHO | H | H | N | O | CMe |
| XL-277 | NCOMe | H | H | N | O | CMe |
| XL-278 | CH$_2$ | Me | H | N | O | CMe |
| XL-279 | O | Me | H | N | O | CMe |
| XL-280 | CHMe | Me | H | N | O | CMe |
| XL-281 | CH$_2$ | H | H | N | S | CH |
| XL-282 | CHMe | H | H | N | S | CH |
| XL-283 | CHEt | H | H | N | S | CH |
| XL-284 | CHF | H | H | N | S | CH |
| XL-285 | C=CH$_2$ | H | H | N | S | CH |
| XL-286 | O | H | H | N | S | CH |
| XL-287 | S | H | H | N | S | CH |
| XL-288 | NH | H | H | N | S | CH |
| XL-289 | NMe | H | H | N | S | CH |
| XL-290 | NCHO | H | H | N | S | CH |
| XL-291 | NCOMe | H | H | N | S | CH |
| XL-292 | CH$_2$ | Me | H | N | S | CH |
| XL-293 | O | Me | H | N | S | CH |
| XL-294 | CHMe | Me | H | N | S | CH |
| XL-295 | CH$_2$ | H | H | N | S | CMe |
| XL-296 | CHMe | H | H | N | S | CMe |
| XL-297 | CHEt | H | H | N | S | CMe |
| XL-298 | CHF | H | H | N | S | CMe |
| XL-299 | C=CH$_2$ | H | H | N | S | CMe |
| XL-300 | O | H | H | N | S | CMe |
| XL-301 | S | H | H | N | S | CMe |
| XL-302 | NH | H | H | N | S | CMe |
| XL-303 | NMe | H | H | N | S | CMe |
| XL-304 | NCHO | H | H | N | S | CMe |
| XL-305 | NCOMe | H | H | N | S | CMe |
| XL-306 | CH$_2$ | Me | H | N | S | CMe |
| XL-307 | O | Me | H | N | S | CMe |
| XL-308 | CHMe | Me | H | N | S | CMe |
| XL-309 | CH$_2$ | H | H | CH | NMe | N |
| XL-310 | CHMe | H | H | CH | NMe | N |
| XL-311 | CHEt | H | H | CH | NMe | N |
| XL-312 | CHF | H | H | CH | NMe | N |
| XL-313 | C=CH$_2$ | H | H | CH | NMe | N |
| XL-314 | O | H | H | CH | NMe | N |
| XL-315 | S | H | H | CH | NMe | N |
| XL-316 | NH | H | H | CH | NMe | N |
| XL-317 | NMe | H | H | CH | NMe | N |
| XL-318 | NCHO | H | H | CH | NMe | N |
| XL-319 | NCOMe | H | H | CH | NMe | N |
| XL-320 | CH$_2$ | Me | H | CH | NMe | N |
| XL-321 | O | Me | H | CH | NMe | N |
| XL-322 | CHMe | Me | H | CH | NMe | N |
| XL-323 | CH$_2$ | H | H | CMe | NMe | N |
| XL-324 | CHMe | H | H | CMe | NMe | N |
| XL-325 | CHEt | H | H | CMe | NMe | N |
| XL-326 | CHF | H | H | CMe | NMe | N |
| XL-327 | C=CH$_2$ | H | H | CMe | NMe | N |
| XL-328 | O | H | H | CMe | NMe | N |
| XL-329 | S | H | H | CMe | NMe | N |
| XL-330 | NH | H | H | CMe | NMe | N |
| XL-331 | NMe | H | H | CMe | NMe | N |
| XL-332 | NCHO | H | H | CMe | NMe | N |
| XL-333 | NCOMe | H | H | CMe | NMe | N |
| XL-334 | CH$_2$ | Me | H | CMe | NMe | N |
| XL-335 | O | Me | H | CMe | NMe | N |
| XL-336 | CHMe | Me | H | CMe | NMe | N |
| XL-337 | CH$_2$ | H | H | CH | O | N |
| XL-338 | CHMe | H | H | CH | O | N |
| XL-339 | CHEt | H | H | CH | O | N |
| XL-340 | CHF | H | H | CH | O | N |
| XL-341 | C=CH$_2$ | H | H | CH | O | N |
| XL-342 | O | H | H | CH | O | N |
| XL-343 | S | H | H | CH | O | N |
| XL-344 | NH | H | H | CH | O | N |
| XL-345 | NMe | H | H | CH | O | N |
| XL-346 | NCHO | H | H | CH | O | N |
| XL-347 | NCOMe | H | H | CH | O | N |
| XL-348 | CH$_2$ | Me | H | CH | O | N |
| XL-349 | O | Me | H | CH | O | N |
| XL-350 | CHMe | Me | H | CH | O | N |
| XL-351 | CH$_2$ | H | H | CMe | O | N |
| XL-352 | CHMe | H | H | CMe | O | N |
| XL-353 | CHEt | H | H | CMe | O | N |
| XL-354 | CHF | H | H | CMe | O | N |
| XL-355 | C=CH$_2$ | H | H | CMe | O | N |
| XL-356 | O | H | H | CMe | O | N |
| XL-357 | S | H | H | CMe | O | N |
| XL-358 | NH | H | H | CMe | O | N |
| XL-359 | NMe | H | H | CMe | O | N |
| XL-360 | NCHO | H | H | CMe | O | N |
| XL-361 | NCOMe | H | H | CMe | O | N |
| XL-362 | CH$_2$ | Me | H | CMe | O | N |
| XL-363 | O | Me | H | CMe | O | N |
| XL-364 | CHMe | Me | H | CMe | O | N |
| XL-365 | CH$_2$ | H | H | CH | S | N |
| XL-366 | CHMe | H | H | CH | S | N |
| XL-367 | CHEt | H | H | CH | S | N |
| XL-368 | CHF | H | H | CH | S | N |
| XL-369 | C=CH$_2$ | H | H | CH | S | N |

TABLE 7-continued

| Compound No | Y | R1 | R2 | Td | Te | Tf |
|---|---|---|---|---|---|---|
| XL-370 | O | H | H | CH | S | N |
| XL-371 | S | H | H | CH | S | N |
| XL-372 | NH | H | H | CH | S | N |
| XL-373 | NMe | H | H | CH | S | N |
| XL-374 | NCHO | H | H | CH | S | N |
| XL-375 | NCOMe | H | H | CH | S | N |
| XL-376 | $CH_2$ | Me | H | CH | S | N |
| XL-377 | O | Me | H | CH | S | N |
| XL-378 | CHMe | Me | H | CH | S | N |
| XL-379 | $CH_2$ | H | H | CMe | S | N |
| XL-380 | CHMe | H | H | CMe | S | N |
| XL-381 | CHEt | H | H | CMe | S | N |
| XL-382 | CHF | H | H | CMe | S | N |
| XL-383 | C=$CH_2$ | H | H | CMe | S | N |
| XL-384 | O | H | H | CMe | S | N |
| XL-385 | S | H | H | CMe | S | N |
| XL-386 | NH | H | H | CMe | S | N |
| XL-387 | NMe | H | H | CMe | S | N |
| XL-388 | NCHO | H | H | CMe | S | N |
| XL-389 | NCOMe | H | H | CMe | S | N |
| XL-390 | $CH_2$ | Me | H | CMe | S | N |
| XL-391 | O | Me | H | CMe | S | N |
| XL-392 | CHMe | Me | H | CMe | S | N |

Table XLI provides 336 compounds of formula Iao

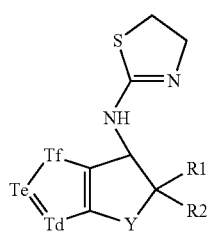

(Iao)

wherein the values of Y, $R^1$, $R^2$, $T^d$, $T^e$ and $T^f$ are given in Table 8.

TABLE 8

| Compound No | Y | R1 | R2 | Td | Te | Tf |
|---|---|---|---|---|---|---|
| XLI-1 | $CH_2$ | H | H | CH | CH | NH |
| XLI-2 | CHMe | H | H | CH | CH | NH |
| XLI-3 | CHEt | H | H | CH | CH | NH |
| XLI-4 | CHF | H | H | CH | CH | NH |
| XLI-5 | C=$CH_2$ | H | H | CH | CH | NH |
| XLI-6 | O | H | H | CH | CH | NH |
| XLI-7 | S | H | H | CH | CH | NH |
| XLI-8 | NH | H | H | CH | CH | NH |
| XLI-9 | NMe | H | H | CH | CH | NH |
| XLI-10 | NCHO | H | H | CH | CH | NH |
| XLI-11 | NCOMe | H | H | CH | CH | NH |
| XLI-12 | $CH_2$ | Me | H | CH | CH | NH |
| XLI-13 | O | Me | H | CH | CH | NH |
| XLI-14 | CHMe | Me | H | CH | CH | NH |
| XLI-15 | $CH_2$ | H | H | CMe | CH | NH |
| XLI-16 | CHMe | H | H | CMe | CH | NH |
| XLI-17 | CHEt | H | H | CMe | CH | NH |
| XLI-18 | CHF | H | H | CMe | CH | NH |
| XLI-19 | C=$CH_2$ | H | H | CMe | CH | NH |
| XLI-20 | O | H | H | CMe | CH | NH |
| XLI-21 | S | H | H | CMe | CH | NH |
| XLI-22 | NH | H | H | CMe | CH | NH |
| XLI-23 | NMe | H | H | CMe | CH | NH |
| XLI-24 | NCHO | H | H | CMe | CH | NH |
| XLI-25 | NCOMe | H | H | CMe | CH | NH |
| XLI-26 | $CH_2$ | Me | H | CMe | CH | NH |
| XLI-27 | O | Me | H | CMe | CH | NH |
| XLI-28 | CHMe | Me | H | CMe | CH | NH |
| XLI-29 | $CH_2$ | H | H | CH | CMe | NH |
| XLI-30 | CHMe | H | H | CH | CMe | NH |
| XLI-31 | CHEt | H | H | CH | CMe | NH |
| XLI-32 | CHF | H | H | CH | CMe | NH |
| XLI-33 | C=$CH_2$ | H | H | CH | CMe | NH |
| XLI-34 | O | H | H | CH | CMe | NH |
| XLI-35 | S | H | H | CH | CMe | NH |
| XLI-36 | NH | H | H | CH | CMe | NH |
| XLI-37 | NMe | H | H | CH | CMe | NH |
| XLI-38 | NCHO | H | H | CH | CMe | NH |
| XLI-39 | NCOMe | H | H | CH | CMe | NH |
| XLI-40 | $CH_2$ | Me | H | CH | CMe | NH |
| XLI-41 | O | Me | H | CH | CMe | NH |
| XLI-42 | CHMe | Me | H | CH | CMe | NH |
| XLI-43 | $CH_2$ | H | H | CH | CH | NMe |
| XLI-44 | CHMe | H | H | CH | CH | NMe |
| XLI-45 | CHEt | H | H | CH | CH | NMe |
| XLI-46 | CHF | H | H | CH | CH | NMe |
| XLI-47 | C=$CH_2$ | H | H | CH | CH | NMe |
| XLI-48 | O | H | H | CH | CH | NMe |
| XLI-49 | S | H | H | CH | CH | NMe |
| XLI-50 | NH | H | H | CH | CH | NMe |
| XLI-51 | NMe | H | H | CH | CH | NMe |
| XLI-52 | NCHO | H | H | CH | CH | NMe |
| XLI-53 | NCOMe | H | H | CH | CH | NMe |
| XLI-54 | $CH_2$ | Me | H | CH | CH | NMe |
| XLI-55 | O | Me | H | CH | CH | NMe |
| XLI-56 | CHMe | Me | H | CH | CH | NMe |
| XLI-57 | $CH_2$ | H | H | CMe | CH | NMe |
| XLI-58 | CHMe | H | H | CMe | CH | NMe |
| XLI-59 | CHEt | H | H | CMe | CH | NMe |
| XLI-60 | CHF | H | H | CMe | CH | NMe |
| XLI-61 | C=$CH_2$ | H | H | CMe | CH | NMe |
| XLI-62 | O | H | H | CMe | CH | NMe |
| XLI-63 | S | H | H | CMe | CH | NMe |
| XLI-64 | NH | H | H | CMe | CH | NMe |
| XLI-65 | NMe | H | H | CMe | CH | NMe |
| XLI-66 | NCHO | H | H | CMe | CH | NMe |
| XLI-67 | NCOMe | H | H | CMe | CH | NMe |
| XLI-68 | $CH_2$ | Me | H | CMe | CH | NMe |
| XLI-69 | O | Me | H | CMe | CH | NMe |
| XLI-70 | CHMe | Me | H | CMe | CH | NMe |
| XLI-71 | $CH_2$ | H | H | CH | CMe | NMe |
| XLI-72 | CHMe | H | H | CH | CMe | NMe |
| XLI-73 | CHEt | H | H | CH | CMe | NMe |
| XLI-74 | CHF | H | H | CH | CMe | NMe |
| XLI-75 | C=$CH_2$ | H | H | CH | CMe | NMe |
| XLI-76 | O | H | H | CH | CMe | NMe |
| XLI-77 | S | H | H | CH | CMe | NMe |
| XLI-78 | NH | H | H | CH | CMe | NMe |
| XLI-79 | NMe | H | H | CH | CMe | NMe |
| XLI-80 | NCHO | H | H | CH | CMe | NMe |
| XLI-81 | NCOMe | H | H | CH | CMe | NMe |
| XLI-82 | $CH_2$ | Me | H | CH | CMe | NMe |
| XLI-83 | O | Me | H | CH | CMe | NMe |
| XLI-84 | CHMe | Me | H | CH | CMe | NMe |
| XLI-85 | $CH_2$ | H | H | CH | CH | O |
| XLI-86 | CHMe | H | H | CH | CH | O |
| XLI-87 | CHEt | H | H | CH | CH | O |
| XLI-88 | CHF | H | H | CH | CH | O |
| XLI-89 | C=$CH_2$ | H | H | CH | CH | O |
| XLI-90 | O | H | H | CH | CH | O |
| XLI-91 | S | H | H | CH | CH | O |
| XLI-92 | NH | H | H | CH | CH | O |
| XLI-93 | NMe | H | H | CH | CH | O |
| XLI-94 | NCHO | H | H | CH | CH | O |
| XLI-95 | NCOMe | H | H | CH | CH | O |
| XLI-96 | $CH_2$ | Me | H | CH | CH | O |
| XLI-97 | O | Me | H | CH | CH | O |
| XLI-98 | CHMe | Me | H | CH | CH | O |
| XLI-99 | $CH_2$ | H | H | CMe | CH | O |
| XLI-100 | CHMe | H | H | CMe | CH | O |
| XLI-101 | CHEt | H | H | CMe | CH | O |
| XLI-102 | CHF | H | H | CMe | CH | O |
| XLI-103 | C=$CH_2$ | H | H | CMe | CH | O |
| XLI-104 | O | H | H | CMe | CH | O |
| XLI-105 | S | H | H | CMe | CH | O |
| XLI-106 | NH | H | H | CMe | CH | O |

TABLE 8-continued

| Compound No | Y | R1 | R2 | Td | Te | Tf |
|---|---|---|---|---|---|---|
| XLI-107 | NMe | H | H | CMe | CH | O |
| XLI-108 | NCHO | H | H | CMe | CH | O |
| XLI-109 | NCOMe | H | H | CMe | CH | O |
| XLI-110 | CH$_2$ | Me | H | CMe | CH | O |
| XLI-111 | O | Me | H | CMe | CH | O |
| XLI-112 | CHMe | Me | H | CMe | CH | O |
| XLI-113 | CH$_2$ | H | H | CH | CMe | O |
| XLI-114 | CHMe | H | H | CH | CMe | O |
| XLI-115 | CHEt | H | H | CH | CMe | O |
| XLI-116 | CHF | H | H | CH | CMe | O |
| XLI-117 | C=CH$_2$ | H | H | CH | CMe | O |
| XLI-118 | O | H | H | CH | CMe | O |
| XLI-119 | S | H | H | CH | CMe | O |
| XLI-120 | NH | H | H | CH | CMe | O |
| XLI-121 | NMe | H | H | CH | CMe | O |
| XLI-122 | NCHO | H | H | CH | CMe | O |
| XLI-123 | NCOMe | H | H | CH | CMe | O |
| XLI-124 | CH$_2$ | Me | H | CH | CMe | O |
| XLI-125 | O | Me | H | CH | CMe | O |
| XLI-126 | CHMe | Me | H | CH | CMe | O |
| XLI-127 | CH$_2$ | H | H | CH | CH | S |
| XLI-128 | CHMe | H | H | CH | CH | S |
| XLI-129 | CHEt | H | H | CH | CH | S |
| XLI-130 | CHF | H | H | CH | CH | S |
| XLI-131 | C=CH$_2$ | H | H | CH | CH | S |
| XLI-132 | O | H | H | CH | CH | S |
| XLI-133 | S | H | H | CH | CH | S |
| XLI-134 | NH | H | H | CH | CH | S |
| XLI-135 | NMe | H | H | CH | CH | S |
| XLI-136 | NCHO | H | H | CH | CH | S |
| XLI-137 | NCOMe | H | H | CH | CH | S |
| XLI-138 | CH$_2$ | Me | H | CH | CH | S |
| XLI-139 | O | Me | H | CH | CH | S |
| XLI-140 | CHMe | Me | H | CH | CH | S |
| XLI-141 | CH$_2$ | H | H | CMe | CH | S |
| XLI-142 | CHMe | H | H | CMe | CH | S |
| XLI-143 | CHEt | H | H | CMe | CH | S |
| XLI-144 | CHF | H | H | CMe | CH | S |
| XLI-145 | C=CH$_2$ | H | H | CMe | CH | S |
| XLI-146 | O | H | H | CMe | CH | S |
| XLI-147 | S | H | H | CMe | CH | S |
| XLI-148 | NH | H | H | CMe | CH | S |
| XLI-149 | NMe | H | H | CMe | CH | S |
| XLI-150 | NCHO | H | H | CMe | CH | S |
| XLI-151 | NCOMe | H | H | CMe | CH | S |
| XLI-152 | CH$_2$ | Me | H | CMe | CH | S |
| XLI-153 | O | Me | H | CMe | CH | S |
| XLI-154 | CHMe | Me | H | CMe | CH | S |
| XLI-155 | CH$_2$ | H | H | CH | CMe | S |
| XLI-156 | CHMe | H | H | CH | CMe | S |
| XLI-157 | CHEt | H | H | CH | CMe | S |
| XLI-158 | CHF | H | H | CH | CMe | S |
| XLI-159 | C=CH$_2$ | H | H | CH | CMe | S |
| XLI-160 | O | H | H | CH | CMe | S |
| XLI-161 | S | H | H | CH | CMe | S |
| XLI-162 | NH | H | H | CH | CMe | S |
| XLI-163 | NMe | H | H | CH | CMe | S |
| XLI-164 | NCHO | H | H | CH | CMe | S |
| XLI-165 | NCOMe | H | H | CH | CMe | S |
| XLI-166 | CH$_2$ | Me | H | CH | CMe | S |
| XLI-167 | O | Me | H | CH | CMe | S |
| XLI-168 | CHMe | Me | H | CH | CMe | S |
| XLI-169 | CH$_2$ | H | H | N | CH | NMe |
| XLI-170 | CHMe | H | H | N | CH | NMe |
| XLI-171 | CHEt | H | H | N | CH | NMe |
| XLI-172 | CHF | H | H | N | CH | NMe |
| XLI-173 | C=CH$_2$ | H | H | N | CH | NMe |
| XLI-174 | O | H | H | N | CH | NMe |
| XLI-175 | S | H | H | N | CH | NMe |
| XLI-176 | NH | H | H | N | CH | NMe |
| XLI-177 | NMe | H | H | N | CH | NMe |
| XLI-178 | NCHO | H | H | N | CH | NMe |
| XLI-179 | NCOMe | H | H | N | CH | NMe |
| XLI-180 | CH$_2$ | Me | H | N | CH | NMe |
| XLI-181 | O | Me | H | N | CH | NMe |
| XLI-182 | CHMe | Me | H | N | CH | NMe |
| XLI-183 | CH$_2$ | H | H | N | CMe | NMe |
| XLI-184 | CHMe | H | H | N | CMe | NMe |
| XLI-185 | CHEt | H | H | N | CMe | NMe |
| XLI-186 | CHF | H | H | N | CMe | NMe |
| XLI-187 | C=CH$_2$ | H | H | N | CMe | NMe |
| XLI-188 | O | H | H | N | CMe | NMe |
| XLI-189 | S | H | H | N | CMe | NMe |
| XLI-190 | NH | H | H | N | CMe | NMe |
| XLI-191 | NMe | H | H | N | CMe | NMe |
| XLI-192 | NCHO | H | H | N | CMe | NMe |
| XLI-193 | NCOMe | H | H | N | CMe | NMe |
| XLI-194 | CH$_2$ | Me | H | N | CMe | NMe |
| XLI-195 | O | Me | H | N | CMe | NMe |
| XLI-196 | CHMe | Me | H | N | CMe | NMe |
| XLI-197 | CH$_2$ | H | H | N | CH | O |
| XLI-198 | CHMe | H | H | N | CH | O |
| XLI-199 | CHEt | H | H | N | CH | O |
| XLI-200 | CHF | H | H | N | CH | O |
| XLI-201 | C=CH$_2$ | H | H | N | CH | O |
| XLI-202 | O | H | H | N | CH | O |
| XLI-203 | S | H | H | N | CH | O |
| XLI-204 | NH | H | H | N | CH | O |
| XLI-205 | NMe | H | H | N | CH | O |
| XLI-206 | NCHO | H | H | N | CH | O |
| XLI-207 | NCOMe | H | H | N | CH | O |
| XLI-208 | CH$_2$ | Me | H | N | CH | O |
| XLI-209 | O | Me | H | N | CH | O |
| XLI-210 | CHMe | Me | H | N | CH | O |
| XLI-211 | CH$_2$ | H | H | N | CMe | O |
| XLI-212 | CHMe | H | H | N | CMe | O |
| XLI-213 | CHEt | H | H | N | CMe | O |
| XLI-214 | CHF | H | H | N | CMe | O |
| XLI-215 | C=CH$_2$ | H | H | N | CMe | O |
| XLI-216 | O | H | H | N | CMe | O |
| XLI-217 | S | H | H | N | CMe | O |
| XLI-218 | NH | H | H | N | CMe | O |
| XLI-219 | NMe | H | H | N | CMe | O |
| XLI-220 | NCHO | H | H | N | CMe | O |
| XLI-221 | NCOMe | H | H | N | CMe | O |
| XLI-222 | CH$_2$ | Me | H | N | CMe | O |
| XLI-223 | O | Me | H | N | CMe | O |
| XLI-224 | CHMe | Me | H | N | CMe | O |
| XLI-225 | CH$_2$ | H | H | N | CH | S |
| XLI-226 | CHMe | H | H | N | CH | S |
| XLI-227 | CHEt | H | H | N | CH | S |
| XLI-228 | CHF | H | H | N | CH | S |
| XLI-229 | C=CH$_2$ | H | H | N | CH | S |
| XLI-230 | O | H | H | N | CH | S |
| XLI-231 | S | H | H | N | CH | S |
| XLI-232 | NH | H | H | N | CH | S |
| XLI-233 | NMe | H | H | N | CH | S |
| XLI-234 | NCHO | H | H | N | CH | S |
| XLI-235 | NCOMe | H | H | N | CH | S |
| XLI-236 | CH$_2$ | Me | H | N | CH | S |
| XLI-237 | O | Me | H | N | CH | S |
| XLI-238 | CHMe | Me | H | N | CH | S |
| XLI-239 | CH$_2$ | H | H | N | CMe | S |
| XLI-240 | CHMe | H | H | N | CMe | S |
| XLI-241 | CHEt | H | H | N | CMe | S |
| XLI-242 | CHF | H | H | N | CMe | S |
| XLI-243 | C=CH$_2$ | H | H | N | CMe | S |
| XLI-244 | O | H | H | N | CMe | S |
| XLI-245 | S | H | H | N | CMe | S |
| XLI-246 | NH | H | H | N | CMe | S |
| XLI-247 | NMe | H | H | N | CMe | S |
| XLI-248 | NCHO | H | H | N | CMe | S |
| XLI-249 | NCOMe | H | H | N | CMe | S |
| XLI-250 | CH$_2$ | Me | H | N | CMe | S |
| XLI-251 | O | Me | H | N | CMe | S |
| XLI-252 | CHMe | Me | H | N | CMe | S |
| XLI-253 | CH$_2$ | H | H | CH | N | NMe |
| XLI-254 | CHMe | H | H | CH | N | NMe |
| XLI-255 | CHEt | H | H | CH | N | NMe |
| XLI-256 | CHF | H | H | CH | N | NMe |
| XLI-257 | C=CH$_2$ | H | H | CH | N | NMe |
| XLI-258 | O | H | H | CH | N | NMe |
| XLI-259 | S | H | H | CH | N | NMe |
| XLI-260 | NH | H | H | CH | N | NMe |
| XLI-261 | NMe | H | H | CH | N | NMe |
| XLI-262 | NCHO | H | H | CH | N | NMe |

TABLE 8-continued

| Compound No | Y | R1 | R2 | Td | Te | Tf |
|---|---|---|---|---|---|---|
| XLI-263 | NCOMe | H | H | CH | N | NMe |
| XLI-264 | CH$_2$ | Me | H | CH | N | NMe |
| XLI-265 | O | Me | H | CH | N | NMe |
| XLI-266 | CHMe | Me | H | CH | N | NMe |
| XLI-267 | CH$_2$ | H | H | CMe | N | NMe |
| XLI-268 | CHMe | H | H | CMe | N | NMe |
| XLI-269 | CHEt | H | H | CMe | N | NMe |
| XLI-270 | CHF | H | H | CMe | N | NMe |
| XLI-271 | C=CH$_2$ | H | H | CMe | N | NMe |
| XLI-272 | O | H | H | CMe | N | NMe |
| XLI-273 | S | H | H | CMe | N | NMe |
| XLI-274 | NH | H | H | CMe | N | NMe |
| XLI-275 | NMe | H | H | CMe | N | NMe |
| XLI-276 | NCHO | H | H | CMe | N | NMe |
| XLI-277 | NCOMe | H | H | CMe | N | NMe |
| XLI-278 | CH$_2$ | Me | H | CMe | N | NMe |
| XLI-279 | O | Me | H | CMe | N | NMe |
| XLI-280 | CHMe | Me | H | CMe | N | NMe |
| XLI-281 | CH$_2$ | H | H | CH | N | O |
| XLI-282 | CHMe | H | H | CH | N | O |
| XLI-283 | CHEt | H | H | CH | N | O |
| XLI-284 | CHF | H | H | CH | N | O |
| XLI-285 | C=CH$_2$ | H | H | CH | N | O |
| XLI-286 | O | H | H | CH | N | O |
| XLI-287 | S | H | H | CH | N | O |
| XLI-288 | NH | H | H | CH | N | O |
| XLI-289 | NMe | H | H | CH | N | O |
| XLI-290 | NCHO | H | H | CH | N | O |
| XLI-291 | NCOMe | H | H | CH | N | O |
| XLI-292 | CH$_2$ | Me | H | CH | N | O |
| XLI-293 | O | Me | H | CH | N | O |
| XLI-294 | CHMe | Me | H | CH | N | O |
| XLI-295 | CH$_2$ | H | H | CMe | N | O |
| XLI-296 | CHMe | H | H | CMe | N | O |
| XLI-297 | CHEt | H | H | CMe | N | O |
| XLI-298 | CHF | H | H | CMe | N | O |
| XLI-299 | C=CH$_2$ | H | H | CMe | N | O |
| XLI-300 | O | H | H | CMe | N | O |
| XLI-301 | S | H | H | CMe | N | O |
| XLI-302 | NH | H | H | CMe | N | O |
| XLI-303 | NMe | H | H | CMe | N | O |
| XLI-304 | NCHO | H | H | CMe | N | O |
| XLI-305 | NCOMe | H | H | CMe | N | O |
| XLI-306 | CH$_2$ | Me | H | CMe | N | O |
| XLI-307 | O | Me | H | CMe | N | O |
| XLI-308 | CHMe | Me | H | CMe | N | O |
| XLI-309 | CH$_2$ | H | H | CH | N | S |
| XLI-310 | CHMe | H | H | CH | N | S |
| XLI-311 | CHEt | H | H | CH | N | S |
| XLI-312 | CHF | H | H | CH | N | S |
| XLI-313 | C=CH$_2$ | H | H | CH | N | S |
| XLI-314 | O | H | H | CH | N | S |
| XLI-315 | S | H | H | CH | N | S |
| XLI-316 | NH | H | H | CH | N | S |
| XLI-317 | NMe | H | H | CH | N | S |
| XLI-318 | NCHO | H | H | CH | N | S |
| XLI-319 | NCOMe | H | H | CH | N | S |
| XLI-320 | CH$_2$ | Me | H | CH | N | S |
| XLI-321 | O | Me | H | CH | N | S |
| XLI-322 | CHMe | Me | H | CH | N | S |
| XLI-323 | CH$_2$ | H | H | CMe | N | S |
| XLI-324 | CHMe | H | H | CMe | N | S |
| XLI-325 | CHEt | H | H | CMe | N | S |
| XLI-326 | CHF | H | H | CMe | N | S |
| XLI-327 | C=CH$_2$ | H | H | CMe | N | S |
| XLI-328 | O | H | H | CMe | N | S |
| XLI-329 | S | H | H | CMe | N | S |
| XLI-330 | NH | H | H | CMe | N | S |
| XLI-331 | NMe | H | H | CMe | N | S |
| XLI-332 | NCHO | H | H | CMe | N | S |
| XLI-333 | NCOMe | H | H | CMe | N | S |
| XLI-334 | CH$_2$ | Me | H | CMe | N | S |
| XLI-335 | O | Me | H | CMe | N | S |
| XLI-336 | CHMe | Me | H | CMe | N | S |

Table XLII provides 612 compounds of formula Iap

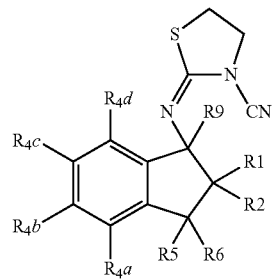

(Iap)

wherein the values of $R^1$, $R^2$, $R^{4a}$, $R^{4b}$, $R^{4c}$, $R^{4d}$, $R^5$, $R^6$ and $R^9$ are given in Table 3.

Table XLIII provides 612 compounds of formula Iaq

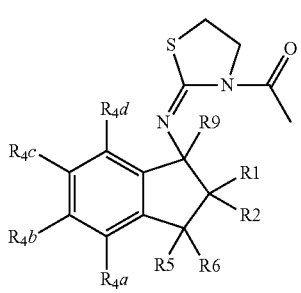

(Iaq)

wherein the values of $R^1$, $R^2$, $R^{4a}$, $R^{4b}$, $R^{4c}$, $R^{4d}$, $R^5$, $R^6$ and given in Table 3.

The following tables provide characterising data for some of the compounds in Tables I-XLIII; other compounds are only described in these tables.

TABLE 1

Characterising Data

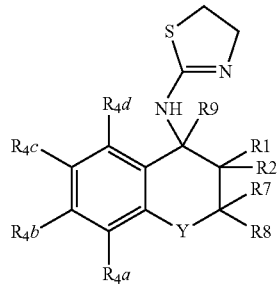

| Cpd.No | R1 | Y | R4a | R4b | R4c | R4d | Mp [° C.] |
|---|---|---|---|---|---|---|---|
| 1.001 | H | CH$_2$ | F | H | H | F | Solid |
| 1.002 | H | CH$_2$ | H | H | Br | H | 167-169 |

TABLE 1-continued

Characterising Data

R2, R7, R8, R9 = H

| Cpd.No | R1 | Y | R4a | R4b | R4c | R4d | Mp [° C.] |
|---|---|---|---|---|---|---|---|
| 1.003 | H | CH$_2$ | H | H | Cl | H | 164-166 |
| 1.004 | H | CH$_2$ | H | H | Me | H | 156-157 |
| 1.005 | H | CH$_2$ | F | H | F | H | 175-178 |
| 1.006 | H | CH$_2$ | MeO | H | H | MeO | 163-165 |
| 1.007 | H | CH$_2$ | Me | H | Me | H | 153-155 |
| 1.008 | H | CH$_2$ | H | H | MeO | H | 159-161 |
| 1.009 | H | CH$_2$ | H | MeO | H | H | 148-150 |
| 1.010 | H | CH$_2$ | MeO | H | H | H | 178-179 |
| 1.011 | H | CH$_2$ | H | Me | MeO | H | 141-143 |
| 1.012 | H | CHMe | H | H | H | H | 112-115 |
| 1.013 | Me | CH$_2$ | H | H | H | H | 166-168 |
| 1.014 | H | S | H | Me | H | H | 234-235 |
| 1.015 | H | O | H | Me | H | H | 133-134 |
| 1.016 | H | CH$_2$ | OH | H | H | H | Decomp. 100 |
| 1.017 | H | CH$_2$ | OCH2OMe | H | H | H | 171 |
| 1.018 | H | CH$_2$ | H | H | H | H | 160 |
| 1.019 | H | O | Cl | H | H | H | 185 |
| 1.020[a] | Me | CH$_2$ | H | H | H | H | resin |
| 1.021 | H | S | H | H | H | H | resin |

[a] R2 = Me

TABLE 2

Characterising Data

| Cpd.No | R1 | R2 | R5 | R6 | R4a | R4b | R4c | R4d | Mp [° C.] |
|---|---|---|---|---|---|---|---|---|---|
| 2.001[a] | H | H | H | H | H | H | H | H | Solid |
| 2.002 | H | H | H | H | H | H | H | H | 137 |
| 2.003[b] | H | H | H | H | H | H | H | H | 123 |
| 2.004[c] | H | H | H | H | H | H | H | H | 123 |
| 2.005 | H | H | H | H | H | F | H | H | 136 |
| 2.006 | H | H | H | H | Me | H | H | H | 134 |
| 2.007 | H | H | H | H | H | H | Me | H | 181 |
| 2.008 | H | H | H | H | Br | H | H | Me | Solid |
| 2.009 | H | H | H | H | Me | H | Br | | Solid |
| 2.010 | H | H | H | H | H | H | H | OCH$_2$OMe | Oil |
| 2.011 | H | H | H | H | OCH$_2$OMe | H | H | H | Solid |
| 2.012 | H | H | H | H | OH | H | H | H | 191 |
| 2.013 | H | H | H | H | OTf | H | H | H | Resin |
| 2.014 | H | H | H | H | Et | H | H | H | Solid |
| 2.015 | H | H | H | H | OH | H | H | H | 125 Decomp. |
| 2.016 | H | H | H | H | H | H | H | Me | 117-120 |
| 2.017 | H | H | H | H | H | OCH$_2$OMe | H | H | 150-153 |
| 2.018 | H | H | H | H | OMe | H | H | H | Solid |
| 2.019 | H | H | H | H | F | H | H | H | 149 |
| 2.020 | H | H | H | H | Cl | H | H | H | 124-127 |
| 2.021[e] | H | H | H | H | Me | H | H | H | 119 |
| 2.022[b] | H | H | H | H | Me | H | H | H | 122 |
| 2.023 | H | H | H | H | F | F | H | H | 161 |
| 2.024 | H | H | H | H | F | H | F | H | 145-152 |
| 2.025 | H | H | H | H | F | H | H | F | 182 |
| 2.026 | H | H | H | H | F | H | Br | H | 156 |
| 2.027 | H | H | Me | Me | H | H | H | H | 60-66 |

TABLE 2-continued

Characterising Data

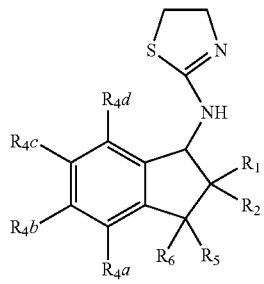

| Cpd.No | R1 | R2 | R5 | R6 | R4a | R4b | R4c | R4d | Mp [° C.] |
|---|---|---|---|---|---|---|---|---|---|
| 2.028 | H | H | H | H | F | F | F | H | 123 |
| 2.029 | H | H | H | H | H | OH | H | H | 75 Decomp. |
| 2.030 | H | H | H | H | F | H | F | F | 172 |
| 2.031 | H | H | H | H | F | H | Me | H | 184 |
| 2.032[d] | Me | H | H | H | H | H | H | H | Solid |
| 2.033 | Me | Me | H | H | H | H | H | H | 119 |
| 2.034 | Pr | Pr | H | H | H | H | H | H | 101-103 |
| 2.035 | H | H | H | H | H | Me | OMe | H | 152-153 |
| 2.036 | H | H | H | H | F | F | F | F | 165 |
| 2.037 | H | H | H | H | F | H | Ph | H | Solid |
| 2.038 | H | H | H | H | F | H | Et | H | 148-149 |
| 2.039 | H | H | H | H | COOMe | H | H | H | 131 |
| 2.040[e] | H | =CH$_2$ | H | H | H | H | H | H | 173-175 |
| 2.041 | H | H | H | H | PhO | H | H | H | 143-146 |
| 2.042 | H | H | H | H | NO$_2$ | H | H | H | 144-145 |
| 2.043 | H | H | H | H | (mCF$_3$)PhO | H | H | H | 115-116 |
| 2.044 | H | H | H | H | CN | H | H | H | Resin |
| 2.045 | H | H | H | H | pClPhO | H | H | H | 163-164 |
| 2.046 | H | H | H | H | I | H | H | H | 170-171 |
| 2.047 | H | H | H | H | Me$_3$SiC≡C | H | H | H | Solid |
| 2.048 | H | H | H | H | HC≡C | H | H | H | Oil |
| 2.048 | H | H | OBn | H | F | H | F | H | Cis Oil |
| 2.049 | H | H | H | H | H | H | Br | H | solid |
| 2.050 | H | H | H | H | H | H | H | Cl | solid |
| 2.051 | H | H | H | H | H | H | H | NHAc | solid |
| 2.052 | H | H | H | H | H | H | H | F | 171-172 |
| 2.053 | H | H | H | H | m-CF$_3$-phenyl | H | H | H | 103-105 |
| 2.054 | H | H | H | H | PhCC— | H | H | H | 160-161 |
| 2.055 | H | H | H | H | p-Cl-phenyl | H | H | H | 187-188 |
| 2.056 | H | H | H | H | vinyl | H | H | H | solid |
| 2.057 | H | H | H | H | formyl | H | H | H | 142-143 |
| 2.058 | H | H | H | H | CHF$_2$ | H | H | H | 116-117 |
| 2.059 | H | H | H | H | MeOCH=N— | H | H | H | resin |
| 2.060 | H | H | N$_3$ | H | F | H | F | H | Cis Resin |
| 2.061 | H | H | SMe | H | F | H | F | H | Cis Resin |
| 2.062 | H | H | H | H | CCl$_3$ | H | H | H | Solid |
| 2.063 | H | H | NH$_2$ | H | F | H | F | H | Trans Resin |
| 2.064 | =CH$_2$ | H | H | H | H | H | H | H | 107-111 |
| 2.066 | H | —CH$_2$— | H | H | H | H | H | H | Exo124-129 |
| 2.067 | F | H | H | H | F | H | H | H | Trans 142-144 |
| 2.068 | H | H | SMe | H | SMe | H | F | H | Trans 143-149 |
| 2.069 | F | H | S(O)Me | H | F | H | H | H | Cis solid |
| 2.070 | H | H | COOMe | H | H | H | H | H | Cis 105-107 |

[a] HCl salt
[b] S-isomer
[c] R-isomer
[d] mixture of cis and trans
[e] endo

TABLE 3

Characterising Data

| Cpd.No. | Y | CR9-CR1R2 | R4a | R4b | R4c | R4d | Mp [° C.] |
|---|---|---|---|---|---|---|---|
| 3.002 | O | CH—CF2 | Me | H | H | H | 162 |
| 3.004 | CH$_2$ | CMe—CH2 | H | H | H | H | a) | a) $^1$H-NMR (300 MHz CDCl$_3$) 1.68 (3H, s, Me); 2.18 (1H, m); 2.73 (1H, m); 2.88 (1H, m); 3.03 (1H, m); 3.22 (2H, t); 3.98 (2H, m); 7.27 (4H, m).

TABLE 4

Characterising Data

| Cpd.No. | Td | Te | Tf | R7 | R8 | Mp |
|---|---|---|---|---|---|---|
| 4.001 | S | CH | CH | H | H | 147-149 |
| 4.002 | NMe | CH | H | H | H | 154-156 |
| 4.003 | O | N | CMe | H | H | 141-143 |
| 4.004 | O | CMe | CH | H | H | 148-150 |

TABLE 4-continued

Characterising Data

| Cpd.No. | Td | Te | Tf | R7 | R8 | Mp |
|---|---|---|---|---|---|---|
| 4.005 | O | CMe | CH | Me | Me | 87-89 |
| 4.006 | O | CH | CH | Me | Me | resin |

Characterising Data-5

| Cpd. No. | Ta | Tb | Tc | Td | Y | R10 | Phys. Data |
|---|---|---|---|---|---|---|---|
| 5.001 | N | CMe | N | CH | CH$_2$CH$_2$ | H | Oil |
| 5.002 | N | C—CF$_3$ | CH | CH | CH$_2$ | H | solid |
| 5.003 | N | C—CHF$_2$ | CH | CH | CH$_2$CH$_2$ | H | solid |
| 5.004 | N | C—CF$_3$ | CH | CH | CH$_2$CMe$_2$ | H | 74-75 |
| 5.005 | N | CH | CH | CH | CH$_2$ | H | solid |
| 5.006 | N | C—CF$_3$ | CH | CH | CH$_2$ | CN | solid |
| 5.007 | N | C—CF$_3$ | CH | CH | CH$_2$ | Boc | 144-147 |

TABLE 6

Characterising Data

| Cpd.No. | R1 | R2 | Y | R4a | R4b | R4c | R4d | Isomer | Mp [° C.] |
|---|---|---|---|---|---|---|---|---|---|
| 6.001 | H | H | C=O | H | H | H | H | | 145-147 |
| 6.002 | F | F | CHF | H | H | H | H | | a) |
| 6.003 | H | H | CH$_2$ | H | H | H | Et | | 98-100 |
| 6.004 | H | H | CHOH | F | H | F | H | cis | 167 |
| 6.005 | H | H | SO$_2$ | H | H | H | H | | 164-166 |
| 6.006 | H | H | CH$_2$ | H | Br | H | H | | 137-139 |
| 6.007 | H | H | CH$_2$ | OCHF$_2$ | H | H | H | | Oil |
| 6.008 | H | H | CH$_2$ | OCSNMe$_2$ | H | H | H | | Resin |
| 6.009 | Me | H | CH$_2$ | H | H | H | H | trans | 122 |
| 6.010 | H | H | CHOH | H | H | H | H | trans | 149 |

TABLE 6-continued

Characterising Data

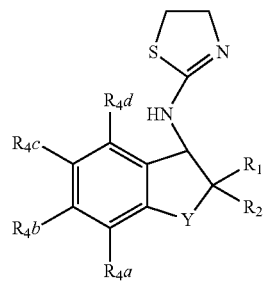

| Cpd.No. | R1 | R2 | Y | R4a | R4b | R4c | R4d | Isomer | Mp [° C.] |
|---|---|---|---|---|---|---|---|---|---|
| 6.011 | H | H | CH₂ | H | H | H | nPr | | 72-75 |
| 6.012 | Me | H | CH₂ | H | H | H | H | cis | Solid |
| 6.013 | iPr | H | CH₂ | H | H | H | H | cis | Solid |
| 6.014 | H | H | CH₂ | COOBu | H | H | H | | Resin |
| 6.015 | Et | H | CH₂ | H | H | H | H | cis | Solid |
| 6.016 | Et | H | CH₂ | H | H | H | H | trans | Solid |
| 6.017 | H | H | CHEt | H | H | H | H | 1:5 c:t | brown solid |
| 6.018 | H | H | CHiPr | H | H | H | H | 1:1 c:t | oil |
| 6.019 | H | H | CHMe | H | H | H | H | cis | 126 |
| 6.020 | H | H | CHMe | H | H | H | H | 1:3 c:t | 139 |
| 6.021 | H | H | C=O | F | H | F | H | | 144-155 |
| 6.022 | F | H | H | F | H | H | H | cis | 159 |
| 6.023 | H | H | CHF | F | H | F | H | trans | brown crystals |
| 6.024 | H | H | CHF | F | H | F | H | cis | brown crystals |
| 6.025 | COOBu | H | CH₂ | H | H | H | H | trans | 99-109 |
| 6.026 | COOMe | H | CH₂ | H | H | H | H | trans | yellow oil |
| 6.027 | CH₂OH | H | CH₂ | H | H | H | H | cis | 147-148 |
| 6.028 | COONa | H | CH₂ | H | H | H | H | cis | >200 |
| 6.029 | CONHBn | H | CH₂ | H | H | H | H | cis | 194-198 |
| 6.030 | H | H | CHOMe | F | H | F | H | cis | 115-116 |
| 6.031 | H | H | O | H | H | H | H | | 135-156 |
| 6.032 | OH | H | CH₂ | H | H | H | H | trans | 182-202 |
| 6.033 | H | H | CH₂ | H | H | H | OTf | | brown resin |
| 6.034 | H | H | O | CH₃ | H | H | H | | 137-138 |
| 6.035 | H | H | O | H | H | F | H | | 107-108 |
| 6.036 | H | H | O | OMe | H | H | H | | 144-144 |
| 6.037 | H | H | O | Cl | H | H | H | | 150-151 |
| 6.038 | H | H | O | Cl | H | Cl | H | | b) |
| 6.039 | H | H | O | CHF₂ | H | H | H | | 130-131 |
| 6.040 | H | H | O | H | F | H | H | | 113-114 |
| 6.041 | H | H | NC(O)Me | H | H | H | H | | 160-161 | a)¹H-NMR (300 MHz, CDCl₃) 3.39 (2H, t); 3.98 (2H, m); 5.44 (1H, t, J = 8); 5.79 (1H, ddd, J = 49, 8, 6); 7.50 4H, m).
b)¹H-NMR (300 MHz CDCl₃) 3.34 (2H, t); 3.88 (2H, m); 4.38 (NH, b), 4.52 (1H, m); 4.80 (1H, m), 5.40 (1H, m), 7.24 (4H, m).

TABLE 7

Characterising Data

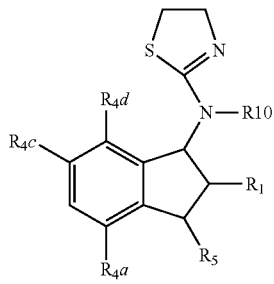

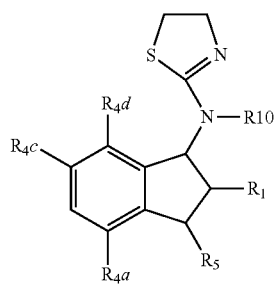

| Cpd.No | R1 | R5 | R4a | R4c | R4d | R¹⁰ | isomer | Mp [° C.] |
|---|---|---|---|---|---|---|---|---|
| 7.001 | H | H | Cl | H | H | OH | | 115-117 |
| 7.002 | H | H | H | H | H | NHBoc | | 63-64 |
| 7.003 | H | H | H | H | H | N=CMe₂ | | oil |
| 7.004 | H | H | H | H | H | N(Ac)₂ | | 91-92 |
| 7.005 | H | H | H | H | H | NHAc | | solid |
| 7.006 | H | H | F | H | H | OH | | 142-143 |
| 7.007 | H | H | H | H | H | OH | | white crystals |
| 7.008 | H | Me | H | H | H | OH | cis | 178-179 |

TABLE 7-continued

Characterising Data

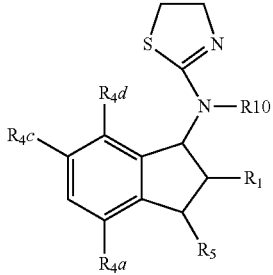

| Cpd.No | R1 | R5 | R4a | R4c | R4d | R10 | isomer | Mp [° C.] |
|---|---|---|---|---|---|---|---|---|
| 7.009 | H | Me | H | H | H | OH | trans | white crystals |
| 7.010 | H | H | Me | H | H | OH | | 183 |
| 7.011 | H | H | H | H | H | Me | | orange oil |

TABLE 7-continued

Characterising Data

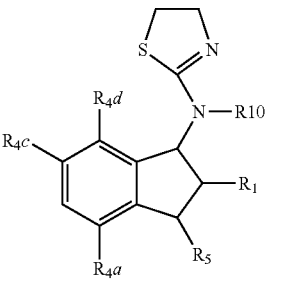

| Cpd.No | R1 | R5 | R4a | R4c | R4d | R10 | isomer | Mp [° C.] |
|---|---|---|---|---|---|---|---|---|
| 7.012 | H | H | H | H | H | OMe | | orange oil |
| 7.013 | H | H | H | H | H | $NH_2$ | | 103-105 |

TABLE 8

Characterising Data

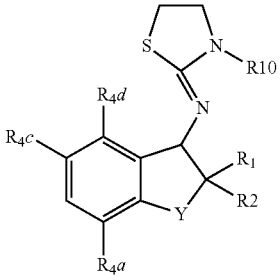

| Cpd.No | R1 | R2 | Y | R4a | R4c | R4d | R10 | isomer | Mp [° C.] |
|---|---|---|---|---|---|---|---|---|---|
| 8.001 | H | H | $CH_2$ | Br | H | Me | 2-thiazolyl | | white solid |
| 8.002 | H | H | $CH_2$ | Me | H | Br | 2-thiazolyl | | 176-181 |
| 8.003 | H | H | O | H | H | H | 2-thiazolyl | | beige crystals |
| 8.004 | H | H | CHMe | H | H | H | Boc | | 187-8 |
| 8.005 | H | H | CHMe | H | H | H | thexyl$Me_2$Si | | orange solid |
| 8.006 | H | H | CHMe | H | H | H | $iPr_3$Si | | solid |
| 8.007 | Me | Me | $CH_2$ | H | H | H | 2-thiazolyl | | 162-3 |
| 8.008 | H | H | $CH_2$ | H | Et | H | 2-thiazolyl | | 111 |
| 8.009 | H | H | $CH_2$ | H | H | Me | 2-thiazolyl | | 125 |
| 8.010 | H | H | C=O | F | F | H | 2-thiazolyl | | 150-162 |
| 8.011 | H | H | C=O | H | H | H | 2-thiazolyl | | 188 |
| 8.012 | H | H | CHOH | F | F | H | 2-thiazolyl | | white foam |
| 8.013 | H | H | $CH_2$ | F | H | H | 2-thiazolyl | | 152-3 |
| 8.014 | iPr | H | $CH_2$ | H | H | H | Boc | cis | oil |
| 8.015 | H | H | $CH_2$ | m($CF_3$)PhO | H | H | CN | | resin |
| 8.016 | H | H | $CH_2$ | I | H | H | Boc | | oil |
| 8.017 | H | H | $CH_2$ | H | H | H | CN | | 90-91 |
| 8.018 | H | H | $CH_2$ | F | H | H | CN | | 99-100 |
| 8.019 | H | H | $CH_2$ | $OCHF_2$ | H | H | CN | | resin |
| 8.020 | H | H | CHOBoc | F | F | H | Me | Cis | 101-105 |
| 8.021 | H | H | CHOH | F | F | H | Me | Cis | 170-173 |
| 8.022 | H | H | CHOH | F | F | H | Boc | Cis | 119 |
| 8.023 | H | H | C=O | F | F | H | Boc | | 158 |
| 8.024 | H | H | $CH_2$ | $OCHF_2$ | H | H | CN | | solid |
| 8.025 | H | H | $CH_2$ | F | H | H | acetyl | | solid |
| 8.026 | H | H | $CH_2$ | Me | H | H | CN | | resin |
| 8.027 | H | H | $CH_2$ | $NO_2$ | H | H | CN | | solid |
| 8.028 | H | H | $CH_2$ | 3-$CF_3$-phenyl | H | H | CN | | resin |
| 8.029 | H | H | $CH_2$ | PhCC | H | H | CN | | solid |
| 8.030 | H | H | $CH_2$ | I | H | H | CN | | solid |
| 8.031 | H | H | $CH_2$ | Me | H | H | acetyl | | resin |
| 8.032 | H | H | $CH_2$ | $CHF_2$ | H | H | CN | | solid |

TABLE 8-continued

Characterising Data

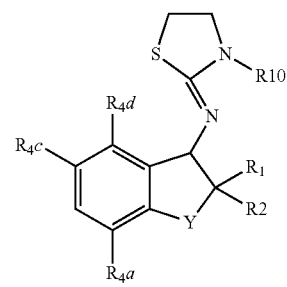

| Cpd.No | R1 | R2 | Y | R4a | R4c | R4d | R10 | isomer | Mp [° C.] |
|---|---|---|---|---|---|---|---|---|---|
| 8.033 | H | H | CH$_2$ | H | H | H | Me$_2$NCO— | | resin |
| 8.034 | H | H | CH$_2$ | F | H | H | Me$_2$NCO | | resin |
| 8.035 | H | H | CH$_2$ | I | H | H | MeOCH$_2$ | | oil |

Characterising Data-9

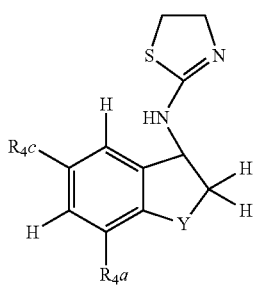

| Cpd. No. | Y | R4a | R4c | Isomer | Mp [° C.] or retention time[a] |
|---|---|---|---|---|---|
| 9.001 | CHOC(CF$_3$)Ph$_2$ | F | F | cis | 96-103 |
| 9.002 | C=NOiBu | F | F | | 0.85 |
| 9.003 | C=NOCH$_2$(2,4,5-Cl$_3$Ph) | F | F | | 1.27 |
| 9.004 | C=NOBn | F | F | | 0.95 |
| 9.005 | C=NNHC(O)(1-Me-3-CF$_3$-pyrazol-4-yl) | F | F | | 0.47 |
| 9.006 | C=NNHC(O)NHPh | F | F | | 0.92 |
| 9.007 | C=NO-allyl | F | F | | 0.43 |
| 9.008 | C=NNHC(O)OPh | F | F | | 0.43 |
| 9.009 | C=NNHSO$_2$Ph | F | F | | 0.79 |
| 9.010 | C=NOtBu | F | F | | 1.00 |
| 9.011 | C=NNHC(O)(benzo[1,2,5]thiadiazole-5-yl) | F | F | | 0.31 |
| 9.012 | C=NO-pentafluorophenyl | F | F | | 1.13 |
| 9.013 | C=NNHC(S)NHiPr | F | F | | 0.83 |
| 9.014 | C=NNHSO$_2$Me | F | F | | 0.17 |
| 9.015 | C=NNHC(S)NHMe | F | F | | 0.18 |
| 9.016 | C=NNHC(O)(2-benzylthio-phenyl) | F | F | | 1.01 |
| 9.017 | C=NOnBu | F | F | | 0.91 |
| 9.018 | C=NNHTroc | F | F | | 0.85 |
| 9.019 | C=NOEt | F | F | | 0.25 |
| 9.020 | C=CH$_2$ | F | F | | Solid |
| 9.021 | C=CF$_2$ | H | H | | 106-108 |
| 9.022 | C=NOH | F | F | | Decomp. 155 |
| 9.023 | C=NOMe | F | F | | 104-114 |

[a] On a Waters 2795 HPLC using an Atlantis dC18 3ym, 3 x 20 mm column two mobile phases were used. Eluant A contained 90% water, 10% MeCN, 0.1% formic acid. Eluant B contained 0.1% formic acid in MeCN. For the first 2.5 min a linear gradient change of eluant was made from 90% eluant A/10% eluant B to 100% eluant B. Then 100% eluant B was used. The flow rate was 1.7 ml/min throughout. Compounds were detected by UV at using a diode array measuring wavelengths between 200 nm and 400 nm.

Characterising Data-10

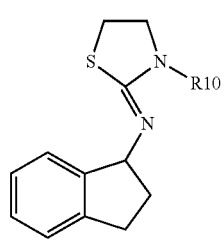

| Cpd.No | R10 | retention time[a] |
|---|---|---|
| 10.001 | C(O)(2,5-dimethyl-furan-3-yl) | 1.02 |
| 10.002 | C(O)(1,3-dimethyl-pyrazol-5-yl) | 1.05 |
| 10.003 | C(O)CH$_2$OBn | 1.58 |
| 10.004 | C(O)OnBu | 0.78 |
| 10.005 | C(O)NEt$_2$ | 0.42 |
| 10.006 | C(O)iPr | 0.70 |
| 10.007 | C(O)NPh$_2$ | 1.28 |
| 10.008 | C(O)n-heptyl | 1.57 |
| 10.009 | C(O)-2-furyl | 0.63 |
| 10.010 | C(O)CH=CH(p-nitrophenyl) | 1.69 |
| 10.011 | C(O)Et | 0.36 |
| 10.012 | C(O)OPh | 0.81 |
| 10.013 | C(O)cyclopropyl | 0.39 |
| 10.014 | C(O)Ph | 1.15 |
| 10.015 | C(O)OMe | 0.18 |
| 10.016 | C(O)-1-piperidyl | 0.70 |
| 10.017 | C(O)-3,5-dimethyl-isoxazol-4-yl | 1.47 |
| 10.018 | C(O)isopropenyl | 0.27 |
| 10.019 | C(O)—O-isopropenyl | 0.33 |
| 10.020 | C(O)OEt | 0.49 |
| 10.021 | C(O)CH$_2$C(O)OEt | 1.56 |
| 10.022 | C(O)CH$_2$-2-thienyl | 1.33 |
| 10.023 | benzyl | Oil |
| 10.024 | CH$_2$OMe | Oil |
| 10.025 | C(O)Me | 86-97 |
| 10.026 | 3-methoxybenzyl | Oil |

[a] On a Waters 2795 HPLC using an Atlantis dC18 3ym, 3 x 20 mm column two mobile phases were used. Eluant A contained 90% water, 10% MeCN, 0.1% formic acid. Eluant B contained 0.1% formic acid in MeCN. For the first 2.5 min a linear gradient change of eluant was made from 90% eluant A /10% eluant B to 100% eluant B. Then 100% eluant B was used. The flow rate was 1.7 ml/min throughout. Compounds were detected by UV at using a diode array measuring wavelengths between 200 nm and 400 nm.

Characterising Data-11

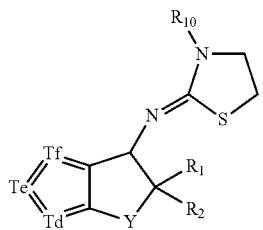

| Cpd.No | Td | Te | Tf | Y | $R_1$ | $R_2$ | $R_{10}$ | Mp [° C.] |
|---|---|---|---|---|---|---|---|---|
| 11.001 | S | CH | CH | $CH_2$ | H | H | H | 144-145 |
| 11.002 | S | CH | CH | $CH_2$ | H | H | $CH_2C\equiv CH$ | a) |
| 11.003 | CH | CH | S | $CH_2$ | H | H | H | 146-147 |
| 11.004 | S | CMe | CH | $CH_2$ | H | H | H | 170-172 |
| 11.005 | S | CH | CH | $CH_2$ | H | H | $C(O)NM2_2$ | b) | a) $^1$H-NMR (300 MHz CDCl$_3$) 2.21 (1H, t), 2.38 (1H, m), 2.83 (2H, m), 3.03 (1H, m), 3.32 (2H, m); 3.56 (2H, m), 4.16 (2H, m); 4.56 (1H, m), 6,83 (1H, d), 7.13 (1H, d).
b) $^1$H-NMR (300 MHz CDCl$_3$) 2.38 (1H, m), 2.82 (2H, m), 2.90 (6H, S), 3.02 (1H, m), 3.20 (2H, m); 3.80 (2H, m), 4.16 (2H, m); 4.53 (1H, m), 6,82 (1H, d), 7.13 (1H, d).

Characterising Data-12

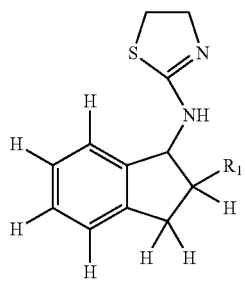

| Cpd.No | R1 | Mp [° C.] |
|---|---|---|
| 12.001 | nBu | Cis 91-94 |
| 12.002 | nBu | Trans 80-82 |
| 12.003 | COnPr | Cis 105-106 |
| 12.004 | F | Cis Resin |
| 12.005 | C(O)Me | Cis 128-129 |
| 12.006 | C(O)Et | Cis 104-105 |
| 12.007 | $CH_2OH$ | Trans144-145 |
| 12.008 | OAc | Trans Oil |
| 12.009 | $CH_2OAc$ | Trans Resin |
| 12.010 | OMe | Trans 96-98 |
| 12.011 | OBz | Trans 117-119 |
| 12.012 | $CH_2OMe$ | Trans Resin |
| 12.013 | $CH_2OMs$ | Trans Solid |
| 12.014 | $CH_2OBn$ | Trans 140 Decomp. |
| 12.015 | $CH_2SMe$ | trans resin |
| 12.016 | $CH_2Ocinnamyl$ | Trans Oil |
| 12.017 | $CH_2OCH_2CO_2tBu$ | Trans Oil |
| 12.018 | $CH_2S(O)Me$ | trans resin |
| 12.019 | $CH_2SO_2Me$ | trans resin |
| 12.020 | SePh | Trans Oil |
| 12.021$^{g)}$ | $CH_2SH$ | Trans 141-147 |
| 12.022 | $CH_2SePH$ | Trans 99-101 |
| 12.023 | $CH_2SC(S)NEt_2$ | Trans Resin |
| 12.024 | $CH_2CN$ | Trans 110-113 |
| 12.025 | $CH_2SCN$ | Trans Oil |
| 12.026 | $CH_2OpFPh$ | Trans 127-133 |
| 12.027 | $CH_2OPh$ | Trans 100 Decomp. |
| 12.028 | $CH_2SC(S)OEt$ | Trans Resin |
| 12.029 | $CO_2H$ | trans solid |

$^{g)}$TFA salt

The compounds of the invention may be made by a variety of methods, for example those described in Tet. 2006, 62, 513

The compounds of the formula I can be prepared from amines of the formula II.

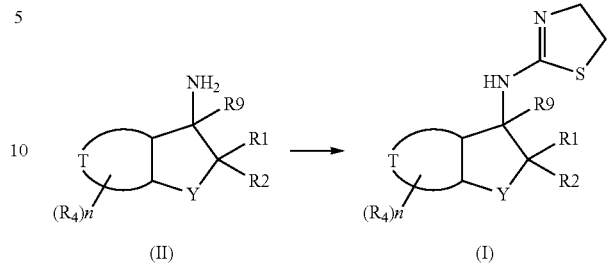

Methods for performing this transformation include A. Treatment with haloethylisothiocyanate as used in Examples 3, 8 (step 6) and 9 (step 6) using the procedures of for example DE 3133918, Indian J. Chem. 1984, 23B, 1243-57 or Heterocycles 1990, 30, 463-9; and B. Treatment with 2-methylthio-2-thiazoline as described in Example 1 following the procedures in for example J. Am. Chem. Soc. 1958, 80, 3339, J. Org. Chem. 1961, 26, 1666 or J. Med. Chem. 1982, 25, 735-42.

In a further aspect of the invention there is provided the use of 2-alkoxy-2-thiazolines, or 2-aryloxy-2-thiazolines of the formula (III)

where $R_z$ is optionally substituted alkyl and aryl as reagents for the preparation of compounds of formula I. The transformation using III is described in Examples 2 and 4. The use of these reagents offers considerable advantages over the use of the corresponding 2-methylthio-2-thiazoline (see Example 3), as the reaction takes place at lower temperature (see Examples 2 and 4).

Additional methods for converting amines into aminothiazolines are described in the literature and can be adapted for transforming amines (II) into aminothiazolines (I). Thus the amines can be converted to thioureas and then treated with 1,2-dibromoethane as described in for example J. Het. Chem. 1986, 23, 1439-42, or also in Ind. J. Chem 1983, 22B, 249-51, or the amines can be treated at higher temperature with an 2-amino-thiazoline following the method of CH 667652.

Alternatively the amines can be converted to thioureas and then treated with 2-bromo-ethylamine as described in Bioorg. Med. Chem. 2001, 9, 2025.

As a further alternative the amines (II) can be converted into isothiocyanates (VI) and then treated with 2-halo-ethylamine as described in for example J. Org. Chem. 1983, 48, 3901-8 or also in J. Med. Chem. 1987, 30, 1955-62.

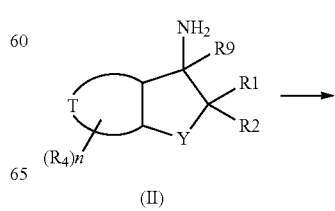

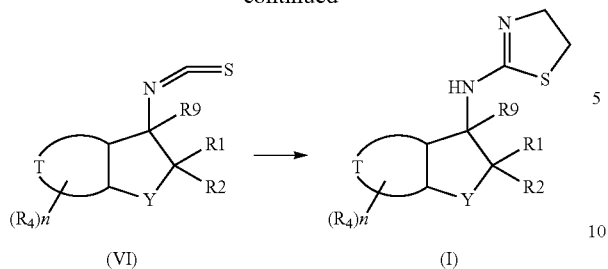

The amines (II$_i$) can be used to make 2-hydroxyethyl-thioureas (VII$_i$), according to methods found in Houben-Weyl E4, (1983) 484, for example using in a first step thiophosgene, and then in a second step 2-hydroxyethylamine. The thioureas (VII$_{ii}$) can be prepared from the isothiocyanates (VI) as described in Example 11. Each of these thioureas can be cyclised to the corresponding thiazolines (I), for example with acid as described for example in U.S. Pat. No. 4,398,028 and in Tet. Lett. 2003, 44, 795-9, or with Ph$_3$P and DEAD as described in Tet. Lett. 1999, 40, 3125 and also described in Example 11. If R$^{10}$ is H, then (II) and (II$_i$) are identical, (VII$_1$) and VII$_{ii}$) are identical, and (I$_i$), (I$_{ii}$) and (Iiii) are tautomers of the same compound.

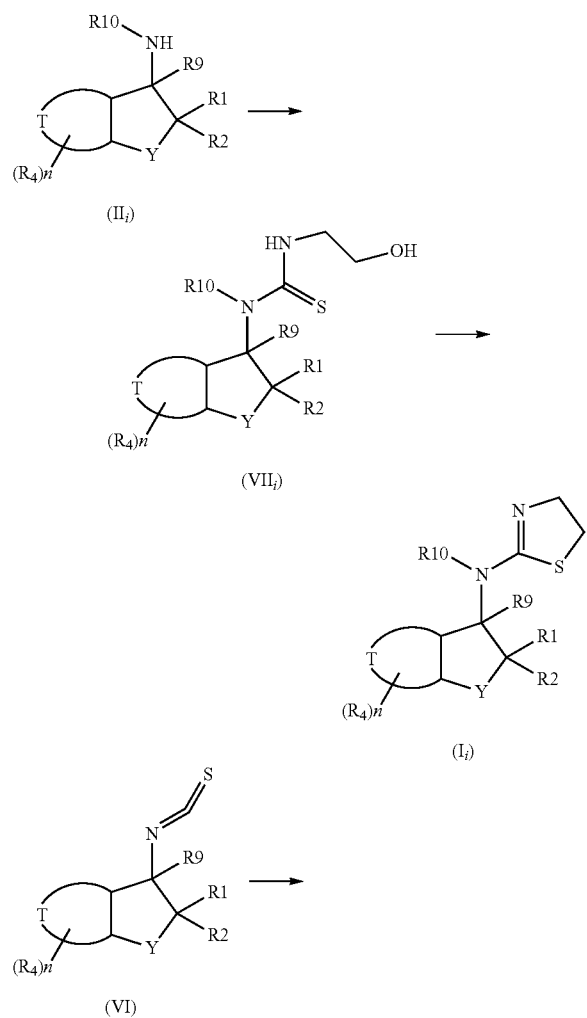

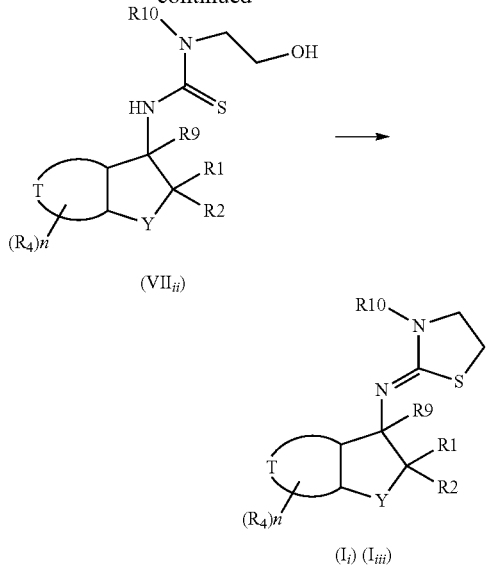

The amines (II) can be converted into isothiocyanates (VI) and then treated with aziridine to the corresponding thioureas which can then be rearranged to the aminothiazolines as described for example in Arch. Pharm. 1958, 291, 457 or also in J. Amer. Chem. Soc. 1961, 83, 2570.

Compounds of the formula I and R$^9$ and R$^{10}$ are H can be prepared from ketones of the formula IV.

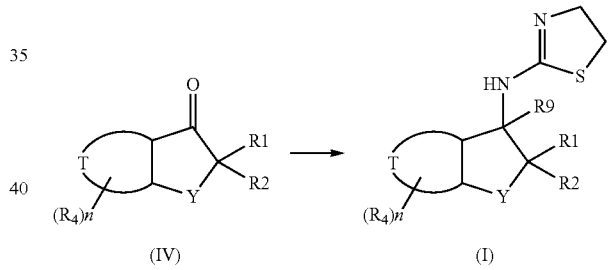

Thus the ketone and 2-aminothiazoline are treated with an agent, which adsorbs, absorbs, or reacts with water such as titanium tetraalkoxide to yield an imine or enamine intermediate, which is then treated with a reducing agent such as sodium borohydride to yield the aminothiazoline (I). An example of this method is described in Example 8. The reaction of ketones with primary amines using drying and reducing agents to form secondary amines is known as reductive amination and is described in for example Organic Reactions 2002, 59, 1-714.

Compounds of the formula I where R$^{10}$ is not H can be prepared from compounds of the formula I where R$^{10}$ is hydrogen, by treatment with a suitable derivatising agent. When R$^{10}$ is an acyl group, acylating agents can be used. When R$^{10}$ is an alkyl group, alkylating agents can be used. When R$^{10}$ is a sulfenyl group, sulfenylating agents can be used. Derivatisation is this manner is well known. Descriptions and methods for these transformations can be found in T. W. Greene and P. G. M. Wuts "Protective Groups in Organic Synthesis" 3$^{rd}$ Edition, Wiley, N.Y., 1999. The group R$^{10}$ can also be introduced via a synthetic precursor of compounds of the formula I, for example via an amine of the formula II$_i$, or via a N—R$^{10}$ substituted hydroxyethylamine.

Amines of the formula (II) can be prepared in various ways. Thus ketones (IV) can be converted into amines of the formula (II) wherein $R^9$ is H. One method for this transformation involves reductive amination for example according to Example 7 and Tetrahedron 2004, 60, 1463-71. This transformation can also be performed in two steps via an oxime and subsequent reduction as exemplified in Examples 9 and intermediate example 1.

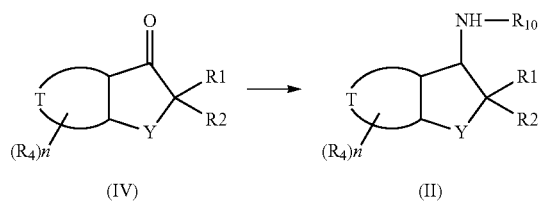

(IV)                    (II)

Amines of the formula (II) can also be prepared from carboxylic acids (V), by a Curtius degradation as shown in Example 5.

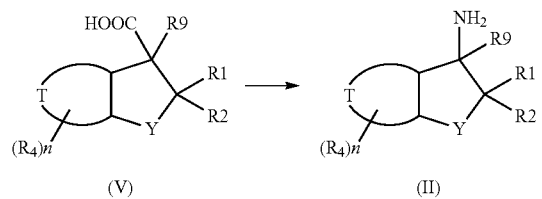

(V)                    (II)

Amines of formula (II), wherein Y is oxygen are partially known or may be prepared by the known methods as described in Chimica Acta Turica, 13(3), 403-412 (1985) and Farmaco, Edizione Scientifica, 43(7-8), 643-655 (1988).

Certain of the isothiocyanates of the formula (VI) are new and are part of this invention.

The novel compounds are those of the formula VIA

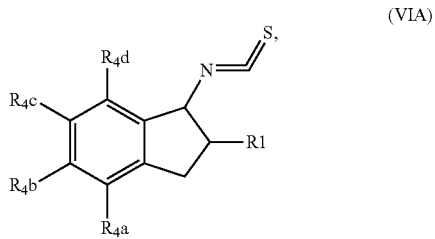

(VIA)

where $R_1$, $R_4a$, $R_4b$, $R_4c$ and $R_4d$ are each independently H, halogen, $C_1$-$C_6$ alkyl or $C_1$-$C_6$ haloalkyl, and where at least one of these substituent must be different to H.

Preferred compounds of the formula (VIA) are those wherein the values $R_1$, $R_4a$, $R_4b$, $R_4c$ and $R_4d$ are given in Table 9.

TABLE 9

| Compound No | R1 | $R_4a$ | $R_4b$ | $R_4c$ | $R_4d$ |
|---|---|---|---|---|---|
| VIA-1 | H | F | H | H | H |
| VIA-2 | H | CH$_3$ | H | H | H |
| VIA-3 | H | F | H | F | H |
| VIA-4 | H | F | H | CH$_3$ | H |

TABLE 9-continued

| Compound No | R1 | $R_4a$ | $R_4b$ | $R_4c$ | $R_4d$ |
|---|---|---|---|---|---|
| VIA-5 | H | F | H | H | F |
| VIA-6 | H | CH$_3$ | H | F | H |
| VIA-7 | F | H | H | H | H |
| VIA-8 | CH$_3$ | H | H | H | H |
| VIA-9 | F | F | H | H | H |
| VIA-10 | F | CH$_3$ | H | H | H |
| VIA-11 | F | F | H | F | H |
| VIA-12 | F | F | H | CH$_3$ | H |
| VIA-13 | F | F | H | H | F |
| VIA-14 | CH$_3$ | F | H | H | H |
| VIA-15 | CH$_3$ | CH$_3$ | H | H | H |
| VIA-16 | CH$_3$ | F | H | F | H |
| VIA-17 | CH$_3$ | F | H | CH$_3$ | H |
| VIA-18 | CH$_3$ | F | H | H | F |

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides* fells (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus*, *Reticulitermes flavipes*, *R. speratu*, *R. virginicus*, *R. hesperus*, and *R. santonensis*) and the *Ter-*

*mitidae* (for example *Globitermes sulphureus*), *Solenopsis geminata* (fire ant), *Monomorium pharaonis* (pharaoh's ant), *Damalinia* spp. and *Linognathus* spp. (biting and sucking lice), and *Deroceras reticulatum* (slug).

The invention therefore provides a method of combating and controlling insects, acarines, or molluscs which comprises applying an insecticidally, acaricidally, nematicidally or molluscicidally effective amount of a compound of formula (I), or a composition containing a compound of formula (I), to a pest, a locus of pest, or to a plant susceptible to attack by a pest, The compounds of formula (I) are preferably used against insects or acarines.

The term "plant" as used herein includes seedlings, bushes and trees.

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

In a still further aspect the invention provides a method of combating and controlling pests at a locus which comprises treating the pests or the locus of the pests with an insecticidally, acaricidally, nematicidally or molluscicidally effective amount of a composition comprising a compound of formula (I). The compounds of formula (I) are preferably used against insects, acarines or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Chloronicotinyl compounds such as imidacloprid, thiacloprid, acetamiprid, nitenpyram or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr; or q) Pymetrozine.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethyl-benzimidazole-1-sulphonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N([methyl(methyl-thioethylideneaminooxycarbonyl)amino]thio)-β-alani nate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples:

Mass spectra data were obtained for selected compounds of the following examples using LCMS: LC5: 254 nm—gradient 10% A to 100% B A=$H_2O$+0.01% HCOOH B=$CH_3CN/CH_3OH$+0.01% HCOOH positive electrospray 150-1000 M/z.

EXAMPLE 1

This Example illustrates the preparation of compound No 2.002

Example 1

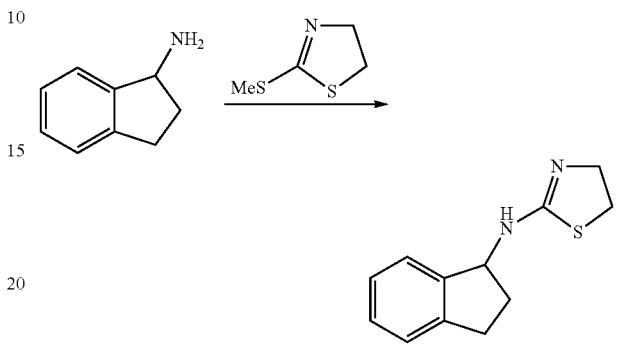

A solution of 1-aminoindane (0.5 ml, 3.87 mmol), 2-methylthio-2-thiazoline (0.421 ml, 3.87 mmol), and methanesulfonic acid (0.251 ml, 3.87 mmol) in butanol (5 ml) was heated under reflux at 125° C. bath temperature for 16 hours. The solvent was evaporated, the crude product separated between HCl (2M) and diethyl ether. The organic phase was made basic with NaOH (32%) and the product extracted into dichloromethane, dried ($MgSO_4$) and evaporated to yield 912 mg of product as beige crystals m.p. 137° C.

EXAMPLE 2

This Example illustrates the preparation of compound No 2.002

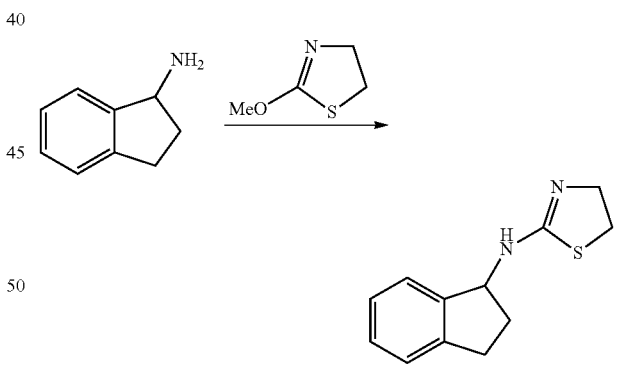

A solution of 1-aminoindane (0.2 ml, 1.55 mmol), 2-methoxy-2-thiazoline (182 mg, 1.55 mmol), and methanesulfonic acid (0.050 ml, 0.77 mmol) in butanol (1 ml) was left at room temperature for 15 days. The mixture was shaken between NaOH (1M) and dichloromethane, and the organic phase dried ($MgSO_4$) and evaporated to yield 286 mg of product as beige crystals m.p. 137° C.

EXAMPLE 3

This Example illustrates the preparation of compound No 2.019

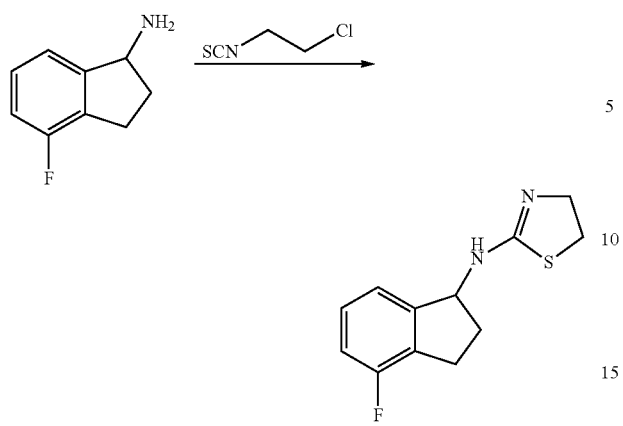

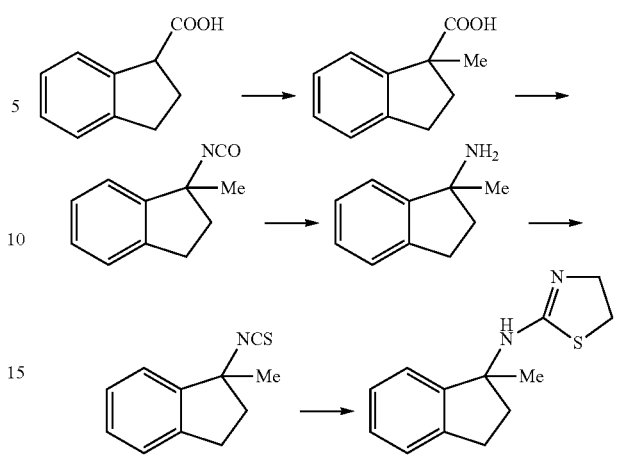

A solution of 4-fluoro-1-indanamine (300 mg, 1.98 mmol) in THF (2.5 ml) was stirred at 0° C. A solution of chloroethyl isothiocyanate (0.200 ml, 2.08 mmol) in THF (0.5 ml) was added, and the mixture stirred at room temperature overnight. The supernatant was decanted and the remaining crystals washed twice with ether, dissolved in water, basified with NaOH (32%) and the product extracted into dichloromethane, dried (MgSO$_4$) and evaporated to leave a dark yellow solid, which was washed twice with ether to yield the product as a fine white powder. m.p. 149° C.

EXAMPLE 4

This Example illustrates the preparation of compound number 6.011

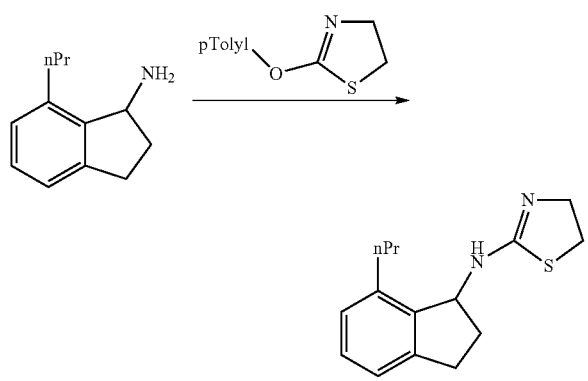

A solution of 7-propyl-1-indanamine (184 mg, 1.05 mmol), 2-(p-tolyloxy)-2-thiazoline (0.174 ml, 203 mg, 1.05 mmol) and methansulfonic acid (0.034 ml, 50 mg, 0.527 mmol) in nBuOH (1 ml) was heated at 110° C. for 2 hours. The solvent was evaporated and the mixture shaken with tBuOMe, NaOH (2M) and NaCl (satd). The product was taken into HCl (2M), and after basification with NaOH (32%) back into tBuOMe, which was washed with NaCl (satd), dried (MgSO$_4$), and evaporated to yield 272 mg as a syrup, which crystallised on standing. m.p. 72-75° C.

EXAMPLE 5

This Example illustrates the preparation of compound number 3.004.

Step 1

A solution of indane-1-carboxylic acid (4.1 g, 25.3 mmol) in THF (30 ml) was added in portions to a solution of lithium diisopropylamide in THF (2M, 27.8 ml, 55.6 mmol) with stirring at −20° C. The solution was then stirred at 35° C. for 1 hour, then cooled again to −20° C. and a solution of methyl iodide (2.05 ml, 32.89 mmol) in THF (10 ml) was added. The light yellow solution was warmed at 35° C. for 4 hours before extracting between HCl (2M) and EtOAc to yield the crude product (4.5 g) as a brown oil. This mixture was cromatographed on HPLC with EtOAc/hexane to yield 1-methyl-1-indanecarboxylic acid (1 g) and recovered starting material (700 mg)

Step 2

A solution of 1-methyl-1-indanecarboxylic acid (864 mg, 4.9 mmol), diphenylphosphoryl azide (1.3 ml, 6.02 mmol) and triethylamine (0.95 ml, 6.87 mmol) in tBuOH (10 ml) was stirred with 5 g of 4A molecular sieves at 95° C. for 5 hours, while a gas was evolved. The mixture was cooled, diluted with EtOAc, filtered and the solvent evaporated. The crude product was redissolved in EtOAc, washed with water, dried with MgSO4, and evaporated to give the isocyanate as a brown oil (700 mg)

Step 3

The isocyanate from step 2 (300 mg, 1.73 mmol) was dissolved in THF (3 ml) and stirred with NaOH (2M, 2.4 ml) for 4 hours, then shaken between HCl (2M) and AcOEt. The aqueous phase was made basic with NaOH (conc.) and the product extracted into EtOAc, dried, and evaporated to give the amine (52 mg, 20%) as an oil.

Step 4

A solution of the amine from step 3 (110 mg, 0.748 mmol) in dichloromethane was added slowly to a stirred solution of thiophosgene (0.063 ml, 0.823 mmol) in dichloromethane (1 ml) and 103 mg potassium carbonate in water (1 ml)at 0° C. After 15 min a cold solution of KOH (1.496 mmol) in water (1 ml) was added and the mixture shaken between dichloromethane and water. The organic phase was dried and evaporated to give the isothiocyanate (90 mg) as an unstable oil.

Step 5

NaOH (2M, 0.237 ml) was added to a solution of 2-bromoethylamine hydrobromide (97 mg, 0.476 mmol) in water (0.1 ml) and stirred with ether (0.5 ml) at 0° C. A solution of the isothiocyanate from step 4 (90 mg, 0.476 mmol) in ether (1 ml) was added slowly and the mixture stirred at 0° C. for 30 minutes. The mixture was shaken between ether and water, and the ether phase extracted with HCl (2M). The aqueous phase was made basic with NaOH (2M) and the product extracted into EtOAc, which was dried and evaporated to yield 11 mg (10%) of the product. $^1$H-NMR (300 MHz CDCl$_3$) 1.68 (3H, s); 2.18 (1H, m); 2.73 (1H, m); 2.88 (1H, m); 3.03 (1H, m); 3.22 (2H, t); 3.98 (2H, m); 7.27 (4H, m).

EXAMPLE 6

This Example illustrates the preparation of compound number 6.002.

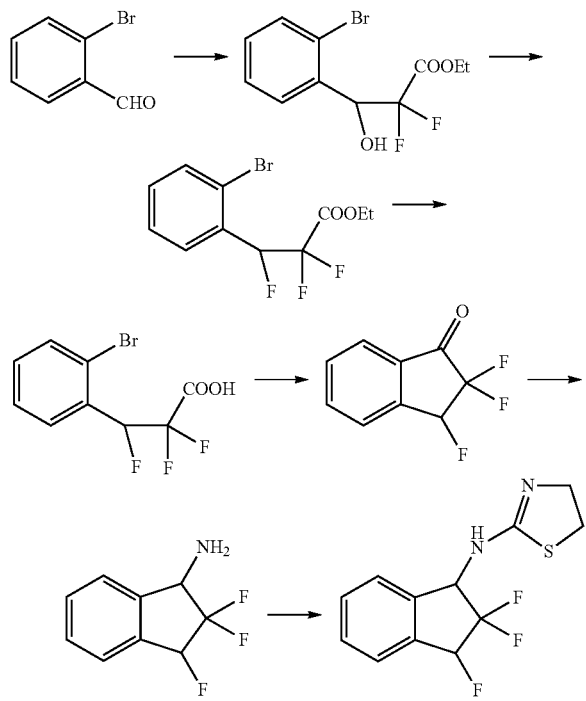

Step 1.

Zinc dust (6 g) was washed with HCl (20% aq. 10 ml), then water, acetone and ether, then added to a solution of 2-bromobenzaldehyde (7.03 ml, 60.8 mmol) in THF (60 ml). Ethyl bromodifluoroacetate (9.5 ml, 73 mmol) in THF (30 ml) was added in portions. After the exothermic reaction was over the mixture was stirred for 3 hours, then shaken between EtOAc, NH$_4$Cl (sat.) and NaCl (sat.). The organic phase was dried and evaporated to yield the product (12 g) as a yellow oil.

Step 2.

A solution of the product from step 1 (12 g, 38.8 mmol) in dichloromethane (30 ml) was added slowly to a solution of DAST in dichloromethane (50 ml) at −70° C. After 30 minutes at this temperature it was allowed to warm to room temperature and stirred for 2 hours, then cooled and poured onto cooled NaHCO$_3$ (1M). The product was extracted into dichloromethane, dried and the solvent evaporated to yield the product (10 g) as a brown oil.

Step 3.

A solution of the product from step 2 (10 g, 32 mmol) in EtOH (200 ml) and NaOH (32%, 100 ml) was stirred at 90° C. for 5 hours, then cooled and shaken between ether and water. The aqueous phase was acidified with HCl (conc.) and the product extracted into ether, dried and evaporated to yield the acid (3.2 g) as a brown oil.

Step 4

A solution of BuLi in hexane (1.6 M, 1.47 ml, 2.36 mmol) was added slowly to a solution of the product from step 3 (304 mg, 1.07 mmol) at −10° C. After 10 minutes at this temperature it was warmed up to room temperature, poured onto HCl (2M aq.) and extracted into ether. The ether phase was dried and evaporated to yield 212 mg crude product, which was chromatographed on silica gel with 50% EtOAc/hexane to yield the 2,2,3-trifluoro-indanone (45 mg).

Step 5

A solution of 2,2,3-trifluoro-indanone (282 mg, 1.5 mmol), titanium isopropoxide (0.886 ml, 2.99 mmol) and ammonia (2M in EtOH, 2.5 ml) in EtOH was stirred for 5 hours. The mixture was cooled to 0° C. and NaBH4 (85 mg, 2.25 mmol) added. After stirring for 2 hours the mixture was left at room temperature overnight, then poured onto NH$_4$OH (25%, 10 ml) and extracted with EtOAc. The organic phase was washed with water, dried, and evaporated to yield the crude product (205 mg) as a brown oil. This was shaken between ether and HCl (2M aq.), basified with NaOH (2M) and extracted into ether. Evaporation yielded 1-amino-2,2,3-trifluoro-indane (90 mg) as an oil.

Step 6

Chloroethylisothiocyanate (0.045 ml, 0.470 mmol) was added to a solution of 1-amino-2,2,3-trifluoro-indane (80 mg, 0.427 mmol) in THF (0.5 ml). The white precipitate was filtered off to yield 40 mg of the product as an HCl salt. This was shaken between NaOH (aq.) and dichloromethane, the organic phase dried and evaporated to yield 31 mg of the product. $^1$H-NMR (300 MHz, CDCl$_3$) 3.39 (2H, t); 3.98 (2H, m); 5.44 (1H, t, J=8); 5.79 (1H, ddd, J=49, 8, 6); 7.50 (4H, m).

EXAMPLE 7

This Example illustrates the preparation of compound number 6.002.

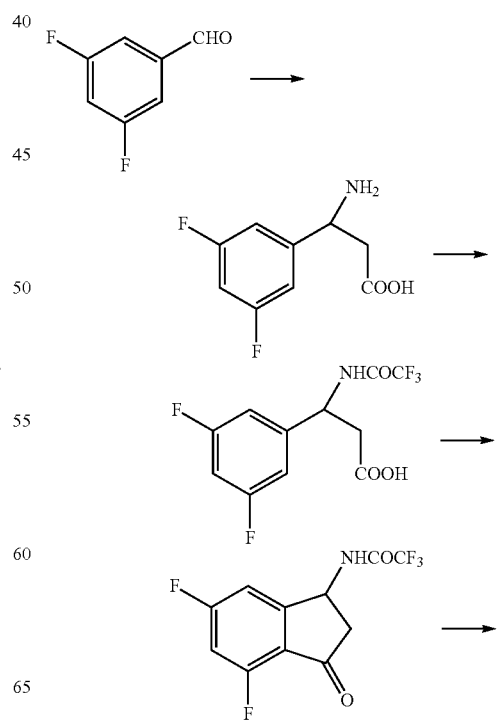

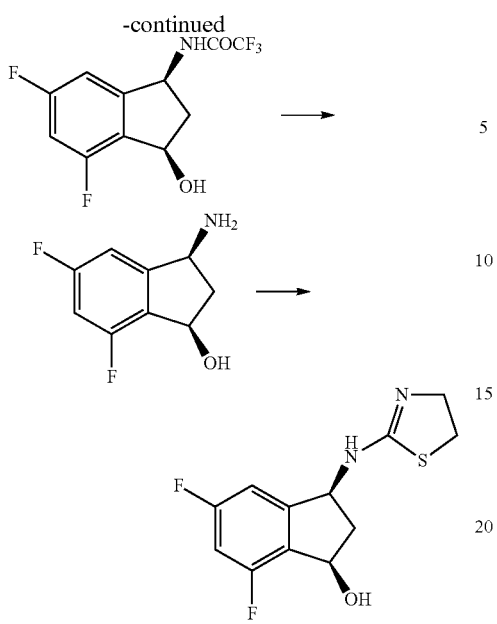

Step 1

A suspension of ammonium acetate (27.12 g, 351.8 mmol), malonic acid (18.31 g, 175.92 mmol) and 3,5-difluoro-benzaldehyde (25 g, 175.92 mmol) in ethanol (53 ml) was heated overnight under reflux, cooled to room temperature, the product filtered off, washed with ethanol and ether, and dried under vacuum to yield 21.07 g of product as a white powder.

Step 2.

TFAA (15 ml) was added to a solution of the product from step 1 (5 g, 24.85 mmol) in TFA (15 ml). After 45 minutes the mixture was poured onto 350 ml cold water and the product filtered off. It was washed with water and dried overnight in the air to yield 6.06 g of the trifluoroacetate as white crystals.

Step 3

Sulfuric acid (0.036 ml, 0.67 mmol) was added to a solution of the product from step 2 (2.0 g, 6.78 mmol) in TFA (10 ml) and TFAA (10 ml), and the mixture heated for 4 hours under reflux. The solvent was evaporated and the crude product stirred with ice/water (50 ml). The product was filtered off and washed with water and dried under vacuum to yield the indanone (1.48 g) as beige crystals.

Step 4.

Sodium borohydride (712 mg, 18.8 mmol) was added in portions to a suspension of the product from step 3 (5 g, 17.9 mmol) in MeOH (50 ml) at 0° C. After 2 hours at 0° C. acetic acid (0.5 ml) and water (2 ml) was added and the solvent evaporated. The crude product was taken up in dichloromethane, washed with HCl (1M) and NaHCO3 (sat.), dried and evaporated to give the product (4.87 g) as a mixture of cis and trans isomers. This mixture was stirred with a little ether and the pure cis isomer filtered off, washed with ether and dried to yield 2.48 g. Chromatography of the mother liquors on silica with 5% MeOH/dichloromethane led to the pure trans isomer (537 mg) as white crystals.

Step 5.

A solution of the cis isomer from step 4 (600 mg, 2.13 mmol) and potassium carbonate (1.47 g, 10.6 mmol) in methanol (20 ml) and water (4.5 ml) was heated under reflux for 2 hours, cooled and the solvent evaporated. The crude product was shaken between NaOH (2M) and dichloromethane. The organic phase was dried and evaporated to yield 160 mg product as brown crystals.

Step 6.

Chloroethylisothiocyanate (0.073 ml, 0.754 mmol) was added to a solution of the product from step 5 (133 mg, 0.718 mmol) in THF (3 ml), and the solution left overnight. The mixture was shaken between HCl (1M) and ether, the aqueous phase was basified with NaOH (32%), and the product extracted into dichloromethane, which was then dried and evaporated. The crude product was washed with ether (1×2 ml, and 2×0.5 ml) to yield the product (105 mg) as beige crystals. m.p. 167° C.

EXAMPLE 8

This Example illustrates the preparation of compound number 1.003

(7-Chloro-1,2,3,4-tetrahydro-naphthalen-1-yl)-(4,5-dihydro-thiazol-2-yl)-amine

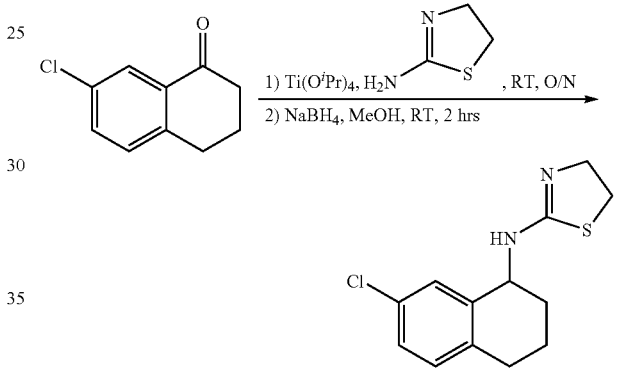

Titanium isopropoxide (710 mg, 0.74 mls, 2.5 mmol) is added to a mixture of 7-chloro-1-tetralone (360 mg, 2 mmol) and 2-aminothiazoline (224 mg, 2.2 mmol). The reaction mixture is stirred for 16 hours at room temperature, then diluted with dry methanol (5 ml). Excess sodium borohydride is added carefully portionwise over a period of 45 minutes. The reaction mixture is stirred for a further 2 hours, then added to a saturated aqueous solution of Rochelle's salt and extracted with dichloromethane (2×25 mls). The organic phases are combined, washed sequentially with water and saturated brine, then filtered through a pad of magnesium sulphate. The filtrate is concentrated under reduced pressure to give the crude product as a pale yellow gum. The crude product is purified by column chromatography on silica, eluting with ethyl acetate to give the title compound as a white solid Mp 164-6° C. Nmr data: ($CDCl_3$): 7.39 (1H, s, CH), 7.13 (1H, dd, CH), 7.01 (1H, s, CH), 4.90 (1H, m, CH), 4.06 (2H, m), 3.37 (2H, m), 2.72 (2H, m), 2.08 (1H, m), 1.85 (3H, m)

EXAMPLE 9

This Example illustrates the preparation of compound number 1.014.

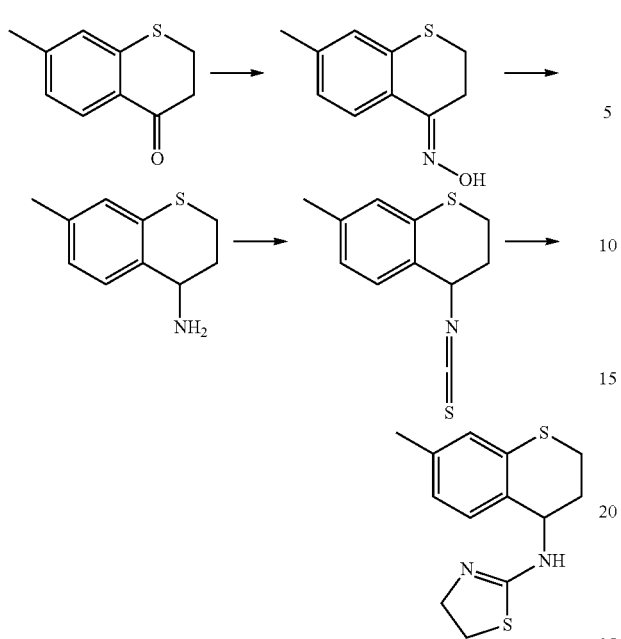

Step 1.

Hydroxylamine hydrochloride (590 mg, 8.4 mmol) was added in one portion to a stirring solution of ketone (1 g, 5.6 mmol) in methanol (15 ml) and the resultant yellow solution was stirred at room temperature for 16 hours. The reaction was then concentrated and triturated with ether and hexane to give a beige solid. This solid was collected and dried by filtration and NMR and MS confirmed this to be the desired oxime (0.802 g, 4.15 mmol, 74%).

Step 2.

Raney nickel (500 mg) was washed and added to a solution of oxime (532 mg, 2.8 mmol) in methanolic ammonia (7M, 10 ml). This suspension was then subjected to 3.85 bar hydrogen pressure at room temperature for 2.5 hours. The reaction was then filtered through hyflo and concentrated in vacuo to a light green solid. This solid was found by NMR to be the desired product (310 mg, 1.6 mmol, 57%) which was used crude in the next step.

Step 3.

1,1'-thiocarbonyldiimidazole (144 mg, 0.81 mmol) was added to a solution of amine (145 mmol, 0.81 mmol, slight presence of nickel) in DMF and stirred at room temperature for 16 hours. Ethyl acetate and water were then added and the organic phase washed with water and brine, dried (MgSO$_4$) and concentrated in vacuo. The crude orange oil was analysed by NMR, MS and IR, found to be desired isothiocyanate and was used immediately in the next step.

Step 4.

Triethylamine (0.15 ml, 1.1 mmol) was added to a suspension of 2-chloroethylamine hydrochloride (130 mg, 1.1 mmol) in DCM and the solution was stirred for 30 mins. Isothiocyanate (1.1 mmol) in DCM was then added. A GCMS was taken after an hour and showed the presence of desired product and SM. The reaction was stirred overnight. GCMS showed complete reaction and the solvent was removed in vacuo to give a crude orange solid. This was recrystallised from ethanol to give the product as a white solid (crop 1, 31 mg, 0.117 mmol, 14%) and a second crop as a beige solid (21 mg, 0.08 mmol, 10%). Overall yield for two steps 24%. m.p. 234-235° C.

EXAMPLE 10

This Example illustrates the preparation of Compound No 8.017

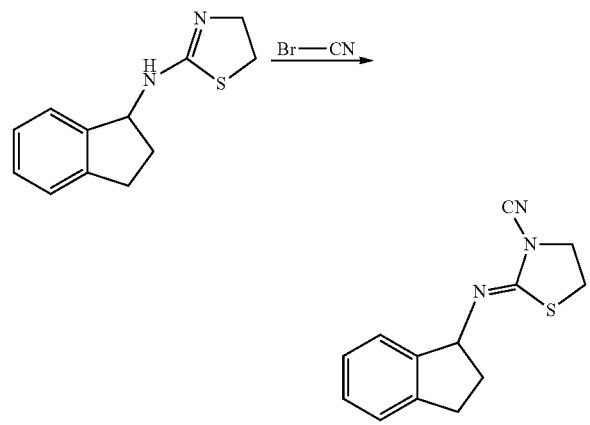

A suspension of 0.70 g (3.2 mmol) (4,5-Dihydro-thiazol-2-yl)-indan-1-yl-amine, 0.52 g (4.8 mmol) cyanogen bromide and 1.56 g (4.8 mmol) CsCO$_3$ in 10 ml acetonitrile— was stirred at 20° C. for 16 hours. The suspension was filtered and the solvent evaporated. The crude product was purified by flash chromatography using EtOAc/n-hexane (1:5) as eluent to yield 0.50 g of 2-(Indan-1-ylimino)-thiazolidine-3-carbonitrile (white crystals, m.p. 90-91° C.). $^1$H-NMR (400 MHz, CDCl$_3$): 2.0-2.15 (1H, m); 2.40-2.50 (1H, m); 2.85-2.95 (1H, m); 3.0-3.10 (1H, m); 3.35-3.45 (2H, m), 3.90-4.0 (2H, m), 4.65 (1H, t), 7.10-7.30 (4H, m).

EXAMPLE 11

This example illustrates the preparation of compound 2.006

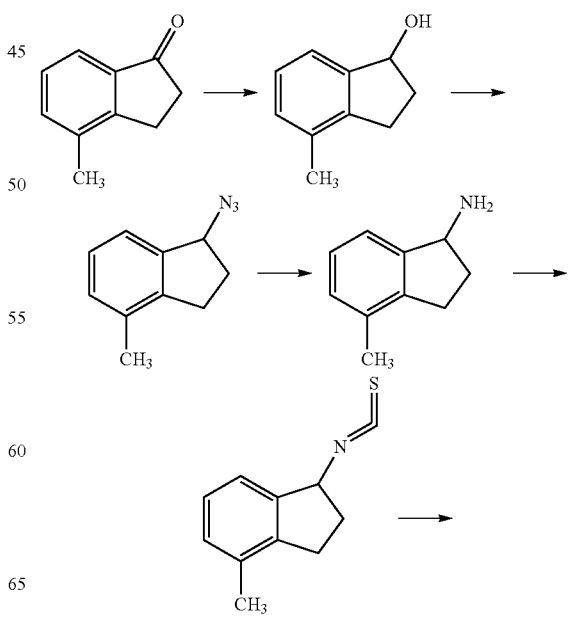

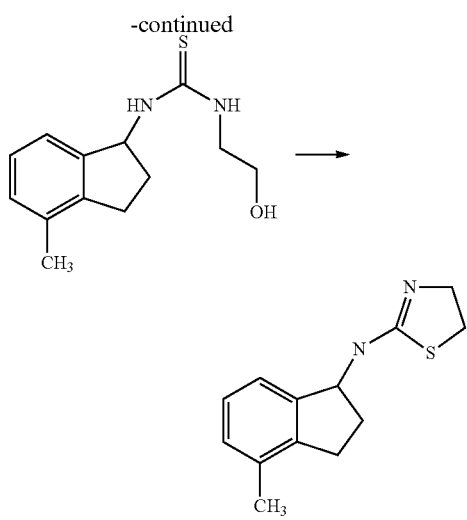

Step 1.

15.0 g (102.6 mmol) 4-methyl-indan-1-one is dissolved in 125 ml MeOH. The solution is cooled to 0-5° C. and 4.3 g (112.9 mmol) NaBH$_4$ is added portionwise while maintaining the temperature between 0-8° C. After the addition of NaBH$_4$ the cool-bath is removed and the reaction mixture is stirred till TLC indicates completion of the reaction. The reaction mixture is poured into water and extracted three times with EtOAc. The collected organic layers are washed with water and brine, dried over MgSO$_4$ and filtered. After evaporation of EtOAc 4-methyl-indan-1-ol is isolated in 98% yield. The crude material may be used directly without further purification.

$^1$H-NMR (ppm, CDCl$_3$): 1.95-2.03 (m, 1H); 2.30 (s, 3H); 2.45-2.55 (m, 1H); 2.70-2.80 (m, 1H); 2.95-3.05 (m, 1H); 5.25-5.30 (dd, 1H); 7.12 (d, 1H); 7.18 (t, 1H); 7.28 (d, 1H).

Step 2.

4.34 g (29.28 mmol) 4-methyl-indan-1-ol and 7.8 ml (35.14 mmol) diphenylphosphoryl azide are dissolved in dry THF at room temperature under argon. To this mixture is added slowly 5.0 ml (35.14 mmol) 1,8-diazabicyclo[5.4.0]undec-7-ene. The reaction is stirred for 6 h at room temperature (TLC monitoring). Then the mixture is poured into water and extracted three times with toluene. The organic layers are combined, dried over MgSO$_4$ and concentrated in vacuo. Purification using silica gel chromatography (hexane/EtOAc 9:1) affords pure 1-azido-4-methyl-indane as light orange liquid.

$^1$H-NMR (ppm, CDCl$_3$): 2.05-2.15 (m, 1H); 2.25 (s, 3H); 2.35-2.45 (m, 1H); 2.72-3.02 (m, 1H); 4.82-4.88 (dd, 1H); 7.10 (d, 1H); 7.15 (t, 1H); 7.22 (d, 1H).

Step 3.

1.0 g (5.8 mmol) 1-azido-4-methyl-indane is treated with 4.54 g (17.3 mmol) triphenylphosphine in 26 ml THF and 1.4 ml H$_2$O at room temperature overnight. Completion of the reaction is achieved by heating up the mixture for additional 2.5 hours. The reaction mixture is then cooled to room temperature and diluted with water. The pH is adjusted to 2 by adding cold (ca 0° C.) aqueous HCl (1M). After extraction with EtOAc the aqueous layer is separated, basified with NaOH (2M) and extracted into EtOAc. The organic layer is then dried (MgSO$_4$) and concentrated in vacuo to give 4-methyl-indan-1-yl-amine as a light yellow liquid.

$^1$H-NMR (ppm, CDCl$_3$): 1.55 (br s, 1H); 1.60-1.70 (m, 1H); 2.25 (s, 3H); 2.45-2.52 (m, 1H); 2.62-2.72 (m, 1H); 2.85-2.94 (m, 1H); 4.33 (t, 1H); 6.98-7.05 (m, 1H); 7.10-7.15 (m, 2H).

Step 4.

A mixture of 0.36 ml (4.32 mmol) thiophosgene in 4 ml dichloromethane is cooled to 0° C. after which a cold (0° C.) solution of 0.5 g (3.60 mmol) K$_2$CO$_3$ in 4 ml water is added. The mixture is stirred for 10 min and 0.53 g (3.60 mmol) indan-1-ylamine is then added drop wise with vigorous stirring at 0° C. After an additional 10 min a cold solution of 0.40 g (7.20 mmol) KOH in 4 ml water is added in one portion with cooling. The organic layer and three extracts (Et$_2$O) are combined, dried over MgSO$_4$, filtered and concentrated to give 1-isothiocyanato-4-methyl-indane as an orange brown liquid. The product is used directly without further purification.

$^1$H-NMR (ppm, CDCl$_3$): 2.18-2.28 (m, 1H); 2.28 (s, 3H); 2.50-2.60 (m, 1H); 2.75-2.85 (m, 1H); 2.95-3.05 (m, 1H); 5.19 (t, 1H), 7.11 (d, 1H); 7.18 (t, 1H); 7.25 (d, 1H).

Step 5.

680 mg (3.59 mmol) 1-isothiocyanato-4-methyl-indane is dissolved in 13 ml THF at room temperature under argon. Then 0.21 ml (3.59 mmol) 2-amino-ethanol is added slowly. The reaction mixture is stirred at room temperature overnight. After completion of the reaction as indicated by TLC the solvent is removed under reduced pressure to give the crude product. Subsequent purification by column chromatography on silica gel (CH$_2$Cl$_2$/MeOH 15:1) and stirring in Et$_2$O affords the title compound 1-(2-hydroxy-ethyl)-3-(4-methyl-indan-1-yl)-thiourea as a white powder (Mp 90-93° C.).

$^1$H-NMR (ppm, CDCl$_3$): 1.85-1.95 (m, 1H); 2.25 (s, 3H); 2.55 (br s, 1H); 2.60-2.70 (m, 1H); 2.71-2.81 (m, 1H); 2.86-2.99 (m, 1H); 3.62 (br s, 2H); 3.78 (t, 2H); 5.67 (br s, 1H); 6.47 (br s, 1H), 6.11 (br s, 1H); 7.07 (d, 1H); 7.12 (t, 1H); 7.18 (d, 1H).

Step 6.

500 mg (2.0 mmol) 1-(2-Hydroxy-ethyl)-3-(4-methyl-indan-1-yl)-thiourea and 786 mg (3.0 mmol) triphenylphosphine (TPP) were solved in 25 ml dry tetrahydrofuran (THF) at room temperature under Argon. After 15 minute stirring at 20° C. a solution of 606 mg (3.0 mmol) disopropyl azodicarboxylate (DIAD) in 10 ml THF was added drop wise while maintaining the temperature below 20° C. The reaction was complete after 3 hours indicated by TLC. Then the reaction mixture was concentrated under vacuo and 1 M HCl and ethyl acetate were added. The water layer was separated and three times extracted with ethyl acetate. The ph of the water phase was then adjusted to ca 8-9 by adding solid NaOH. The crude product was extracted into CH$_2$Cl$_2$ and thoroughly washed with water and brine. After drying over MgSO$_4$ and evaporation 428 mg (4,5-Dihydro-thiazol-2-yl)-(4-methyl-indan-1-yl)-amine were obtained as a white powder (Mp. 135-135° C.).

$^1$H-NMR (CDCl$_3$, ppm): 1.80-1.90 (m, 1H), 2.1.9 (s, 3H), 2.51-2.61 (m, 1H), 2.61-2.72 (m, 1H), 2.80-2.90 (m, 1H), 3.30 (t, 2H), 3.92-4.05 (m, 2H), 5.18 (t, 1H), 6.99 (d, 1H), 7.08 (t, 1H), 7.15 (d, 1H).

INTERMEDIATE EXAMPLE 1

This Example illustrates the preparation of 4,5-difluoro-1-indanamine.

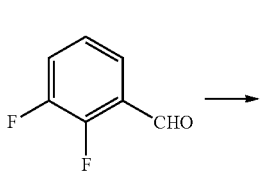

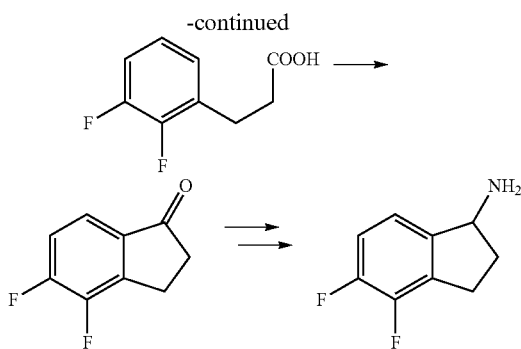

Step 1 (According to G Toth et al. Synth. Comm. 1995, 25(19), 3067-74)

Triethylamine (30 ml) was added dropwise with stirring to formic acid (19 ml) at 0° C. To this solution was added 2,3-difluorobenzaldehyde (25 g, 176 mmol) and Meldrum's acid (25.4 g, 176 mmol) and the mixture heated at 100° C. for 2 hours, during which time gas evolved and 5 ml distillate was collected. The mixture was heated for a further 2 hours, then treated with ice/water (140 ml), and HCl (conc. aq.) to pH 1-2. The mixture was left at 5° C. overnight, and the product then filtered off, washed with water, dried first in the air then on the vacuum to yield 29.11 g white crystals of the (2,3-difluoro)-3-propionic acid.

Step 2

Thionyl chloride (6.43 ml, 88.64 mmol) was added to a suspension of (2,3-difluoro)-3-propionic acid (15 g, 80.58 mmol) in DMF (0.17 ml) and hexane (60 ml) with stirring. After stirring for one hour at room temperature the brown solution was heated at 50° C. for 2 hours then the solvent evaporated leaving the acid chloride as a brown oil. This was dissolved in dichloromethane (60 ml), AlCl$_3$ was added in three portions with stirring, and the dark brown/black mixture stirred overnight at room temperature. The mixture was poured onto ice/water, acidified with HCl (conc. 15 ml) and the product extracted into dichloromethane, which was washed with HCl (2M) and NaOH (2M), dried (MgSO$_4$), and evaporated to yield 7.21 g 4,5-difluoro-1-indanone as a brown solid (m.p. 28-32° C.).

Step 3

4,5-difluoro-1-indanone (5.0 g, 35.68 mmol) and hydroxylamine hydrochloride (3.72 g, 53.52 mmol) were dissolved in pyridine (16 ml) and the dark brown solution left at room temperature overnight, then poured onto 40 ml of ice/water. The product was filtered off, washed with water, and dried first in the air then under vacuum to yield 6.21 g of the oxime as a light beige powder.

Step 4

Sodium borohydride (4.34 g, 114.6 mmol) was added to a solution of TiCl$_4$ (6.3 ml, 57.3 mmol) in DME (120 ml) at 0° C. under stirring. A gas evolved, the temperature rose to 20° C., and the solution became light blue. After cooling to 0° C. a suspension of the oxime from step 3 (5.0 g, 27.3 mmol) in DME (20 ml) was poured in. The temperature rose to 20° C. and the mixture was stirred at room temperature overnight. The dark blue suspension was added in portions to a mixture of potassium tartrate (200 mmol), water (100 ml), and NaOH (32%, 50 ml), which was stirred at 0° C. This quenching was exothermic. After stirring for 2 hours the opalescent mixture was extracted with diethyl ether. The product was then extracted into HCl (1M), washed with ether, and after basifying with NaOH (32%), it was extracted into dichloromethane, which was dried and evaporated to yield 1.5 g of 4,5-difluoro-1-aminoindane as a light brown oil. $^1$H-NMR (300 MHz, CDCl$_3$) 1.57 (3H, s, NH$_2$); 1.78 (1H, m); 2.57 (1H, m); 2.81 (1H, m); 3.09 (1H, m); 4.37 (1H, t) 7.00 (2H, m).

INTERMEDIATE EXAMPLE 2

This Example illustrates the preparation of dimethyl-thiocarbamic acid O-(1-oxo-indan-4-yl) ester

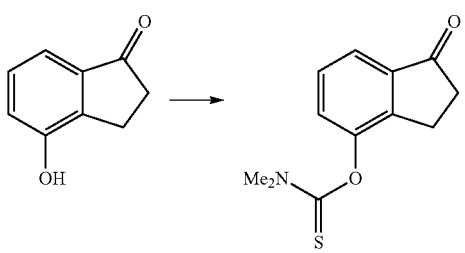

13.3 g (87 mmol) 4-hydroxy-indan-1-one was added portion wise to a suspension of 2.3 g (91.3 mmol) NaH in 200 ml dry DMF and stirred at 20° C. After hydrogen evolution had ceased, a solution of 11.8 g (95.6 mmol) N,N'-dimethylthiocarbamoyl chloride in 50 ml dry DMF was slowly added. The resulting mixture was stirred overnight at 20° C. After completion of the reaction indicated by TLC the reaction mixture was poured into ice water and extracted several times with EtOAc. The organic extract was thoroughly washed with 10% aq K2CO3, dried over MgSO4, and evaporated to dryness in vacuo. The crude product was purified by flash chromatography (hexane/EtOAc 3:1) to give 13.3 g (65%) of dimethyl-thiocarbamic acid O-(1-oxo-indan-4-yl) ester as a slight yellow solid compound. 1H-NMR (ppm, CDCl3): 2.65-2.7 (m, 2H), 3.05-3.1 (m, 2H), 3.4 (s, 3H), 3.5 (s, 3H), 7.25 (d, 1H), 7.4 (t, 1H), 7.7 (d, 1H).

INTERMEDIATE EXAMPLE 3

This Example illustrates the preparation of 4-difluoromethoxy-indan-1-one

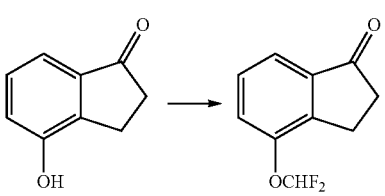

10.0 g (76.5 mmol) 4-hydroxy-indan-1-one was added to a suspension of 28.0 g (202 mmol) K$_2$CO$_3$ in 100 ml dry DMF and stirred overnight at 20° C. The suspension was heated to 85° C. and treated with 17.0 g (202 mmol) gaseous CHClF2 for 45 minutes while maintaining the temperature at 85° C. The resulting dark suspension was cooled to room temperature and poured into 1500 ml water. The mixture was extracted with EtOAc. After separation the organic layer was washed with water and brine, dried over MgSO$_4$ and evaporated to dryness. The crude product was purified by flash chromatography (hexane/EtOAc 9:1) to give 7.0 g (52%) of 4-difluoro-methoxy-indan-1-one with mp 61-67° C.

1H-NMR (ppm, CDCl$_3$): 2.70-2.75 (m, 2H), 3.15-3.2 (m, 2H), 6.65 (t, broad, 1H) 7.35-7.45 (m, 2H), 7.65 (d, 1H).

INTERMEDIATE EXAMPLE 4

This Example illustrates the preparation of 2-p-tolyloxy-thiazoline

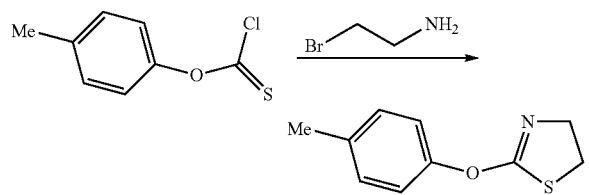

(according to Iwakura at al. J. Org. Chem. 1967, 32, 2362) Solid 2-aminoethylbromide hydrobromide (6.57 g, 32.1 mmol) was added to a solution of para tolylchlorothionoformate (5 ml, 6.05 g, 32.1 mmol) in tBuOMe (50 ml) with stirring at 0° C. NaOH (2M, 35 ml) was slowly added causing an exotherm to 29° C. After stirring at 0° C. for ca 30 minutes, NaOH (8M, ca 30 ml) was added to make the mixture basic. The product was extracted into tBuOMe, washed with NaHCO$_3$ (1M) and NaCl (sat.), dried (MgSO$_4$) and evaporated to yield 5.125 g (83%) of the product as a colourless oil. $^1$H-NMR (300 MHz, CDCl$_3$): 2.32 (3H, s, Me); 3.51 (2H, t, J=8); 4.06 (2H, t, J=8); 7.09 (2H, d, J=8); 7.18 (2H, d, J=8).

EXAMPLE 12

This Example illustrates the pesticidal/insecticidal properties of compounds of formula (I).

Test against were performed as follows:

*Heliothis virescens* (Tobacco Budworm):

Eggs (0-24 h old) were placed in 24-well microtiter plate on artificial diet and treated with test solutions at an application rate of 200 ppm by pipetting. After an incubation period of 4 days, samples were checked for egg mortality, larval mortality, and growth regulation. The following compounds gave at least 80% control of *Heliothis virescens:* 2.025, 2.024, 2.022, 2.001, 2.020, 2.031, 2.003, 2.019, 2.026, 7.010, 2.030, 2.032, 1.007, 2.028, 2.040, 2.048, 2.049, 2.052, 2.058, 2.067, 6.022, 6.023, 6.026, 6.027, 6.032, 6.035, 6.038, 8.017, 8.018, 8.025, 8.031, 8.033, 8.034, 9.018, 9.019, 9.020, 10.001, 10.009, 10.011, 10.013, 10.015, 10.017, 10.020, 10.022, 10.025, 12.008, 12.012, 12.017.

*Myzus persicae* (Green Peach Aphid):

Sunflower leaf discs were placed on agar in a 24-well microtiter plate and sprayed with test solutions at an application rate of 200/50/12.5 ppm. After drying, the leaf discs were infested with an aphid population of mixed ages. After an incubation period of 6 DAT, samples were checked for mortality.

The following compounds gave at least 80% control of *Myzus persicae:* 2.025, 2.024, 2.022, 2.001, 7.006, 2.020, 2.031, 6.019, 4.001, 2.002, 2.003, 2.006, 2.019, 2.016, 7.007, 2.026, 7.008, 2.014, 7.010, 2.030, 1.012, 2.014, 2.031, 2.032, 2.052, 2.058, 2.066, 6.020, 6.022, 6.032, 6.042, 8.017, 8.018, 8.030, 8.031, 8.032, 8.036, 9.001, 9.020, 10.002, 10.012, 10.013, 10.014, 10.015, 10.019, 10.020, 10.021, 10.022, 10.025, 12.008, 12.010, 12.011.

*Myzus persicae* (Green Peach Aphid):

Roots of pea seedlings, infested with an aphid population of mixed ages, were placed directly in the test solutions of 24 ppm. 6 days after introduction, samples were checked for mortality.

The following compounds gave at least 80% control of *Myzus persicae:* 2.025, 2.024, 2.022, 2.001, 2.031, 4.001, 2.003, 2.006, 2.019, 2.030, 2.058, 2.066, 2.067, 7.006, 8.025, 10.002, 10.006, 10.009, 10.011, 10.015.

*Tetranychus urticae* (Two-Spotted Spider Mite):

Bean leaf discs on agar in 24-well microtiter plates were sprayed with test solutions at an application rate of 200/50/12.5 ppm. After drying, the leaf discs are infested with mite populations of mixed ages. 8 days later, discs are checked for egg mortality, larval mortality, and adult mortality.

The following compounds gave at least 80% control of *Tetranychus urticae:* 2.024, 2.022, 7.006, 2.020, 2.006, 2.019, 7.010, 2.030, 2.058, 2.066, 2.067, 6.022, 6.032, 7.006, 8.018, 8.025, 8.026, 8.027, 8.031, 8.032.

The invention claimed is:

1. A compound of formula IC

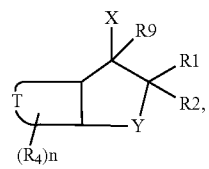

wherein

X is (i), (ii) or (iii)

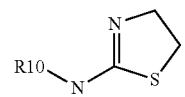

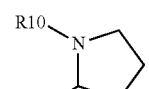

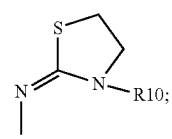

Y is O, S(O)$_m$, NR$^3$ or CR$^5$R$^6$;

m is 0, 1, or 2;

the ring (T)

is a 5- or 6-membered aromatic or heteroaromatic ring;

R$^1$, R$^2$, R$^5$ and R$^6$ are each independently H, OH, halogen, nitro, cyano, rhodano, carboxy, formyl, formyloxy, G-, G-O—, G-S—, G-A-, R$^{21}$R$^{22}$N—, R$^{21}$R$^{22}$N-A-, G-O-A-, G-S-A-, G-A-O—, G-A-S—, G-A-NR$^{23}$—, R$^{21}$R$^{22}$N-A-O—, R$^{21}$R$^{22}$N-A-S—, R$^{21}$R$^{22}$N-A-NR$^{23}$—, G-O-A-O—, G-O-A-S—, G-O-A-NR$^{23}$—, G-S-A-O, G-S-A-NR$^{23}$—, or R$^{20}$S(O)(=NR$^{17}$)—, or two of the groups $R^1$, $R^2$, $R^5$ and $R^6$ attached to the same carbon atom are =O, =S, =NR$^{11}$ or =CR$^{12}$R$^{13}$, or the groups $R^1$ and $R^2$ or $R^5$ and $R^6$ together with the carbon atom to which they are attached form a three to six membered ring containing at least 2 carbon atoms and optionally containing (i) one or two sulfur atoms, (ii) one or two non-adjacent oxygen atoms, (iii) or a combination of (i) and (ii), or a group NR$^{14}$, the ring being optionally substituted by $C_1$-$C_6$ alkyl; or two of the groups $R^1$, $R^2$, $R^5$ and $R^6$ attached to different atoms together with the atoms they are attached form a three to seven membered ring that optionally contains (i) one or two sulfur atoms, (ii) one or two non-adjacent oxygen atoms, (iii) or a combination of (i) and (ii), or a group NR$^{14}$, the ring being optionally substituted by $C_1$-$C_6$ alkyl or two of the groups $R^1$, $R^2$, $R^5$ and $R^6$ attached to adjacent atoms combine to form a bond;

$R^{10}$ is H, OH, cyano, formyl, tri($C_1$-$C_6$ alkyl)silyl, G-, G-O—, G-S—, G-S—S—, G-A-, $R^{24}R^{25}$N—, $R^{24}R^{25}$N—S—, $R^{24}R^{25}$N-A-, $R^{18}$N=C($R^{19}$)—, G-A-NR$^{69}$—, $R^{70}R^{71}$C=N, G-O-A- or G-S-A-, $R^{11}$ is H, OH, nitro, cyano, formyl, formyloxy, G-, G-O—, G-A-, $R^{36}R^{37}$N—, G-C(O)—O—, G-C(O)—NR$^{26}$—, $R^{36}R^{37}$N—C(O)—, G-OC(O)O—, or G-OC(O)—NR$^{26}$—;

$R^{12}$ and $R^{13}$ are each independently H, halogen, nitro, cyano, formyl, formyloxy, G-, G-O—, G-S—, G-A-, $R^{40}R^{41}$N—, $R^{40}R^{41}$N-A-, G-O-A-, G-A-O—, $R^{40}R^{41}$N-A-O—, $R^{40}R^{41}$N-A-S—, G-O-A-O—, G-O-A-S—, or G-O-A-NR$^{30}$—, or $R^{12}$ and $R^{13}$ together with the carbon atom to which they are attached form a 3 to 6 membered carbocyclic ring;

$R^3$, $R^{14}$, $R^{15}$ and $R^{16}$ are each independently H, OH, cyano, formyl, G-, G-O—, G-S—, G-A-, $R^{27}R^{28}$N—, $R^{27}R^{28}$N-A-, G-O-A-, G-S-A-, G-A-NR$^{29}$—, $R^{27}R^{28}$N-A-NR$^{29}$—, G-O-A-NR$^{29}$— or G-S-A-NR$^{29}$—;

each $R^4$ is independently OH, halogen, nitro, cyano, azido, rhodano, isothiocyanato, carboxy, formyl, formyloxy, G-, G-O—, G-S—, G-A-, $R^{31}R^{32}$N—, $R^{31}R^{32}$N-A-, G-O-A-, G-S-A-, G-A-O—, G-A-S—, G-A-NR$^{33}$—, $R^{31}R^{32}$N-A-O—, $R^{31}R^{32}$N-A-S—, $R^{31}R^{32}$N-A-NR$^{33}$—, G-O-A-O—, G-O-A-S—, G-O-A-NR$^{33}$—, G-S-A-O, G-S-A-NR$^{33}$—, $R^{20}$S(O)(=NR$^{17}$)—, $R^{18}$N=C($R^{19}$)—, $R^{44}R^{45}$P(O)— or $R^{44}R^{45}$P(S)—, or 2 adjacent groups $R^4$ together with the carbon atoms to which they are attached form a 4, 5, 6, or 7 membered carbocyclic or heterocyclic ring which may be optionally substituted by halogen, or a group $R^4$ together with a group $R^3$, $R^5$ or $R^9$ and the atoms to which they are attached form a 5-7 membered ring optionally containing an NR$^{15}$ group or an S or O atom, the ring being optionally substituted by $C_1$-$C_6$ alkyl;

n is 0, 1, 2, 3 or 4;

$R^9$ is H, formyl, G, G-A-, $R^{34}R^{35}$N-A-, G-O-A- or G-S-A-, or $R^9$ together with a group $R^1$ or $R^5$ and the atoms to which they are attached may form a three to seven membered ring that optionally may contain (i) one or two sulfur atoms, (ii) one or two non-adjacent oxygen atoms, (iii) or a combination of (i) and (ii), or a group NR$^{16}$;

$R^{17}$ is H, G-, G-C(O)— or G-OC(O)—;

$R^{18}$ is H, OH, cyano, nitro, G-, G-O— or $R^{38}R^{39}$N—;

$R^{19}$ is H, cyano, G-, G-O—, G-S— or $R^{42}R^{43}$N—;

$R^{20}$ is $C_{1-6}$ alkyl, optionally substituted phenyl, or optionally substituted benzyl;

each of the groups $R^{21}$ to $R^{43}$ inclusive are independently H or G-, or two $R^{21}$, $R^{22}$, $R^{27}$, $R^{28}$, $R^{31}$, $R^{32}$, $R^{34}$, $R^{35}$, $R^{36}$, $R^{37}$, $R^{38}$, $R^{39}$, $R^{42}$ or $R^{43}$ groups, together with the N atom to which they are attached, form a group N=CR$^a$R$^b$ where R$^a$ and R$^b$ are each independently H or $C_{1-6}$-alkyl, $R^{21}$, $R^{22}$, $R^{24}$, $R^{25}$, $R^{27}$, $R^{28}$, $R^{31}$, $R^{32}$, $R^{34}$, $R^{35}$, $R^{36}$, $R^{37}$, $R^{38}$, $R^{39}$, $R^{42}$ or $R^{43}$ groups, together with the N atom to which they are attached, form a five, six or seven-membered heterocyclic ring which may contain one or two further heteroatoms selected from O, N or S and which may be optionally substituted by one to four $C_{1-6}$ alkyl groups;

$R^{44}$ and $R^{45}$ are each independently $C_{1-6}$alkyl, $C_{1-6}$-alkoxy, phenyl, or phenoxy;

G is optionally substituted $C_{1-12}$ alkyl, optionally substituted $C_{2-12}$ alkenyl, optionally substituted $C_{2-12}$ alkynyl, optionally substituted $C_{3-8}$ cycloalkyl, optionally substituted $C_{3-8}$ cycloalkenyl, optionally substituted aryl, optionally substituted heteroaryl or optionally substituted heterocyclyl;

$R^{69}$ is H, G-, G-C(O)— or G-OC(O)—;

$R^{70}$ and $R^{71}$ are each independently H, cyano, nitro, G-, G-O—, or G-S—, or $R^{70}$ and $R^{71}$ together with the carbon atom to which they are attached form a five, six or seven-membered heterocyclic ring which may contain one or two further heteroatoms selected from O, N or S and which may be optionally substituted by one to four $C_{1-6}$ alkyl groups;

A is S(O), SO$_2$, C(O) or C(S);

or salts or N-oxides thereof, provided that any compound having formulae (IC1) to (IC3) is excluded:

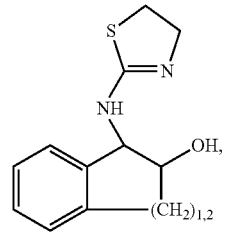

(IC1)

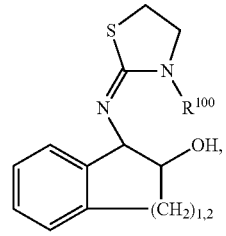

(IC2)

wherein $R^{100}$ is hydrogen or acetyl, and

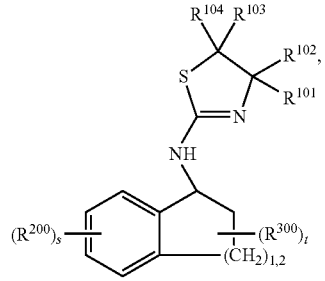

(IC3)

wherein $R^{101}$, $R^{102}$, $R^{103}$ and $R^{104}$ are hydrogen, $R^{200}$ and $R^{300}$ are independently of each other halogen, $C_{1-4}$ alkyl, $C_{1-4}$ alkoxy, $C_{1-4}$ alkylthio, trifluoromethyl or trifluoromethoxy, s and t are independently of each other 0, 1, 2 or 3, and the total of s+t is not greater than 3.

2. Compounds according to claim 1 of the formula ID

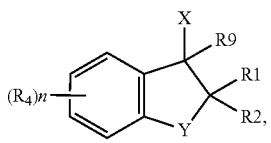
(ID)

or salts or N-oxides thereof, wherein Y is $CR^5R^6$, and at least one of $R^1$, $R^2$, $R^4$, $R^5$, $R^6$ or $R^9$ is fluorine.

3. Compounds according to claim 1 of formula IE

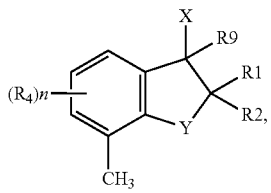
(IE)

or salts or N-oxides thereof, wherein Y is $CR^5R^6$, and n is 0, 1, 2 or 3.

4. Compounds according to claim 1, wherein Y is $CR^5R^6$.

5. Compounds according to claim 1, wherein the ring (T) is a 6-membered aromatic ring.

6. Compounds according to claim 1, wherein X is (ii).

7. Compounds according to claim 6, wherein $R^{10}$ is cyano.

8. Compounds according to claim 4, wherein the ring (T) is a 6-membered aromatic ring.

9. Compounds according to claim 8, wherein X is (ii).

10. Compounds according to claim 9, wherein $R^{10}$ is cyano.

11. Compounds according to claim 10, wherein n is 0.

12. Compounds according to claim 11, wherein $R^1$, $R^2$, $R^5$, $R^6$, and $R^9$ are H.

13. Compounds according to claim 5, wherein n is 0.

14. Compounds according to claim 5, wherein X is (ii).

15. Compounds according to claim 14, wherein $R^{10}$ is cyano.

16. Compounds according to claim 14, wherein n is 0.

* * * * *